United States Patent
Frackenpohl et al.

(10) Patent No.: US 9,006,265 B2
(45) Date of Patent: Apr. 14, 2015

(54) SUBSTITUTED FUSED PYRIMIDINONES AND DIHYDROPYRIMIDINONES

(75) Inventors: Jens Frackenpohl, Frankfurt (DE); Hans-Joachim Zeiβ, Sulzbach (DE); Ines Heinemann, Hofheim (DE); Lothar Willms, Hofheim (DE); Thomas Müller, Frankfurt (DE); Marco Busch, St. Cyr du Pont d'Or (FR); Pascal Von Koskull-Döring, Frankfurt (DE); Isolde Häuser-Hahn, Leverkusen (DE); Christopher Hugh Rosinger, Hofheim (DE); Jan Dittgen, Frankfurt (DE); Martin Jeffrey Hills, Idstein (DE); Monika H. Schmitt, Frankfurt (DE)

(73) Assignee: Bayer Intellectual Property GmbH, Monheim (DE)

( * ) Notice: Subject to any disclaimer, the term of this patent is extended or adjusted under 35 U.S.C. 154(b) by 253 days.

(21) Appl. No.: 13/224,375

(22) Filed: Sep. 2, 2011

(65) Prior Publication Data

US 2012/0157306 A1 Jun. 21, 2012

Related U.S. Application Data

(60) Provisional application No. 61/381,558, filed on Sep. 10, 2010.

(30) Foreign Application Priority Data

Sep. 3, 2010 (EP) .................................. 10175309

(51) Int. Cl.
| | |
|---|---|
| *C07D 239/90* | (2006.01) |
| *A01N 43/653* | (2006.01) |
| *A01N 43/90* | (2006.01) |
| *A01N 43/84* | (2006.01) |
| *A01N 43/56* | (2006.01) |
| *C07D 401/06* | (2006.01) |
| *C07D 239/91* | (2006.01) |
| *C07D 403/04* | (2006.01) |
| *C07D 409/04* | (2006.01) |
| *C07D 405/04* | (2006.01) |
| *A01N 43/82* | (2006.01) |

(52) U.S. Cl.
CPC ............ *C07D 239/90* (2013.01); *A01N 43/653* (2013.01); *A01N 43/82* (2013.01); *A01N 43/84* (2013.01); *A01N 43/90* (2013.01); *C07D 239/91* (2013.01); *C07D 401/06* (2013.01); *C07D 403/04* (2013.01); *C07D 405/04* (2013.01); *C07D 409/04* (2013.01); *A01N 43/56* (2013.01)

(58) Field of Classification Search
USPC ............. 514/303; 504/246; 546/116
See application file for complete search history.

(56) References Cited

U.S. PATENT DOCUMENTS

| | | | |
|---|---|---|---|
| 4,431,440 A * | 2/1984 | Bhalla et al. .................. 504/240 |
| 5,945,423 A | 8/1999 | Bereznak et al. | |
| 6,274,383 B1 | 8/2001 | Gao | |
| 6,337,332 B1 | 1/2002 | Carpino | |
| 2006/0178386 A1 | 8/2006 | Ahmad et al. | |
| 2009/0105283 A1 | 4/2009 | Koltun et al. | |

FOREIGN PATENT DOCUMENTS

| | | |
|---|---|---|
| DE | 289525 | 5/1991 |
| EP | 0239362 | 12/1991 |
| EP | 0897915 | 2/1999 |
| EP | 1396488 | 3/2004 |
| JP | 52051378 | 4/1977 |
| WO | WO 95/24379 | 9/1995 |
| WO | WO 97/10221 | 3/1997 |
| WO | WO 98/11438 | 3/1998 |
| WO | WO 98/26664 | 6/1998 |
| WO | WO 98/33802 | 8/1998 |
| WO | WO 01/81346 | 11/2001 |
| WO | WO 02/48117 | 6/2002 |
| WO | WO 03/035075 | 5/2003 |
| WO | WO 03/055865 | 7/2003 |

(Continued)

OTHER PUBLICATIONS

Dorwald; "Side Reactions in Organic Synthesis: A Guide to Successful Synthesis Design" 2005 Wiley-VCH Verlag GmbH & Co. KGaA, Wienheim, chapter 1.*
Christian; Journal of Experimental Botany, 2008, 59, 2757-2767.*
Somasekhara; Current Science, 1964, 33, 645-646.*
Silverman; The Organic Chemistry of Drug Design and Drug Action, 2004, 2nd Ed, Elsevier pp. 29 to 34.*
International Search Report for EP 10 17 5309 mailed Jan. 19, 2011.
De Block et al., "Poly(ADP-ribose) polymerase in plants affects energy homeostasis, cell death and stress tolerance", The Plant Journal, 2005, pp. 95-106, vol. 41, Blackwell Publishing Ltd., United Kingdom.

(Continued)

*Primary Examiner* — John Mabry
*Assistant Examiner* — Daniel Carcanague
(74) *Attorney, Agent, or Firm* — Frommer Lawrence & Haug LLP

(57) ABSTRACT

The use of substituted fused pyrimidinones and dihydropyrimidinones of the formula (I) or salts thereof

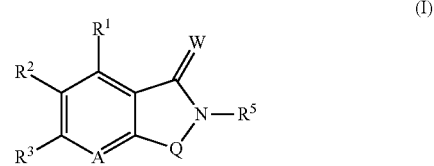

where the radicals of the formula (I) are each as defined in the description, for enhancing stress tolerance in plants to abiotic stress, and for invigorating plant growth and/or for increasing plant yield.

11 Claims, No Drawings

(56) References Cited

FOREIGN PATENT DOCUMENTS

| WO | WO 03/062226 | 7/2003 |
| WO | WO 03/063874 | 8/2003 |
| WO | WO 2004/041755 | 5/2004 |
| WO | WO 2004/096779 | 11/2004 |
| WO | WO 2007/149907 | 2/2007 |
| WO | WO 2007/144669 | 12/2007 |
| WO | WO 2008/090379 | 7/2008 |
| WO | WO 2009/030224 | 3/2009 |
| WO | WO 2009/158404 | 12/2009 |

* cited by examiner

SUBSTITUTED FUSED PYRIMIDINONES AND DIHYDROPYRIMIDINONES

The invention relates to substituted fused pyrimidinones and dihydropyrimidinones and the analogs thereof, to processes for preparation thereof and to the use thereof for enhancing stress tolerance in plants to abiotic stress, and for invigorating plant growth and/or for increasing plant yield.

It is known that particular fused pyrimidinones, in this case 4(3H)-quinazolinone, can be used as active antibacterial ingredients (cf. JP52051378). It is also known that 3-substituted quinazolinones can be used as active fungicidal ingredients (cf. WO9826664 and U.S. Pat. No. 5,945,423). The fungicidal action of 3-substituted dihydroquinazolinones has also been described (cf. DD289525).

It is additionally known that substituted fused pyrimidinones of the quinazolinone type can be used as active pharmaceutical ingredients for regulation of apolipoprotein A-I (cf. WO2009158404), for treatment of obesity (cf. U.S. Pat. No. 6,337,332), as calcium receptor antagonists (cf. WO2004041755), as inhibitors of phosphatidylinositol 3-kinase (cf. WO2003035075 and WO2001081346) and for treatment of diabetes (cf. US2009105283), and also as active antitumor ingredients (cf. EP239362 and WO2009030224). The action of substituted fused dihydropyrimidinones of the dihydroquinazolinone type as serotonin modulators is detailed in US2006178386, while U.S. Pat. No. 6,337,332 describes the preparation of particular substituted fused dihydropyrimidinones of the dihydroquinazolinone type and use as neuropeptide Y receptor antagonists for treatment of obesity and circulation disorders. WO97/10221, WO98/11438 and U.S. Pat. No. 6,274,383 describe the solid phase-supported combinatorial preparation of substituted quinazolinones and dihydroquinazolinones, while WO2008090379 and WO2007149907 describe the preparation and pharmaceutical use of pyrazoloquinazolinones. It is additionally known that 2,3-dihydroquinazolin-4(1H)-ones can be used as tubulin inhibitors and active antitumor ingredients (cf. J. Med. Chem. 2008, 51, 4620).

In contrast, there has been no description to date of the use of the substituted fused pyrimidinones and dihydropyrimidinones described in the patent applications and publications cited above for enhancement of stress tolerance in plants to abiotic stress, for invigorating plant growth and/or for increasing plant yield.

It is known that plants can react to natural stress conditions, for example cold, heat, drought, injury, pathogenic attack (viruses, bacteria, fungi, insects), etc., but also to herbicides, with specific or unspecific defense mechanisms [Pflanzenbiochemie, p. 393-462, Spektrum Akademischer Verlag, Heidelberg, Berlin, Oxford, Hans W. Heldt, 1996; Biochemistry and Molecular Biology of Plants, p. 1102-1203, American Society of Plant Physiologists, Rockville, Md., eds. Buchanan, Gruissern, Jones, 2000].

In plants, numerous proteins involved in defense reactions to abiotic stress (e.g. cold, heat, drought, salinity, flooding), and the genes that code for them, are known. Some of these form part of signal transduction chains (for example transcription factors, kinases, phosphatases) or cause a physiological response of the plant cell (for example ion transport, deactivation of reactive oxygen species). The signaling chain genes of the abiotic stress reaction include transcription factors of the DREB and CBF classes (Jaglo-Ottosen et al., 1998, Science 280: 104-106). The reaction to salinity stress involves phosphatases of the ATPK and MP2C types. In addition, in the event of salinity stress, the biosynthesis of osmolytes such as proline or sucrose is often activated. This involves, for example, sucrose synthase and praline transporters (Hasegawa et al., 2000, Annu Rev Plant Physiol Plant Mol Biol 51: 463-499). The stress defense of the plants to cold and drought uses some of the same molecular mechanisms. There is a known accumulation of what are called late embryogenesis abundant proteins (LEA proteins), which include the dehydrins as an important class (Ingram and Bartels, 1996, Annu Rev Plant Physiol Plant Mol Biol 47: 277-403, Close, 1997, Physiol Plant 100: 291-296). These are chaperones which stabilize vesicles, proteins and membrane structures in stressed plants (Bray, 1993, Plant Physiol 103: 1035-1040). In addition, there is frequently induction of aldehyde dehydrogenases, which deactivate the reactive oxygen species (ROS) which form in the event of oxidative stress (Kirch et al., 2005, Plant Mol Biol 57: 315-332). Heat shock factors (HSF) and heat shock proteins (HSP) are activated in the event of heat stress and play a similar role here as chaperones to that of dehydrins in the event of cold and drought stress (Yu et al., 2005, Mol Cells 19: 328-333).

A number of signaling substances which are endogenous to plants and are involved in stress tolerance or pathogenic defense are already known. Examples here include salicylic acid, benzoic acid, jasmonic add or ethylene [Biochemistry and Molecular Biology of Plants, p. 850-929, American Society of Plant Physiologists, Rockville, Md., eds. Buchanan, Gruissem, Jones, 2000]. Some of these substances or the stable synthetic derivatives and derived structures thereof are also effective on external application to plants or in seed dressing, and activate defense reactions which cause elevated stress tolerance or pathogen tolerance of the plant [Sembdner, and Parthier, 1993, Ann. Rev. Plant Physiol. Plant Mol. Bid. 44: 569-589].

It is additionally known that chemical substances can increase the tolerance of plants to abiotic stress. Such substances are applied by seed dressing, by leaf spraying or by soil treatment. For instance, an increase in the abiotic stress tolerance of crop plants by treatment with elicitors of systemic acquired resistance (SAR) or abscisic acid derivatives is described (Schading and Wei, WO200028055; Abrams and Gusta, U.S. Pat. No. 5,201,931; Abrams et al., WO97/23441, Churchill et al., 1998, Plant Growth Regul 25: 35-45). In addition, effects of growth regulators on the stress tolerance of crop plants have been described (Morrison and Andrews, 1992, J Plant Growth Regul 11: 113-117, RD-259027). In this context, it is likewise known that a growth-regulating naphthylsulfonamide (4-bromo-N-(pyridin-2-ylmethyl)naphthalene-1-sulfonamide) influences the germination of plant seeds in the same way as abscisic acid (Park et al. Science 2009, 324, 1068-1071). It is also known that a further naphthylsulfonamide, N-(6-aminohexyl)-5-chloronaphthalene-1-sulfonamide, influences the calcium level in plants which have been exposed to cold shock (Cholewa at al. Can. J. Botany 1997, 75, 375-382).

Similar effects are also observed on application of fungicides, especially from the group of the strobilurins or of the succinate dehydrogenase inhibitors, and are frequently also accompanied by an increase in yield (Draber et al., DE3534948, Bartlett et al., 2002, Pest Manag Sci 60: 309). It is likewise known that the herbicide glyphosate in low dosage stimulates the growth of some plant species (Cedergreen, Env. Pollution 2008, 156, 1099).

In the event of osmotic stress, a protective effect has been observed as a result of application of osrnolytes, for example glycine betaine or the biochemical precursors thereof, e.g. choline derivatives (Chen at al., 2000, Plant Cell Environ 23: 609-618, Bergmann et al., DE4103253). The effect of antioxidants, for example naphthols and xanthines, to increase abiotic stress tolerance in plants has also already been described (Bergmann at al., DD-277832, Bergmann at al., DD-277835). The molecular causes of the antistress action of these substances are, however, largely unknown.

It is additionally known that the tolerance of plants to abiotic stress can be increased by a modification of the activity of endogenous poly-ADP-ribose polymerases (PARP) or poly-(ADP-ribose) glycohydrolases (PARG) (de Block et al., The Plant Journal, 2004, 41, 95; Levine et al., FEBS Lett. 1998, 440, 1; WO0004173; WO04090140).

It is thus known that plants possess several endogenous reaction mechanisms which can bring about effective defense against a wide variety of different harmful organisms and/or natural abiotic stress.

Since the ecologic and economic demands on modern plant treatment compositions are increasing constantly, for example with respect to toxicity, selectivity, application rate, formation of residues and favorable manufacture, there is a constant need to develop novel plant treatment compositions which have advantages over those known, at least in some areas.

It was therefore an object of the present invention to provide further compounds which increase tolerance to abiotic stress in plants, bring about invigoration of plant growth and/or contribute to an increase in plant yield.

The present invention accordingly provides for the use of substituted fused pyrimidinones and dihydropyrimidinones of the formula (I) or salts thereof (I)

for increasing tolerance to abiotic stress in plants, where Q represents the moieties

Q-1

Q-2

Q-3

Q-4 where $R^6$, $R^7$, $R^8$, $R^9$ and $R^{10}$ are each as defined below and where the arrow represents a bond to the $N-R^5$ group;
W is oxygen or sulfur;
A is N (nitrogen) or the $C-R^4$ moiety, where $R^4$ in the $C-R^4$ moiety is in each case as defined below;
$R^1$, $R^2$, $R^3$, $R^4$ are each independently hydrogen, nitro, amino, hydroxyl, halogen, cyano, alkyl, cycloalkyl, alkenyl, alkynyl, aryl, arylalkyl, arylalkenyl, arylalkynyl, heteroaryl, cycloalkylalkyl, cycloalkylalkenyl, cycloalkylalkynyl, heteroarylalkyl, heteroarylalkenyl, heteroarylalkynyl, haloalkyl, halocycloalkyl, haloalkenyl, halocycloalkenyl, haloalkyalkynyl, alkysilylalkynyl, alkoxyalkyl, alkoxy, haloalkoxy, alkenyoxyalkyl, alkyalkoxy, arylalkoxy, alkoxycarbonyl, hydroxycarbonyl, aminocarbonyl, alkylaminocarbonyl, cycloalkylaminocarbonyl, alkylamino, alkenylamino, alkynylamino, hydrothio, alkylthio, haloalkylthio, bisalkylamino, cycloalkylamino, alkycarbonylamino, cycloalkylcarbonylamino, haloalkylcarbonylamino, alkoxycarbonylamino, alkylaminocarbonylamino, alkysulfonyamino, cycloalkysulfonylamino, arylsulfonylamino, hetarylsulfonylamino, sulfonylhaloalkylamino, aminoalkylsulfonyl, aminohaloalkylsulfonyl, alkylsulfonyl, cycloalkylsulfonyl, arylsulfonyl, alkysulfinyl, cycloalkylsulfinyl, arylsulfinyl, N,S-dialkysulfonimidoyl, S-alkylsulfonimidoyl, alkylsulfonylaminocarbonyl, cycloalkylsulfonyaminocarbonyl, cycloalkylaminosulfonyl, cycloalkylalkoxy, alkynyalkoxy, alkenylalkoxy, alkenyloxyalkoxy, alkyloxyalkoxy, alkylaminoalkoxy, bisalkylaminoalkoxy, cycloalkylaminoalkoxy;
$R^5$ is hydrogen, alkyl, cycloalkyl, halogen, alkynylalkyl, alkynylalkyl, haloalkyl, alkoxyalkyl, alkynyl, alkenyl, cycloalkylalkyl, cyanoalkyl, nitroalkyl, arylalkyl, heteroarylalkyl, alkylaminoalkyl, bisalkylaminoalkyl, aminocarbonylalkyl, alkylaminocarbonylalkyl, bisalkylaminocarbonylalkyl, alkoxycarbonylalkyl, hydroxycarbonylalky, alkycarbonyl, cycloalkylcarbonyl, haloalkycarbonyl, alkoxycarbonyl, alkysulfonyl, arylsulfony, cycloalkysulfonyl, arylalkylsulfonyl, alkenylsulfonyl, heteroarylsulfonyl, alkynylsulfonyl, alkylsulfinyl, arylsulfinyl, cycloalkylsulfinyl, alkenylsulfinyl, alkynylsulfinyl, arylcarbonyl, heteroarylcarbonyl, alkoxycarbonylalkyl, cyanoalkylaminocarbonyl, alkynylaminocarbonyl, heterocycloalkylcarbonyl, heteroarylalkylaminocarbonyl, alkenyloxycarbonyl, cycloalkylalkoxycarbonyl, cycloalkylalkylaminocarbonyl, arylalkylaminocarbonyl or a negative charge;
$R^6$ is hydrogen, hydroxyl, formyl, amino, bisalkylamino, alkyl, cycloalkyl, cyanoalkyl, alkenyalkyl, haloalkyl, alkynyl, alkenyl, cycloalkylalkyl, cyanoalkyalkenyl, arylalkyl, arylalkenyl, arylalkynyl, heteroarylalkyl, heteroarylalkenyl, heteroarylalkynyl, alkylcarbony, haloalkylcarbonyl, cycloalkylcarbonyl, arylcarbonyl, heteroarylcarbonyl, alkoxycarbonyl, aminocarbonyl, alkylaminocarbonyl, alkylsulfonyl, alkenylsulfonyl, heteroarylsulfonyl, arylsulfonyl, cycloalkylsulfonyl, alkylsulfinyl, arylsulfinyl, cycloalkylsulfinyl, alkoxycarbonylalkyl, cycloalkylaminocarbonyl, haloalkylaminocarbonyl, alkynylaminocarbonyl, cyanoalkylaminocarbonyl, heterocycloalkylcarbonyl, heteroarylalkylaminocarbonyl, alkenyloxycarbonyl, cycloalkylalkoxycarbonyl, cycloalkylalkylaminocarbonyl, arylalkylaminocarbonyl, alkylaminoalkyl, bisalkylaminoalkyl, aminocarbonylalkyl, alkylaminocarbonylalkyl, bisalkylaminocarbonylalkyl;
$R^7$ is hydrogen, alkyl, cycloalkyl, haloalkyl, alkenyl, alkynyl, cycloalkylalkyl, cyanoalkyl, alkylsilylalkyl, alkenylalkyl, alkynylalkyl, aryl, heteroaryl, heterocycloalkyl, arylalkenyl, arylalkynyl, heteroarylalkenyl, heteroarylalkynyl, haloalkenyl, arylhaloalkenyl, heteroarylhaloalkenyl, arylalkyl, heteroarylalkyl, alkoxyalkyl, haloalkoxyalkyl, aryloxyalkyol, heteroaryloxyalkyl, arylalkyloxyalkyl, heteroaylalkyloxyalkyl, cycloaalkylalkoxyalkyl, alkynylalkoxyalkyl, alkenylalkoxyalkyl, alkenyloxyalkoxyalkyl, alkyloxyalkoxyalkyl, alkylaminoalkoxyalkyl, bisalkylaminoalkoxyalkyl, cycloaalkyrlaminoalkoxyalkyl, arminoalkyl, alkylaminoalkyl, bisalkylaminoalkyl, cycloalkylaminoalkyl, cycloalkoxyaminoalkyl, arylaminoalkyl, arylalkylaminoalkyl, heteroarylalkylaminoalkyl, bisalkylamino, cycloalkylamino, alkylcarbonylamino, cycloalkylcarbonylamino, haloalkylcarbonylamino, alkoxycarbonyolamino, alkylaminocarbonylamino, alkylsulfonylamino, cycloalkylsulfonylamino, arylsulfonylamino, heteroarylsulfonyrlamino, sulfonylhaloalkylamino, arylalkynyol, arylalkynylheteroaryl, cycloalkoxyalkyol, alkylcarbonyloxyalkyl, cycloalkylcarbonyloxyalkyl, arylcarbonyloxyalkyl, heteroarylcarbonyloxyalkyl, heteroarylalkylcarbonyloxyalkyl, alkylthioalkyl, cycloalkylthioalkyl, haloalkylthioalkyl, arylthioalkyl, heteroarylthioalkyl, alkylcarbonyloxyalkylheteroaryl, alkoxycarbonylaminoalkyl, alkylcarbonylaminoalkyl, cycloalkylcarbonylaminoalkylo, haloalkylcarbonylaminoalkyl, arylcarbonylaminoalkyl, heteroarylcarbonylaminoalkyl, alkoxycarbonylaminoalkyl, alkylaminocarbonylaminoalkyl, alkylsulfonylaminoalkyl, cycloalkylsulfonylaminoalkyl, arylsulfonylaminoalkyl, heteroarylsulfonylaminoalkyl, sulfonylhaloalkylaminoalkyl, (heteroaryl)alkylaminoalkyl, (aryl)alkylaminocarbonyl, (heteroarylalkyl)alkylaminoalkyl, alkylcarbonylalkyl, alkoxycarbonylalkyl, arylalkoxycarbonylalkyl, aminocarbonylalkyl, alkylaminocarbonylalkyl, cycloalkylaminocarbonylalkyl, heteroarylalkylaminocarbonylalkyl, arylalkylaminocarbonylalkyl, heteroarylaminocarbonylalkyl, heterocycloalkyl-N-alkyl, arylheterocycloalkenyl-N-alkyl, arylheterocycloalkyl-N-alkyl, heterocycloalkyl, heterocycloalkenyl, heterocycloalkylalkynyl, heterocyloalkenylalkynyl, heterocycloalkylaylkenyl, heterocyloalkenylalknylalkenyl, heterocycloalkylalkyl, heterocyloalkenylalkyl, where the heteroatom in heteroaryl, heterocycloalkyl and heterocycloalkenyl optionally bears a charge; and $R^8$ is hydrogen, alkyl, haloalkyl, alkoxyalkyl, haloalkoxyalkyl, cycloalkyl, cycloalkylalkyl, alkylthioalkyl, cyanoalkyl, alkenylalkyl, alkynylalkyl, alkenyl; or $R^7$ and $R^8$ with the atom to which they are bonded are a fully saturated or partly saturated 4 to 7-membered ring optionally interrupted by heteroatoms and optionally further substituted by one or more radicals, where any substituents present correspond to the definition described for $R^1$;

$R^9$ is hydrogen, alkyl, aryl, alkenyl, haloalkyl, cycloalkyl, arylalkyl, heteroaryl, hydroxycarbonyl, alkoxycarbonyl, alkylaminocarbonyl, cycloalkylaminocarbonyl, cyanoalkylaminocarbonyl, heteroarylalkylaminocarbonyl, cycloalkylalkylaminocarbonyl, arylalkylaminocarbonyl, alkynylaminocarbonyl, heterocycloalkylcarbonyl, alkenyloxycarbonyl, cycloalkylalkoxycarbonyl; and $R^{10}$ is hydrogen, alkyl, alkenyl, haloalkyl, cycloalkyl, arylalkyl, aryl, heteroaryl, alkenylalkyl.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. These salts then contain the conjugate base of the acid as the anion.

Suitable substituents present in deprotonated form, for example sulfonic acids or carboxylic acids, can form internal salts with groups which are themselves protonatable, such as amino groups. The compounds of the formula (I) used in accordance with the invention and salts thereof are referred to hereinafter as "compounds of the formula (I)".

Preference is given to the inventive use of compounds of the formula (I) in which
Q represents the moieties

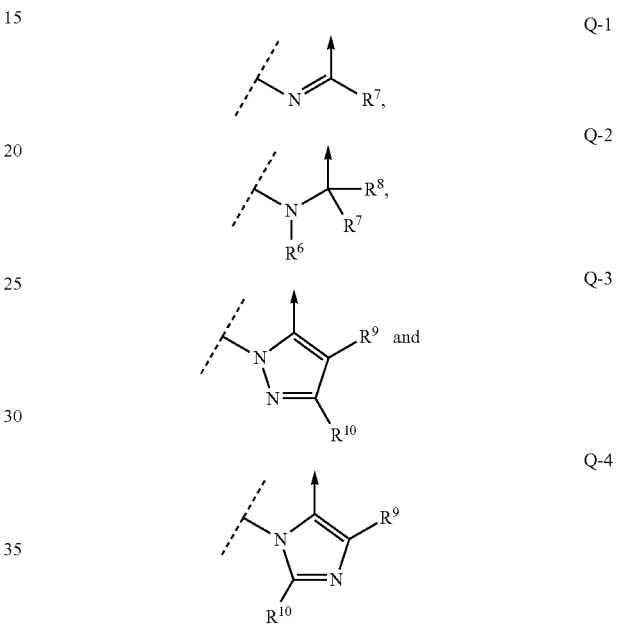

where $R^6$, $R^7$, $R^8$, $R^9$ and $R^{10}$ are each as defined below and where the arrow represents a bond to the N—$R^5$ group;

W is oxygen or sulfur;

A is N (nitrogen) or the C—$R^4$ moiety, where in the C—$R^4$ moiety is in each case as defined below;

$R^1$, $R^2$, $R^3$, $R^4$ are each independently hydrogen, nitro, amino, hydroxyl, cyano, $(C_1-C_{16})$-alkyl, $(C_3-C_8)$-cycloalkyl, $(C_2-C_8)$-alkenyl, $(C_2-C_8)$-alkynyl, aryl, aryl-$(C_2-C_8)$-alkenyl, aryl-$(C_2-C_8)$-alkynyl, heteroaryl, $(C_3-C_8)$-cycloalkyl-$(C_1-C_8)$-alkyl, $(C_3-C_8)$-cycloalkyl-$(C_2-C_8)$-alkenyl, $(C_3-C_8)$-cycloalkyl-$(C_2-C_8)$-alkynyl, heteroaryl-$(C_1-C_8)$-alkyl, heteroaryl-$(C_2-C_8)$-alkenyl, heteroaryl-$(C_2-C_8)$-alkynyl, $(C_1-C_8)$-haloalkyl, $(C_3-C_8)$-halocycloalkyl, $(C_2-C_8)$-haloalkenyl, $(C_3-C_8)$-halocycloalkenyl, $(C_2-C_8)$-haloalkylkynyl, $(C_1-C_6)$-alkylsilyl-$(C_2-C_8)$-alkynyl, $(C_1-C_8)$-alkoxy-$(C_1-C_8)$-alkyl, $(C_1-C_8)$-alkoxy, $(C_1-C_8)$-haloalkoxy, $(C_2-C_8)$-alkenyloxy-$(C_1-C_8)$-alkyl, aryl-$(C_1-C_8)$-alkoxy, $(C_1-C_8)$-alkoxycarbonyl, hydroxycarbonyl, aminocarbonyl, $(C_1-C_8)$-alkylaminocarbonyl, $(C_3-C_8)$-cycloalkylaminocarbonyl, $(C_1-C_8)$-alkylamino, $(C_2-C_8)$-alkenylamino, $(C_2-C_8)$-alkynylamino, hydrothio, $(C_1-C_8)$-alkylthio, $(C_1-C_8)$-haloalkylthio, bis-$(C_1-C_8)$-alkylamino, $(C_3-C_8)$-cycloalkylamino, $(C_3-C_8)$-haloalkylamino, $(C_1-C_8)$-alkylcarbonylamino, $(C_3-C_8)$-cycloalkylcarbonylamino, $(C_1-C_8)$-haloalkylcarbonylamino, $(C_1-C_8)$-alkoxycarbonylamino, $(C_1-C_8)$-alkylaminocarbonylamino, $(C_1-C_8)$-alkylsulfonylamino, $(C_1-C_8)$-cycloalkylsulfonylamino, arylsulfonylamino, hetarylsulfonylamino, $(C_3-C_8)$-haloalkylsulfonylamino, amino-$(C_1-C_8)$-alkylsulfonyl, amino-$(C_1-C_8)$-haloalkylsulfonyl, $(C_1-C_8)$-alkylsulfonyl, $(C_3-C_8)$-cycloalkylsulfonyl, $(C_1-C_8)$-haloalkylsulfonyl, arylsulfonyl, $(C_1-C_8)$-alkylsulfinyl, $(C_3-C_8)$-cycloalkylsulfinyl, $(C_1-C_8)$-haloalkylsulfinyl, arylsulfinyl, N,S-bis-$(C_1-C_8)$-alkylsulfonimidoyl, S—$(C_1-C_8)$-alkylsulfonimidoyl, $(C_1-C_8)$-alkylsulfonylaminocarbonyl, $(C_3-C_8)$-cycloalkylsulfonylaminocarbonyl, $(C_3-C_8)$-cycloalkylaminosulfonyl, $(C_3-C_8)$-cycloalkyl-$(C_1-C_8)$-alkoxy, $(C_1-C_8)$-alkynyl-$(C_1-C_8)$-alkoxy, $(C_2-C_8)$-alkenyl-$(C_1-C_8)$-alkoxy, $(C_2-C_8)$-alkenyloxy-$(C_1-C_8)$-alkoxy, $(C_1-C_8)$-alkyloxy-$(C_1-C_8)$-alkoxy, $(C_1-C_8)$-alkylamino-$(C_1-C_8)$-alkoxy, bis-$(C_1-C_8)$-alkylamino-$(C_1-C_8)$-alkoxy, $(C_3-C_8)$-cycloalkylamino-$(C_1-C_8)$-alkoxy $(C_3-C_8)$-heterocycloalkyl;

$R^5$ is hydrogen, $(C_1-C_{16})$-alkyl, $(C_3-C_8)$-cycloalkyl, halogen, $(C_2-C_8)$-alkenyl-$(C_1-C_8)$-alkyl, $(C_2-C_8)$-alkynyl-$(C_1-C_8)$-alkyl, $(C_1-C_8)$-haloalkyl, $(C_1-C_8)$-alkoxy-$(C_1-C_8)$-alkyl, $(C_2-C_8)$-alkynyl, $(C_2-C_8)$-alkenyl, $(C_3-C_8)$-cycloalkyl-$(C_1-C_8)$-alkyl, cyano-$(C_1-C_8)$-alkyl, nitro-$(C_1-C_8)$-alkyl, heteroaryl-$(C_1-C_8)$-alkyl, $(C_1-C_8)$-alkylamino-$(C_1-C_8)$-alkyl, bis-$(C_1-C_8)$-alkylamino-$(C_1-C_8)$-alkyl, aminocarbonyl-$(C_1-C_8)$-alkyl, $(C_1-C_8)$-alkylaminocarbonyl-$(C_1-C_8)$-alkyl, bis-$(C_1-C_8)$-alkylaminocarbonyl-$(C_1-C_8)$-alkyl, $(C_1-C_8)$-alkoxycarbonyl-$(C_1-C_8)$-alkyl, hydroxycarbonyl-$(C_1-C_8)$-alkyl, $(C_1-C_8)$-alkylcarbonyl, $(C_3-C_8)$-cycloalkylcarbonyl, $(C_1-C_8)$-haloalkylcarbonyl, $(C_1-C_8)$-alkoxycarbonyl, $(C_1-C_8)$-alkylsulfonyl, arylsulfonyl, $(C_3-C_8)$-cycloalkylsulfonyl, aryl-$(C_1-C_8)$-alkylsulfonyl, $(C_2-C_8)$-alkenylsulfonyl, heteroarylsulfonyl, $(C_2-C_8)$-alkynylsulfonyl, $(C_1-C_8)$-alkylsulfinyl, arylsulfinyl, $(C_3-C_8)$-cycloalkylsulfinyl, $(C_2-C_8)$-alkenylsulfinyl, $(C_2-C_6)$-alkynylsulfinyl, arylcarbonyl, heteroarylcarbonyl, $(C_1-C_8)$-alkoxycarbonyl-cyano-$(C_1-C_8)$-alkylaminocarbonyl, $(C_3-C_8)$-alkynylaminocarbonyl, $(C_4-C_7)$-heterocycloalkylcarbonyl, heteroaryl-$(C_1-C_8)$-alkylaminocarbonyl, $(C_2-C_7)$-alkenyloxycarbonyl, $(C_3-C_8)$-cycloalkyl-$(C_1-C_8)$-alkoxycarbonyl, $(C_3-C_8)$-cycloalkyl-$(C_1-C_8)$-alkylaminocarbonyl, aryl-$(C_1-C_8)$-alkylaminocarbonyl or a negative charge;

$R^6$ is hydrogen, hydroxyl, formyl, amino, bis-$(C_1-C_8)$-alkylamino, $(C_1-C_8)$-alkyl, $(C_3-C_8)$-cycloalkyl, cyano-$(C_1-C_8)$-alkyl, $(C_2-C_8)$-alkenyl-$(C_1-C_8)$-alkyl, $(C_1-C_8)$-haloalkyl, $(C_2-C_8)$-alkynyl, $(C_2-C_8)$-alkenyl, $(C_3-C_8)$-cycloalkyl-$(C_1-C_8)$-alkyl, cyano-$(C_1-C_8)$-alkyl-$(C_2-C_8)$-alkenyl, aryl-$(C_2-C_8)$-alkenyl, aryl-$(C_2-C_8)$-alkynyl, heteroaryl-$(C_1-C_8)$-alkyl, heteroaryl-$(C_2-C_8)$-alkenyl, heteroaryl-$(C_2-C_8)$-alkynyl, $(C_1-C_8)$-alkylcarbonyl, $(C_1-C_8)$-haloalkylcarbonyl, $(C_3-C_8)$-cycloalkylcarbonyl, arylcarbonyl, heteroarylcarbonyl, $(C_1-C_8)$-alkoxycarbonyl, aminocarbonyl, $(C_1-C_8)$-alkylaminocarbonyl, $(C_1-C_8)$-alkylsulfonyl, $(C_1-C_8)$-alkenylsulfonyl, heteroarylsulfonyl, arylsulfonyl, $(C_3-C_8)$-cycloalkylsulfonyl, $(C_1-C_8)$-alkylsulfinyl, arylsulfinyl, $(C_3-C_8)$-cycloalkylsulfinyl, $(C_1-C_8)$-alkoxycarbonyl-$(C_1-C_8)$-alkyl, $(C_3-C_6)$-cycloalkylaminocarbonyl, $(C_1-C_6)$-haloalkylaminocarbonyl, $(C_2-C_7)$-alkynylaminocarbonyl, cyano-$(C_1-C_7)$-alkylaminocarbonyl, $(C_4-C_7)$-heterocycloalkylcarbonyl, heteroaryl-$(C_1-C_7)$-alkylaminocarbonyl, $(C_2-C_7)$-alkenyloxycarbonyl, $(C_3-C_7)$-cycloalkyl-$(C_1-C_6)$-alkoxycarbonyl, $(C_3-C_7)$-cycloalkyl-$(C_1-C_6)$-alkylaminocarbonyl, aryl-$(C_1-C_6)$-alkylaminocarbonyl, $(C_1-C_7)$-alkylamino-$(C_1-C_7)$-alkyl, bis-$(C_1-C_7)$-alkylamino-aminocarbonyl-$(C_1-C_7)$-alkyl, $(C_1-C_7)$-alkylaminocarbonyl, bis-$(C_1-C_7)$-alkylaminocarbonyl-$(C_1-C_7)$-alkyl;

$R^7$ is hydrogen, $(C_1-C_{16})$-alkyl, $(C_3-C_8)$-cycloalkyl, $(C_1-C_8)$-haloalkyl, $(C_2-C_{16})$-alkenyl, $(C_2-C_{16})$-alkynyl, $(C_3-C_8)$-cycloalkyl-$(C_1-C_8)$-alkyl, cyano-$(C_1-C_8)$-alkyl, $(C_2-C_8)$-alkenyl-$(C_1-C_8)$-alkyl, $(C_2-C_8)$-alkynyl-$(C_1-C_8)$-alkyl, aryl, heteroaryl, $(C_3-C_8)$-heterocycloalkyl, aryl-$(C_2-C_8)$-alkenyl, aryl-$(C_2-C_8)$-alkynyl, heteroaryl-$(C_2-C_8)$-alkenyl, heteroaryl-$(C_2-C_8)$-alkynyl, $(C_2-C_8)$-haloalkenyl, aryl-$(C_2-C_8)$-haloalkenyl, heteroaryl-$(C_2-C_8)$-haloalkenyl, aryl-$(C_1-C_8)$-alkyl, heteroaryl-$(C_1-C_8)$-alkyl, $(C_1-C_8)$-alkoxy-$(C_1-C_8)$-alkyl, $(C_1-C_8)$-haloalkoxy-$(C_1-C_8)$-alkyl, aryloxy-$(C_1-C_8)$-alkyl, heteroaryloxy-$(C_1-C_8)$-alkyl, aryl-$(C_1-C_8)$-alkyloxy-$(C_1-C_8)$-alkyl, heteroaryl-$(C_1-C_8)$-alkyloxy-$(C_1-C_8)$-alkyl, $(C_3-C_8)$-cycloalkyl-$(C_1-C_8)$-alkoxy-$(C_1-C_8)$-alkyl, $(C_2-C_8)$-alkynyl-$(C_1-C_8)$-alkoxy-$(C_1-C_8)$-alkyl, $(C_2-C_8)$-alkenyl-$(C_1-C_8)$-alkoxy-$(C_1-C_8)$-alkyl, $(C_2-C_8)$-alkenyloxy-$(C_1-C_8)$-alkoxy-$(C_1-C_8)$-alkyl, $(C_1-C_8)$-alkyloxy-$(C_1-C_8)$-alkoxy-$(C_1-C_8)$-alkyl, $(C_1-C_8)$-alkylamino-$(C_1-C_8)$-alkoxy-$(C_1-C_8)$-alkyl, bis-$(C_1-C_8)$-alkylamino-$(C_1-C_8)$-alkoxy-$(C_1-C_8)$-alkyl, $(C_3-C_8)$-cycloalkylamino-$(C_1-C_8)$-alkoxy-$(C_1-C_8)$-alkyl, amino-$(C_1-C_8)$-alkyl, $(C_1-C_8)$-alkylamino-$(C_1-C_8)$-alkyl, bis-$(C_1-C_8)$-alkylamino-$(C_1-C_8)$-alkyl, $(C_1-C_8)$-cycloalkylamino-$(C_1-C_8)$-alkyl, $(C_3-C_8)$-cycloalkoxyamino-$(C_1-C_8)$-alkyl, arylamino-$(C_1-C_8)$-alkyl, aryl-$(C_1-C_8)$-alkylamino-$(C_1-C_8)$-alkyl, heteroaryl-$(C_1-C_8)$-alkylamino-$(C_1-C_8)$-alkyl, bis-$(C_1-C_8)$-alkylamino, $(C_3-C_8)$-cycloalkylamino, $(C_1-C_8)$-alkylcarbonylamino, $(C_3-C_8)$-cycloalkylcarbonylamino, $(C_1-C_8)$-haloalkylcarbonylamino, $(C_1-C_8)$-alkoxycarbonylamino, $(C_1-C_8)$-alkylaminocarbonylamino, $(C_1-C_8)$-alkylsulfonylamino, $(C_3-C_8)$-cycloalkylsulfonylamino, arylsulfonylamino, heteroarylsulfonylamino, sulfonyl-$(C_1-C_8)$-haloalkylamino, aryl-$(C_2-C_8)$-alkynyl, aryl-$(C_2-C_8)$-alkynylheteroaryl, $(C_3-C_8)$-cycloalkoxy-$(C_1-C_8)$-alkyl, $(C_1-C_8)$-alkylcarbonyloxy-$(C_1-C_8)$-alkyl, $(C_3-C_8)$-cycloalkylcarbonyloxy-$(C_1-C_8)$-alkyl, arylcarbonyloxy-$(C_1-C_8)$-alkyl, heteroarylcarbonyloxy-$(C_1-C_8)$-alkyl, heteroaryl-$(C_1-C_8)$-alkylcarbonyloxy-$(C_1-C_8)$-alkyl, $(C_1-C_8)$-alkylthio-$(C_1-C_8)$-alkyl, $(C_3-C_8)$-cycloalkylthio-$(C_1-C_8)$-alkyl, $(C_3-C_8)$-cycloalkyl-$(C_1-C_8)$-alkylthio-$(C_1-C_8)$-alkyl, $(C_1-C_8)$-haloalkylthio-$(C_1-C_8)$-alkyl, arylthio-$(C_1-C_8)$-alkyl, heteroarylthio-$(C_1-C_8)$-alkyl, $(C_1-C_8)$-alkylcarbonyloxy-$(C_1-C_8)$-alkylheteroaryl, $(C_1-C_8)$-alkoxycarbonylamino-$(C_1-C_8)$-alkyl, $(C_1-C_8)$-alkylaminocarbonylamino-$(C_1-C_8)$-alkyl, $(C_3-C_8)$-cycloalkylcarbonylamino-$(C_1-C_8)$-alkyl, haloalkylcarbonylamino-$(C_1-C_8)$-alkyl, arylcarbonylamino-$(C_1-C_8)$-alkyl, heteroarylcarbonylamino-$(C_1-C_8)$-alkyl, $(C_1-C_8)$-alkoxycarbonylamino-$(C_1-C_8)$-alkyl, $(C_1-C_8)$-alkylaminocarbonylamino-$(C_1-C_8)$-alkyl, $(C_1-C_8)$-alkylsulfonylamino-$(C_1-C_8)$-alkyl, $(C_3-C_8)$-cycloalkylsulfonylamino-$(C_1-C_8)$-alkyl, arylsulfonylamino-$(C_1-C_8)$-alkyl, heteroarylsulfonylamino-$(C_1-C_8)$-alkyl, sulfonyl-$(C_1-C_8)$-haloalkylamino-$(C_1-C_8)$-alkyl, (heteroaryl)-$(C_1-C_8)$-alkylamino-$(C_1-C_8)$-alkyl, (aryl)-$(C_1-C_8)$-alkylaminocarbonyl, (heteroaryl-$(C_1-C_8)$-alkyl)-$(C_1-C_8)$-alkylamino-$(C_1-C_8)$-alkyl, $(C_1-C_8)$-alkylcarbonyl-$(C_1-C_8)$-alkyl, $(C_1-C_8)$-alkoxycarbonyl-$(C_1-C_8)$-alkyl, aryl-$(C_1-C_8)$-alkoxycarbonyl-$(C_1-C_8)$-alkyl, aminocarbonyl-$(C_1-C_8)$-alkyl, $(C_1-C_8)$-alkylaminocarbonyl-$(C_1-C_8)$-alkyl, $(C_3-C_8)$-cycloalkylaminocarbonyl-$(C_1-C_8)$-alkyl, heteroaryl-$(C_1-C_8)$-alkylaminocarbonyl-$(C_1-C_8)$-alkyl, aryl-$(C_1-C_8)$-alkylaminocarbonyl-$(C_1-C_8)$-alkyl, heteroarylaminocarbonyl-$(C_1-C_8)$-alkyl, $(C_1-C_8)$-heterocycloalkyl-N—$(C_1-C_8)$-alkyl, aryl-$(C_4-C_8)$-heterocycloalkenyl-N—$(C_1-C_8)$-alkyl, aryl-$(C_3-C_8)$-heterocycloalkyl-N—$(C_1-C_8)$-alkyl, $(C_3-C_8)$- heterocycloalkyl, (C₃-C₈)-heterocycloalkenyl, (C₃-C₈)-heterocycloalkyl-(C₂-C₈)-alkynyl, (C₃-C₈)-heterocycloalkenyl-(C₂-C₈)-alkynyl, (C₃-C₈)-heterocycloalkyl-(C₂-C₈)-alkenyl, (C₃-C₈)-heterocycloalkenyl-(C₂-C₈)-alkenyl, (C₃-C₈)-heterocycloalkyl-(C₁-C₈)-alkyl, (C₃-C₈)-heterocycloalkenyl-(C₁-C₈)-alkyl, where the heteroatom in heteroaryl, heterocycloalkyl and heterocycloalkenyl optionally bears a charge; and R⁸ is hydrogen, (C₁-C₈)-alkyl, (C₁-C₈)-haloalkyl, (C₁-C₈)-alkoxy-(C₁-C₈)-alkyl, (C₁-C₈)-haloalkoxy-(C₁-C₈)-alkyl, (C₃-C₈)-cycloalkyl, (C₃-C₈)-cycloalkyl-(C₁-C₈)-alkyl, (C₁-C₈)-alkylthio-(C₁-C₈)-alkyl, cyano-(C₁-C₈)-alkyl, (C₂-C₈)-alkenyl-(C₁-C₈)-alkyl, (C₇-C₈)-alkynyl-(C₁-C₈)-alkyl, (C₂-C₈)-alkenyl, (C₃-C₈)-heterocycloalkyl; or R⁷ and R⁸ with the atom to which they are bonded are a fully saturated or partly saturated 4 to 7-membered ring optionally interrupted by heteroatoms and optionally further substituted by one or more radicals, where any substituents present correspond to the definition described for R¹;

R⁹ is hydrogen, (C₁-C₈)-alkyl, substituted or unsubstituted phenyl, (C₂-C₈)-alkenyl, (C₁-C₈)-haloalkyl, (C₃-C₈)-cycloalkyl, aryl-(C₁-C₈)-alkyl, heteroaryl, hydroxycarbonyl, (C₁-C₈)-alkoxycarbonyl, (C₁-C₈)-alkylaminocarbonyl, (C₃-C₈)-cycloalkylaminocarbonyl, cyano-(C₁-C₈)-alkylaminocarbonyl, heteroaryl-(C₁-C₈)-alkylaminocarbonyl, (C₃-C₈)-cycloalkyl-(C₁-C₈)-alkylaminocarbonyl, aryl-(C₁-C₈)-alkylaminocarbonyl, (C₃-C₈)-alkynylaminocarbonyl, (C₄-C₇)-heterocycloalkylcarbonyl, hetaroalyl-(C₁-C₈)-alkylaminocarbonyl, (C₂-C₇)-alkenyloxycarbonyl, (C₃-C₈)-cycloalkyl-(C₁-C₈)-alkoxycarbonyl; and R¹⁰ is hydrogen, (C₁-C₈)-alkyl, (C₂-C₈)-alkenyl, (C₁-C₈)-haloalkyl, (C₃-C₈)-cycloalkyl, aryl-(C₁-C₈)-alkyl, aryl, heteroaryl, (C₂-C₈)-alkenyl-(C₁-C₈)-alkyl.

Particular preference is given to the inventive use of compounds of the formula (I) in which
Q represents the moieties

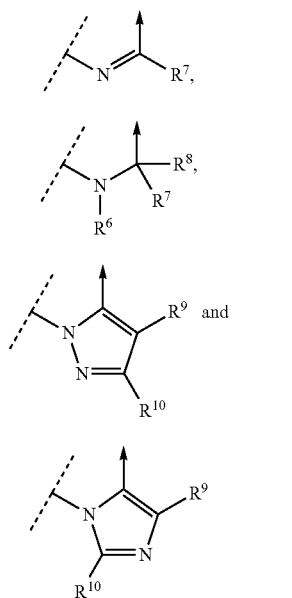

where R⁶, R⁷, R⁸, R⁹ and R¹⁰ are each as defined below and where the arrow represents a bond to the N—R⁶ group;
W is oxygen or sulfur;

A is N (nitrogen) or the C—R⁴ moiety; where R⁴ in the C—R⁴ moiety is in each case as defined below;

R¹, R², R⁴ are each independently hydrogen, nitro, amino, hydroxyl, halogen, cyano, (C₁-C₁₄)-alkyl, (C₃-C₇)-cycloalkyl, (C₂-C₇)-alkenyl, (C₂-C₇)-alkynyl, substituted or unsubstituted phenyl, aryl-(C₁-C₇)-alkyl, aryl-(C₂-C₇)-alkenyl, aryl-(C₂-C₇)-alkynyl, heteroaryl, (C₃-C₇)-cycloalkyl-(C₁-C₇)-alkyl, (C₃-C₇)-cycloalkyl-(C₂-C₇)-alkenyl, (C₃-C₇)-cycloalkyl-(C₂-C₇)-alkynyl; heteroaryl-(C₁-C₇)-alkyl, heteroaryl-(C₂-C₇)-alkenyl, heteroaryl-(C₂-C₇)-alkynyl, (C₁-C₇)-haloalkyl, (C₃-C₇)-halocycloalkyl, (C₂-C₇)-haloalkenyl, (C₃-C₇)-halocycloalkenyl, (C₂-C₇)-haloalkylalkynyl, (C₁-C₅)-alkylsilyl-(C₂-C₇)-alkynyl, (C₁-C₇)-alkoxy-(C₁-C₇)-alkyl, (C₁-C₇)-alkoxy, (C₁-C₇)-haloalkoxy, (C₂-C₇)-alkenyloxy-(C₁-C₇)-alkyl, aryl-(C₁-C₇)-alkoxy, (C₁-C₇)-alkoxycarbonyl, hydroxycarbonyl, aminocarbonyl, (C₁-C₇)-alkylaminocarbonyl, (C₃-C₇)-cycloalkylaminocarbonyl, (C₁-C₇)-alkylamino, (C₂-C₇)-alkenylamino, (C₂-C₇)-alkynylamino, hydrothio, (C₁-C₇)-alkylthio, (C₁-C₇)-haloalkylthio, bis-(C₁-C₇)-alkylamino, (C₃-C₇)-cycloalkylamino, (C₃-C₇)-haloalkylamino, (C₁-C₇)-alkylcarbonylamino, (C₃-C₇)-cycloalkylcarbonylamino, (C₁-C₇)-haloalkylcarbonylamino, (C₁-C₇)-alkoxycarbonylamino, (C₁-C₇)-alkylaminocarbonylamino, (C₁-C₇)-alkylsulfonylamino, (C₃-C₇)-cycloalkylsulfonylamino, arylsulfonylamino, hetarylsulfonylamino, (C₃-C₇)-haloalkylsulfonylamino, amino-(C₁-C₇)-alkylsulfonyl, amino-(C₁-C₇)-haloalkylsulfonyl, (C₁-C₇)-alkylsulfonyl, (C₃-C₇)-cycloalkylsulfonyl, (C₁-C₇)-haloalkylsulfonyl, arylsulfonyl, (C₁-C₇)-alkylsulfinyl, (C₃-C₇)-cycloalkylsulfinyl, arylsulfinyl, N,S-bis-(C₁-C₇)-alkylsulfonimidoyl, S—(C₁-C₇)-alkylsulfonimidoyl, (C₁-C₇)-alkylsulfonylaminocarbonyl, (C₃-C₇)-cycloalkylsulfonylaminocarbonyl, (C₃-C₇)-cycloalkylaminosulfonyl, (C₃-C₇)-cycloalkyl-(C₁-C₇)-alkoxy, (C₁-C₇)-alkynyl-(C₁-C₇)-alkoxy, (C₂-C₇)-alkenyl-(C₁-C₇)-alkoxy, (C₂-C₇)-alkenyloxy-(C₁-C₇)-alkoxy, (C₁-C₇)-alkyloxy-(C₁-C₇)-alkoxy, (C₁-C₇)-alkylamino-(C₁-C₇)-alkoxy, bis-(C₁-C₇)-alkylamino-(C₁-C₇)-alkoxy, (C₃-C₇)-cycloalkylamino-(C₁-C₇)-alkoxy (C₃-C₇)-heterocycloalkyl;

R⁵ is hydrogen, (C₁-C₁₄)-alkyl, (C₃-C₇)-cycloalkyl, halogen, (C₂-C₇)-alkenyl-(C₁-C₇)-alkyl, (C₂-C₇)-alkynyl-(C₁-C₇)-alkyl, (C₁-C₇)-haloalkyl, (C₁-C₇)-alkoxy-(C₁-C₇)-alkyl, (C₂-C₇)-alkynyl, (C₂-C₇)-alkenyl, (C₃-C₇)-cycloalkyl-(C₁-C₇)-alkyl, cyano-(C₁-C₇)-alkyl, nitro-(C₁-C₇)-alkyl, heteroaryl-(C₁-C₇)-alkyl, (C₁-C₇)-alkylamino-(C₁-C₇)-alkyl, bis-(C₁-C₇)-alkylamino-(C₁-C₇)-alkyl, aminocarbonyl-(C₁-C₇)-alkyl, (C₁-C₇)-alkylaminocarbonyl-(C₁-C₇)-alkyl, bis-(C₁-C₇)-alkylaminocarbonyl-(C₁-C₇)-alkyl, (C₁-C₇)-alkoxycarbonyl-(C₁-C₇)-alkyl, hydroxycarbonyl-(C₁-C₇)-alkyl, (C₁-C₇)-alkylcarbonyl, (C₃-C₇)-cycloalkylcarbonyl, (C₁-C₇)-haloalkylcarbonyl, (C₁-C₇)-alkoxycarbonyl, (C₁-C₇)-alkylsulfonyl, arylsulfonyl, (C₃-C₇)-cycloalkylsulfonyl, aryl-(C₁-C₇)-alkylsulfonyl, (C₂-C₇)-alkenylsulfonyl, heteroarylsulfonyl, (C₂-C₇)-alkynylsulfonyl, (C₁-C₇)-alkylsulfinyl, arylsulfinyl, (C₃-C₇)-cycloalkylsulfinyl, (C₂-C₇)-alkenylsulfinyl, (C₂-C₇)-alkynylsulfinyl, arylcarbonyl, heteroarylcarbonyl, (C₁-C₇)-alkoxycarbonyl-(C₁-C₇)-alkyl, aryl-(C₁-C₇)-alkyl, heteroaryl, hydroxycarbonyl, (C₁-C₇)-alkoxycarbonyl, (C₁-C₇)-alkylaminocarbonyl, (C₃-C₇)-cycloalkylaminocarbonyl, cyano-(C₁-C₇)-alkylaminocarbonyl, (C₃-C₇)-alkynylaminocarbonyl, (C₄-C₇)-heterocycloalkylcarbonyl, hetaroary-(C₁-C₇)-alkylaminocarbonyl, (C₂-C₆)-alkenyloxycarbonyl, (C₃-C₇)-cycloalkyl-(C₁-C₇)-alkoxycarbonyl, (C₃-C₇)- cycloalkyl-($C_1$-$C_7$)-alkylaminocarbonyl, aryl-($C_1$-$C_7$)-alkylaminocarbonyl or a negative charge;

$R^6$ is hydrogen, hydroxyl, formyl, amino, bis-($C_1$-$C_8$)-alkylamino, ($C_1$-$C_7$)-alkyl, ($C_3$-$C_7$)-cycloalkyl, cyano-($C_1$-$C_7$)-alkyl, ($C_2$-$C_7$)-alkenyl-($C_1$-$C_7$)-alkyl, ($C_1$-$C_7$)-haloalkyl, ($C_2$-$C_7$)-alkynyl, ($C_2$-$C_7$)-alkenyl, ($C_3$-$C_7$)-cycloalkyl-($C_1$-$C_7$)-alkyl, cyano-($C_1$-$C_7$)-alkyl-($C_2$-$C_7$)-alkenyl, aryl-($C_1$-$C_7$)-alkyl, aryl-($C_2$-$C_7$)-alkenyl, aryl-($C_2$-$C_7$)-alkynyl, heteroaryl-($C_1$-$C_7$)-alkyl, heteroaryl-($C_2$-$C_7$)-alkenyl, heteroaryl-($C_2$-$C_7$)-alkynyl, ($C_1$-$C_7$)-alkylcarbonyl, ($C_1$-$C_7$)-haloalkylcarbonyl, ($C_3$-$C_7$)-cycloalkylcarbonyl, arylcarbonyl, heteroarylcarbonyl, ($C_1$-$C_7$)-alkoxycarbonyl, aminocarbonyl, ($C_1$-$C_7$)-alkylaminocarbonyl, ($C_1$-$C_7$)-alkylsulfonyl, ($C_1$-$C_7$)-alkenylsulfonyl, heteroarylsulfonyl, arylsulfonyl, ($C_3$-$C_7$)-cycloalkylsulfonyl, ($C_1$-$C_7$)-alkylsulfinyl, arylsulfinyl, ($C_3$-$C_7$)-cycloalkylsulfinyl, ($C_1$-$C_7$)-alkoxycarbonyl-($C_1$-$C_7$)-alkyl, ($C_1$-$C_6$)-alkoxycarbonyl, ($C_3$-$C_6$)-cycloalkylaminocarbonyl, ($C_1$-$C_4$)-haloalkylaminocarbonyl, ($C_2$-$C_6$)-alkynylaminocarbonyl, cyano-($C_1$-$C_6$)-alkylaminocarbonyl, ($C_1$-$C_7$)-heterocycloalkylcarbonyl, heteroaryl-($C_1$-$C_7$)-alkylaminocarbonyl, ($C_2$-$C_6$)-alkenyloxycarbonyl, ($C_3$-$C_7$)-cycloalkyl-($C_1$-$C_4$)-alkoxycarbonyl, ($C_3$-$C_7$)-cycloalkyl-($C_1$-$C_4$)-alkylaminocarbonyl, aryl-($C_1$-$C_4$)-alkylaminocarbonyl, ($C_1$-$C_7$)-alkylamino-($C_1$-$C_7$)-alkyl, aminocarbonyl-($C_1$-$C_7$)-alkyl, ($C_1$-$C_7$)-alkylaminocarbonyl-($C_1$-$C_7$)-alkyl, bis-($C_1$-$C_7$)-alkylaminocarbonyl-($C_1$-$C_7$)-alkyl;

$R^7$ is hydrogen, ($C_1$-$C_{14}$)-alkyl, ($C_3$-$C_7$)-cycloalkyl, ($C_2$-$C_{14}$)-alkenyl, ($C_2$-$C_{14}$)-alkynyl, ($C_3$-$C_7$)-cycloalkyl-($C_1$-$C_7$)-alkyl, cyano-($C_1$-$C_7$)-alkyl, ($C_1$-$C_5$)-alkylsilyl-($C_1$-$C_7$)-alkyl, ($C_2$-$C_7$)-alkenyl-($C_1$-$C_7$)-alkyl, ($C_2$-$C_7$)-alkynyl-($C_1$-$C_7$)-alkyl, aryl, heteroaryl, ($C_3$-$C_7$)-heterocycloalkyl, aryl-($C_2$-$C_7$)-alkenyl, aryl-($C_2$-$C_7$)-alkynyl, heteroaryl-($C_2$-$C_7$)-alkenyl, heteroaryl-($C_2$-$C_7$)-alkynyl, ($C_2$-$C_7$)-haloalkenyl; aryl-($C_2$-$C_7$)-haloalkenyl, heteroaryl-($C_2$-$C_7$)-haloalkenyl, heteroaryl-($C_1$-$C_7$)-alkyl, ($C_1$-$C_7$)-alkoxy-($C_1$-$C_7$)-alkyl, ($C_1$-$C_7$)-haloalkoxy-($C_1$-$C_7$)-alkyl, aryloxy-($C_1$-$C_7$)-alkyl, heteroaryloxy-($C_1$-$C_7$)-alkyl, aryl-($C_1$-$C_7$)-alkyloxy-($C_1$-$C_7$)-alkyl, heteroaryl-($C_1$-$C_7$)-alkyloxy-($C_1$-$C_7$)-alkyl, ($C_3$-$C_7$)-cycloalkyl-($C_1$-$C_7$)-alkoxy-($C_1$-$C_7$)-alkyl, ($C_2$-$C_7$)-alkynyl-($C_1$-$C_7$)-alkoxy-($C_1$-$C_7$)-alkyl, ($C_2$-$C_7$)-alkenyl-($C_1$-$C_7$)-alkoxy-($C_1$-$C_7$)-alkyl, ($C_2$-$C_7$)-alkenyloxy-($C_1$-$C_7$)-alkoxy-($C_1$-$C_7$)-alkyl, ($C_1$-$C_7$)-alkyloxy-($C_1$-$C_7$)-alkoxy-($C_1$-$C_7$)-alkyl, ($C_1$-$C_7$)-alkylamino-($C_1$-$C_7$)-alkoxy-($C_1$-$C_7$)-alkyl, bis-($C_1$-$C_7$)-alkylamino-($C_1$-$C_7$)-alkoxy-($C_1$-$C_7$)-alkyl, ($C_3$-$C_7$)-cycloalkylamino-($C_1$-$C_7$)-alkoxy-($C_1$-$C_7$)-alkyl, amino-($C_1$-$C_7$)-alkyl, ($C_1$-$C_7$)-alkylamino-($C_1$-$C_7$)-alkyl, bis-($C_1$-$C_7$)-alkylamino-($C_1$-$C_7$)-cycloalkylamino-($C_1$-$C_7$)-alkyl, ($C_3$-$C_7$)-cycloalkoxyamino-($C_1$-$C_7$)-alkyl, arylamino-($C_1$-$C_7$)-alkyl, aryl-($C_1$-$C_7$)-alkylamino-($C_1$-$C_7$)-alkyl, heteroaryl-($C_1$-$C_7$)-alkylamino-($C_1$-$C_7$)-alkyl, bis-($C_1$-$C_7$)-alkylamino, ($C_3$-$C_7$)-cycloalkylamino, ($C_1$-$C_7$)-alkylcarbonylamino, ($C_3$-$C_7$)-cycloalkylcarbonylamino, ($C_1$-$C_7$)-haloalkylcarbonylamino, ($C_1$-$C_7$)-alkoxycarbonylamino, ($C_1$-$C_7$)-alkylaminocarbonylamino, ($C_1$-$C_7$)-alkylsulfonylamino, ($C_3$-$C_7$)-cycloalkylsulfonylamino, arylsulfonylamino, heteroarylsulfonylamino, sulfonyl-($C_1$-$C_7$)-haloalkylamino, aryl-($C_2$-$C_7$)-alkynyl, aryl-($C_2$-$C_7$)-alkynylheteroaryl, ($C_3$-$C_7$)-cycloalkyloxy-($C_1$-$C_7$)-alkyl, ($C_1$-$C_7$)-alkylcarbonyloxy-($C_1$-$C_7$)-alkyl, ($C_3$-$C_7$)-cycloalkylcarbonyloxy-($C_1$-$C_7$)-alkyl, arylcarbonyloxy-($C_1$-$C_7$)-alkyl, heteroarylcarbonyloxy-($C_1$-$C_7$)-alkyl, heteroaryl-($C_1$-$C_7$)-alkylcarbonyloxy-($C_1$-$C_7$)-alkyl, ($C_3$-$C_7$)-cycloalkylthio-($C_1$-$C_7$)-alkyl, ($C_3$-$C_7$)-cycloalkyl-($C_1$-$C_7$)-alkylthio-($C_1$-$C_7$)-alkyl, ($C_1$-$C_7$)-haloalkylthio-($C_1$-$C_7$)-alkyl, arylthio-($C_1$-$C_7$)-alkyl, heteroarylthio-($C_1$-$C_7$)-alkyl, ($C_1$-$C_7$)-alkylcarbonyloxy-($C_1$-$C_7$)-alkylheteroaryl, ($C_1$-$C_7$)-alkoxycarbonylamino-($C_1$-$C_7$)-alkyl, ($C_1$-$C_7$)-alkylcarbonylamino-($C_1$-$C_7$)-alkyl, ($C_3$-$C_7$)-cycloalkylcarbonylamino-($C_1$-$C_7$)-alkyl, ($C_1$-$C_7$)-haloalkylcarbonylamino-($C_1$-$C_7$)-alkyl, arylcarbonylamino-($C_1$-$C_7$)-alkyl, heteroarylcarbonylamino-($C_1$-$C_7$)-alkyl, ($C_1$-$C_7$)-alkoxycarbonylamino-($C_1$-$C_7$)-alkyl, ($C_1$-$C_7$)-alkylaminocarbonylamino-($C_1$-$C_7$)-alkyl, ($C_1$-$C_7$)-alkylsulfonylamino-($C_1$-$C_7$)-alkyl, ($C_3$-$C_7$)-cycloalkylsulfonylamino-($C_1$-$C_7$)-alkyl, arylsulfonylamino-($C_1$-$C_7$)-alkyl, heteroarylsulfonylamino-($C_1$-$C_7$)-alkyl, sulfonyl-($C_1$-$C_7$)-haloalkylamino-($C_1$-$C_7$)-alkyl, heteroaryl-($C_1$-$C_7$)-alkylamino-($C_1$-$C_7$)-alkyl, (aryl)-($C_1$-$C_7$)-alkylaminocarbonyl, (heteroaryl-($C_1$-$C_7$)-alkyl)-($C_1$-$C_7$)-alkylamino-($C_1$-$C_7$)-alkyl, ($C_1$-$C_7$)-alkylcarbonyl-($C_1$-$C_7$)-alkyl, ($C_1$-$C_7$)-alkoxycarbonyl-($C_1$-$C_7$)-alkyl, aryl-($C_1$-$C_7$)-alkoxycarbonyl-($C_1$-$C_7$)-alkyl, aminocarbonyl-($C_1$-$C_7$)-alkyl, ($C_1$-$C_7$)-alkylaminocarbonyl-($C_1$-$C_7$)-alkyl, ($C_3$-$C_7$)-cycloalkylaminocarbonyl-($C_1$-$C_7$)-alkyl, heteroaryl-($C_1$-$C_7$)-alkylaminocarbonyl-($C_1$-$C_7$)-alkyl, aryl-($C_1$-$C_7$)-alkylaminocarbonyl-(C alkyl, heteroarylaminocarbonyl-($C_1$-$C_7$)-alkyl, ($C_3$-$C_7$)-heterocycloalkyl-N—($C_1$-$C_7$)-alkyl, aryl-($C_4$-$C_7$)-heterocycloalkenyl-N—($C_1$-$C_7$)-alkyl, aryl-($C_3$-$C_7$)-heterocycloalkyl-N—($C_1$-$C_7$)-alkyl, ($C_3$-$C_7$)-heterocycloalkyl, ($C_3$-$C_7$)-heterocycloalkenyl, ($C_3$-$C_7$)-heterocycloalkyl-($C_2$-$C_7$)-alkynyl, ($C_3$-$C_7$)-heterocyloalkenyl-($C_2$-$C_7$)-alkynyl, ($C_3$-$C_7$)-heterocycloalkyl-($C_2$-$C_7$)-alkenyl, ($C_3$-$C_7$)-heterocycloalkenyl-($C_2$-$C_7$)-alkenyl, ($C_3$-$C_7$)-heterocycloalkyl-($C_1$-$C_7$)-alkyl, ($C_3$-$C_7$)-heterocyloalkenyl-($C_1$-$C_7$)-alkyl, where the heteroatom in heteroaryl, heterocycloalkyl and heterocycloalkenyl optionally bears a charge; and $R^8$ is hydrogen, ($C_1$-$C_7$)-alkyl, ($C_1$-$C_7$)-haloalkyl, ($C_1$-$C_7$)-alkoxy-($C_1$-$C_7$)-alkyl, ($C_1$-$C_7$)-haloalkoxy-($C_1$-$C_7$)-alkyl, ($C_3$-$C_7$)-cycloalkyl, ($C_3$-$C_7$)-cycloalkyl-($C_1$-$C_7$)-alkyl, ($C_1$-$C_7$)-alkylthio-($C_1$-$C_7$)-alkyl, cyano-($C_1$-$C_7$)-alkyl, ($C_2$-$C_7$)-alkynyl-($C_1$-$C_7$)-alkyl, ($C_2$-$C_7$)-alkenyl, ($C_3$-$C_7$)-heterocycloalkyl; or $R^7$ and $R^8$ with the atom to which they are bonded are a fully saturated or partly saturated 4 to 7-membered ring optionally interrupted by heteroatoms and optionally further substituted by one or more radicals, where any substituents present correspond to the definition described for $R^1$;

$R^9$ is hydrogen, ($C_1$-$C_7$)-alkyl, substituted or unsubstituted phenyl, ($C_2$-$C_7$)-alkenyl, ($C_1$-$C_7$)-haloalkyl, ($C_3$-$C_7$)-cycloalkyl, aryl-($C_1$-$C_7$)-alkyl, heteroaryl, hydroxycarbonyl, ($C_1$-$C_7$)-alkoxycarbonyl, ($C_1$-$C_7$)-alkylaminocarbonyl, ($C_3$-$C_7$)-cycloalkylaminocarbonyl, cyano-($C_1$-$C_7$)-alkylaminocarbonyl, ($C_3$-$C_7$)-alkynylaminocarbonyl, ($C_4$-$C_7$)-heterocycloalkylcarbonyl, heteroaryl-($C_1$-$C_7$)-alkylaminocarbonyl, ($C_2$-$C_6$)-alkenyloxycarbonyl, ($C_3$-$C_7$)-cycloalkyl-($C_1$-$C_7$)-alkoxycarbonyl, ($C_3$-$C_7$)-cycloalkyl-($C_1$-$C_7$)-alkylaminocarbonyl, aryl-($C_1$-$C_7$)-alkylaminocarbonyl; and $R^{10}$ is hydrogen, ($C_1$-$C_7$)-alkyl, ($C_2$-$C_7$)-alkenyl, ($C_1$-$C_7$)-haloalkyl, ($C_3$-$C_7$)-cycloalkyl, aryl-($C_1$-$C_7$)-alkyl, aryl, heteroaryl, ($C_2$-$C_7$)-alkenyl-($C_1$-$C_7$)-alkyl.

Very particular preference is given to the inventive use of compounds of the general formula (I) in which Q represents the moieties

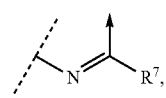
Q-1

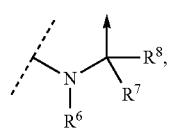
Q-2

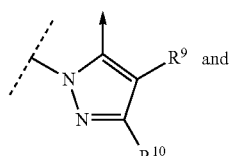
Q-3

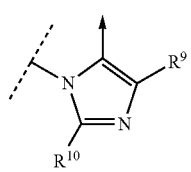
Q-4 where $R^6$, $R^7$, $R^8$, $R^9$ and $R^{10}$ are each as defined below and where the arrow represents a bond to the N—$R^6$ group;

W is oxygen or sulfur;

A is N (nitrogen) or the C—$R^4$ moiety, where $R^4$ in the C—$R^4$ moiety is in each case as defined below;

$R^1$, $R^2$, $R^3$, $R^4$ are each independently hydrogen, nitro, amino, hydroxyl, fluorine, chlorine, bromine, iodine, cyano, hydrothio, ($C_1$-$C_4$)-alkyl, ($C_3$-$C_6$)-cycloalkyl, ($C_2$-$C_6$)-alkenyl, ($C_2$-$C_6$)-alkynyl, substituted or unsubstituted phenyl, aryl-($C_1$-$C_4$)-alkyl, aryl-($C_2$-$C_6$)-alkenyl, aryl-($C_2$-$C_6$)-alkynyl, heteroaryl, ($C_3$-$C_6$)-cycloalkyl-($C_1$-$C_4$)-alkyl, ($C_3$-$C_6$)-cycloalkyl-($C_2$-$C_6$)-alkenyl, ($C_3$-$C_6$)-cycloalkyl-($C_2$-$C_6$)-alkynyl, heteroaryl-($C_1$-$C_4$)-alkyl, heteroaryl-($C_2$-$C_6$)-alkenyl, heteroaryl-($C_2$-$C_6$)-alkynyl, ($C_1$-$C_4$)-haloalkyl, ($C_3$-$C_6$)-halocycloalkyl, ($C_2$-$C_6$)-haloalkenyl, ($C_3$-$C_6$)-halocycloalkenyl, ($C_2$-$C_6$)-haloalkylalkynyl, ($C_1$-$C_4$)-trialkylsilyl-($C_2$-$C_6$)-alkynyl, ($C_1$-$C_4$)-alkoxy-($C_1$-$C_4$)-alkyl, ($C_1$-$C_4$)-alkoxy, ($C_1$-$C_4$)-haloalkoxy, ($C_2$-$C_6$)-alkenyloxy-($C_1$-$C_4$)-alkyl, aryl-($C_1$-$C_4$)-alkoxy, ($C_1$-$C_6$)-alkoxycarbonyl, hydroxycarbonyl, aminocarbonyl, ($C_1$-$C_6$)-alkylaminocarbonyl, ($C_3$-$C_6$)-cycloalkylaminocarbonyl, ($C_1$-$C_6$)-alkylamino, ($C_2$-$C_6$)-alkenylamino, ($C_2$-$C_6$)-alkynylamino, ($C_1$-$C_4$)-alkylthio, ($C_1$-$C_4$)-haloalkylthio, bis-($C_1$-$C_6$)-alkylamino, ($C_3$-$C_6$)-cycloalkylamino, ($C_3$-$C_6$)-haloalkylamino, ($C_1$-$C_6$)-alkylcarbonylamino, ($C_3$-$C_6$)-cycloalkylcarbonylamino, ($C_1$-$C_4$)-haloalkylcarbonylamino, ($C_1$-$C_4$)-alkoxycarbonylamino, ($C_1$-$C_4$)-alkylaminocarbonylamino, ($C_1$-$C_4$)-alkylsulfonylamino, ($C_3$-$C_6$) cycloalkylsulfonylamino, arylsulfonylamino, hetarylsulfonylamino, ($C_3$-$C_6$)-haloalkylsulfonylamino, amino-($C_1$-$C_4$)-alkylsulfonyl, amino-($C_1$-$C_4$)-haloalkylsulfonyl, ($C_1$-$C_4$)-alkylsulfonyl, ($C_3$-$C_6$)-cycloalkylsulfonyl, haloalkylsulfonyl; arylsulfonyl, ($C_1$-$C_4$)-alkylsulfinyl, ($C_3$-$C_6$)-cycloalkylsulfinyl, ($C_1$-$C_4$)-haloalkylsulfinyl, arylsulfinyl, N,S-bis-($C_1$-$C_6$)-alkylsulfonimidoyl, S—($C_1$-$C_6$)-alkylsulfonimidoyl, ($C_1$-$C_4$)-alkylsulfonylaminocarbonyl, ($C_3$-$C_6$)-cycloalkylsulfonylaminocarbonyl, ($C_3$-$C_6$)-cycloalkylaminosulfonyl, ($C_3$-$C_6$)-cycloalkyl-($C_1$-$C_4$)-alkoxy, ($C_1$-$C_6$)-alkynyl-($C_1$-$C_4$)-alkoxy, ($C_2$-$C_6$)-alkenyl-($C_1$-$C_4$)-alkoxy, ($C_2$-$C_6$)-alkenyloxy-($C_1$-$C_4$)-alkoxy, ($C_1$-$C_4$)-alkyloxy-($C_1$-$C_4$)-alkoxy, ($C_1$-$C_4$)-alkylamino-($C_1$-$C_4$)-alkoxy, bis-($C_1$-$C_6$)-alkylamino-($C_1$-$C_4$)-alkoxy, ($C_3$-$C_6$)-cycloalkylamino-($C_1$-$C_4$)-alkoxy, ($C_3$-$C_6$)-heterocycloalkyl;

$R^5$ is hydrogen or one of the following groups: G-1 to G-6, G-43, G-51 to G-54, G-69, G-71, G-72, G-89, G-163 to G-168, G-197 to G-199, G-202 to G-210, G212 to G-216 and G-222 to G-240;

$R^6$ is hydrogen, hydroxyl or one of the following groups: G-1 to G-6. G-43, G-51 to G-54, G-69, G-71, G-72, G-89, G-163 to G-168, G-197 to G-199, G-202 to G-210, G212 to G-216 and G-222 to G-240;

$R^7$ is one of the following groups: G-1 to G-195, G-199, G-211 to G-221, G-223 to G-231, G-237 to G-282;

$R^8$ is hydrogen or one of the following groups: G-1 to G-6, G-43 and G-51;

$R^9$ is hydrogen or one of the following groups: G-1 to G-42, G-3, G-74, G-79 to G-87, G-155 to G-180, G-192 to G-210 and G-222; and $R^{10}$ is additionally hydrogen or one of the following groups: G-1 to G-6, G-43 to G-45, G-51 to G-54, G-70 to G-72, G-163 to G-168, G-195, G-201 and G-237 to G-240; and where the aforementioned groups G-1 to G-282 are each defined as follows:

G-1

G-2

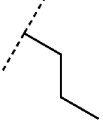
G-3

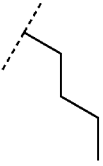
G-4

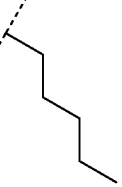
G-5

-continued
G-6
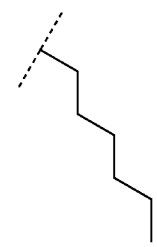
G-7
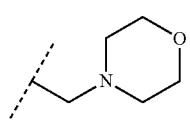
G-8
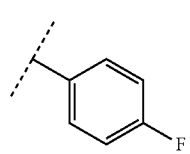
G-9
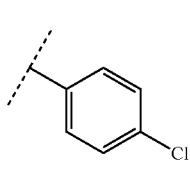
G-10
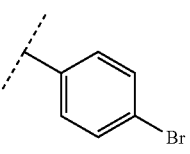
G-11
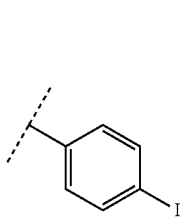
G-12
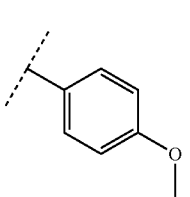
G-13
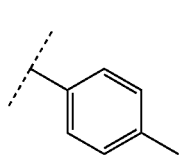
G-14
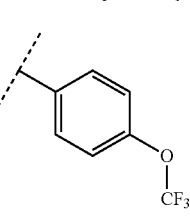
-continued
G-15
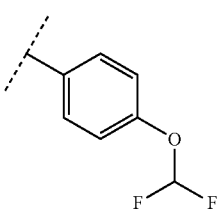
G-16
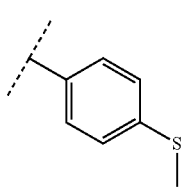
G-17
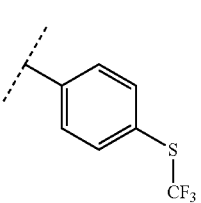
G-18
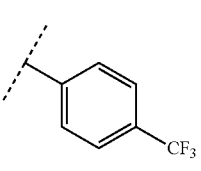
G-19
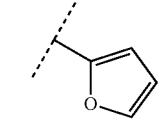
G-20
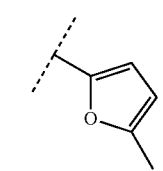
G-21
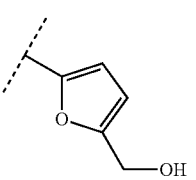
G-22

-continued
G-23 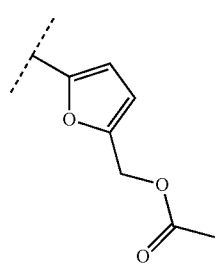
G-24 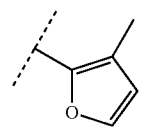
G-25 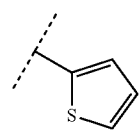
G-26 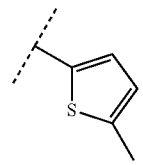
G-27 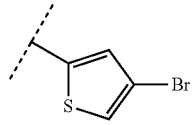
G-28 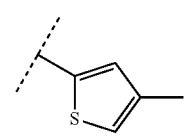
G-29 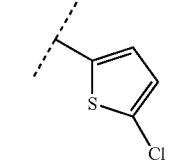
G-30 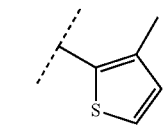
G-31 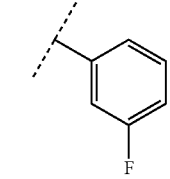
-continued
G-32 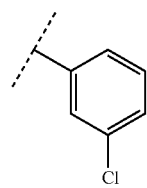
G-33 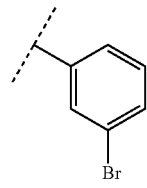
G-34 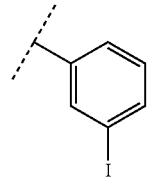
G-35 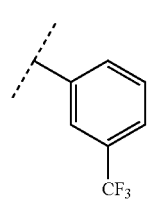
G-36 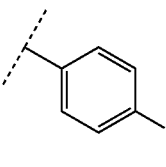
G-37 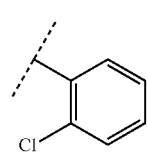
G-38 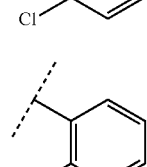
G-39 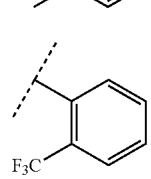
G-40 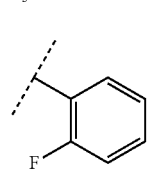

G-41 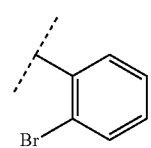
G-42 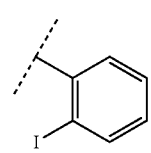
G-43 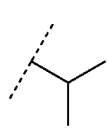
G-44 
G-45 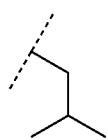
G-46 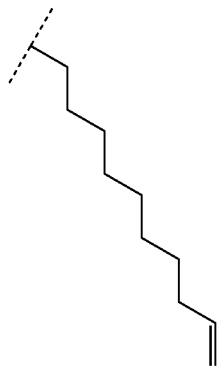
G-47 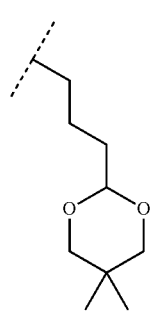
G-48 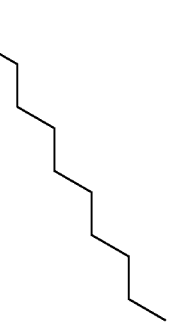
G-49 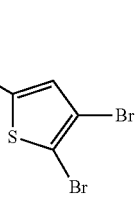
G-50 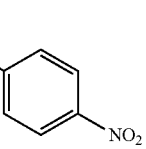
G-51 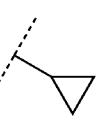
G-52 
G-53 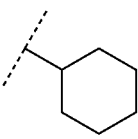
G-54 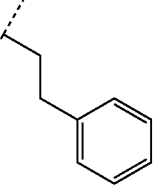
G-55

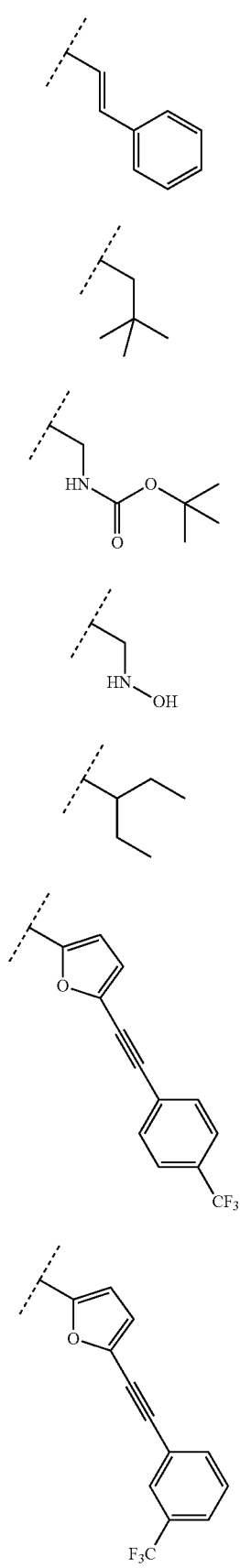
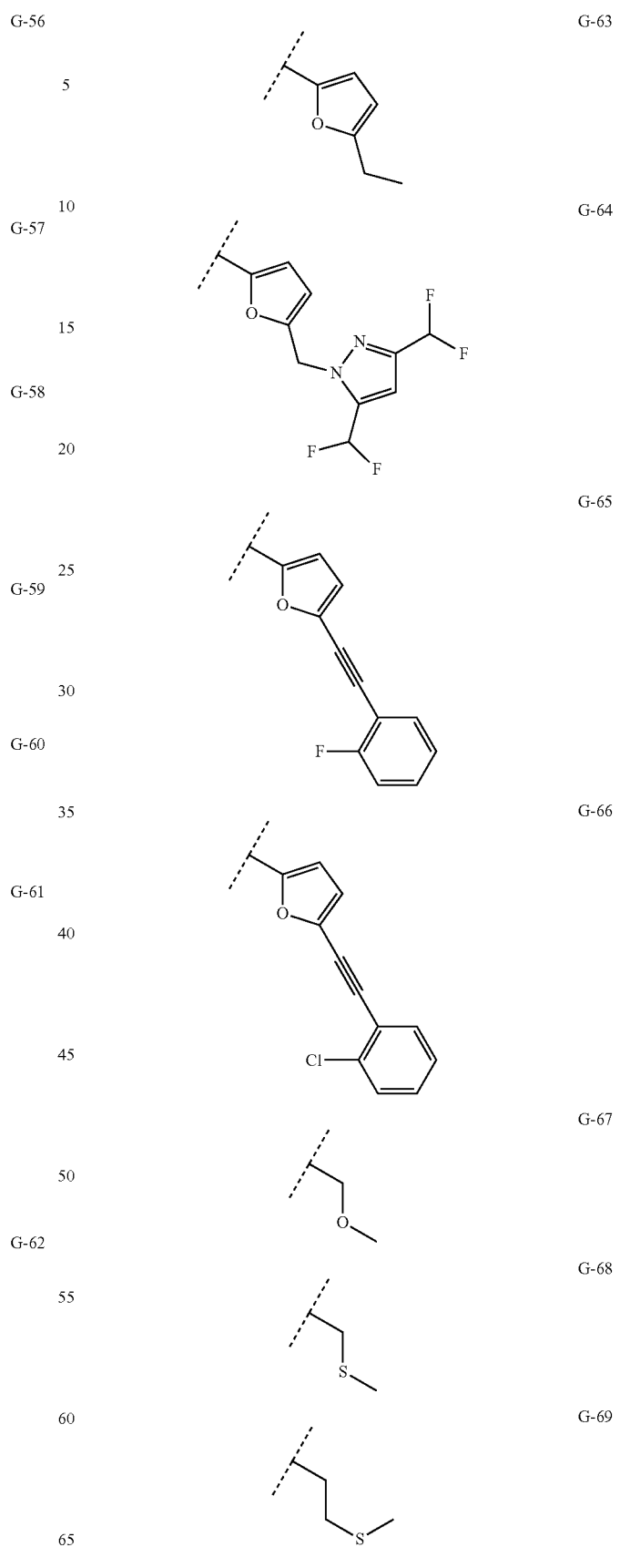

-continued
G-70 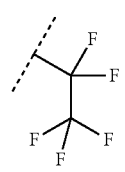
G-71 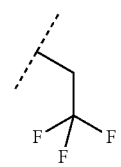
G-72 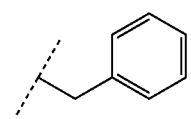
G-73 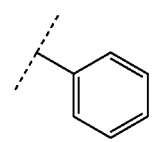
G-74 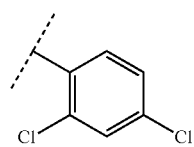
G-75 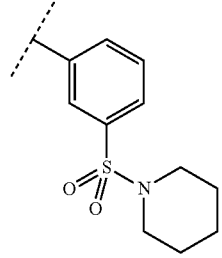
G-76 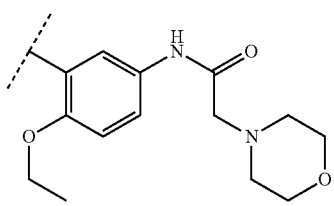
G-77 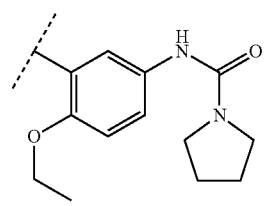
-continued
G-78 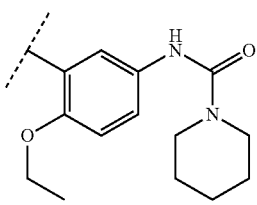
G-79 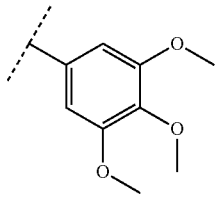
G-80 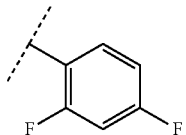
G-81 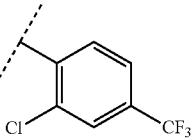
G-82 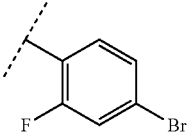
G-83 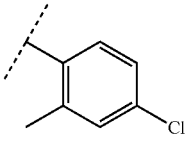
G-84 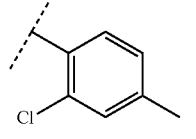
G-85 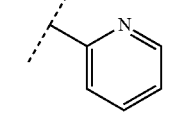
G-86 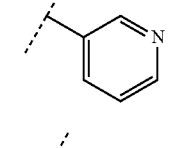
G-87 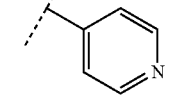

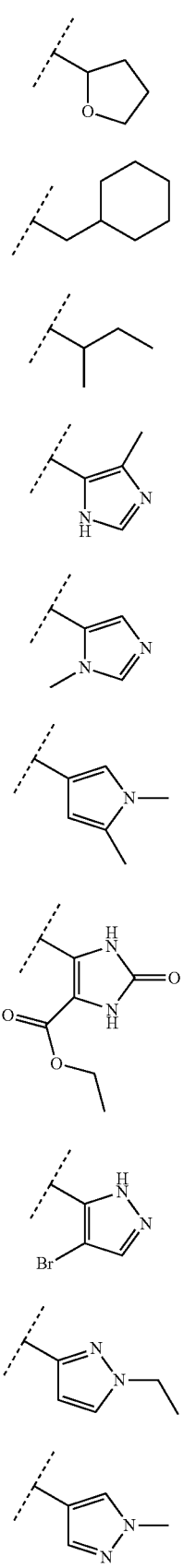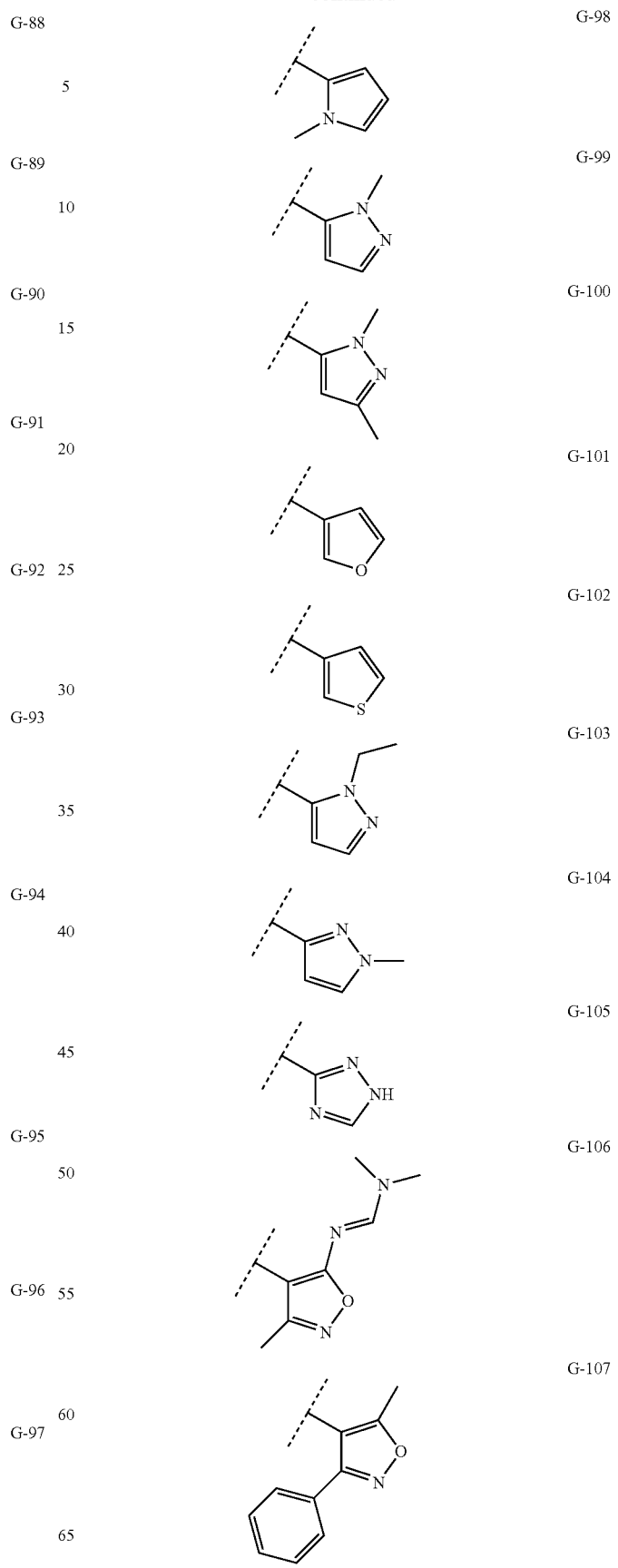

G-108 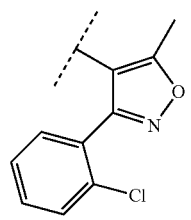
G-109 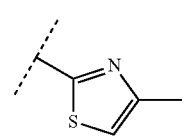
G-110 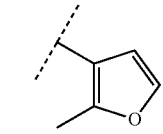
G-111 
G-112 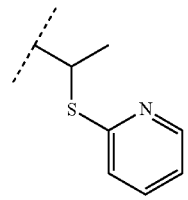
G-113 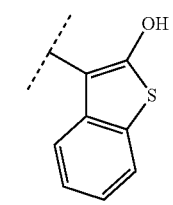
G-114 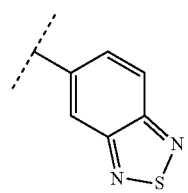
G-115 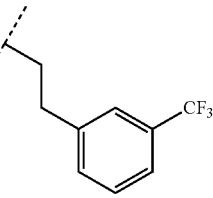
G-116 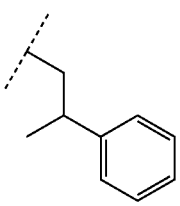
G-117 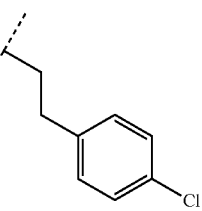
G-118 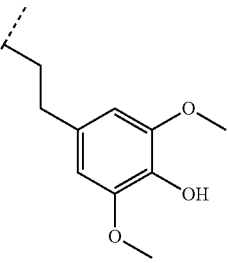
G-119 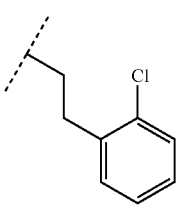
G-120 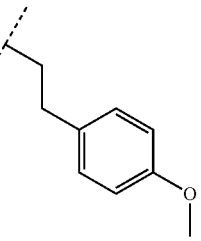
G-121 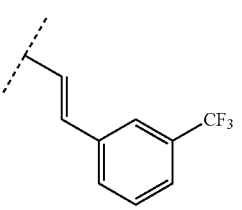
G-122 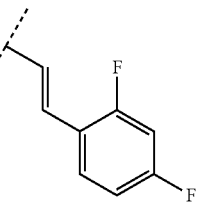

G-123 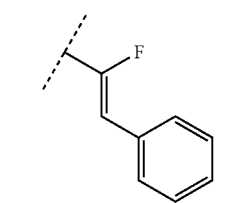
G-124 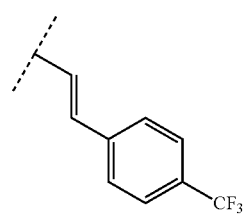
G-125 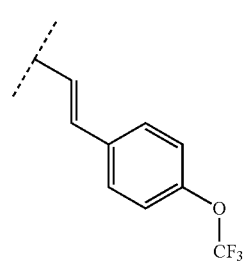
G-126 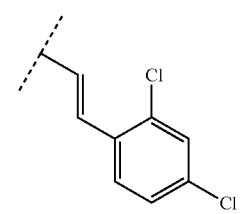
G-127 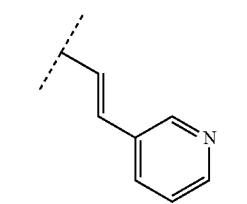
G-128 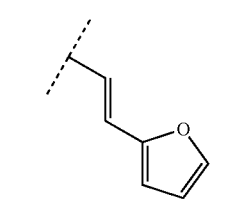
G-129 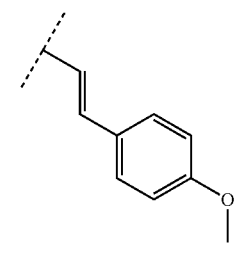
G-130 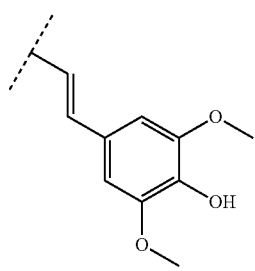
G-131 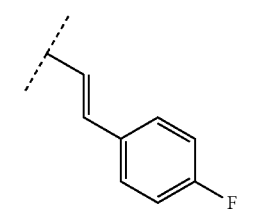
G-132 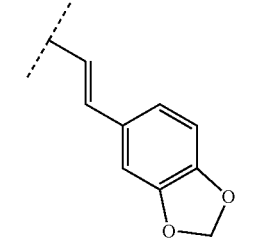
G-133 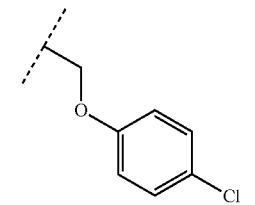
G-134 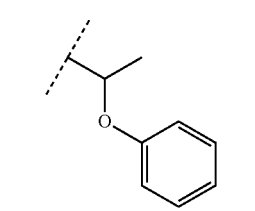
G-135 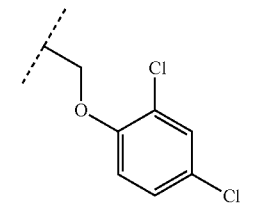
G-136 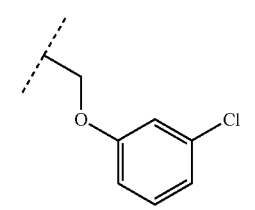

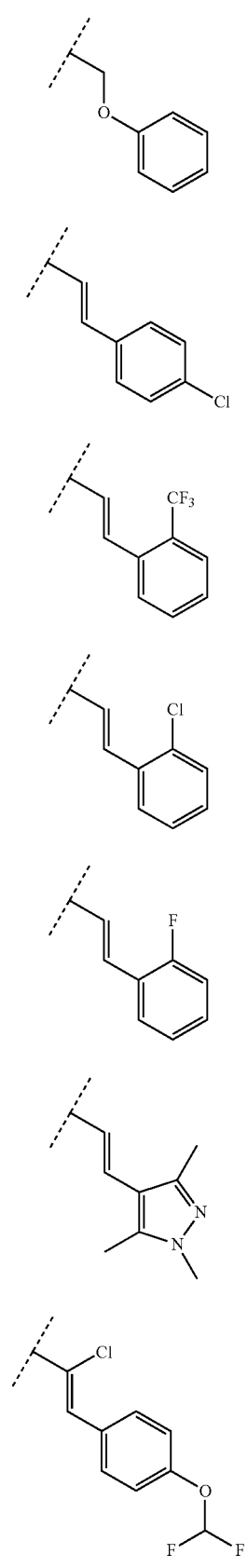
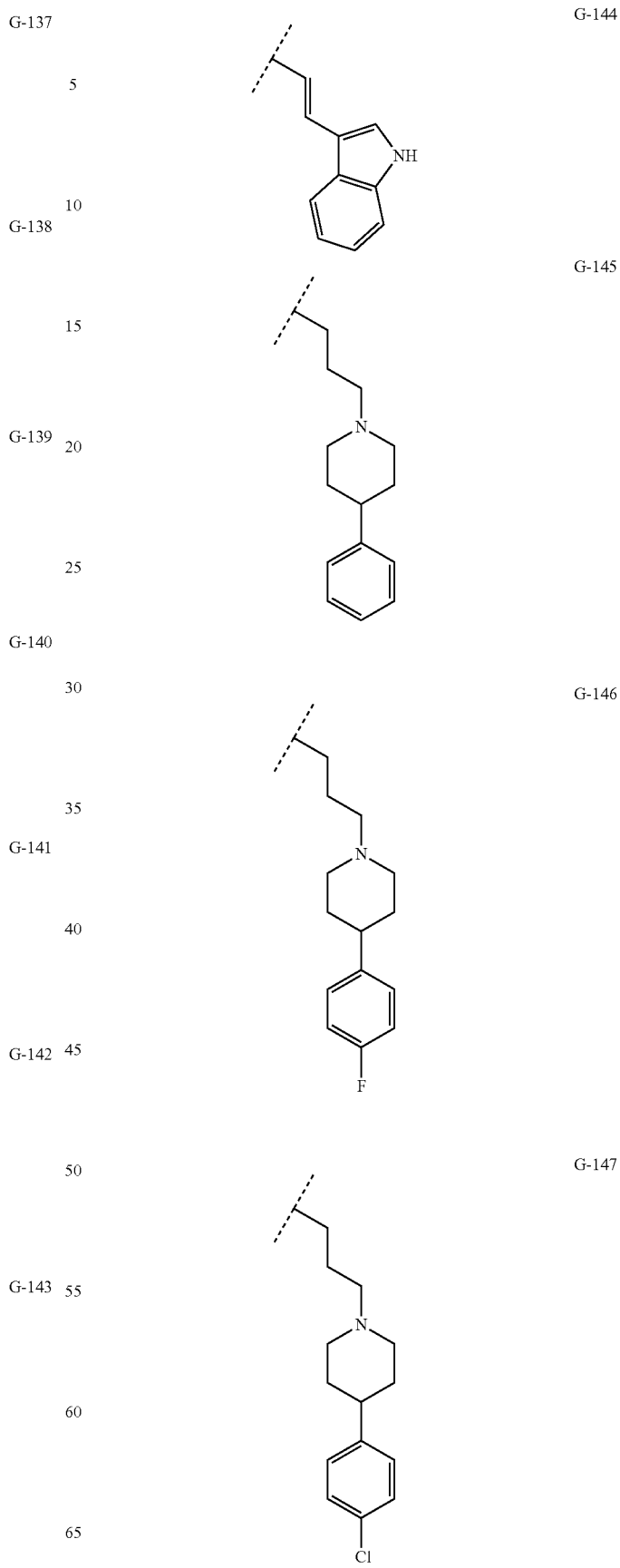

G-148 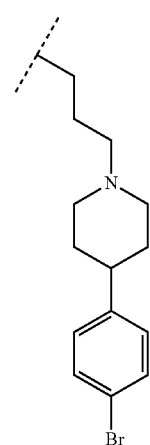
G-149 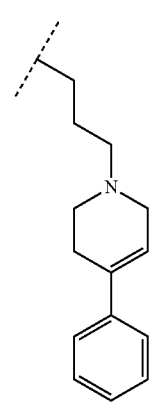
G-150 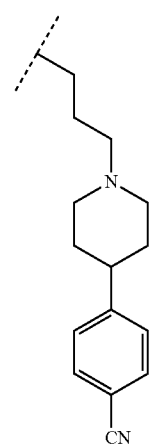
G-151 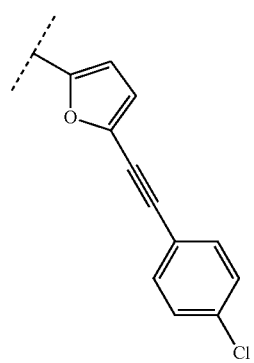
G-152 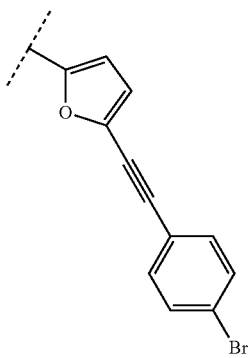
G-153 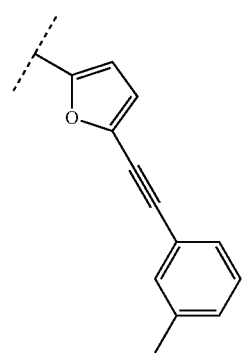
G-154 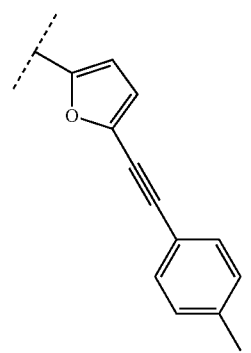
G-155 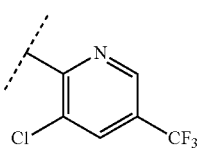
G-156 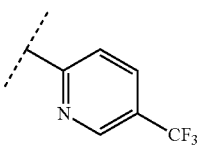
G-157 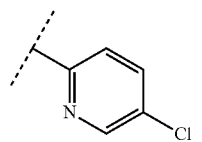

G-158 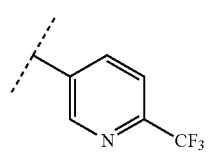
G-159 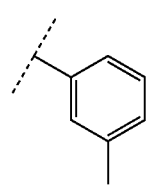
G-160 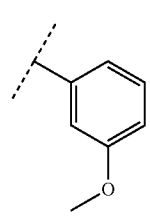
G-161 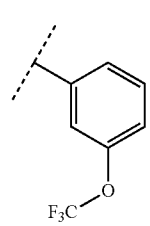
G-162 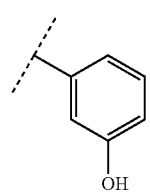
G-163 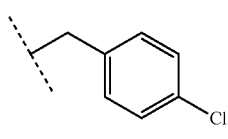
G-164 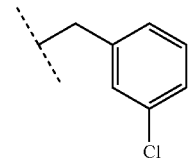
G-165 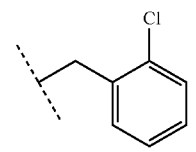
G-166 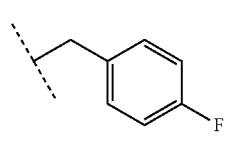
G-167 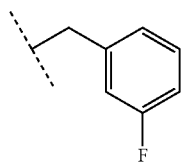
G-168 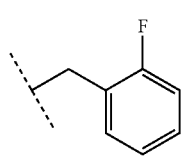
G-169 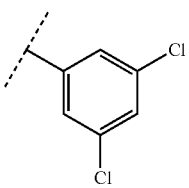
G-170 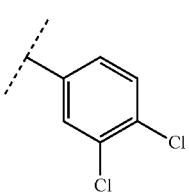
G-171 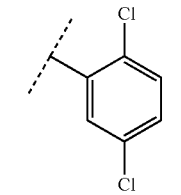
G-172 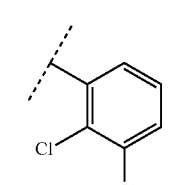
G-173 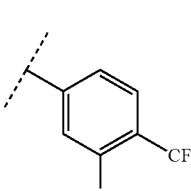
G-174 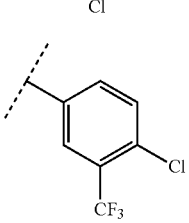

-continued
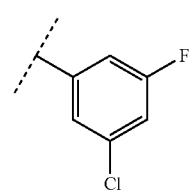 G-175
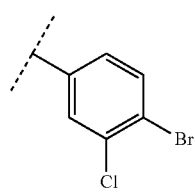 G-176
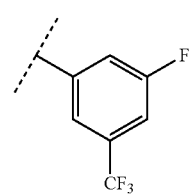 G-177
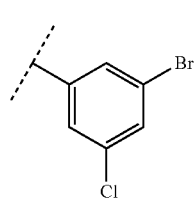 G-178
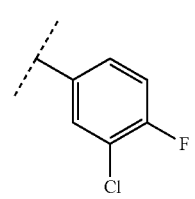 G-179
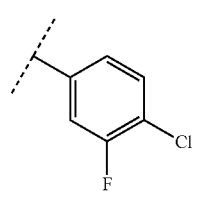 G-180
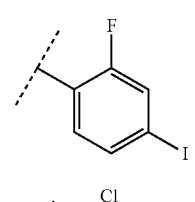 G-175
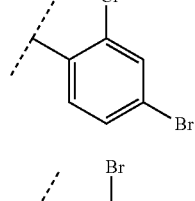 G-176
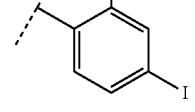 G-177
-continued
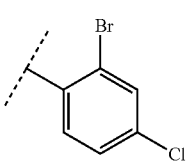 G-178
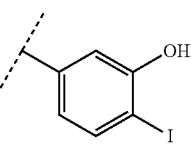 G-179
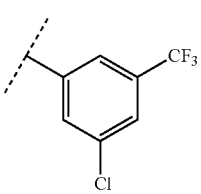 G-180
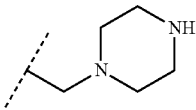 G-181
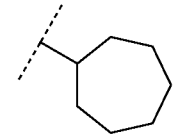 G-182
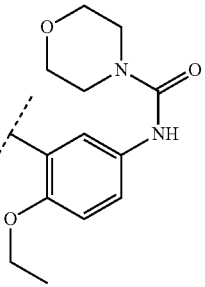 G-183
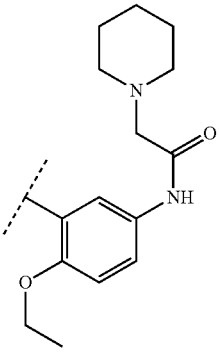 G-184
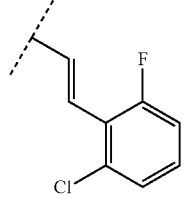 G-185

-continued
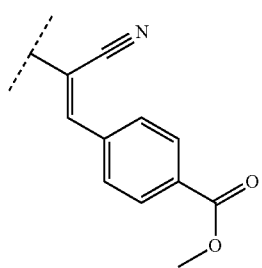 G-186
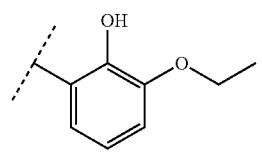 G-187
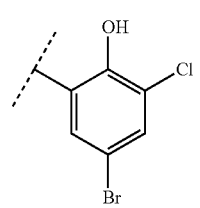 G-188
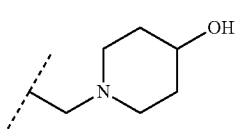 G-189
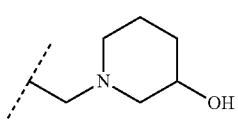 G-190
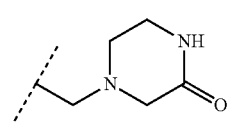 G-191
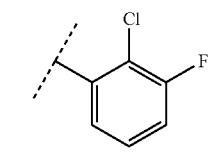 G-192
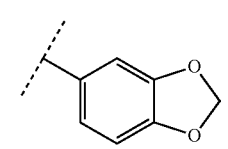 G-193
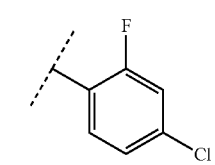 G-194
 G-195
-continued
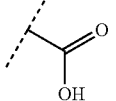 G-196
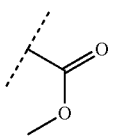 G-197
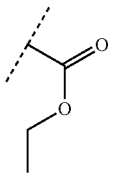 G-198
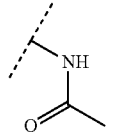 G-199
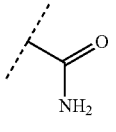 G-200
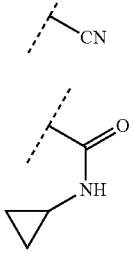 G-201
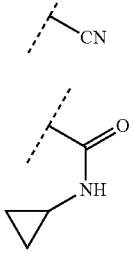 G-202
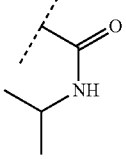 G-203
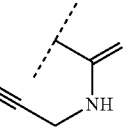 G-204
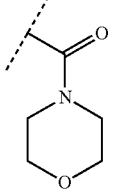 G-205

-continued

| G-206 | G-216 |
| G-207 | G-217 |
| G-208 | |
| G-209 | G-218 |
| G-210 | |
| G-211 | |
| G-212 | G-219 |
| G-213 | |
| G-214 | |
| G-215 | |

| | |
|---|---|
| G-220 | G-228 |
| G-221 | G-229 |
| G-222 | G-230 |
| G-223 | G-231 |
| G-224 | G-232 |
| G-225 | G-233 |
| G-226 | G-234 |
| G-227 | G-235 |
| | G-236 |

G-237 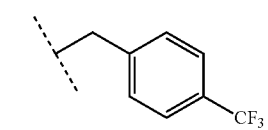
G-238 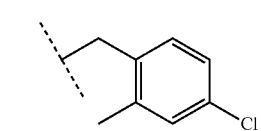
G-239 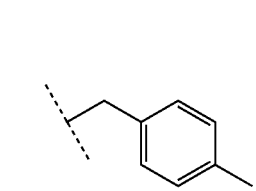
G-240 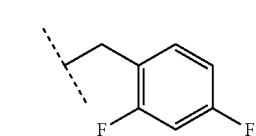
G-241 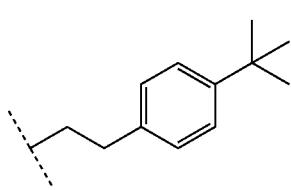
G-242 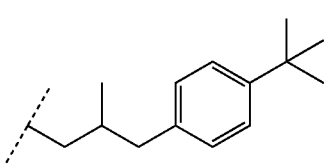
G-243 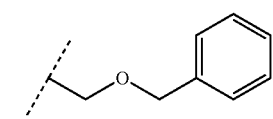
G-244 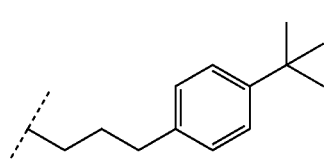
G-245 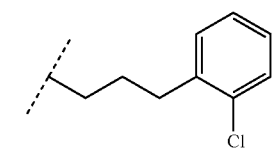
G-246 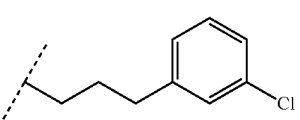
G-247 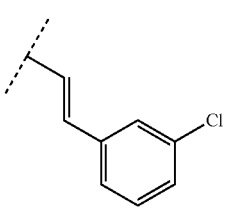
G-248 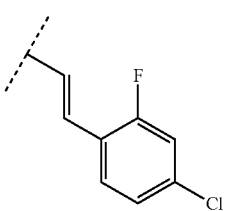
G-249 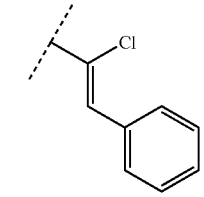
G-250 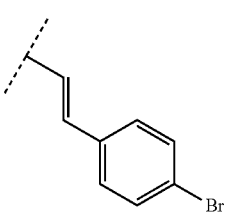
G-251 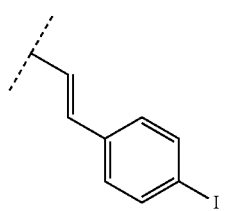
G-252 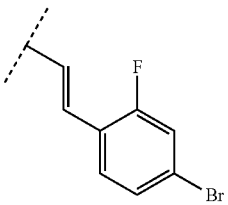
G-253 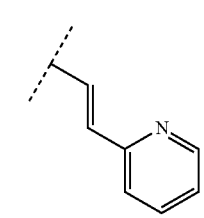

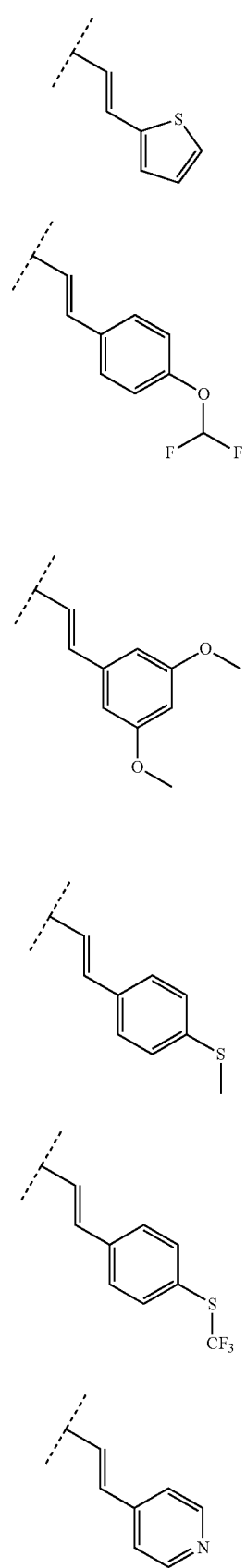
G-254
G-255
G-256
G-257
G-258
G-259
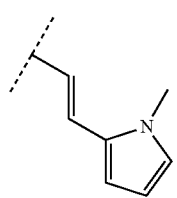
G-260
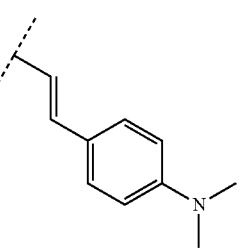
G-261
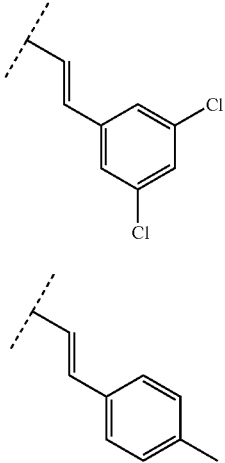
G-262
G-263
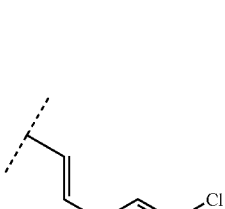
G-264
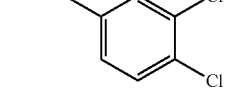
G-265
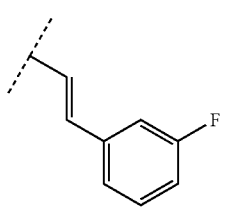
G-266
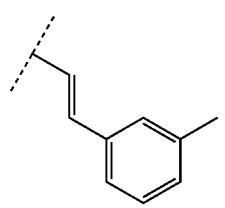

G-267 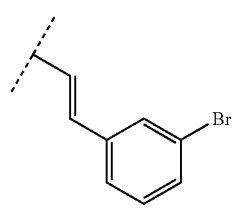
G-268 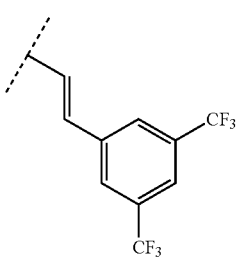
G-269 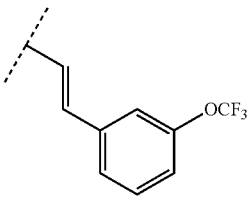
G-270 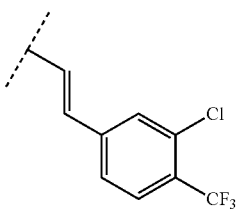
G-271 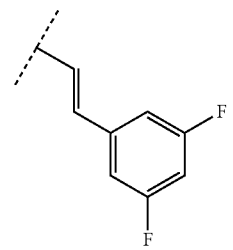
G-272 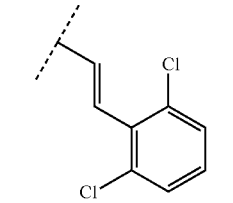
G-273 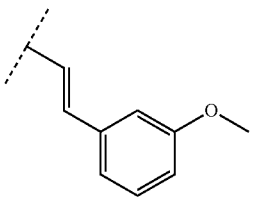
G-274 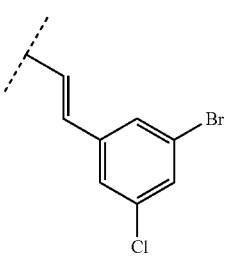
G-275 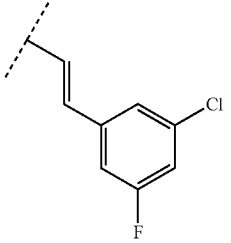
G-276 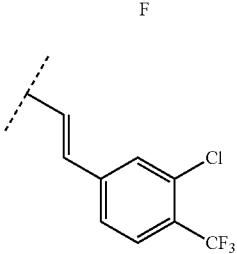
G-277 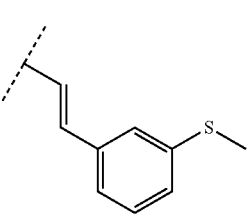
G-278 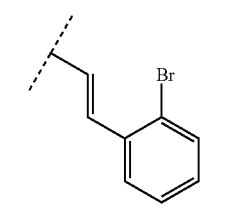
G-279 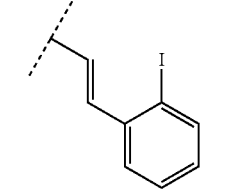
G-280 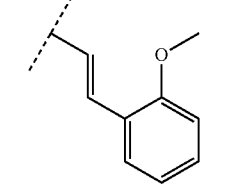

-continued

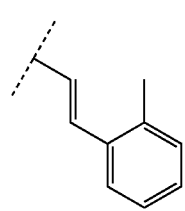
G-281

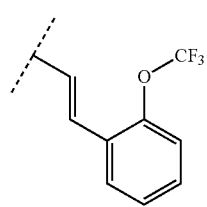
G-282

Particular aforementioned substituted fused dihydropyrimidinones of the formula (I) are likewise not yet known in the prior art. Thus, a further part of the invention is that of substituted fused dihydropyrimidinones of the formula (I), or salts thereof,

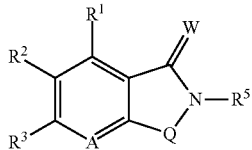
(I)

in which
Q is the moiety

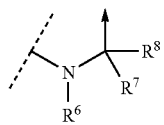
Q-2 where $R^6$, $R^7$ und $R^8$ are each as defined below and where the arrow represents a bond to the N—$R^5$ group;
W is oxygen or sulfur;
A is the C—$R^4$ moiety, where $R^4$ in the C—$R^4$ moiety is in each case as defined below;
$R^1$, $R^2$, $R^3$ are each hydrogen or fluorine;
$R^4$ is nitro, amino, hydroxyl, fluorine, chlorine, bromine, iodine, cyano, hydrothio, $(C_1-C_4)$-alkyl, $(C_3-C_6)$-cycloalkyl, $(C_2-C_6)$-alkenyl, $(C_2-C_6)$-alkynyl, aryl, aryl-aryl-$(C_2-C_6)$-alkenyl, aryl-$(C_2-C_6)$-alkynyl, heteroaryl, $(C_3-C_6)$-cycloalkyl-$(C_1-C_4)$-alkyl, heteroaryl-$(C_2-C_6)$-alkenyl, heteroaryl-$(C_2-C_6)$-alkynyl, $(C_1-C_4)$-haloalkyl, $(C_3-C_6)$-halocycloalkyl, $(C_2-C_6)$-haloalkenyl, $(C_2-C_6)$-haloalkylalkynyl, $(C_1-C_4)$-trialkylsilyl-$(C_2-C_6)$-alkynyl, $(C_1-C_4)$-alkoxy-$(C_1-C_4)$-alkyl, $(C_1-C_4)$-alkoxy, $(C_1-C_4)$-haloalkoxy, $(C_2-C_6)$-alkenyloxy-$(C_1-C_4)$-alkyl, aryl-$(C_1-C_4)$-alkoxy, $(C_1-C_6)$-alkylamino, $(C_2-C_6)$-alkenylamino, $(C_2-C_6)$-alkynylamino, $(C_1-C_4)$-alkylthio, $(C_1-C_4)$-haloalkylthio, bis-$(C_1-C_6)$-alkylamino, $(C_3-C_6)$-cycloalkylamino, $(C_3-C_6)$-haloalkylamino, $(C_1-C_6)$-alkylcarbonylamino, $(C_3-C_6)$-cycloalkylcarbonylamino, $(C_1-C_4)$-haloalkylcarbonylamino, $(C_1-C_4)$-alkoxycarbonylamino, $(C_1-C_4)$-alkylaminocarbonylamino, $(C_1-C_4)$-alkylsulfonylamino, $(C_3-C_6)$-cycloalkylsulfonylamino, arylsulfonylamino, hetarylsulfonylamino, $(C_3-C_6)$-haloalkylsulfonylamino, $(C_1-C_4)$-alkylsulfonyl, $(C_1-C_6)$-haloalkylsulfonyl, arylsulfonyl, arylsulfinyl, $(C_3-C_6)$-cycloalkyl-$(C_1-C_4)$-alkoxy, $(C_1-C_6)$-alkynyl-$(C_1-C_4)$-alkoxy, $(C_2-C_6)$-alkenyl-$(C_1-C_4)$-alkoxy, $(C_2-C_6)$-alkenyloxy-$(C_1-C_4)$-alkoxy, $(C_1-C_4)$-alkyloxy-$(C_1-C_4)$-alkoxy, $(C_1-C_4)$-alkylamino-$(C_1-C_4)$-alkoxy, bis-$(C_1-C_6)$-alkylamino-$(C_1-C_4)$-alkoxy, $(C_3-C_6)$-cycloalkylamino-$(C_1-C_4)$-alkoxy;

$R^5$ is hydrogen, $(C_1-C_6)$-alkyl, $(C_2-C_6)$-alkenyl, $(C_3-C_6)$-alkynyl, $(C_3-C_6)$-cycloalkyl, $(C_1-C_6)$-alkoxy-$(C_1-C_6)$-alkyl, $(C_1-C_4)$-haloalkyl, $(C_3-C_6)$-cycloalkyl-$(C_1-C_4)$-alkyl, $(C_1-C_6)$-alkoxycarbonyl, $(C_1-C_6)$-alkylcarbonyl, $(C_3-C_6)$-cycloalkylcarbonyl, $(C_1-C_6)$-alkylaminocarbonyl, $(C_3-C_6)$-cycloalkylaminocarbonyl, $(C_1-C_4)$-haloalkylaminocarbonyl, $(C_2-C_6)$-alkynylaminocarbonyl, cyano-$(C_1-C_6)$-alkylaminocarbonyl, $(C_4-C_7)$-heterocycloalkylcarbonyl, heteroaryl-$(C_1-C_7)$-alkylaminocarbonyl, $(C_2-C_6)$-alkenyloxycarbonyl, $(C_3-C_7)$-cycloalkyl-$(C_1-C_4)$-alkoxycarbonyl, $(C_3-C_7)$-cycloalkyl-$(C_1-C_4)$-alkylaminocarbonyl, aryl-$(C_1-C_4)$-alkylaminocarbonyl, cyano-$(C_1-C_6)$-alkyl, nitro-$(C_1-C_6)$-alkyl, $(C_1-C_7)$-alkylamino-$(C_1-C_7)$-alkyl, bis-$(C_1-C_7)$-alkylamino-$(C_1-C_7)$-alkyl, aminocarbonyl-$(C_1-C_7)$-alkyl, $(C_1-C_7)$-alkylaminocarbonyl-$(C_1-C_7)$-alkyl, bis-$(C_1-C_7)$-alkylaminocarbonyl-$(C_1-C_7)$-alkyl, $(C_1-C_7)$-alkoxycarbonyl-$(C_1-C_7)$-alkyl;

$R^6$ is hydrogen, formyl, hydroxyl, amino, $(C_1-C_6)$-alkyl, $(C_2-C_6)$-alkenyl, $(C_2-C_6)$-alkynyl, $(C_3-C_6)$-cycloalkyl, $(C_1-C_6)$-alkoxy-$(C_1-C_6)$-alkyl, $(C_1-C_4)$-haloalkyl, aryl-$(C_2-C_6)$-alkenyl, $(C_3-C_6)$-cycloalkyl-$(C_1-C_4)$-alkyl, $(C_1-C_6)$-alkoxycarbonyl, $(C_1-C_6)$-alkylcarbonyl, $(C_3-C_6)$-cycloalkylcarbonyl, $(C_1-C_6)$-alkylaminocarbonyl, $(C_3-C_6)$-cycloalkylaminocarbonyl, $(C_1-C_4)$-haloalkylaminocarbonyl, $(C_2-C_6)$-alkynylaminocarbonyl, cyano-$(C_1-C_6)$-alkylaminocarbonyl, $(C_4-C_7)$-heterocycloalkylcarbonyl, heteroaryl-$(C_1-C_7)$-alkylaminocarbonyl, $(C_2-C_6)$-alkenyloxycarbonyl, $(C_3-C_7)$-cycloalkyl-$(C_1-C_4)$-alkoxycarbonyl, $(C_3-C_7)$-cycloalkyl-$(C_1-C_4)$-alkylaminocarbonyl, aryl-$(C_1-C_4)$-alkylaminocarbonyl, cyano-$(C_1-C_6)$-alkyl, nitro-$(C_1-C_6)$-alkyl, heteroaryl-$(C_1-C_4)$-alkyl, $(C_1-C_7)$-alkylamino-$(C_1-C_7)$-alkyl, aminocarbonyl-$(C_1-C_7)$-alkyl, $(C_1-C_7)$-alkylaminocarbonyl-$(C_1-C_7)$-alkyl, bis-$(C_1-C_7)$-alkylaminocarbonyl-$(C_1-C_7)$-alkyl, $(C_1-C_7)$-alkoxycarbonyl-$(C_1-C_7)$-alkyl;

$R^7$ is aryl-$(C_2-C_4)$-alkenyl, aryl-$(C_2-C_4)$-haloalkenyl, heteroaryl-$(C_2-C_4)$-alkenyl, heteroaryl-$(C_7-C_4)$-haloalkenyl, $(C_3-C_7)$-heterocycloalkyl-$(C_2-C_4)$-alkynyl, $(C_3-C_7)$-heterocyloalkenyl-$(C_2-C_4)$-alkynyl, $(C_3-C_7)$-heterocyloalkyl-$(C_2-C_4)$-alkenyl, $(C_3-C_7)$-heterocyloalkenyl-$(C_2-C_4)$-alkenyl, $(C_3-C_7)$-heterocyloalkyl-$(C_1-C_4)$-alkyl, $(C_3-C_7)$-heterocyloalkenyl-$(C_1-C_4)$-alkyl, where the heteroatom in heteroaryl, heterocycloalkyl and heterocyloalkenyl optionally bears a charge; and $R^8$ is H or $(C_1-C_6)$-alkyl.

Preference is given to compounds of the formula (I) in which

Q is the moiety

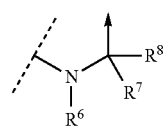

where $R^6$, $R^7$ and $R^8$ are each as defined below and where the arrow represents a bond to the N—$R^5$ group;

W is oxygen or sulfur;

A is the C—$R^4$ moiety, where $R^4$ in the C—$R^4$ moiety is in each case as defined below;

$R^1$, $R^2$, $R^3$ are each hydrogen;

$R^4$ is nitro, amino, hydroxyl, fluorine, chlorine, bromine, iodine, cyano, hydrothio, ($C_1$-$C_4$)-alkyl, ($C_3$-$C_6$)-cycloalkyl, ($C_2$-$C_6$)-alkenyl, ($C_2$-$C_6$)-alkynyl, aryl, aryl-($C_1$-$C_4$)-alkyl, aryl-($C_2$-$C_6$)-alkenyl, aryl-($C_2$-$C_6$)-alkynyl, heteroaryl, ($C_3$-$C_6$)-cycloalkyl-($C_1$-$C_4$)-alkyl, heteroaryl-($C_2$-$C_6$)-alkenyl, heteroaryl-($C_2$-$C_6$)-alkynyl, ($C_1$-$C_4$)-haloalkyl, ($C_3$-$C_6$)-halocycloalkyl, ($C_2$-$C_6$)-haloalkenyl, ($C_2$-$C_6$)-haloalkylalkynyl, ($C_1$-$C_4$)-trialkylsilyl-($C_2$-$C_6$)-alkynyl, ($C_1$-$C_4$)-alkoxy-($C_1$-$C_4$)-alkyl, ($C_1$-$C_4$)-alkoxy, ($C_1$-$C_4$)-haloalkoxy, ($C_2$-$C_6$)-alkenyloxy-($C_1$-$C_4$)-alkyl, aryl-($C_1$-$C_4$)-alkoxy, ($C_1$-$C_6$)-alkylamino, ($C_2$-$C_6$)-alkenylamino, ($C_2$-$C_6$)-alkynylamino, ($C_1$-$C_4$)-alkylthio, ($C_1$-$C_4$)-haloalkylthio, bis-($C_1$-$C_6$)-alkylamino, ($C_3$-$C_6$)-cycloalkylamino, ($C_3$-$C_6$)-haloalkylamino, ($C_1$-$C_6$)alkylcarbonylamino, ($C_3$-$C_6$)-cycloalkylcarbonylamino, ($C_1$-$C_4$)-haloalkylcarbonylamino, ($C_1$-$C_4$)alkoxycarbonylamino, ($C_1$-$C_4$)-alkylaminocarbonylamino, ($C_1$-$C_4$)-alkylsulfonylamino, ($C_3$-$C_6$)-cycloalkylsulfonylamino, arylsulfonylamino, hetarylsulfonylamino, ($C_3$-$C_6$)-haloalkylsulfonylamino, ($C_1$-$C_4$)-alkylsulfonyl, ($C_1$-$C_6$)-haloalkylsulfonyl, arylsulfonyl, ($C_1$-$C_4$)-haloalkylsulfinyl, ($C_3$-$C_6$)-cycloalkyl-($C_1$-$C_4$)-alkoxy, ($C_1$-$C_6$)-alkynyl-($C_1$-$C_4$)-alkoxy, ($C_2$-$C_6$)-alkenyl-($C_1$-$C_4$)-alkoxy, ($C_2$-$C_6$)-alkenyloxy-($C_1$-$C_4$)-alkoxy, ($C_1$-$C_4$)-alkyloxy-($C_1$-$C_4$)-alkoxy, ($C_1$-$C_4$)-alkylamino-($C_1$-$C_4$)-alkoxy, bis-($C_1$-$C_6$)-alkylamino-($C_1$-$C_4$)-alkoxy, ($C_3$-$C_6$)-cycloalkylamino-($C_1$-$C_4$)-alkoxy;

$R^5$ is H or one of the above-defined groups: G-1 to G-6. G-43, G-51 to G-54, G-69, G-71, G-89, G-197 to G-198, G-202 to G-210, G212 to G-216 and G-222 to G-236;

$R^6$ is one of the above-defined groups: G-1 to G-6, G-43, G-51 to G-54, G-69, G-71, G-72, G-89, G-163 to G-168, G-197 to G-198, G-202 to G-210, G212 to G-216 and G-222 to G-240;

$R^7$ is one of the above-defined G-56, G-121 to G-132, G-138 to G-144, G-185 and G-247 to G-282 groups; and $R^8$ is H or one of above-defined G-1 to G-6 groups.

The definitions of radicals stated above in general terms or in areas of preference apply both to the end products of the formula (I) and correspondingly to the starting materials or intermediates required in each case for preparation thereof. These radical definitions can be combined with one another as desired, i.e. including combinations between the given preferred ranges.

With regard to the inventive compounds, the terms used above and below will be elucidated. These are familiar to the person skilled in the art and especially have the definitions elucidated hereinafter:

"Alkoxy" is an alkyl radical bonded via an oxygen atom, alkenyloxy is an alkenyl radical bonded via an oxygen atom, alkynyloxy is an alkynyl radical bonded via an oxygen atom, cycloalkyloxy is a cycloalkyl radical bonded via an oxygen atom, and cycloalkenyloxy is a cycloalkenyl radical bonded via an oxygen atom.

The term "aryl" is an optionally substituted mono-, bi- or polycyclic aromatic system having preferably 6 to 14, especially 6 to 10, ring carbon atoms, for example phenyl, naphthyl, anthryl, phenanthrenyl and the like, preferably phenyl.

The term "optionally substituted aryl" also includes polycyclic systems, such as tetrahydronaphthyl, indenyl, indanyl, fluorenyl, biphenylyl, where the bonding site is on the aromatic system. In systematic terms, "aryl" is generally also encompassed by the term "optionally substituted phenyl".

According to the invention, the expression "heteroaryl" represents heteroaromatic compounds, i.e. fully unsaturated aromatic heterocyclic compounds, preferably 5- to 7-membered rings having 1 to 3, preferably 1 or 2, identical or different heteroatoms, preferably O, S or N. Inventive heteroaryls are, for example, 1H-pyrrol-1-yl; 1H-pyrrol-2-yl; 1H-pyrrol-3-yl; furan-2-yl; furan-3-yl; thien-2-yl; thien-3-yl, 1H-imidazol-1-yl; 1H-imidazol-2-yl; 1H-imidazol-4-yl; 1H-imidazol-5-yl; 1H-pyrazol-1-yl; 1H-pyrazol-3-yl; 1H-pyrazol-4-yl; 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 4H-1,2,4-triazol-4-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, azepinyl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, oxepinyl, thiepinyl, 1,2,4-triazolonyl and 1,2,4-diazepinyl. The inventive heteroaryl groups may also be substituted by one or more identical or different radicals. When two adjacent carbon atoms are part of a further aromatic ring, the systems are fused heteroaromatic systems, such as benzofused or polyannulated heteroaromatics. Preference is given, for example, to quinoline; isoquinoline; quinoxaline; quinazoline; cinnoline; 1,5-naphthyridine; 1,6-naphthyridine; 1,7-naphthyridine; 1,8-naphthyridine; 2,6-naphthyridine; 2,7-naphthyridine; phthalazine; pyridopyrazine; pyridopyrimidine; pyridopyridazine; pteridine; pyrimidopyrimidine.

The term "halogen" means, for example, fluorine, chlorine, bromine or iodine. When the term is used for a radical, "halogen" means, for example, a fluorine, chlorine, bromine or iodine atom.

According to the invention, "alkyl" means a straight-chain or branched open-chain, saturated hydrocarbyl radical which is optionally mono- or polysubstituted. Preferred substituents are halogen atoms, alkoxy, haloalkoxy, cyano, alkylthio, haloalkylthio, amino or nitro groups, particular preference being given to methoxy, methyl, fluoroalkyl, cyano, nitro, fluorine, chlorine, bromine or iodine.

"Haloalkyl", "-alkenyl" and "-alkynyl" mean, respectively, alkyl, alkenyl and alkynyl partly or fully substituted by identical or different halogen atoms, for example monohaloalkyl, for example $CH_2CH_2Cl$, $CH_2CH_2Br$, $CHClCH_3$, $CH_2Cl$, $CH_2F$; perhaloalkyl, for example $CCl_3$, $CClF_2$, $CFCl_2$, $CF_2CClF_2$, $CF_2CClFCF_3$; polyhaloalkyl, for example $CH_2CHFCl$, $CF_2CClFH$, $CF_2CBrFH$, $CH_2CF_3$; the term "perhaloalkyl" also encompasses the term "perfluoroalkyl".

"Fluoroalkyl" means a straight-chain or branched open-chain, saturated and fluorine-substituted hydrocarbyl radical, where at least one fluorine atom is at one of the possible positions.

"Perfluoroalkyl" means a straight-chain or branched open-chain, saturated and fully fluorine-substituted hydrocarbyl radical, for example $CF_3$, $CF_2CF_3$, $CF_2CF_2CF_3$.

"Partly fluorinated alkyl" means a straight-chain or branched, saturated hydrocarbon which is mono- or polysubstituted by fluorine, where the fluorine atoms in question may be present as substituents on one or more different carbon atoms of the straight-chain or branched hydrocarbyl chain, for example $CHFCH_3$, $CH_2CH_2F$, $CH_2CH_2CF_3$, $CHF_2$, $CH_2F$, $CHFCF_2CF_3$.

"Partly fluorinated haloalkyl" means a straight-chain or branched, saturated hydrocarbon which is substituted by different halogen atoms with at least one fluorine atom, where any other halogen atoms are all selected from the group of fluorine, chlorine or bromine, iodine. The halogen atoms in question may be present as substituents on one or more different carbon atoms of the straight-chain or branched hydrocarbyl chain. Partly fluorinated haloalkyl also includes full substitution of the straight or branched chain by halogen including at least one fluorine atom.

Haloalkoxy is, for example, $OCF_3$, $OCHF_2$, $OCH_2F$, $OCF_2CF_3$, $OCH_2CF_3$ and $OCH_2CH_2Cl$; the situation is equivalent for haloalkenyl and other halogen-substituted radicals.

The expression "$(C_1-C_4)$-alkyl" mentioned here by way of example is a brief notation for alkyl having one to 4 carbon atoms according to the range stated for carbon atoms, i.e. comprises the methyl, ethyl, 1-propyl, 2-propyl, 1-butyl, 2-butyl, 2-methylpropyl or tert-butyl radicals. General alkyl radicals with a larger specified range of carbon atoms, e.g. "$(C_1-C_6)$-alkyl", correspondingly also encompass straight-chain or branched alkyl radicals with a greater number of carbon atoms, i.e. according to the example also the alkyl radicals having 5 and 6 carbon atoms.

Unless stated specifically, for the hydrocarbyl radicals such as alkyl, alkenyl and alkynyl radicals, including in composite radicals, preference is given to the lower carbon skeletons, for example having 1 to 6 carbon atoms, or having 2 to 6 carbon atoms in the case of unsaturated groups. Alkyl radicals, including in composite radicals such as alkoxy, haloalkyl, etc., are, for example, methyl, ethyl, n-propyl or i-propyl, n-, i- or t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals, where at least one double bond or triple bond is present. Preference is given to radicals having one double bond or triple bond.

Alkenyl especially also includes straight-chain or branched open-chain hydrocarbyl radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl. Alkenyl is, for example, vinyl which may optionally be substituted by further alkyl radicals, for example prop-1-en-1-yl, but-1-en-1-yl, allyl, 1-methylprop-2-en-1-yl, 2-methylprop-2-en-1-yl, but-2-en-1-yl, 1-methylbut-3-en-1-yl and 1-methylbut-2-en-1-yl, 2-methylprop-1-en-1-yl, 1-methylprop-1-en-1-yl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl, pentenyl, 2-methylpentenyl or hexenyl.

Alkynyl especially also includes straight-chain or branched open-chain hydrocarbyl radicals having more than one triple bond, or else having one or more triple bonds and one or more double bonds, for example 1,3-butatrienyl or 3-penten-1-yn-1-yl. $(C_2-C_5)$-Alkynyl is, for example, ethynyl, propargyl, 1-methylprop-2-yn-1-yl, 2-butynyl, 2-pentynyl or 2-hexynyl, preferably propargyl, but-2-yn-1-yl, but-3-yn-1-yl or 1-methylbut-3-yn-1-yl.

The term "cycloalkyl" means a carbocyclic saturated ring system having preferably 3-8 ring carbon atoms, for example cyclopropyl, cyclobutyl, cyclopentyl or cyclohexyl. In the case of optionally substituted cycloalkyl, cyclic systems with substituents are included, also including substituents with a double bond on the cycloalkyl radical, for example an alkylidene group such as methylidene. In the case of optionally substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), bicyclo[2.2.2]octan-2-yl, adamantan-1-yl and adamantan-2-yl. The expression "$(C_3-C_7)$-cycloalkyl" means a brief notation for cycloalkyl having three to 7 carbon atoms corresponding to the range specified for carbon atoms.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl.

"Cycloalkenyl" means a carbocyclic, nonaromatic, partly unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cycloalkyl apply correspondingly.

The term "alkylidene", for example including in the form of $(C_1-C_{10})$-alkylidene, means the radical of a straight-chain or branched open-chain hydrocarbyl radical bonded via a double bond. Possible bonding sites for alkylidene are naturally only positions on the skeleton where two hydrogen atoms can be replaced by the double bond; radicals are, for example, $=CH_2$, $=CH-CH_3$, $=C(CH_3)-CH_3$, $=C(CH_3)-C_2H_5$ or $=C(C_2H_5)-C_2H_5$. Cycloalkylidene is a carbocyclic radical bonded via a double bond.

A heterocyclic radical (heterocyclyl) comprises at least one heterocyclic ring (=carbocyclic ring in which at least one carbon atom is replaced by a heteroatom, preferably by a heteroatom from the group consisting of N, O, S, P, B, Si, Se), which is saturated, unsaturated or heteroaromatic and may be unsubstituted or substituted, where the point of attachment is located at a ring atom. When the heterocyclyl radical or the heterocyclic ring is optionally substituted, it may be fused to other carbocyclic or heterocyclic rings. Optionally substituted heterocyclyl also includes polycyclic systems, such as, for example, 8-aza-bicyclo[3.2.1]octanyl or 1-aza-bicyclo[2.2.1]heptyl. In the case of optionally substituted heterocyclyl, spirocyclic systems are also included, for example 1-oxa-5-azaspiro[2.3]hexyl. Unless defined differently, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group of N, O and S, though no two oxygen atoms should be directly adjacent, for example with one heteroatom from the group of N, O and S like 1- or 2- or 3-pyrrolidinyl, 3,4-dihydro-2H-pyrrol-2- or 3-yl, 2,3-dihydro-1H-pyrrol-1- or 2- or 3- or 4- or 5-yl; 2,5-dihydro-1H- pyrrol-1- or 2- or 3-yl, 1- or 2- or 3- or 4-piperidinyl; 2,3,4,5-tetrahydropyridin-2- or 3- or 4- or 5-yl or 6-yl; 1,2,3,6-tetrahydropyridin-1- or 2- or 3- or 4- or 5- or 6-yl; 1,2,3,4-tetrahydropyridin-1- or 2- or 3- or 4- or 5- or 6-yl; 1,4-dihydropyridin-1- or 2- or 3- or 4-yl; 2,3-dihydropyridin-2- or 3- or 4- or 5- or 6-yl; 2,5-dihydropyridin-2- or 3- or 4- or 5- or 6-yl, 1- or 2- or 3- or 4-azepanyl; 2,3,4,5-tetrahydro-1H-azepin-1- or 2- or 3- or 4- or 5- or 6- or 7-yl; 2,3,4,7-tetrahydro-1H-azepin-1- or 2- or 3- or 4- or 5- or 6- or 7-yl; 2,3,6,7-tetrahydro-1H-azepin-1- or 2- or 3- or 4-yl; 3,4,5,6-tetrahydro-2H-azepin-2- or 3- or 4- or 5- or 6- or 7-yl; 4,5-dihydro-1H-azepin-1- or 2- or 3- or 4-yl; 2,5-dihydro-1H-azepin-1- or -2- or 3- or 4- or 5- or 6- or 7-yl; 2,7-dihydro-1H-azepin-1- or -2- or 3- or 4-yl; 2,3-dihydro-1H-azepin-1- or -2- or 3- or 4- or 5- or 6- or 7-yl; 3,4-dihydro-2H-azepin-2- or 3- or 4- or 5- or 6- or 7-yl; 3,6-dihydro-2H-azepin-2- or 3- or 4- or 5- or 6- or 7-yl; 5,6-dihydro-2H-azepin-2- or 3- or 4- or 5- or 6- or 7-yl; 4,5-dihydro-3H-azepin-2- or 3- or 4- or 5- or 6- or 7-yl; 1H-azepin-1- or -2- or 3- or 4- or 5- or 6- or 7-yl; 2H-azepin-2- or 3- or 4- or 5- or 6- or 7-yl; 3H-azepin-2- or 3- or 4- or 5- or 6- or 7-yl; 4H-azepin-2- or 3- or 4- or 5- or 6- or 7-yl. Preferred 3-membered and 4-membered heterocyclic rings are, for example, 1- or 2-aziridinyl, oxiranyl, thiiranyl, 1- or 2- or 3-azetidinyl, 2- or 3-oxetanyl, 2- or 3-thietanyl, 1,3-dioxetan-2-yl.

In the case of a partly or fully saturated nitrogen heterocycle, this may be joined to the rest of the molecule either via carbon or via the nitrogen.

According to the invention, "arylsulfonyl" represents optionally substituted phenylsulfonyl or optionally substituted polycyclic arylsulfonyl, here especially optionally substituted naphthylsulfonyl, for example substituted by halogen, cyano, nitro, alkyl, haloalkyl, haloalkoxy, amino, alkylamino, alkylcarbonylamino, dialkylamino or alkoxy groups.

According to the invention, "cycloalkylsulfonyl"—alone or as part of a chemical group—represents optionally substituted cycloalkylsulfonyl, preferably having 3 to 6 carbon atoms, for example cyclopropylsulfonyl, cyclobutylsulfonyl, cyclopentylsulfonyl or cyclohexylsulfonyl.

According to the invention, "alkylsulfonyl"—alone or as part of a chemical group—represents straight-chain or branched alkylsulfonyl, preferably having 1 to 8, or more preferably having 1 to 6 carbon atoms, for example methylsulfonyl, ethylsulfonyl, n-propylsulfonyl, isopropylsulfonyl, n-butylsulfonyl, isobutylsulfonyl, sec-butylsulfonyl and tert-butylsulfonyl.

According to the invention, "alkylthio"—alone or as part of a chemical group—represents straight-chain or branched S-alkyl, preferably having 1 to 8, more preferably having 1 to 6 carbon atoms, for example methylthio, ethylthio, n-propylthio, isopropylthio, n-butylthio, isobutylthio, sec-butylthio and tert-butylthio. Alkenylthio is an alkenyl radical bonded via a sulfur atom, alkynylthio is an alkynyl radical bonded via a sulfur atom, cycloalkylthio is a cycloalkyl radical bonded via a sulfur atom, and cycloalkenylthio is a cycloalkenyl radical bonded via a sulfur atom.

According to the nature and the bonding of the substituents, the compounds of the formula (I) may be present as stereoisomers. The formula (I) embraces all possible stereoisomers defined by their specific three-dimensional form, such as enantiomers, diastereomers. Z and E isomers. When, for example, one or more alkenyl groups are present, diastereamers (Z and E isomers) may occur. When, for example, one or more asymmetric carbon atoms are present, enantiomers and diastereomers may occur. Stereoisomers can be obtained from the mixtures obtained in the preparation by customary separation methods. The chromatographic separation can be effected either on the analytical scale to find the enantiomeric excess or the diastereomeric excess, or on the preparative scale to prepare test specimens for biological testing. It is equally possible to selectively prepare stereoisomers by using stereoselective reactions using optically active starting materials and/or auxiliaries. The invention thus also relates to all stereoisomers which are embraced by the formula (I) but are not shown in their specific stereomeric form, and to mixtures thereof.

Synthesis of substituted quinazolinones ($A^1$=C—$R^4$), pyridopyrimidinones ($A^1$=N) and dihydroquinazolinones as preferred subclasses of the pyrimidinones and dihydropyrimidinones of the formula I Substituted fused pyrimidinones of the quinazolinone and pyridopyrimidinone type can be prepared by known processes (cf. J. Comb. Chem. 2009, 11, 653; J. Heterocyclic Chem, 2009, 46, 178; J. Comb. Chem. 2009, 11, 676; Bioorg Med, Chem. 2010, 18, 526; Molecules 2009, 14, 4246; Bioorg. Med. Chem. 2009, 17, 119; Anti-Cancer Drug Des. 1995, 10, 507; Tetrahedron 2004, 60, 4107; J. Med. Chem. 1998, 41, 5247; Org. Prep. Proc. 1980, 12, 219; Ind. J. Chem. 1995, 34B, 587; Synthesis 2008, 3974; J. Org. Chem., 2006, 71, 382; Angew. Chem. 2009, 121, 354; WO97/10221; WO98/11438). The subclass of the pyrazolo- and imidazolo-quinazolinones is likewise obtainable via the use of synthesis routes known from the literature (cf. Tetrahedron 2010, 66, 128: WO2008090379: WO2007149907). Dihydroquinazolin-4(1H)-ones can likewise be prepared by methods known from the literature (cf. Synthesis 2006, 344; Bioorg Med. Chem. 2006, 14, 1378; Synth. Comm. 2007, 37, 1965; Tetrahedron Lett. 2008, 49, 3814). Chiral dihydroquinazolin-4(1H)-ones can be obtained by enantioselective synthesis (cf. J. Med. Chem. 2008, 51, 4620; Angew. Chem. 2009, 121, 925) or by preparative HPLC separation of the enantiomers on a chiral phase. Various preparation routes known from the literature for formation of the quinazolinone and pyridopyrimidine core structures and of the dihydroquinazolin-4(1H)-one structures have been used, and some have been optimized. Selected detailed synthesis examples are detailed in the next section. The synthesis routes used and examined proceed from commercially available or easily preparable substituted nitrobenzoic acids, nicotinic acids or 1,3-benzaxazinones (isatoic anhydrides).

The relevant 2-nitrobenzoic acid with optional additional substitution can be converted with the aid of thionyl chloride and aqueous ammonia solution to the corresponding 2-nitrobenzamide, which is reduced either with hydrogen in the presence of a catalyst of the palladium on carbon system in a suitable solvent or with tin(II) chloride to give an optionally further-substituted 2-aminobenzamide. The 2-aminobenzamide thus obtained can be converted to the desired substituted quinazolinone (I)a via various reaction variants, for example by condensation with an aldehyde in a suitable solvent (e.g. DMA) at elevated temperature or by acylation of the amino group with an acyl chloride in a suitable solvent (e.g. tetrahydrofuran) using a suitable base (e.g. triethylamine) with subsequent ring closure mediated by a base (e.g. sodium hydroxide) (scheme 1). Alternatively, the corresponding substituted quinazolinone (I)a can also be obtained by reaction of a corresponding benzaxazinone 2 with aqueous ammonia solution. By reaction of the benzaxazinone 2 with an amine $R^5$—$NH_2$, N-substituted quinazolinones (I)b are preparable. N-Substituted quinazolinones (I)b can likewise be obtained by direct conversion of the quinazolinones (I)a. The optionally substituted benzoxazinones 2 are also prepared proceeding from the particular optionally further-substituted 2-nitrobenzoic acids in two steps by reduction of the nitro group with hydrogen in the presence of a catalyst of the palladium on carbon system in a suitable solvent (e.g. methanol) or with tin(II) chloride in a suitable solvent (e.g. ethanol) and subsequent condensation with an appropriate anhydride at elevated temperature (scheme 1).

carbonyl chloride with the aid of diisopropylethylamine in a suitable solvent (e.g. dichloromethane). In the final reaction step, the cyclization is effected to give the desired target product and the detachment from the resin is effected by reaction with potassium hydroxide in ethanol at elevated temperature.

Scheme 1.

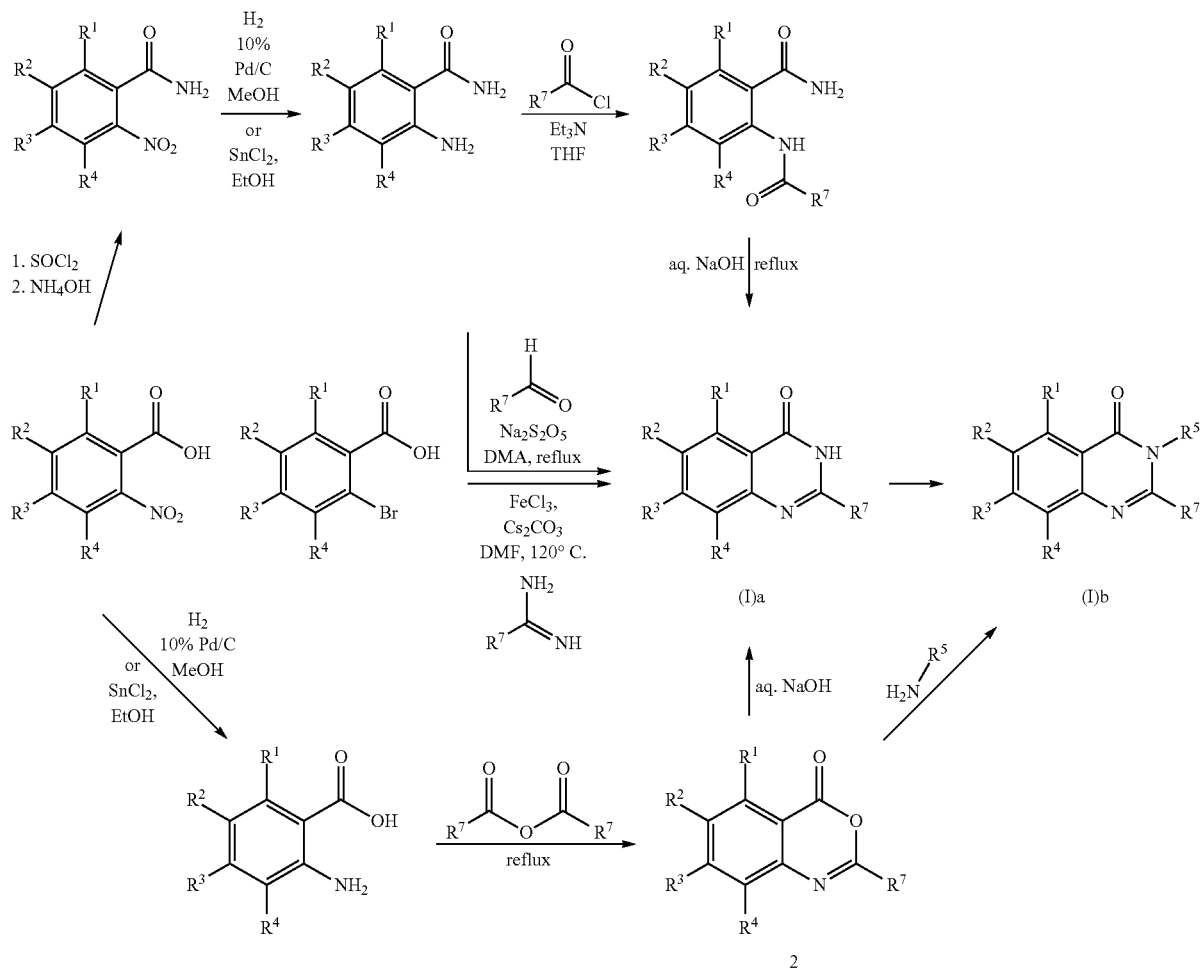

A further variant for preparation of the quinazolinones (I)a is the condensation, mediated by iron(III) chloride and cesium carbonate, of a suitable amidine and of an optionally further-substituted 2-bromobenzoic acid in a suitable polar aprotic solvent (e.g. DMF or dioxane) at elevated temperature. The inventive quinazolinones (I)a can also be prepared via a solid phase-supported synthesis route using a suitable polystyrene resin (scheme 2; the abbreviations used in schemes 1 and 2 are defined as follows: DMA=dimethylacetamide, DMF=N,N-dimethylformamide, RAM-PS polymer resin for the solid phase-bound synthesis, DIC=N,N'-diisopropyl-carbodiimide, HOBt=N-hydroxy-benzotriazole, DIPEA=N,N-diisopropylethylamine, TFA=trifluoroacetic acid). First of all, the appropriate, optionally further-substituted 2-nitrobenzoic acid is bound to an RAM-PS resin, then the nitro group is converted to an amino group with tin(II) chloride in a suitable solvent (e.g. N,N-dimethylformamide) and acylated with an appropriate Scheme 2.

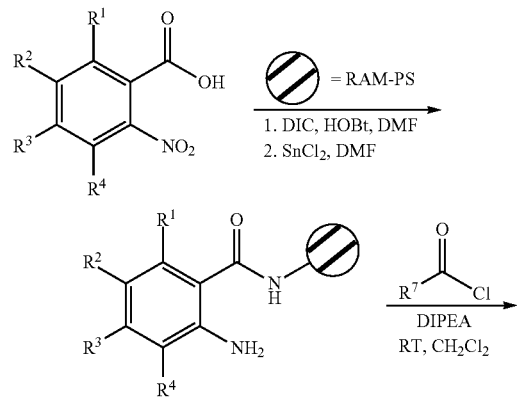

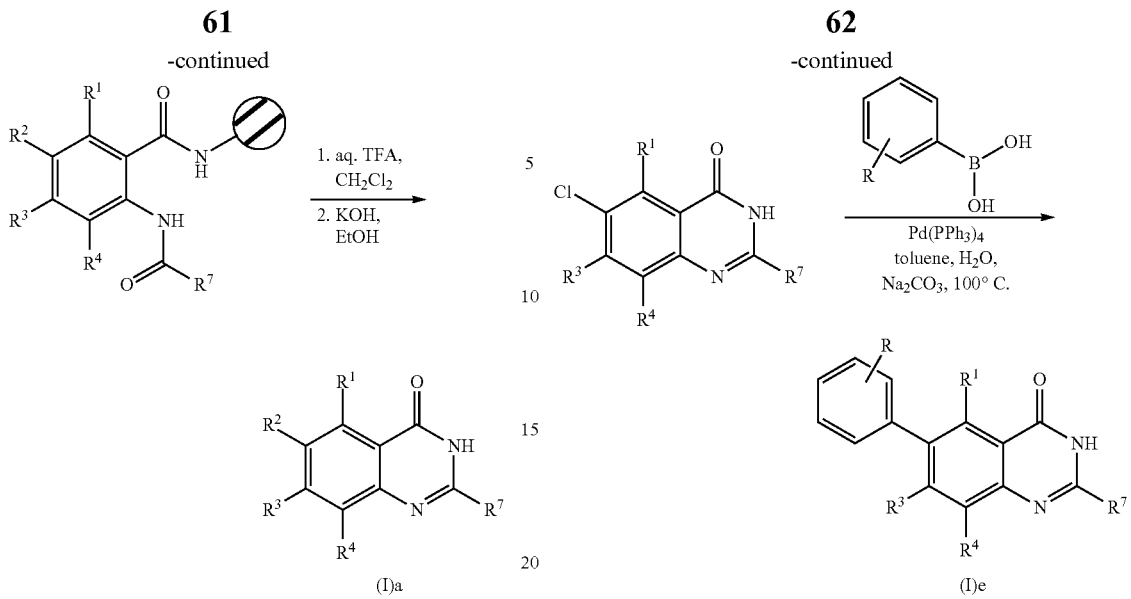

Quinazolinone (I)a with chlorine, bromine or iodine substituents at positions $R^1$, $R^2$, $R^3$ or $R^4$ can be substituted further with the aid of transition metal-catalyzed reactions. Selected examples of this kind of reactions are shown in Scheme 3. The substituents R are not defined specifically in Scheme 3, since these are illustrative reactions. The possible and preferred substituents on the groups introduced are evident from the abovementioned claims and definitions. With the aid of a Sonogashira coupling using copper(I) chloride and bis(triphenylphosphine)palladium dichloride in as suitable solvent, e.g. triethylamine ($Et_3N$) or a mixture of triethylamine and tetrahydrofuran (THF), it is possible, for example, to introduce alkynyl, arylalkynyl, heteroarylalkynyl, alkylsilylalkynyl or alkylalkynyl groups and to form the target molecules (I)d. Via a Suzuki coupling with tetrakis(triphenylphosphine)palladium in a suitable solvent system, it is possible to prepare, for example, aryl-, alkenyl-, cycloalkyl- or heteroaryl-substituted target molecules such as quinazolinones (I)e.

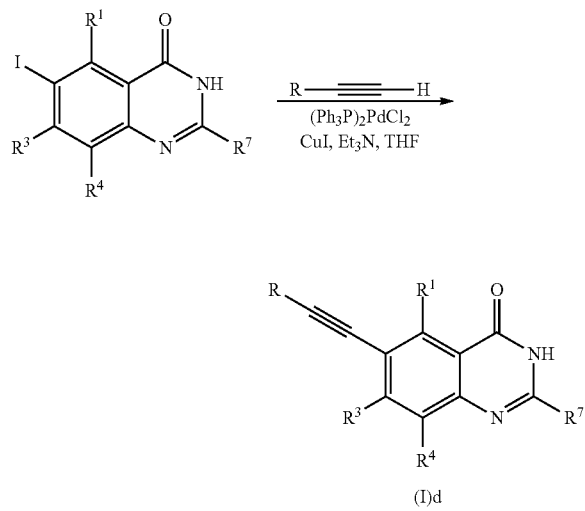

When $R^6$ is hydrogen, 2,3-dihydroquinazolin-4(1H)-ones can be oxidized with suitable oxidizing agents, for example 2,3-dichloro-5,6-dicyano-1,4-benzoquinone (DDQ), to give quinazolinones of the formula (I)a or (I)b.

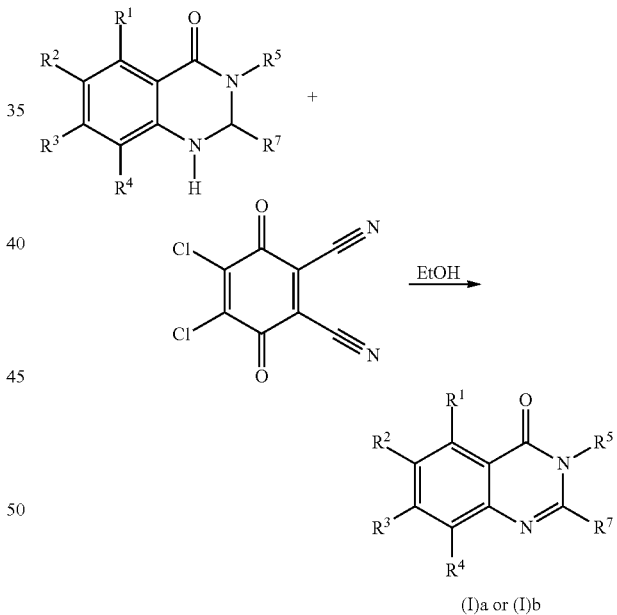

The analogous pyridopyrimidinones (I)c can be prepared in several reaction steps proceeding from commercially available and optionally substituted chloronicotinic acids (Scheme 5). First of all, the chlorine atom is exchanged for an amino group under elevated pressure with the aid of ammonia and copper(I) chloride. The aminonicotinic acid thus obtained is then reacted with an acyl chloride in a suitable solvent (e.g. tetrahydrofuran) using a suitable base (e.g. triethylamine). Reaction with a suitable anhydride and subsequent addition of aqueous ammonia solution forms the desired substituted pyridopyrimidinone (I)c.

Scheme 5.

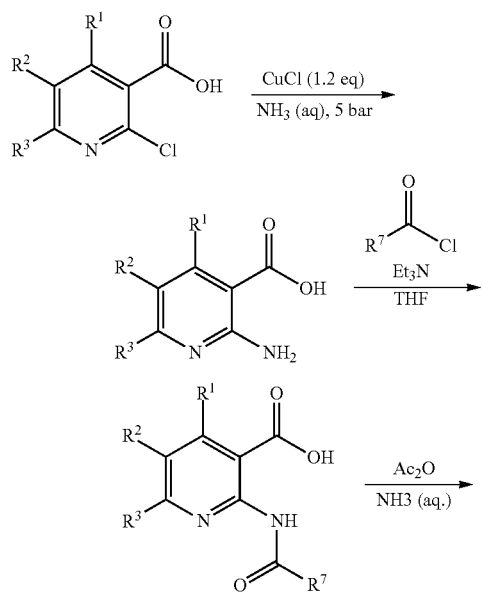

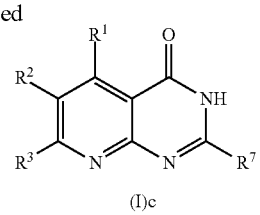

(I)c

By condensation of optionally further-substituted 2-hydrazinobenzamides or 2-hydrazinonicotinamides with substituted α-cyano ketones in glacial acetic acid at elevated temperature, it is possible to prepare substituted pyrazoloquinazolinones (I)i (Scheme 6). Since this reaction proceeds successfully with a multitude of differently substituted α-cyano ketones, it is also possible, for example—as shown in Scheme 6—to introduce a carboxyl group as the $R^9$ substituent. The corresponding pyrazoloquinazolinonecarboxylic esters (I)j can be converted to the corresponding acids (I)k with a suitable base (e.g. sodium hydroxide or lithium hydroxide) and subsequent acidic workup. The acids (I)k thus obtained can be converted further to the corresponding carboxamides (I)l firstly with the aid of thionyl chloride, triethylamine and a suitable amine, but also by use of hydroxybenzotriazole (HOBt) and 1-ethyl-3-(3-dimethylaminopropyl)carbodiimide (EDC) and a suitable amine.

Scheme 6.

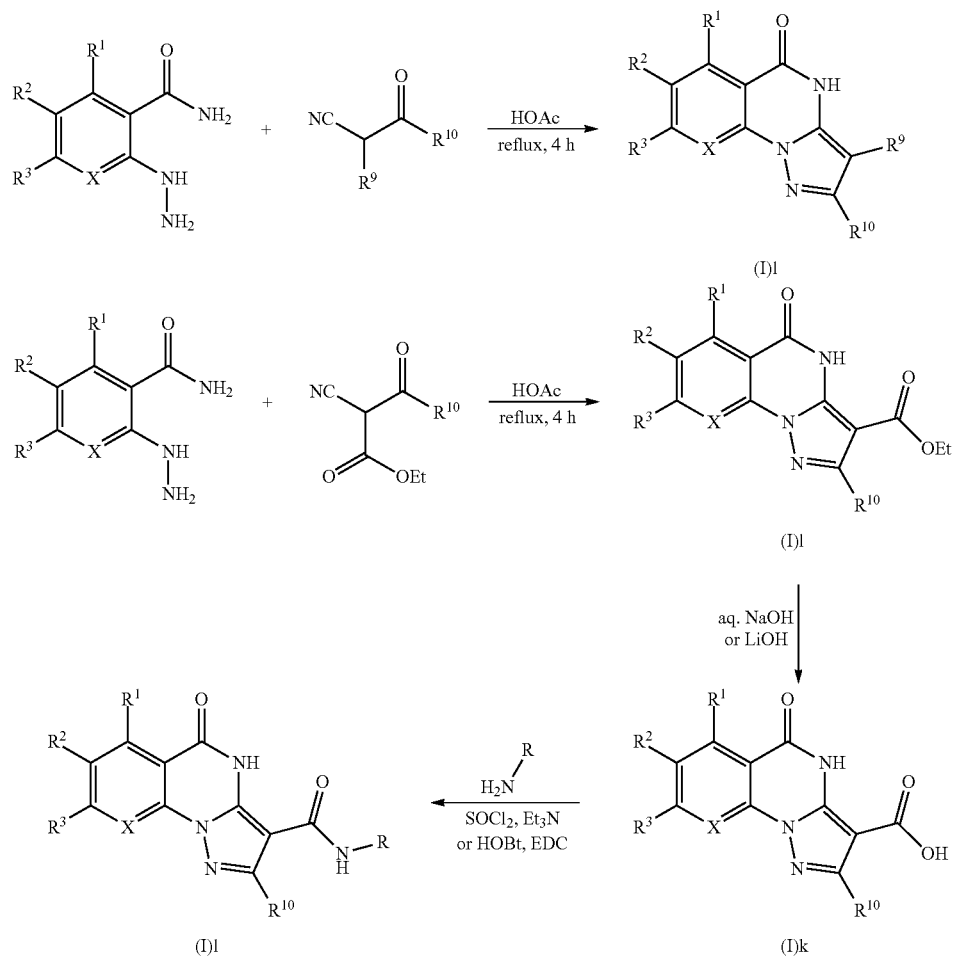

2,3-Dihydroquinazolin-4(1H)-ones (I)f can be obtained by reaction of 1,3-benzoxazinones (isatoic anhydrides) with aldehydes in the presence of an optionally substituted nitrogen source $R^5NH_2$ (Scheme 7). If $R^5$ is to be hydrogen, not only the use of ammonia under elevated pressure but also ammonium formate or ammonium acetate can serve as the nitrogen source.

2,2-Disubstituted dihydroquinazolin-4(1H)-ones (I)g can be prepared proceeding from optionally further-substituted 2-nitrobenzamides in a reaction with an appropriately substituted ketone and tin(II) chloride hydrate in a suitable solvent (e.g. ethanol or toluene) (Scheme 8). The reaction of optionally further-substituted 2-nitrobenzamides kann can, in addition to the dihydroquinazolinone (I)g, also form the corresponding 1-hydroxy-2,3-dihydroquinazolinone (I)h. Optionally further-substituted 2-aminobenzamides, which can also be formed by palladium-mediated hydrogenation of the corresponding 2-nitrobenzamides, can also be converted to the desired 2,2-disubstituted dihydroquinazolinones (I)g by condensation with suitable ketones at elevated temperature in a suitable solvent (e.g. toluene).

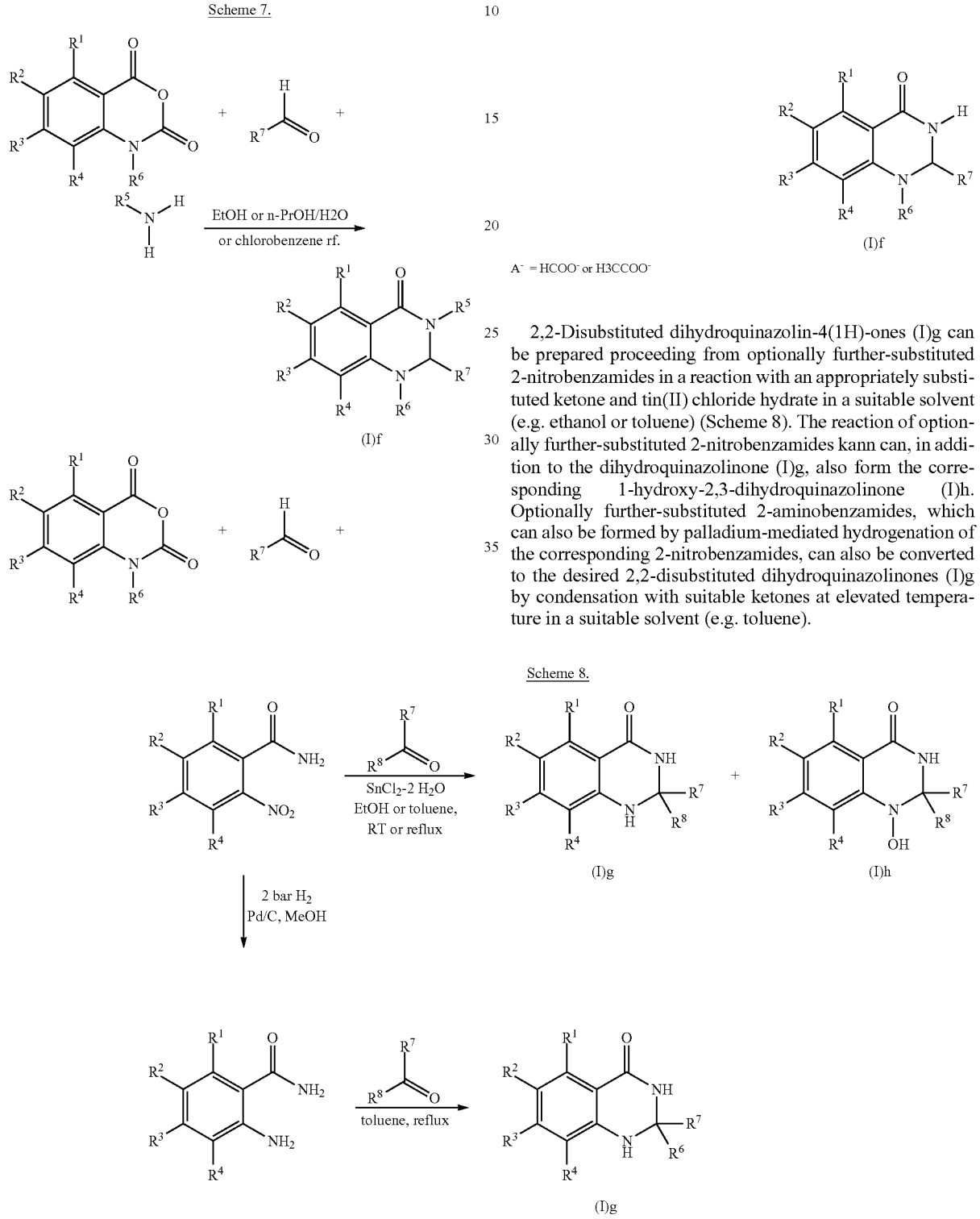

Synthesis Examples for Compounds of the Formula (I)

The substance numbers stated correspond to the numberings stated in tables 1 to 5. The $^1$H NMR, $^{13}$C NMR and $^{19}$F NMR spectroscopy data which are reported for the chemical examples described in the paragraphs which follow (400 MHz for $^1$H NMR and 150 MHz for $^{13}$C NMR and 375 MHz for $^{19}$F NMR, solvent: CDCl$_3$, CD$_3$OD or d$_6$-DMSO, internal standard: tetramethylsilane δ=0.00 ppm), were obtained with a Bruker instrument, and the signals identified are defined as follows: br=broad; s=singlet, d=doublet, t=triplet, dd=double doublet, ddd=doublet of a double doublet, m=multiplet, q=quartet, quint=quintet, sext=sextet, sept=septet, dq=double quartet, dt=double triplet No. I.1-1: 2-Butylquinazolin-4(3H)-one

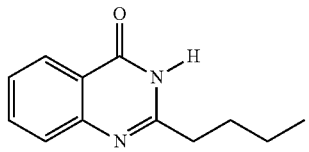

Anthranilamide (300 mg, 2.20 mmol) was dissolved under argon in dimethylacetamide (5 ml), valeraldehyde (199 mg, 2.31 mmol) and Na$_2$S$_2$O$_5$ (628 mg, 3.31 mmol) were added, and the mixture was stirred under reflux conditions for 4 h. After cooling to room temperature, water was added to the reaction mixture. By suction-filtering and thoroughly drying the solid formed, 2-butylquinazolin-4(3H)-one (254 mg, 54% of theory) was obtained as a colorless solid. $^1$H NMR (400 MHz, CDCl$_3$ δ, ppm) 8.26 (d, 1H), 7.74 (dd, 1H), 7.69 (d, 1H), 7.46 (dd, 1H), 7.30 (br. s, 1H, NH), 2.75 (t, 2H), 1.82 (quint, 2H), 1.49 (sext, 2H), 1.00 (t, 3H).

No. I.1-37: 2-(4-Fluorophenyl)-8-methoxyquinazolin-4(3H)-one

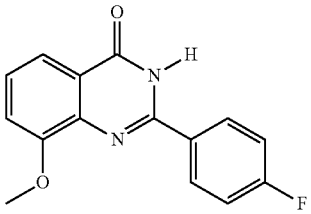 [SMILES: COc1cccc2c(=O)[nH]c(-c3ccc(F)cc3)nc12]

3-Methoxy-2-nitrobenzoic acid (2000 mg, 10.15 mmol) was dissolved under argon in abs. tetrahydrofuran (10 ml), and oxalyl chloride (1288 mg, 10.15 mmol) and a catalytic amount of DMF were added. The resulting reaction mixture was stirred at 60° C. for 2 h and then concentrated under reduced pressure. The crude product was dissolved directly in abs. dioxane (8 ml) under argon and the solution was cooled to 0° C. Thereafter, ammonia gas was introduced for 10 min. After the introduction of gas had ended, the reaction solution was poured onto ice-water and extracted repeatedly with ethyl acetate. The combined organic phases were dried over magnesium sulfate, filtered and concentrated under reduced pressure. The 3-methoxy-2-nitrobenzamide (1950 mg, 9.94 mmol) thus prepared was then dissolved in abs. methanol (60 ml). After the addition of catalytic amounts of palladium on activated carbon (content of 10% in water-moist form; 543 mg, 0.51 mmol), hydrogen was introduced at room temperature until conversion was complete. The catalyst was then filtered off and the solvent was concentrated under reduced pressure. The crude product was used without further purification in the next reaction step, and the 2-amino-3-methoxybenzamide (350 mg, 2.11 mmol) thus obtained was dissolved in abs. tetrahydrofuran (5 ml). After addition of triethylamine (0.32 ml, 2.32 mmol) and stirring at room temperature for a further 10 minutes, 4-fluorobenzoyl chloride (0.28 ml, 2.32 mmol) was added. The resulting reaction mixture was stirred at room temperature for 3 h, then the solvent was removed under reduced pressure, and water and ethyl acetate were added to the residue. The aqueous phase was extracted repeatedly with ethyl acetate, and the combined organic phases were then dried over magnesium sulfate, filtered and concentrated under reduced pressure. Column chromatography purification (ethyl acetate/n-heptane gradient) of the crude product gave 2-[(4-fluorobenzoyl)amino]-3-methoxybenzamide (550 mg, 91% of theory) as a colorless solid. 2-[(4-Fluorobenzoyl)amino]-3-methoxybenzamide (500 mg, 1.73 mmol) was dissolved in aqueous sodium hydroxide solution (2M, 5 ml) and stirred at 60° C. for 5 h. After cooling to room temperature, filtration with suction and thorough drying gave 2-(4-fluorophenyl)-8-methoxyquinazolin-4(3H)-one (462 mg, 98% of theory) as a colorless solid. $^1$H NMR (400 MHz, d$_6$-DMSO δ, ppm) 12.60 (br. s, 1H, NH), 8.24 (m, 2H), 7.70 (dd, 1H), 7.46 (d, 1H), 7.42 (d, 1H), 7.38 (m, 2H), 3.96 (s, 3H).

No. I.1-39: 2-(4-Fluorophenyl)-8-hydroxyquinazolin-4(3H)-one

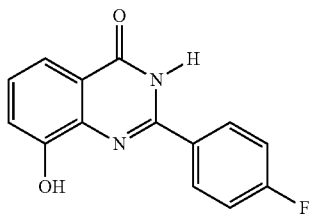 [SMILES: O=c1[nH]c(-c2ccc(F)cc2)nc2c(O)cccc12]

2-(4-Fluorophenyl)-8-methoxyquinazolin-4(3H)-one (460 mg, 1.70 mmol) was dissolved under argon in boron tribromide solution (1M solution in tetrahydrofuran; 5.11 ml, 5.11 mmol) and stirred under reflux conditions for 4 h. After cooling to room temperature, the solvent was removed under reduced pressure, and the residue was taken up in aqueous sodium hydroxide solution (10 ml) and stirred at room temperature for a further 3 h. Subsequently, the reaction solution was neutralized with dilute aqueous hydrochloric acid (1M). Filtration with suction and thorough drying gave 2-(4-fluorophenyl)-8-hydroxyquinazolin-4(3H)-one (370 mg, 85% of theory) as a colorless solid. $^1$H NMR (400 MHz, d$_6$-DMSO δ, ppm) 12.49 (br. s, 1H, NH), 9.65 (br. s, 1H, OH), 8.49 (m, 2H), 7.67 (dd, 1H), 7.38 (m 2H), 7.34 (d, 1H), 7.23 (dd, 1H).

No. I.1-141: 2-(4-Bromo-1H-pyrazol-5-yl)-5-fluoro-quinazolin-4(3H)-one

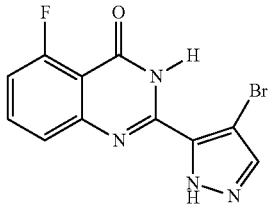 [SMILES: O=c1[nH]c(-c2[nH]ncc2Br)nc2cccc(F)c12]

2-Amino-6-fluorobenzamide (77 mg, 0.50 mmol) was dissolved under argon in dimethylacetamide (5 ml), 4-bromo-1H-pyrazole-5-carbaldehyde (88 mg, 0.50 mmol) and $Na_2S_2O_5$ (143 mg, 0.75 mmol) were added, and the mixture was stirred under reflux conditions for 5 h. After cooling to room temperature, the reaction mixture was concentrated and taken up with a mixture of acetonitrile and N,N-dimethylformamide. Filtration with suction and thorough drying of the remaining solid gave 2-(4-bromo-1H-pyrazol-5-yl)-5-fluoro-quinazolin-4(3H)-one (30 mg, 19% of theory) as a colorless solid. $^1$H NMR (400 MHz, $d_6$-DMSO δ, ppm) 13.91 (br. s, 1H, NH), 12.03 (br. s, 1H, NH), 8.22 (s, 1H), 7.80 (dd, 1H), 7.51 (d, 1H), 7.27 (dd, 1H).

No. I.1-505: 2-(2-Chloro-4-methylphenyl)-8-methylquinazolin-4(3H)-one

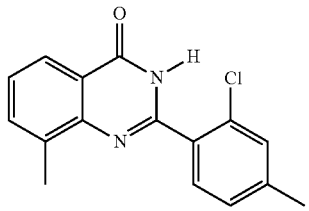 [SMILES: Cc1ccc(-c2nc3c(C)cccc3c(=O)[nH]2)c(Cl)c1]

2-(2-Chloro-4-methylphenyl)-8-methyl-2,3-dihydroquinazolin-4(1H)-one (159 mg, 0.6 mmol) and 2,3-dichloro-5,6-dicyano-1,4-benzoquinone (126 mg, 0.6 mmol) were dissolved in 5 ml of ethanol and then stirred at room temperature for 2 hours. The reaction mixture was filtered and the solid was washed with a little ethanol. This gave 108 mg (65.5% of theory) of 2-(2-chloro-4-methylphenyl)-8-methylquinazolin-4(3H)-one as a colorless said of melting point 234° C. $^1$H NMR (400 MHz, $d_6$-DMSO δ, ppm) 12.54 (br. S, 1H), 8.00 (d, 1H), 7.70 (d, 1H), 7.56 (d, 1H), 7.42 (m, 2H), 7.30 (d, 1H), 2.51 (s, 3H), 2.40 (s, 3H).

No. I.2-8: 2-Cyclobutyl-7-(trifluoromethyl)pyrido[2,3-d]pyrimidin-4(3H)-one

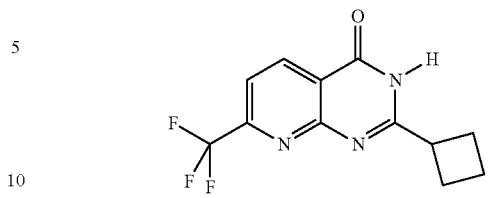

2-Chloro-6-trifluoromethylnicotinic acid (3000 mg, 13.30 mmol) was added under argon to 24% aqueous ammonia solution (5 ml), and copper(I) chloride (1580 mg, 15.96 mmol) was added. The resulting reaction mixture was stirred at a temperature of 100° C. and at an elevated pressure of approx. 5 bar in a pressure vessel for 15 h. After cooling to room temperature and lowering the pressure to standard pressure, ethyl acetate and dilute hydrochloric acid (2N) were added to the reaction mixture. The aqueous phase was extracted repeatedly with ethyl acetate, and the combined organic phases were then dried over magnesium sulfate, filtered and concentrated under reduced pressure. Column chromatography purification (ethyl acetatein-heptane gradient) of the crude product gave 2-amino-6-trifluoromethylnicotinic acid (1640 mg, 58% of theory) as a colorless solid. 2-Amino-6-trifluoromethylnicotinic acid (500 mg, 2.43 mmol) was dissolved in abs. tetrahydrofuran (8 ml), and triethylamine (369 mg, 3.64 mmol) was added. Thereafter, the reaction solution was cooled under argon to 0° C., and cyclobutanecarbonyl chloride (316 mg, 2.69 mmol) was slowly added dropwise. The resulting reaction mixture was stirred at room temperature for a further 7 h, then dist. water and dichloromethane were added. The aqueous phase was extracted repeatedly with dichloromethane, and the combined organic phases were then dried over magnesium sulfate, filtered and concentrated under reduced pressure. Preparative HPLC purification (acetonitrile/water/trifluoroacetic acid gradient) of the crude product gave 2-[(cyclobutylcarbonyl)amino]-6-(trifluoro-methyl)nicotinamide (197 mg, 28% of theory) as a colorless solid. 2-[(Cyclobutyl-carbonyl)amino]-6-(trifluoromethyl)nicatinamide (197 mg, 0.68 mmol) was dissolved in acetic anhydride (5 ml) and stirred under reflux conditions under argon for 5 h. After cooling to room temperature, concentrated ammonia solution was added (10 ml) and the reaction mixture was stirred at room temperature for a further 6 h. The precipitated solid was filtered off with suction and dried. Preparative HPLC purification of the crude product gave 2-cyclobutyl-7-(trifluoromethyl)pyrido[2,3-d]pyrimidin-4 (3H)-one (55 mg, 30% of theory) as a yellowish solid. $^1$H NMR (400 MHz, $CDCl_3$ δ, ppm) 8.79 (d, 1H), 7.78 (d, 1H), 7.28 (br. s, 1H, NH), 3.62 (quint, 1H), 2.64 (m, 2H), 2.48 (m, 2H), 2.18 (m, 1H), 2.02 (m, 1H).

No. I.3-17: 3-(4-Chlorophenyl)-2-(trifluoromethyl)pyrazolo[1,5-a]quinazolin-5(4H)-one

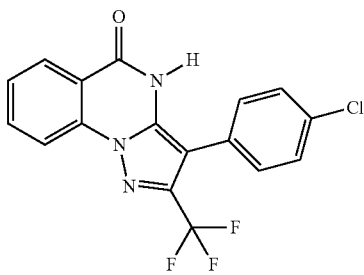 [SMILES: O=c1[nH]c2c(-c3ccc(Cl)cc3)c(C(F)(F)F)nn2c2ccccc12]

2-Hydrazinobenzoic acid hydrochloride (200 mg, 1.06 mmol) and 2-(4-chlorophenyl)-4,4,4-trifluoro-3-oxobutanonitrile (263 mg, 1.06 mmol) were added under argon to conc. acetic acid (3 ml) and stirred under reflux conditions for 10 h. After cooling to room temperature, filtration with suction and thorough drying of the solid which precipitated gave 3-(4-chlorophenyl)-2-(trifluoromethyl)pyrazolo[1,5-a]quinazolin-5(4H)-one (168 mg, 41% of theory) as a light brown solid. $^1$H NMR (400 MHz, $d_6$-DMSO δ, ppm) 12.38 (br. s, 1H, NH), 8.19 (d, 1H), 8.17 (d, 1H), 7.96 (dd, 1H), 7.62 (dd, 1H), 7.53 (d, 2H), 7.40 (d, 2H).

No. I.4-71: 2-(4-Chlorophenyl)-2,3-dihydroquinazolin-4(1H)-one

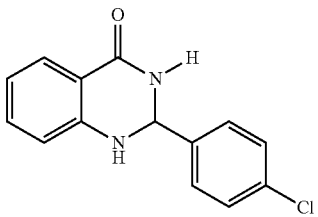 [SMILES: O=C1NC(c2ccc(Cl)cc2)Nc2ccccc21]

Isatoic anhydride (163 mg, 10 003l\ was dissolved under an argon atmosphere in 5 ml of ethanol and, after addition of 4-chlorobenzaldehyde (211 mg, 15 mmol), ammonium acetate (93 mg, 12 mmol) and 4-toluenesulfonic acid (86 mg, 5 mmol), boiled at reflux for 5 hours. The product precipitated in the course of cooling. The precipitated solid was washed with a little ethanol and dried. This gave 150 mg (54.5% of theory) of 2-(4-chlorophenyl)-2,3-dihydroquinazolin-4(1H)-one as a white solid of melting point 190° C. $^1$H NMR (400 MHz, CDCl$_3$ δ, ppm) 7.95 (d, 1H), 7.55 (dd, 2H), 7.42 (dd, 2H), 7.34 (t, 1H), 6.91 (t, 1H), 6.68 (d, 1H), 5.90 (s, 1H), 5.75 (br. S, 1H), 4.35 (br. S, 1H).

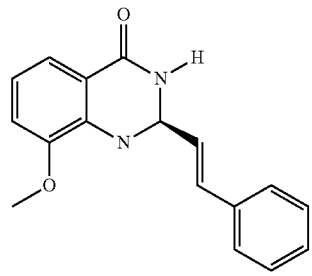

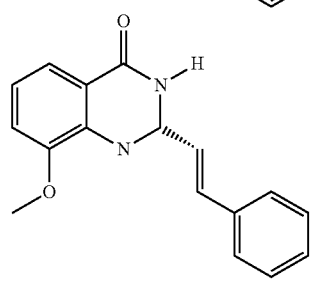

No. I.4-352: 2S-(+)-8-Methoxy-2-[(E)-2-phenylethenyl]-2,3-dihydroquinazolin-4(1H)-one 200 mg of racemic 2R,S-8-methoxy-2-[(E)-2-phenylethenyl]-2,3-dihydroquinazolin-4(1H)-one (example I.4-75) were separated by means of preparative HPLC on a chiral phase (Chiralpak IC 20 μm from Chiral Technologies Europe, Illkirch, France; column dimensions 250×50 mm).

Distilling off the eluent left 43 mg of 2S-(+)-8-methoxy-2-[(E)-2-phenylethenyl]-2,3-dihydroquinazolin-4(1H)-one with an enantiomeric excess of 68.00% (determined by analytical HPLC on Chiralpak IC 5 μm from Chiral Technologies Europe, Illkirch, France; column dimensions 250×4.6 mm).

No. I.4-353: (−)-8-Methoxy-2-[(E)-2-phenylethenyl]-2,3-dihydroquinazolin-4(H)-one 200 mg of racemic 2R,S-8-methoxy-2-[(E)-2-phenylethenyl]-2,3-dihydroquinazolin-4(1H)-one (example I.4-75) were separated by means of preparative HPLC on a chiral phase (Chiralpak IC 20 μm from Chiral Technologies Europe, Illkirch, France; column dimensions 250×50 mm).

Distilling off the eluent left 68 mg of 2R-(−)-8-methoxy-2-[(E)-2-phenylethenyl]-2,3-dihydroquinazolin-4(1H)-one with a specific rotation of $[\alpha]^{23}_{589}$=−180.10°, which corresponds to an enantiomeric excess of 99.40% (determined by analytical HPLC on Chiralpak IC 5 μm from Chiral Technologies Europe, Illkirch, France; column dimensions 250×4.6 mm).

No. I.5-17: 4'-(2,2,2-Trifluoroethoxy)-7-(trifluoromethyl)-1H-spiro[quinazolin-2,1'-cyclohexan]-4(3H)-one

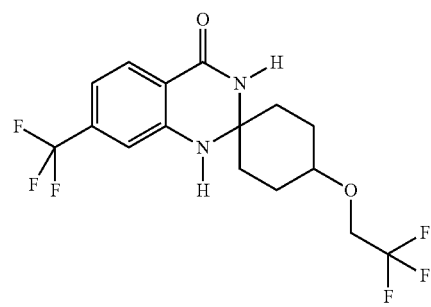 [SMILES: O=C1NC2(CCC(OCC(F)(F)F)CC2)Nc2cc(C(F)(F)F)ccc21]

2-Nitro-4-trifluoromethylbenzamide (347 mg, 1.47 mmol), 4-(2,2,2-trifluoroethoxy)cyclohexanone (303 mg, 1.54 mmol) and tin(II) chloride hydrate (663 mg, 2.94 mmol) were added to toluene (5 ml) under argon and stirred under reflux conditions for 10 h. After cooling to room temperature, filtration with suction and thorough drying of the solid which precipitated gave 4'-(2,2,2-trifluoroethoxy)-7-(trifluoromethyl)-1H-spiro[quinazolin-2,1'-cyclohexan]-4(3H)-one (223 mg, 36% of theory) as a colorless solid. $^1$H NMR (400 MHz, $d_6$-DMSO δ, ppm) 8.23 (br. 5, 1H, NH), 7.73 (d, 1H), 7.21 (br. s, 1H, NH), 7.19 (s, 1H), 6.90 (d, 1H), 4.06 (q, 2H), 3.51 (m, 1H), 1.90 (m, 4H), 1.62 (m, 4H).

In analogy to the preparation examples detailed above, and taking account of the general information regarding the preparation of the compounds of the formula (I), the following compounds are obtained with the base structures I.1-I.5 specified in the tables below:

TABLE 1 with base structure I.1 and the radical definitions specified hereinafter:

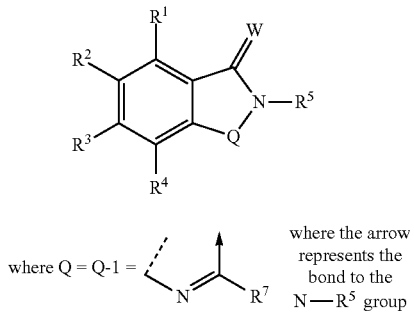

(I.1)

where Q = Q-1 = 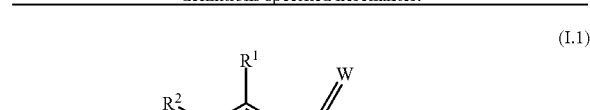  where the arrow represents the bond to the N—$R^5$ group and with $R^7$ selected from the aforementioned G-1 to G-282 radicals

| No. | W | $R^1$ | $R^2$ | $R^3$ | $R^4$ | $R^5$ | $R^7$ |
|---|---|---|---|---|---|---|---|
| I.1-1 | O | H | H | H | H | H | G-4 |
| I.1-2 | O | H | H | Cl | H | H | G-1 |
| I.1-3 | O | H | H | Cl | H | H | G-1 |
| I.1-4 | O | H | $CH_3$ | H | H | H | G-1 |
| I.1-5 | O | H | H | H | H | H | G-7 |
| I.1-6 | O | H | $CH_3$ | H | H | H | G-2 |
| I.1-7 | O | F | H | H | H | H | G-1 |
| I.1-8 | O | H | Cl | H | H | H | G-12 |
| I.1-9 | O | H | $CH_3$ | H | H | H | G-12 |
| I.1-10 | O | H | H | H | H | H | G-9 |
| I.1-11 | O | H | H | H | H | H | G-2 |
| I.1-12 | O | H | Cl | H | H | H | G-1 |
| I.1-13 | O | H | H | H | H | H | G-25 |
| I.1-14 | O | H | Cl | H | H | H | G-25 |
| I.1-15 | O | H | H | H | H | H | G-43 |
| I.1-16 | O | H | H | H | H | H | G-3 |
| I.1-17 | O | H | H | H | H | H | G-32 |
| I.1-18 | O | H | H | H | H | H | G-19 |
| I.1-19 | O | Cl | H | H | H | H | G-1 |
| I.1-20 | O | H | Br | H | H | H | G-1 |
| I.1-21 | O | H | H | $NO_2$ | H | H | G-1 |
| I.1-22 | O | H | $OCH_3$ | $OCH_3$ | H | H | G-44 |
| I.1-23 | O | H | H | Cl | H | H | G-2 |
| I.1-24 | O | H | I | H | H | H | G-44 |
| I.1-25 | O | H | $OCH_3$ | $OCH_3$ | H | H | G-5 |
| I.1-26 | O | H | H | H | H | H | G-120 |
| I.1-27 | O | H | $OCH_3$ | $OCH_3$ | H | H | G-37 |
| I.1-28 | O | H | H | H | $CH_3$ | H | G-1 |
| I.1-29 | O | H | H | Cl | H | H | G-8 |
| I.1-30 | O | H | H | H | H | H | G-105 |
| I.1-31 | O | H | H | H | H | H | G-104 |
| I.1-32 | O | H | H | H | $NO_2$ | H | G-1 |
| I.1-33 | O | H | H | H | $OCH_3$ | H | G-12 |
| I.1-34 | O | H | H | H | OH | H | G-12 |
| I.1-35 | O | H | H | H | $OCH_3$ | H | G-29 |
| I.1-36 | O | H | H | H | $OCH_3$ | H | G-50 |
| I.1-37 | O | H | H | H | $OCH_3$ | H | G-8 |
| I.1-38 | O | H | H | H | OH | H | G-29 |
| I.1-39 | O | H | H | H | OH | H | G-8 |
| I.1-40 | O | H | H | H | OH | H | G-49 |
| I.1-41 | O | H | H | H | OH | H | G-50 |
| I.1-42 | O | H | H | H | OH | H | G-36 |
| I.1-43 | O | H | H | H | H | H | G-45 |
| I.1-44 | O | H | H | H | H | H | G-20 |
| I.1-45 | O | H | H | H | H | H | G-22 |
| I.1-46 | O | H | H | H | H | H | G-23 |
| I.1-47 | O | H | H | H | H | H | G-55 |
| I.1-48 | O | H | H | H | H | H | G-46 |
| I.1-49 | O | H | H | H | H | H | G-47 |
| I.1-50 | O | H | H | H | $CH_3$ | H | G-25 |
| I.1-51 | O | H | H | Cl | H | H | G-19 |
| I.1-52 | O | H | H | Cl | H | H | G-20 |
| I.1-53 | O | H | Br | H | Br | H | G-19 |
| I.1-54 | O | H | H | Cl | H | H | G-22 |
| I.1-55 | O | H | H | Cl | H | H | G-25 |
| I.1-56 | O | H | $CH_3$ | H | H | H | G-19 |
| I.1-57 | O | H | $CH_3$ | H | H | H | G-20 |
| I.1-58 | O | H | $CH_3$ | H | H | H | G-22 |
| I.1-59 | O | H | $CH_3$ | H | H | H | G-25 |
| I.1-60 | O | H | F | H | H | H | G-19 |
| I.1-61 | O | H | F | H | H | H | G-20 |
| I.1-62 | O | H | F | H | H | H | G-23 |
| I.1-63 | O | H | F | H | H | H | G-22 |
| I.1-64 | O | H | F | H | H | H | G-25 |
| I.1-65 | O | H | Cl | H | H | H | G-19 |
| I.1-66 | O | H | Cl | H | H | H | G-20 |
| I.1-67 | O | H | Cl | H | H | H | G-23 |
| I.1-68 | O | H | Cl | H | H | H | G-22 |
| I.1-69 | O | F | H | H | H | H | G-19 |
| I.1-70 | O | F | H | H | H | H | G-20 |
| I.1-71 | O | F | H | H | H | H | G-23 |
| I.1-72 | O | F | H | H | H | H | G-22 |
| I.1-73 | O | F | H | H | H | H | G-25 |
| I.1-74 | O | H | H | H | $CH_3$ | H | G-19 |
| I.1-75 | O | H | H | H | $CH_3$ | H | G-20 |
| I.1-76 | O | H | H | H | $CH_3$ | H | G-23 |
| I.1-77 | O | H | $CH_3$ | H | H | H | G-23 |
| I.1-78 | O | H | Br | H | Br | H | G-23 |
| I.1-79 | O | H | H | H | H | H | G-55 |
| I.1-80 | O | H | H | H | H | H | G-74 |
| I.1-81 | O | H | H | Cl | H | H | G-4 |
| I.1-82 | O | H | H | Cl | H | H | G-43 |
| I.1-83 | O | H | H | Cl | H | H | G-55 |
| I.1-84 | O | H | H | Cl | H | H | G-74 |
| I.1-85 | O | H | $CH_3$ | H | H | H | G-48 |
| I.1-86 | O | H | $CH_3$ | H | H | H | G-4 |
| I.1-87 | O | H | $CH_3$ | H | H | H | G-43 |
| I.1-88 | O | H | $CH_3$ | H | H | H | G-55 |
| I.1-89 | O | H | $CH_3$ | H | H | H | G-74 |
| I.1-90 | O | H | F | H | H | H | G-48 |
| I.1-91 | O | H | Cl | H | H | H | G-4 |
| I.1-92 | O | H | Cl | H | H | H | G-45 |
| I.1-93 | O | H | F | H | H | H | G-44 |
| I.1-94 | O | H | F | H | H | H | G-45 |
| I.1-95 | O | H | F | H | H | H | G-2 |
| I.1-96 | O | H | F | H | H | H | G-43 |
| I.1-97 | O | H | F | H | H | H | G-55 |
| I.1-98 | O | H | F | H | H | H | G-74 |
| I.1-99 | O | H | Cl | H | H | H | G-52 |
| I.1-100 | O | H | Cl | H | H | H | G-43 |
| I.1-101 | O | H | Cl | H | H | H | G-74 |
| I.1-102 | O | H | Cl | H | Br | H | G-1 |
| I.1-103 | O | H | Cl | H | Br | H | G-4 |
| I.1-104 | O | H | Cl | H | Br | H | G-45 |
| I.1-105 | O | H | Cl | H | Br | H | G-2 |
| I.1-106 | O | H | Cl | H | Br | H | G-43 |
| I.1-107 | O | H | Cl | H | Br | H | G-55 |
| I.1-108 | O | F | H | H | H | H | G-48 |
| I.1-109 | O | F | H | H | H | H | G-4 |
| I.1-110 | O | F | H | H | H | H | G-43 |

TABLE 1-continued with base structure I.1 and the radical definitions specified hereinafter:

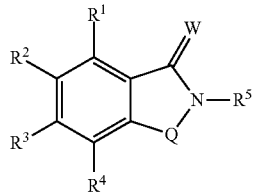

where Q = Q-1 = [structure], where the arrow represents the bond to the N—R⁵ group and with $R^7$ selected from the aforementioned G-1 to G-282 radicals

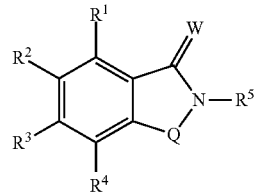

where Q = Q-1 = [structure], where the arrow represents the bond to the N—R⁵ group and with $R^7$ selected from the aforementioned G-1 to G-282 radicals

| No. | W | $R^1$ | $R^2$ | $R^3$ | $R^4$ | $R^5$ | $R^7$ |
|---|---|---|---|---|---|---|---|
| I.1-111 | O | F | H | H | H | H | G-74 |
| I.1-112 | O | H | H | H | CH₃ | H | G-48 |
| I.1-113 | O | F | H | H | H | H | G-45 |
| I.1-114 | O | H | CH₃ | H | H | H | G-91 |
| I.1-115 | O | H | F | H | H | H | G-91 |
| I.1-116 | O | H | Cl | H | H | H | G-91 |
| I.1-117 | O | F | H | H | H | H | G-91 |
| I.1-118 | O | H | H | H | CH₃ | H | G-91 |
| I.1-119 | O | H | F | H | H | H | G-60 |
| I.1-120 | O | H | F | H | H | H | G-57 |
| I.1-121 | O | H | F | H | H | H | G-12 |
| I.1-122 | O | H | Cl | H | H | H | G-60 |
| I.1-123 | O | H | Cl | H | H | H | G-57 |
| I.1-124 | O | F | H | H | H | H | G-60 |
| I.1-125 | O | F | H | H | H | H | G-57 |
| I.1-126 | O | F | H | H | H | H | G-12 |
| I.1-127 | O | H | H | H | CH₃ | H | G-74 |
| I.1-128 | O | H | H | H | CH₃ | H | G-60 |
| I.1-129 | O | H | H | H | CH₃ | H | G-57 |
| I.1-130 | O | H | H | H | H | H | G-60 |
| I.1-131 | O | H | H | H | H | H | G-69 |
| I.1-132 | O | H | H | H | H | H | G-57 |
| I.1-133 | O | H | H | H | H | H | G-12 |
| I.1-134 | O | H | H | Cl | H | H | G-57 |
| I.1-135 | O | H | H | Cl | H | H | G-12 |
| I.1-136 | O | H | CH₃ | H | H | H | G-60 |
| I.1-137 | O | H | CH₃ | H | H | H | G-57 |
| I.1-138 | O | H | H | H | H | H | G-91 |
| I.1-139 | O | H | H | Cl | H | H | G-91 |
| I.1-140 | O | H | Cl | H | H | H | G-95 |
| I.1-141 | O | F | H | H | H | H | G-95 |
| I.1-142 | O | H | Cl | H | H | H | G-59 |
| I.1-143 | O | H | H | Cl | H | H | G-58 |
| I.1-144 | O | H | H | CF₃ | H | H | G-91 |
| I.1-145 | O | H | H | H | CH₃ | H | G-55 |
| I.1-146 | O | H | H | H | OH | H | G-4 |
| I.1-147 | O | H | H | H | OH | H | G-51 |
| I.1-148 | O | H | H | H | OH | H | G-53 |
| I.1-149 | O | H | H | H | OH | H | G-54 |
| I.1-150 | O | H | H | H | OH | H | G-43 |
| I.1-151 | O | H | H | H | OH | H | G-10 |
| I.1-152 | O | H | H | H | OCH₃ | H | G-25 |
| I.1-153 | O | H | H | H | OCH₃ | H | G-4 |
| I.1-154 | O | H | H | H | OCH₃ | H | G-43 |
| I.1-155 | O | H | H | H | OCH₃ | H | G-10 |
| I.1-156 | O | H | H | H | OCH₃ | H | G-54 |
| I.1-157 | O | H | H | H | OCH₃ | H | G-53 |
| I.1-158 | O | H | H | H | OCH₃ | H | G-51 |
| I.1-159 | O | H | H | H | OCH₃ | H | G-9 |
| I.1-160 | O | H | H | H | OCH₃ | H | G-56 |
| I.1-161 | O | H | H | H | OH | H | G-52 |
| I.1-162 | O | H | H | H | OCH₃ | H | G-52 |
| I.1-163 | O | H | H | H | OH | H | G-56 |
| I.1-164 | O | H | H | H | OH | H | G-25 |
| I.1-165 | O | H | Cl | H | CH₃ | H | G-95 |
| I.1-166 | O | H | H | H | CH₃ | H | G-94 |
| I.1-167 | O | H | H | H | CH₃ | H | G-95 |
| I.1-168 | O | H | H | H | Cl | H | G-94 |
| I.1-169 | O | H | H | H | Cl | H | G-95 |
| I.1-170 | O | H | Cl | H | CH₃ | H | G-56 |
| I.1-171 | O | H | H | H | CH₃ | H | G-2 |
| I.1-172 | O | H | H | H | Cl | H | G-55 |
| I.1-173 | O | H | H | Cl | H | H | G-63 |
| I.1-174 | O | F | H | H | H | H | G-63 |
| I.1-175 | O | H | H | H | CH₃ | H | G-63 |
| I.1-176 | O | F | H | H | H | H | G-92 |
| I.1-177 | O | H | H | Cl | H | H | G-92 |
| I.1-178 | O | H | H | H | CH₃ | H | G-92 |
| I.1-179 | O | H | H | Cl | H | H | G-62 |
| I.1-180 | O | H | H | Cl | H | H | G-66 |
| I.1-181 | O | H | H | Cl | H | H | G-65 |
| I.1-182 | O | H | Cl | H | H | H | G-63 |
| I.1-183 | O | H | H | Cl | H | H | G-64 |
| I.1-184 | O | F | H | H | H | H | G-26 |
| I.1-185 | O | F | H | H | H | H | G-65 |
| I.1-186 | O | F | H | H | H | H | G-106 |
| I.1-187 | O | F | H | H | H | H | G-61 |
| I.1-188 | O | F | H | H | H | H | G-66 |
| I.1-189 | O | H | CH₃ | H | H | H | G-26 |
| I.1-190 | O | H | CH₃ | H | H | H | G-63 |
| I.1-191 | O | H | CH₃ | H | H | H | G-28 |
| I.1-192 | O | H | CH₃ | H | H | H | G-101 |
| I.1-193 | O | H | CH₃ | H | H | H | G-109 |
| I.1-194 | O | H | CH₃ | H | H | H | G-106 |
| I.1-195 | O | H | CH₃ | H | H | H | G-98 |
| I.1-196 | O | H | CH₃ | H | H | H | G-21 |
| I.1-197 | O | H | H | Cl | H | H | G-98 |
| I.1-198 | O | H | Cl | H | H | H | G-98 |
| I.1-199 | O | H | H | H | Cl | H | G-25 |
| I.1-200 | O | H | Cl | H | H | H | G-92 |
| I.1-201 | O | H | H | H | Cl | H | G-27 |
| I.1-202 | O | H | H | H | Cl | H | G-26 |
| I.1-203 | O | H | H | H | Cl | H | G-20 |
| I.1-204 | O | H | H | H | Cl | H | G-10 |
| I.1-205 | O | H | Cl | H | H | H | G-56 |
| I.1-206 | O | H | Cl | H | H | H | G-53 |
| I.1-207 | O | H | H | H | Cl | H | G-101 |
| I.1-208 | O | H | H | H | Cl | H | G-30 |
| I.1-209 | O | H | H | H | Cl | H | G-63 |
| I.1-210 | O | H | H | H | Cl | H | G-2 |
| I.1-211 | O | F | H | H | H | H | G-55 |
| I.1-212 | O | H | Cl | H | H | H | G-4 |
| I.1-213 | O | F | H | H | H | H | G-56 |
| I.1-214 | O | H | H | H | SH | H | G-70 |
| I.1-215 | O | H | H | Cl | H | H | G-61 |
| I.1-216 | O | H | H | F | H | H | G-3 |
| I.1-217 | O | H | H | H | CF₃ | H | G-25 |
| I.1-218 | O | H | H | H | H | H | G-72 |
| I.1-219 | O | H | H | H | H | H | G-8 |
| I.1-220 | O | H | H | H | Cl | H | G-51 |

TABLE 1-continued with base structure I.1 and the radical definitions specified hereinafter:

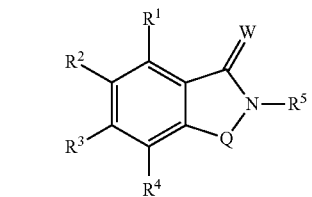

(I.1)

where Q = Q-1 = 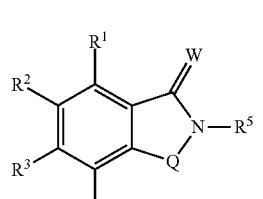 where the arrow represents the bond to the N—$R^5$ group and with $R^7$ selected from the aforementioned G-1 to G-282 radicals

| No. | W | $R^1$ | $R^2$ | $R^3$ | $R^4$ | $R^5$ | $R^7$ |
|---|---|---|---|---|---|---|---|
| I.1-221 | O | H | H | H | Cl | H | G-43 |
| I.1-222 | O | H | H | H | Cl | H | G-45 |
| I.1-223 | O | H | H | H | H | H | G-53 |
| I.1-224 | O | H | H | H | H | H | G-54 |
| I.1-225 | O | H | H | H | Cl | H | G-53 |
| I.1-226 | O | H | H | H | Cl | H | G-4 |
| I.1-227 | O | H | H | H | Cl | H | G-72 |
| I.1-228 | O | H | H | $CF_3$ | H | H | G-8 |
| I.1-229 | O | H | H | $CF_3$ | H | H | G-51 |
| I.1-230 | O | H | H | $CF_3$ | H | H | G-43 |
| I.1-231 | O | H | H | $CF_3$ | H | H | G-45 |
| I.1-232 | O | H | H | $CF_3$ | H | H | G-53 |
| I.1-233 | O | H | H | $CF_3$ | H | H | G-54 |
| I.1-234 | O | H | H | $CF_3$ | H | H | G-4 |
| I.1-235 | O | H | H | $CF_3$ | H | H | G-9 |
| I.1-236 | O | H | H | $CF_3$ | H | H | G-10 |
| I.1-237 | O | H | H | $CF_3$ | H | H | G-73 |
| I.1-238 | O | H | H | $CF_3$ | H | H | G-19 |
| I.1-239 | O | H | H | $CF_3$ | H | H | G-12 |
| I.1-240 | O | H | H | $CF_3$ | H | H | G-72 |
| I.1-241 | O | H | H | $CF_3$ | H | H | G-56 |
| I.1-242 | O | H | H | H | H | H | G-75 |
| I.1-243 | O | H | H | H | H | H | G-76 |
| I.1-244 | O | H | H | H | H | H | G-77 |
| I.1-245 | O | H | H | H | H | H | G-78 |
| I.1-246 | O | H | H | F | H | H | G-52 |
| I.1-247 | O | H | H | F | H | H | G-51 |
| I.1-248 | O | H | H | F | H | H | G-54 |
| I.1-249 | O | H | H | F | H | H | G-4 |
| I.1-250 | O | H | H | F | H | H | G-19 |
| I.1-251 | O | H | H | F | H | H | G-37 |
| I.1-252 | O | H | H | F | H | H | G-53 |
| I.1-253 | O | H | H | F | H | H | G-72 |
| I.1-254 | O | H | H | F | H | H | G-137 |
| I.1-255 | O | H | F | F | H | H | G-51 |
| I.1-256 | O | H | F | F | H | H | G-54 |
| I.1-257 | O | H | F | F | H | H | G-67 |
| I.1-258 | O | H | F | F | H | H | G-32 |
| I.1-259 | O | H | F | F | H | H | G-25 |
| I.1-260 | O | H | F | F | H | H | G-19 |
| I.1-261 | O | H | F | F | H | H | G-37 |
| I.1-262 | O | H | F | F | H | H | G-72 |
| I.1-263 | O | H | Cl | H | H | H | G-51 |
| I.1-264 | O | H | Cl | H | H | H | G-54 |
| I.1-265 | O | H | Cl | H | H | H | G-67 |
| I.1-266 | O | H | Cl | H | H | H | G-3 |
| I.1-267 | O | H | Cl | H | H | H | G-32 |
| I.1-268 | O | H | Cl | H | H | H | G-9 |
| I.1-269 | O | H | Cl | H | H | H | G-37 |
| I.1-270 | O | H | Cl | H | H | H | G-72 |
| I.1-271 | O | H | Cl | H | H | H | G-137 |
| I.1-272 | O | H | H | Cl | H | H | G-51 |
| I.1-273 | O | H | H | Cl | H | H | G-37 |
| I.1-274 | O | H | H | Cl | H | H | G-53 |
| I.1-275 | O | H | $CH_3$ | H | H | H | G-32 |
| I.1-276 | O | H | $CH_3$ | H | H | H | G-72 |
| I.1-277 | O | H | $CH_3$ | H | H | H | G-137 |
| I.1-278 | O | H | F | H | H | H | G-52 |
| I.1-279 | O | H | F | H | H | H | G-51 |
| I.1-280 | O | H | F | H | H | H | G-54 |
| I.1-281 | O | H | F | H | H | H | G-67 |
| I.1-282 | O | H | F | H | H | H | G-3 |
| I.1-283 | O | H | F | H | H | H | G-32 |
| I.1-284 | O | H | F | H | H | H | G-9 |
| I.1-285 | O | H | F | H | H | H | G-56 |
| I.1-286 | O | H | F | H | H | H | G-53 |
| I.1-287 | O | H | F | H | H | H | G-72 |
| I.1-288 | O | H | F | H | H | H | G-137 |
| I.1-289 | O | H | H | F | H | H | G-67 |
| I.1-290 | O | H | H | F | H | H | G-25 |
| I.1-291 | O | H | F | F | H | H | G-52 |
| I.1-292 | O | H | F | F | H | H | G-3 |
| I.1-293 | O | H | F | F | H | H | G-9 |
| I.1-294 | O | H | F | F | H | H | G-53 |
| I.1-295 | O | H | F | F | H | H | G-137 |
| I.1-296 | O | H | H | Cl | H | H | G-52 |
| I.1-297 | O | H | H | Cl | H | H | G-54 |
| I.1-298 | O | H | H | Cl | H | H | G-67 |
| I.1-299 | O | H | H | Cl | H | H | G-3 |
| I.1-300 | O | H | H | Cl | H | H | G-32 |
| I.1-301 | O | H | H | Cl | H | H | G-9 |
| I.1-302 | O | H | H | Cl | H | H | G-56 |
| I.1-303 | O | H | H | Cl | H | H | G-137 |
| I.1-304 | O | H | $CH_3$ | H | H | H | G-52 |
| I.1-305 | O | H | $CH_3$ | H | H | H | G-51 |
| I.1-306 | O | H | $CH_3$ | H | H | H | G-54 |
| I.1-307 | O | H | $CH_3$ | H | H | H | G-67 |
| I.1-308 | O | H | $CH_3$ | H | H | H | G-3 |
| I.1-309 | O | H | $CH_3$ | H | H | H | G-9 |
| I.1-310 | O | H | $CH_3$ | H | H | H | G-56 |
| I.1-311 | O | H | $CH_3$ | H | H | H | G-53 |
| I.1-312 | O | H | H | $CH_3$ | H | H | G-52 |
| I.1-313 | O | H | H | $CH_3$ | H | H | G-51 |
| I.1-314 | O | H | H | $CH_3$ | H | H | G-54 |
| I.1-315 | O | H | H | $CH_3$ | H | H | G-67 |
| I.1-316 | O | H | H | $CH_3$ | H | H | G-3 |
| I.1-317 | O | H | H | $CH_3$ | H | H | G-32 |
| I.1-318 | O | H | H | $CH_3$ | H | H | G-9 |
| I.1-319 | O | H | H | $CH_3$ | H | H | G-25 |
| I.1-320 | O | H | H | $CH_3$ | H | H | G-19 |
| I.1-321 | O | H | H | $CH_3$ | H | H | G-37 |
| I.1-322 | O | H | H | $CH_3$ | H | H | G-56 |
| I.1-323 | O | H | H | $CH_3$ | H | H | G-53 |
| I.1-324 | O | H | H | $CH_3$ | H | H | G-72 |
| I.1-325 | O | H | H | $CH_3$ | H | H | G-137 |
| I.1-326 | O | H | H | H | $CH_3$ | H | G-52 |
| I.1-327 | O | H | H | H | $CH_3$ | H | G-89 |
| I.1-328 | O | H | H | H | $CH_3$ | H | G-90 |
| I.1-329 | O | H | H | H | $CH_3$ | H | G-44 |
| I.1-330 | O | H | H | H | $CH_3$ | H | G-71 |

TABLE 1-continued with base structure I.1 and the radical definitions specified hereinafter:

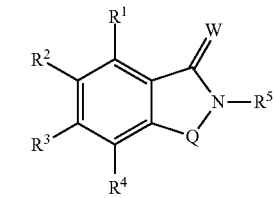

(I.1)

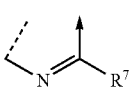

where Q = Q-1 = , where the arrow represents the bond to the N—R⁵ group and with R⁷ selected from the aforementioned G-1 to G-282 radicals

| No. | W | R¹ | R² | R³ | R⁴ | R⁵ | R⁷ |
|---|---|---|---|---|---|---|---|
| I.1-331 | O | H | H | H | CH₃ | H | G-137 |
| I.1-332 | O | H | H | H | CH₃ | H | G-135 |
| I.1-333 | O | H | H | H | CH₃ | H | G-136 |
| I.1-334 | O | H | H | H | CH₃ | H | G-119 |
| I.1-335 | O | H | H | H | CH₃ | H | G-134 |
| I.1-336 | O | H | H | H | CH₃ | H | G-126 |
| I.1-337 | O | H | H | H | CH₃ | H | G-124 |
| I.1-338 | O | H | H | H | CH₃ | H | G-127 |
| I.1-339 | O | H | H | H | CH₃ | H | G-125 |
| I.1-340 | O | H | H | F | H | H | G-32 |
| I.1-341 | O | H | H | F | H | H | G-9 |
| I.1-342 | O | H | H | F | H | H | G-56 |
| I.1-343 | O | H | H | H | CH₃ | H | G-182 |
| I.1-344 | O | H | H | H | CH₃ | H | G-133 |
| I.1-345 | O | H | H | H | CH₃ | H | G-88 |
| I.1-346 | O | H | H | H | CH₃ | H | G-117 |
| I.1-347 | O | H | H | H | CH₃ | H | G-115 |
| I.1-348 | O | H | H | H | CH₃ | H | G-116 |
| I.1-349 | O | H | H | H | CH₃ | H | G-122 |
| I.1-350 | O | H | H | H | CH₃ | H | G-121 |
| I.1-351 | O | H | H | H | CH₃ | H | G-123 |
| I.1-352 | O | H | H | H | CH₃ | H | G-107 |
| I.1-353 | O | H | H | H | CH₃ | H | G-108 |
| I.1-354 | O | H | H | H | CH₃ | H | G-30 |
| I.1-355 | O | H | H | H | CH₃ | H | G-110 |
| I.1-356 | O | H | H | H | CH₃ | H | G-24 |
| I.1-357 | O | H | H | H | CH₃ | H | G-183 |
| I.1-358 | O | H | H | H | CH₃ | H | G-184 |
| I.1-359 | O | H | H | H | H | H | G-144 |
| I.1-360 | O | H | H | H | H | H | G-114 |
| I.1-361 | O | H | H | Cl | H | H | G-113 |
| I.1-362 | O | H | H | H | H | H | G-143 |
| I.1-363 | O | H | H | H | H | H | G-139 |
| I.1-364 | O | H | H | H | H | H | G-142 |
| I.1-365 | O | H | H | H | H | H | G-185 |
| I.1-366 | O | H | H | H | H | H | G-186 |
| I.1-367 | O | H | H | H | H | H | G-187 |
| I.1-368 | O | H | H | H | H | H | G-188 |
| I.1-369 | O | H | H | H | H | H | G-189 |
| I.1-370 | O | H | H | H | H | H | G-190 |
| I.1-371 | O | H | H | H | H | H | G-191 |
| I.1-372 | O | H | H | H | CH₃ | H | G-43 |
| I.1-373 | O | H | H | H | CH₃ | H | G-45 |
| I.1-374 | O | H | H | H | CH₃ | H | G-53 |
| I.1-375 | O | H | H | H | CH₃ | H | G-54 |
| I.1-376 | O | H | H | H | CH₃ | H | G-4 |
| I.1-377 | O | H | H | H | CH₃ | H | G-9 |
| I.1-378 | O | H | H | H | CH₃ | H | G-10 |
| I.1-379 | O | H | H | H | CH₃ | H | G-12 |
| I.1-380 | O | H | H | H | CH₃ | H | G-72 |
| I.1-381 | O | H | H | H | CH₃ | H | G-56 |
| I.1-382 | O | H | H | H | OCH₃ | H | G-18 |
| I.1-383 | O | H | H | H | H | H | G-148 |
| I.1-384 | O | H | H | H | H | H | G-146 |
| I.1-385 | O | H | H | H | H | H | G-147 |
| I.1-386 | O | H | H | H | H | H | G-145 |
| I.1-387 | O | H | H | H | H | H | G-149 |
| I.1-388 | O | H | H | H | H | − (negative charge) | G-217 |
| I.1-389 | O | F | H | H | H | − (negative charge) | G-218 |
| I.1-390 | O | H | H | H | CH₃ | H | G-149 |
| I.1-391 | O | H | H | H | CH₃ | − (negative charge) | G-217 |
| I.1-392 | O | H | H | H | H | − (negative charge) | G-218 |
| I.1-393 | O | H | H | H | H | − (negative charge) | G-219 |
| I.1-394 | O | H | H | H | CH₃ | H | G-147 |
| I.1-395 | O | F | H | H | H | − (negative charge) | G-219 |
| I.1-396 | O | H | H | H | CH₃ | H | G-13 |
| I.1-397 | O | H | OCH₃ | OCH₃ | H | H | G-9 |
| I.1-398 | O | H | OCH₃ | OCH₃ | H | H | G-13 |
| I.1-399 | O | H | OCH₃ | OCH₃ | H | H | G-25 |
| I.1-400 | O | H | OCH₃ | OCH₃ | H | H | G-55 |
| I.1-401 | O | H | OCH₃ | OCH₃ | H | H | G-80 |
| I.1-402 | O | F | H | H | H | − (negative charge) | G-220 |
| I.1-403 | O | H | OCH₃ | OCH₃ | H | H | G-86 |
| I.1-404 | O | H | H | H | OCH₃ | H | G-86 |
| I.1-405 | O | H | H | H | CH₃ | H | G-81 |
| I.1-406 | O | H | H | H | CH₃ | − | G-219 |
| I.1-407 | O | H | H | H | CH₃ | − (negative charge) | G-218 |
| I.1-408 | O | H | H | H | CH₃ | H | G-85 |
| I.1-409 | O | H | OCH₃ | OCH₃ | H | H | G-85 |
| I.1-410 | O | H | OCH₃ | OCH₃ | H | H | G-102 |
| I.1-411 | O | F | H | H | H | H | G-150 |
| I.1-412 | O | Cl | H | H | H | H | G-55 |
| I.1-413 | O | H | H | H | OCH₃ | H | G-102 |
| I.1-414 | O | H | H | H | CH₃ | H | G-102 |
| I.1-415 | O | H | OCH₃ | OCH₃ | H | H | G-74 |
| I.1-416 | O | H | H | H | CH₃ | H | G-87 |
| I.1-417 | O | H | H | H | OCH₃ | H | G-101 |
| I.1-418 | O | H | H | H | OCH₃ | H | G-93 |
| I.1-419 | O | H | H | H | OCH₃ | H | G-87 |
| I.1-420 | O | H | H | H | OCH₃ | H | G-55 |
| I.1-421 | O | H | OCH₃ | OCH₃ | H | H | G-93 |
| I.1-422 | O | H | H | H | OH | H | G-9 |
| I.1-423 | O | H | OCH₃ | OCH₃ | H | H | G-128 |
| I.1-424 | O | H | OCH₃ | OCH₃ | H | H | G-101 |
| I.1-425 | O | H | H | H | CH₃ | H | G-87 |
| I.1-426 | O | H | OCH₃ | OCH₃ | H | H | G-97 |
| I.1-427 | O | H | OCH₃ | OCH₃ | H | H | G-93 |
| I.1-428 | O | H | H | H | CH₃ | H | G-128 |
| I.1-429 | O | H | OCH₃ | OCH₃ | H | H | G-130 |
| I.1-430 | O | H | H | H | CH₃ | H | G-129 |
| I.1-431 | O | H | OCH₃ | OCH₃ | H | H | G-120 |

TABLE 1-continued with base structure I.1 and the radical definitions specified hereinafter:

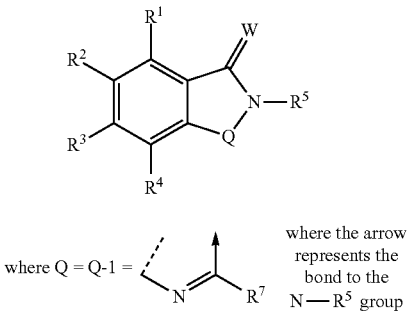

where $Q = Q-1 =$ 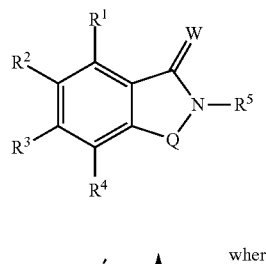 where the arrow represents the bond to the $N-R^5$ group and with $R^7$ selected from the aforementioned G-1 to G-282 radicals

| No. | W | $R^1$ | $R^2$ | $R^3$ | $R^4$ | $R^5$ | $R^7$ |
|---|---|---|---|---|---|---|---|
| I.1-432 | O | H | OCH₃ | OCH₃ | H | H | G-96 |
| I.1-433 | O | H | H | H | OCH₃ | H | G-129 |
| I.1-434 | O | H | OCH₃ | OCH₃ | H | H | G-118 |
| I.1-435 | O | H | OCH₃ | OCH₃ | H | H | G-99 |
| I.1-436 | O | H | H | H | OCH₃ | H | G-127 |
| I.1-437 | O | H | OCH₃ | OCH₃ | H | H | G-100 |
| I.1-438 | O | H | OCH₃ | OCH₃ | H | H | G-8 |
| I.1-439 | O | H | H | H | CH₃ | H | G-131 |
| I.1-440 | O | H | OCH₃ | OCH₃ | H | H | G-35 |
| I.1-441 | O | H | CH₃ | H | H | H | G-102 |
| I.1-442 | O | F | H | H | H | H | G-102 |
| I.1-443 | O | H | H | H | NO₂ | H | G-9 |
| I.1-444 | O | H | H | H | NO₂ | H | G-13 |
| I.1-445 | O | Cl | H | H | H | H | G-102 |
| I.1-446 | O | F | H | H | H | H | G-13 |
| I.1-447 | O | H | CH₃ | H | H | H | G-93 |
| I.1-448 | O | F | H | H | H | H | G-93 |
| I.1-449 | O | Cl | H | H | H | H | G-13 |
| I.1-450 | O | H | CH₃ | H | H | H | G-35 |
| I.1-451 | O | Cl | H | H | H | H | G-56 |
| I.1-452 | O | H | CH₃ | H | H | H | G-55 |
| I.1-453 | O | F | H | H | H | H | G-56 |
| I.1-454 | O | H | H | H | NO₂ | H | G-12 |
| I.1-455 | O | H | CH₃ | H | H | H | G-101 |
| I.1-456 | O | H | CH₃ | H | H | H | G-56 |
| I.1-457 | O | Cl | H | H | H | H | G-85 |
| I.1-458 | O | H | CH₃ | H | H | H | G-85 |
| I.1-459 | O | F | H | H | H | H | G-85 |
| I.1-460 | O | Cl | H | H | H | H | G-128 |
| I.1-461 | O | H | CH₃ | H | H | H | G-128 |
| I.1-462 | O | F | H | H | H | H | G-128 |
| I.1-463 | O | H | CH₃ | H | H | H | G-120 |
| I.1-464 | O | H | CH₃ | H | H | H | G-221 |
| I.1-465 | O | H | CH₃ | H | H | H | G-128 |
| I.1-466 | O | H | H | H | Cl | H | G-85 |
| I.1-467 | O | F | H | H | H | H | G-101 |
| I.1-468 | O | H | CH₃ | H | H | H | G-97 |
| I.1-469 | O | F | H | H | H | H | G-97 |
| I.1-470 | O | Cl | H | H | H | H | G-93 |
| I.1-471 | O | H | H | H | OCH₃ | H | G-80 |
| I.1-472 | O | H | H | H | OCH₃ | H | G-37 |
| I.1-473 | O | H | H | H | OCH₃ | H | G-35 |
| I.1-474 | O | H | H | H | OCH₃ | H | G-19 |
| I.1-475 | O | H | H | H | OCH₃ | H | G-83 |
| I.1-476 | O | H | H | H | OCH₃ | H | G-18 |
| I.1-477 | O | H | H | H | OCH₃ | H | G-13 |
| I.1-478 | O | H | H | H | OCH₃ | H | G-96 |
| I.1-479 | O | H | H | H | OCH₃ | H | G-85 |
| I.1-480 | O | H | H | H | OCH₃ | H | G-99 |
| I.1-481 | O | H | H | H | OCH₃ | H | G-100 |
| I.1-482 | O | H | H | H | OCH₃ | H | G-132 |
| I.1-483 | O | H | H | H | OCH₃ | H | G-103 |
| I.1-484 | O | H | H | H | OCH₃ | H | G-138 |
| I.1-485 | O | H | H | H | OCH₃ | H | G-82 |
| I.1-486 | O | H | H | H | OCH₃ | H | G-84 |
| I.1-487 | O | H | H | H | CH₃ | H | G-37 |
| I.1-488 | O | H | H | H | CH₃ | H | G-80 |
| I.1-489 | O | H | H | H | CH₃ | H | G-18 |
| I.1-490 | O | H | H | H | CH₃ | H | G-83 |
| I.1-491 | O | H | H | H | OCH₃ | H | G-111 |
| I.1-492 | O | H | H | H | OCH₃ | H | G-81 |
| I.1-493 | O | H | H | H | OCH₃ | H | G-74 |
| I.1-494 | O | H | H | H | CH₃ | H | G-96 |
| I.1-495 | O | H | H | H | CH₃ | H | G-86 |
| I.1-496 | O | H | H | H | CH₃ | H | G-82 |
| I.1-497 | O | H | H | H | CH₃ | H | G-93 |
| I.1-498 | O | H | H | H | CH₃ | H | G-97 |
| I.1-499 | O | H | H | H | CH₃ | H | G-101 |
| I.1-500 | O | H | H | H | CH₃ | H | G-132 |
| I.1-501 | O | H | H | H | CH₃ | H | G-100 |
| I.1-502 | O | H | H | H | CH₃ | H | G-103 |
| I.1-503 | O | H | H | H | CH₃ | H | G-138 |
| I.1-504 | O | H | H | H | CH₃ | H | G-35 |
| I.1-505 | O | H | H | H | CH₃ | H | G-84 |
| I.1-506 | O | H | H | H | CH₃ | H | G-126 |
| I.1-507 | O | H | H | H | CH₃ | H | G-211 |
| I.1-508 | O | H | H | H | OCH₃ | G-213 | G-13 |
| I.1-509 | O | H | H | H | OCH₃ | G-215 | G-37 |
| I.1-510 | O | F | H | H | H | H | G-211 |
| I.1-511 | O | Cl | H | H | H | H | G-211 |
| I.1-512 | O | H | H | H | OCH₃ | G-215 | G-80 |
| I.1-513 | O | H | H | H | OCH₃ | G-213 | G-37 |
| I.1-514 | O | H | H | H | OCH₃ | G-213 | G-19 |
| I.1-515 | O | H | H | H | OCH₃ | G-213 | G-55 |
| I.1-516 | O | H | OCH₃ | OCH₃ | H | H | G-211 |
| I.1-517 | O | H | H | H | CH₃ | H | G-241 |
| I.1-518 | O | H | H | H | CH₃ | H | G-242 |
| I.1-519 | O | H | H | Cl | H | H | G-60 |

TABLE 2 with base structure I.2 and the radical definitions specified hereinafter:

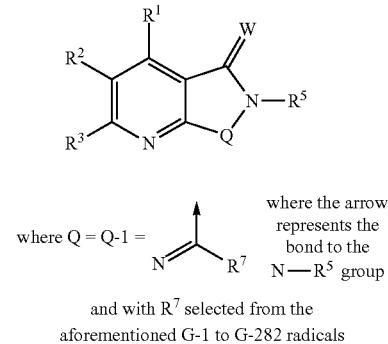

(I.2)

where Q = Q-1 = (structure with N=C-R⁷, where the arrow represents the bond to the N—R⁵ group)

and with R⁷ selected from the aforementioned G-1 to G-282 radicals

| No. | W | R¹ | R² | R³ | R⁵ | R⁷ |
|---|---|---|---|---|---|---|
| I.2-1 | O | H | H | H | H | G-44 |
| I.2-2 | O | H | H | H | H | G-1 |
| I.2-3 | O | H | H | CF₃ | H | G-1 |
| I.2-4 | O | H | Br | H | H | G-1 |
| I.2-5 | O | H | H | CF₃ | H | G-51 |
| I.2-6 | O | H | H | CF₃ | H | G-44 |
| I.2-7 | O | H | H | CF₃ | H | G-3 |
| I.2-8 | O | H | H | CF₃ | H | G-52 |
| I.2-9 | O | H | Br | H | H | G-19 |
| I.2-10 | O | H | H | CH₃ | H | G-1 |
| I.2-11 | O | H | H | H | H | G-43 |
| I.2-12 | O | H | H | H | H | G-181 |
| I.2-13 | O | H | H | H | H | G-79 |
| I.2-14 | O | H | H | H | H | G-2 |
| I.2-15 | O | H | H | H | H | G-199 |
| I.2-16 | O | H | H | H | H | G-3 |
| I.2-17 | O | H | H | H | H | G-4 |
| I.2-18 | O | H | H | H | H | G-5 |
| I.2-19 | O | H | H | H | H | G-6 |
| I.2-20 | O | H | H | H | H | G-51 |
| I.2-21 | O | H | H | H | H | G-25 |
| I.2-22 | O | H | H | H | H | G-52 |
| I.2-23 | O | H | H | H | H | G-45 |
| I.2-24 | O | H | H | H | H | G-53 |
| I.2-25 | O | H | H | H | H | G-54 |
| I.2-26 | O | H | H | H | H | G-19 |
| I.2-27 | O | H | H | H | H | G-57 |
| I.2-28 | O | H | H | H | H | G-60 |
| I.2-29 | O | H | H | CF₃ | H | G-19 |
| I.2-30 | O | H | H | CF₃ | H | G-57 |
| I.2-31 | O | H | H | CF₃ | H | G-60 |
| I.2-32 | O | H | H | CF₃ | H | G-53 |
| I.2-33 | O | H | H | CF₃ | H | G-54 |
| I.2-34 | O | H | H | CF₃ | H | G-43 |
| I.2-35 | O | H | H | CF₃ | H | G-45 |
| I.2-36 | O | H | H | CF₃ | H | G-25 |
| I.2-37 | O | H | H | CF₃ | H | G-20 |
| I.2-38 | O | H | H | CF₃ | H | G-4 |
| I.2-39 | O | H | H | CF₃ | H | G-5 |
| I.2-40 | O | H | H | CF₃ | H | G-6 |

TABLE 3 with base structure I.3 and the radical definitions specified hereinafter:

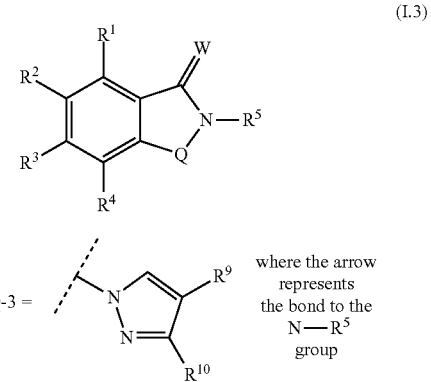

(I.3)

where Q = Q-3 = (pyrazole structure with R⁹ and R¹⁰, where the arrow represents the bond to the N—R⁵ group)

and with R⁹ and R¹⁰ selected from the aforementioned G-1 to G-282 radicals for all cases in which R⁹ and R¹⁰ are not H

| No. | W | R¹ | R² | R³ | R⁴ | R⁵ | R⁹ | R¹⁰ |
|---|---|---|---|---|---|---|---|---|
| I.3-1 | O | H | H | H | H | H | G-73 | G-1 |
| I.3-2 | O | H | F | H | H | H | G-73 | G-1 |
| I.3-3 | O | H | H | Cl | H | H | G-73 | G-1 |
| I.3-4 | O | H | H | Cl | H | H | H | G-1 |
| I.3-5 | O | H | F | H | H | H | G-8 | G-1 |
| I.3-6 | O | H | H | H | H | H | G-8 | G-1 |
| I.3-7 | O | H | Cl | H | H | H | G-8 | G-1 |
| I.3-8 | O | H | H | H | H | H | G-192 | G-1 |
| I.3-9 | O | H | H | Cl | H | H | G-192 | G-1 |
| I.3-10 | O | H | Cl | H | H | H | G-192 | G-1 |
| I.3-11 | O | H | H | Cl | H | H | G-8 | G-1 |
| I.3-12 | O | H | H | H | H | H | G-80 | G-195 |
| I.3-13 | O | H | H | H | H | H | G-198 | G-1 |
| I.3-14 | O | H | F | H | H | H | G-9 | G-195 |
| I.3-15 | O | H | F | H | H | H | G-37 | G-195 |
| I.3-16 | O | H | H | H | H | H | G-193 | G-164 |
| I.3-17 | O | H | H | H | H | H | G-9 | G-195 |
| I.3-18 | O | H | Cl | H | H | H | G-9 | G-195 |
| I.3-19 | O | H | Cl | H | H | H | G-74 | G-1 |
| I.3-20 | O | H | H | H | H | H | G-37 | G-195 |
| I.3-21 | O | H | Cl | H | H | H | G-37 | G-195 |
| I.3-22 | O | H | F | H | H | H | G-74 | G-1 |
| I.3-23 | O | H | H | H | H | H | G-74 | G-1 |
| I.3-24 | O | H | F | H | H | H | G-80 | G-195 |
| I.3-25 | O | H | Cl | H | H | H | H | G-1 |
| I.3-26 | O | H | F | H | H | H | H | G-1 |
| I.3-27 | O | H | H | Cl | H | H | G-74 | G-1 |
| I.3-28 | O | H | Cl | H | H | H | G-80 | G-195 |
| I.3-29 | O | H | Cl | H | H | H | G-73 | G-1 |
| I.3-30 | O | H | H | H | H | H | G-196 | H |
| I.3-31 | O | H | H | H | H | H | G-200 | H |
| I.3-32 | O | H | H | H | H | H | G-198 | G-201 |
| I.3-33 | O | H | H | H | H | H | G-198 | H |
| I.3-34 | O | H | H | H | H | H | G-202 | H |
| I.3-35 | O | H | H | H | H | H | G-203 | H |
| I.3-36 | O | H | H | H | H | H | G-204 | H |
| I.3-37 | O | H | H | H | H | H | G-205 | H |
| I.3-38 | O | H | H | H | H | H | G-206 | H |
| I.3-39 | O | H | H | H | H | H | G-207 | H |
| I.3-40 | O | H | H | H | H | H | G-208 | H |
| I.3-41 | S | H | F | H | H | H | G-73 | G-1 |
| I.3-42 | O | H | F | H | H | H | G-202 | H |
| I.3-43 | O | H | F | H | H | H | G-222 | H |
| I.3-44 | O | H | H | H | H | H | G-210 | H |
| I.3-45 | O | H | H | H | H | H | G-222 | H |
| I.3-46 | O | H | Cl | H | H | H | G-202 | H |
| I.3-47 | O | H | Cl | H | H | H | G-222 | H |
| I.3-48 | O | H | F | H | H | H | G-210 | H |

TABLE 4 with base structure I.4 and the radical definitions specified hereinafter:

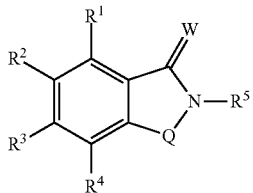

(I.4)

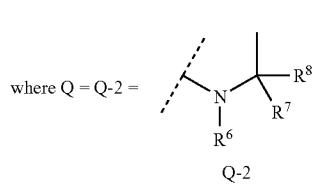

where Q = Q-2 = where the arrow represents the bond to the N—R⁵ group with $R^8$ = H and with $R^7$ selected from the aforementioned G-1 to G-282 radicals for all cases in which $R^6$ and/or $R^7$ are not H

| No. | W | $R^1$ | $R^2$ | $R^3$ | $R^4$ | $R^5$ | $R^6$ | $R^7$ |
|---|---|---|---|---|---|---|---|---|
| I.4-1 | O | H | H | H | CH₃ | H | H | G-9 |
| I.4-2 | O | H | H | H | CH₃ | H | H | G-13 |
| I.4-3 | O | H | H | H | H | H | G-1 | G-9 |
| I.4-4 | O | H | H | H | H | H | G-1 | G-13 |
| I.4-5 | O | H | H | H | OCH₃ | H | H | G-9 |
| I.4-6 | O | H | H | H | OCH₃ | H | H | G-13 |
| I.4-7 | O | H | H | H | CH₃ | H | H | G-19 |
| I.4-8 | O | H | H | H | H | H | G-1 | G-19 |
| I.4-9 | O | H | H | H | CH₃ | H | H | G-55 |
| I.4-10 | O | H | H | H | H | H | G-1 | G-55 |
| I.4-11 | O | H | OCH₃ | OCH₃ | H | H | H | G-19 |
| I.4-12 | O | H | H | H | OCH₃ | H | H | G-19 |
| I.4-13 | O | H | H | H | CH₃ | H | H | G-25 |
| I.4-14 | O | H | H | H | H | H | G-1 | G-25 |
| I.4-15 | O | H | H | H | OCH₃ | H | H | G-25 |
| I.4-16 | O | H | H | H | OCH₃ | H | H | G-55 |
| I.4-17 | O | H | H | H | CH₃ | H | H | G-37 |
| I.4-18 | O | H | H | H | H | H | G-1 | G-37 |
| I.4-19 | O | H | OCH₃ | OCH₃ | H | H | H | G-37 |
| I.4-20 | O | H | H | H | OCH₃ | H | H | G-37 |
| I.4-21 | O | H | H | H | CH₃ | H | H | G-18 |
| I.4-22 | O | H | H | H | H | H | G-1 | G-18 |
| I.4-23 | O | H | OCH₃ | OCH₃ | H | H | G-237 | G-18 |
| I.4-24 | O | H | H | H | OCH₃ | H | H | G-18 |
| I.4-25 | O | H | H | H | CH₃ | H | H | G-74 |
| I.4-26 | O | H | H | H | H | H | G-1 | G-74 |
| I.4-27 | O | H | OCH₃ | OCH₃ | H | H | H | G-74 |
| I.4-28 | O | H | H | H | OCH₃ | H | H | G-74 |
| I.4-29 | O | H | H | H | OCH₃ | H | H | G-80 |
| I.4-30 | O | H | H | H | CH₃ | H | H | G-80 |
| I.4-31 | O | H | H | H | H | H | G-1 | G-80 |
| I.4-32 | O | H | H | H | CH₃ | H | H | G-82 |
| I.4-33 | O | H | H | H | H | H | G-1 | G-82 |
| I.4-34 | O | H | OCH₃ | OCH₃ | H | H | H | G-82 |
| I.4-35 | O | H | H | H | OCH₃ | H | H | G-82 |
| I.4-36 | O | H | H | H | CH₃ | H | H | G-83 |
| I.4-37 | O | H | H | H | H | H | G-1 | G-83 |
| I.4-38 | O | H | OCH₃ | OCH₃ | H | H | H | G-83 |
| I.4-39 | O | H | H | H | OCH₃ | H | H | G-83 |
| I.4-40 | O | H | H | H | CH₃ | H | H | G-81 |
| I.4-41 | O | H | H | H | H | H | G-1 | G-81 |
| I.4-42 | O | H | OCH₃ | OCH₃ | H | H | H | G-81 |
| I.4-43 | O | H | H | H | OCH₃ | H | H | G-81 |
| I.4-44 | O | H | H | H | CH₃ | H | H | G-86 |
| I.4-45 | O | H | H | H | H | H | G-1 | G-86 |
| I.4-46 | O | H | OCH₃ | OCH₃ | H | H | G-238 | G-83 |
| I.4-47 | O | H | H | H | OCH₃ | H | H | G-85 |
| I.4-48 | O | H | OCH₃ | OCH₃ | H | H | CH₂-G-25 | G-46 |
| I.4-49 | O | H | Cl | H | OCH₃ | H | H | G-37 |

TABLE 4-continued with base structure I.4 and the radical definitions specified hereinafter:

(I.4)

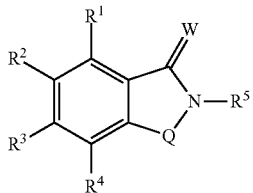

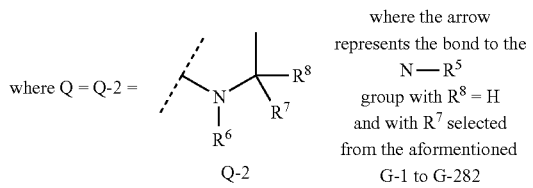

where Q = Q-2 =

Q-2 where the arrow represents the bond to the N—R⁵ group with $R^8$ = H and with $R^7$ selected from the aforementioned G-1 to G-282 radicals for all cases in which $R^6$ and/or $R^7$ are not H

| No. | W | $R^1$ | $R^2$ | $R^3$ | $R^4$ | $R^5$ | $R^6$ | $R^7$ |
|---|---|---|---|---|---|---|---|---|
| I.4-50 | O | H | OCH₃ | OCH₃ | H | H | G-240 | G-25 |
| I.4-51 | O | H | H | H | H | H | H | G-101 |
| I.4-52 | O | H | H | H | H | H | H | G-101 |
| I.4-53 | O | H | OCH₃ | OCH₃ | H | H | H | G-101 |
| I.4-54 | O | H | H | H | OCH₃ | H | H | G-101 |
| I.4-55 | O | H | H | H | CH₃ | H | H | G-102 |
| I.4-56 | O | H | H | H | H | H | G-1 | G-102 |
| I.4-57 | O | H | H | H | OCH₃ | H | H | G-102 |
| I.4-58 | O | H | OCH₃ | OCH₃ | H | H | HCO | G-82 |
| I.4-59 | O | H | OCH₃ | OCH₃ | H | H | HCO | G-25 |
| I.4-60 | O | H | H | H | OCH₃ | H | CH₂-G-102 | G-102 |
| I.4-61 | O | H | OCH₃ | OCH₃ | H | H | CH₂-G-102 | G-102 |
| I.4-62 | O | H | H | H | H | H | G-1 | G-87 |
| I.4-63 | O | H | H | H | H | H | G-1 | G-97 |
| I.4-64 | O | H | OCH₃ | OCH₃ | H | H | H | G-97 |
| I.4-65 | O | H | H | H | OCH₃ | H | H | G-97 |
| I.4-66 | O | H | H | H | H | H | G-1 | G-93 |
| I.4-67 | O | H | OCH₃ | OCH₃ | H | H | H | G-93 |
| I.4-68 | O | H | H | H | H | H | G-1 | G-56 |
| I.4-69 | O | H | H | H | OCH₃ | H | H | G-87 |
| I.4-70 | O | H | OCH₃ | CH₃ | H | H | H | G-56 |
| I.4-71 | O | H | H | H | H | H | H | G-9 |
| I.4-72 | O | H | H | H | OCH₃ | H | H | G-93 |
| I.4-73 | O | H | H | H | CH₃ | H | H | G-93 |
| I.4-74 | O | H | H | H | CH₃ | H | H | G-56 |
| I.4-75 | O | H | H | H | OCH₃ | H | H | G-56 |
| I.4-76 | O | H | H | H | CH₃ | H | H | G-128 |
| I.4-77 | O | H | H | H | H | H | G-1 | G-128 |
| I.4-78 | O | H | OCH₃ | OCH₃ | H | H | H | G-128 |
| I.4-79 | O | H | H | H | H | H | H | G-37 |
| I.4-80 | O | H | OCH₃ | OCH₃ | H | H | H | G-9 |
| I.4-81 | O | H | OCH₃ | OCH₃ | H | H | H | G-13 |
| I.4-82 | O | H | H | H | H | H | H | G-74 |
| I.4-83 | O | H | H | H | H | H | H | G-85 |
| I.4-84 | O | H | H | H | CH₃ | H | H | G-101 |
| I.4-85 | O | H | H | H | H | H | G-1 | G-101 |
| I.4-86 | O | H | H | H | H | H | H | G-87 |
| I.4-87 | O | H | H | H | H | H | H | G-87 |
| I.4-88 | O | H | H | H | H | H | H | G-97 |
| I.4-89 | O | H | H | H | CH₃ | H | H | G-97 |
| I.4-90 | O | H | H | H | H | H | G-1 | G-130 |
| I.4-91 | O | H | H | H | OCH₃ | H | H | G-130 |
| I.4-92 | O | H | H | H | H | H | G-1 | G-129 |
| I.4-93 | O | H | H | H | OCH₃ | H | H | G-129 |
| I.4-94 | O | H | OCH₃ | OCH₃ | H | H | G-239 | G-45 |
| I.4-95 | O | H | H | H | CH₃ | H | H | G-96 |
| I.4-96 | O | H | H | H | H | H | G-1 | G-96 |
| I.4-97 | O | H | H | H | OCH₃ | H | H | G-96 |
| I.4-98 | O | H | H | H | CH₃ | H | H | G-131 |

TABLE 4-continued with base structure I.4 and the radical definitions specified hereinafter:

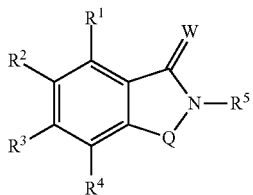

(I.4)

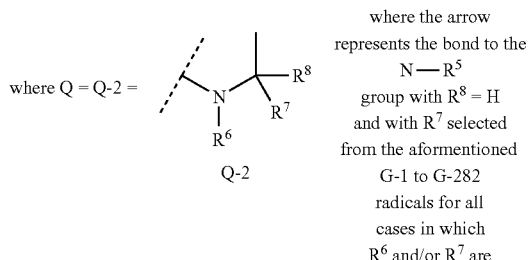

where Q = Q-2 = where the arrow represents the bond to the N—$R^5$ group with $R^8$ = H and with $R^7$ selected from the aforementioned G-1 to G-282 radicals for all cases in which $R^6$ and/or $R^7$ are not H

| No. | W | $R^1$ | $R^2$ | $R^3$ | $R^4$ | $R^5$ | $R^6$ | $R^7$ |
|---|---|---|---|---|---|---|---|---|
| I.4-99  | O | H  | H      | H      | H      | H | G-1   | G-131 |
| I.4-100 | O | H  | H      | H      | $CH_3$ | H | H     | G-132 |
| I.4-101 | O | H  | H      | H      | H      | H | G-1   | G-132 |
| I.4-102 | O | H  | H      | H      | $OCH_3$| H | H     | G-132 |
| I.4-103 | O | H  | H      | H      | $CH_3$ | H | H     | G-100 |
| I.4-104 | O | H  | H      | H      | H      | H | G-1   | G-100 |
| I.4-105 | O | H  | H      | H      | $OCH_3$| H | H     | G-100 |
| I.4-106 | O | H  | $OCH_3$| $OCH_3$| H      | H | H     | G-100 |
| I.4-107 | O | H  | H      | H      | $CH_3$ | H | H     | G-99  |
| I.4-108 | O | H  | H      | H      | H      | H | G-1   | G-99  |
| I.4-109 | O | H  | H      | H      | $OCH_3$| H | H     | G-99  |
| I.4-110 | O | H  | H      | H      | $CH_3$ | H | H     | G-127 |
| I.4-111 | O | H  | H      | H      | H      | H | G-1   | G-127 |
| I.4-112 | O | H  | H      | H      | $OCH_3$| H | H     | G-131 |
| I.4-113 | O | H  | $OCH_3$| $OCH_3$| H      | H | H     | G-132 |
| I.4-114 | O | H  | H      | H      | OH     | H | H     | G-13  |
| I.4-115 | O | H  | H      | H      | $CH_3$ | H | H     | G-103 |
| I.4-116 | O | H  | H      | H      | H      | H | G-1   | G-103 |
| I.4-117 | O | H  | H      | H      | $OCH_3$| H | H     | G-103 |
| I.4-118 | O | H  | $OCH_3$| $OCH_3$| H      | H | H     | G-103 |
| I.4-119 | O | H  | H      | H      | $CH_3$ | H | H     | G-138 |
| I.4-120 | O | H  | H      | H      | H      | H | G-1   | G-138 |
| I.4-121 | O | H  | H      | H      | $OCH_3$| H | H     | G-138 |
| I.4-122 | O | H  | $OCH_3$| $OCH_3$| H      | H | H     | G-138 |
| I.4-123 | O | H  | H      | H      | $CH_3$ | H | H     | G-8   |
| I.4-124 | O | H  | H      | H      | H      | H | G-1   | G-8   |
| I.4-125 | O | H  | H      | H      | $OCH_3$| H | H     | G-8   |
| I.4-126 | O | H  | $OCH_3$| $CH_3$ | H      | H | H     | G-8   |
| I.4-127 | O | H  | H      | H      | $CH_3$ | H | H     | G-35  |
| I.4-128 | O | H  | H      | H      | H      | H | G-1   | G-35  |
| I.4-129 | O | H  | H      | H      | $OCH_3$| H | H     | G-35  |
| I.4-130 | O | H  | $OCH_3$| $OCH_3$| H      | H | H     | G-35  |
| I.4-131 | O | H  | H      | H      | $CH_3$ | H | H     | G-111 |
| I.4-132 | O | H  | H      | H      | H      | H | G-1   | G-111 |
| I.4-133 | O | H  | H      | H      | $OCH_3$| H | H     | G-111 |
| I.4-134 | O | H  | $OCH_3$| $OCH_3$| H      | H | H     | G-111 |
| I.4-135 | O | Cl | H      | H      | H      | H | H     | G-81  |
| I.4-136 | O | H  | $CH_3$ | H      | H      | H | H     | G-81  |
| I.4-137 | O | F  | H      | H      | H      | H | H     | G-81  |
| I.4-138 | O | H  | H      | H      | H      | H | G-223 | G-81  |
| I.4-139 | O | Cl | H      | H      | H      | H | H     | G-25  |
| I.4-140 | O | H  | $CH_3$ | H      | H      | H | H     | G-25  |
| I.4-141 | O | F  | H      | H      | H      | H | H     | G-25  |
| I.4-142 | O | H  | H      | H      | H      | H | G-223 | G-25  |
| I.4-143 | O | Cl | H      | H      | H      | H | H     | G-19  |
| I.4-144 | O | H  | H      | H      | Cl     | H | H     | G-25  |
| I.4-145 | O | H  | H      | H      | Cl     | H | H     | G-19  |
| I.4-146 | O | H  | H      | H      | Cl     | H | H     | G-37  |
| I.4-147 | O | H  | H      | H      | Cl     | H | H     | G-18  |

TABLE 4-continued with base structure I.4 and the radical definitions specified hereinafter:

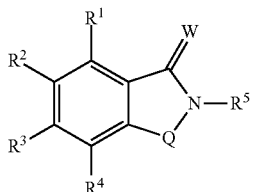
(I.4)

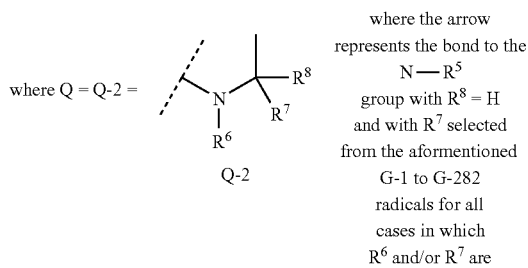

where the arrow represents the bond to the N—R$^5$ group with R$^8$ = H and with R$^7$ selected from the aforementioned G-1 to G-282 radicals for all cases in which R$^6$ and/or R$^7$ are not H

| No. | W | R$^1$ | R$^2$ | R$^3$ | R$^4$ | R$^5$ | R$^6$ | R$^7$ |
|---|---|---|---|---|---|---|---|---|
| I.4-148 | O | Cl | H | H | H | H | H | G-37 |
| I.4-149 | O | H | CH$_3$ | H | H | H | H | G-37 |
| I.4-150 | O | Cl | H | H | H | H | H | G-37 |
| I.4-151 | O | H | H | H | H | H | G-223 | G-37 |
| I.4-152 | O | H | Cl | H | Cl | H | H | G-37 |
| I.4-153 | O | CH$_3$ | H | H | H | H | H | G-37 |
| I.4-154 | O | Cl | H | H | H | H | H | G-18 |
| I.4-155 | O | H | CH$_3$ | H | H | H | H | G-18 |
| I.4-156 | O | F | H | H | H | H | H | G-18 |
| I.4-157 | O | H | CH$_3$ | H | H | H | H | G-19 |
| I.4-158 | O | F | H | H | H | H | H | G-19 |
| I.4-159 | O | H | Cl | H | Cl | H | H | G-19 |
| I.4-160 | O | CH$_3$ | H | H | H | H | H | G-19 |
| I.4-161 | O | CH$_3$ | H | H | H | H | H | G-25 |
| I.4-162 | O | CH$_3$ | H | H | H | H | H | G-18 |
| I.4-163 | O | Cl | H | H | H | H | H | G-9 |
| I.4-164 | O | H | CH$_3$ | H | H | H | H | G-9 |
| I.4-165 | O | F | H | H | H | H | H | G-9 |
| I.4-166 | O | H | H | H | H | H | G-223 | G-9 |
| I.4-167 | O | H | Cl | H | Cl | H | H | G-9 |
| I.4-168 | O | CH$_3$ | H | H | H | H | H | G-9 |
| I.4-169 | O | H | H | H | Cl | H | H | G-9 |
| I.4-170 | O | Cl | H | H | H | H | H | G-80 |
| I.4-171 | O | H | CH$_3$ | H | H | H | H | G-80 |
| I.4-172 | O | F | H | H | H | H | H | G-80 |
| I.4-173 | O | H | Cl | H | Cl | H | H | G-80 |
| I.4-174 | O | CH$_3$ | H | H | H | H | H | G-80 |
| I.4-175 | O | H | H | H | Cl | H | H | G-80 |
| I.4-176 | O | Cl | H | H | H | H | H | G-102 |
| I.4-177 | O | F | H | H | H | H | H | G-102 |
| I.4-178 | O | H | H | H | H | H | G-223 | G-102 |
| I.4-179 | O | H | Cl | H | Cl | H | H | G-102 |
| I.4-180 | O | CH$_3$ | H | H | H | H | H | G-102 |
| I.4-181 | O | H | H | H | Cl | H | H | G-102 |
| I.4-182 | O | Cl | H | H | H | H | H | G-55 |
| I.4-183 | O | H | CH$_3$ | H | H | H | H | G-55 |
| I.4-184 | O | F | H | H | H | H | H | G-55 |
| I.4-185 | O | H | H | H | H | H | G-223 | G-55 |
| I.4-186 | O | H | Cl | H | Cl | H | H | G-55 |
| I.4-187 | O | CH$_3$ | H | H | H | H | H | G-55 |
| I.4-188 | O | H | H | H | Cl | H | H | G-55 |
| I.4-189 | O | Cl | H | H | H | H | H | G-13 |
| I.4-190 | O | F | H | H | H | H | H | G-13 |
| I.4-191 | O | H | CH$_3$ | H | H | H | H | G-13 |
| I.4-192 | O | H | Cl | H | Cl | H | H | G-13 |
| I.4-193 | O | CH$_3$ | H | H | H | H | H | G-13 |
| I.4-194 | O | H | H | H | Cl | H | H | G-13 |
| I.4-195 | O | Cl | H | H | H | H | H | G-35 |
| I.4-196 | O | H | CH$_3$ | H | H | H | H | G-35 |

TABLE 4-continued with base structure I.4 and the radical definitions specified hereinafter:

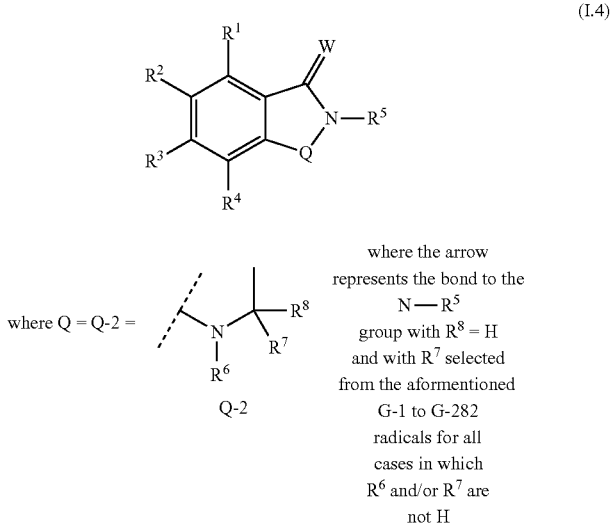

(I.4)

where Q = Q-2 =

Q-2 where the arrow represents the bond to the N—R⁵ group with $R^8$ = H and with $R^7$ selected from the aforementioned G-1 to G-282 radicals for all cases in which $R^6$ and/or $R^7$ are not H

| No. | W | $R^1$ | $R^2$ | $R^3$ | $R^4$ | $R^5$ | $R^6$ | $R^7$ |
|---|---|---|---|---|---|---|---|---|
| I.4-197 | O | F | H | H | H | H | H | G-35 |
| I.4-198 | O | H | Cl | H | Cl | H | H | G-35 |
| I.4-199 | O | CH₃ | H | H | H | H | H | G-35 |
| I.4-200 | O | H | H | H | Cl | H | H | G-35 |
| I.4-201 | O | H | CH₃ | H | H | H | H | G-102 |
| I.4-202 | O | Cl | H | H | H | H | H | G-86 |
| I.4-203 | O | H | CH₃ | H | H | H | H | G-86 |
| I4-204 | O | F | H | H | H | H | H | G-86 |
| I.4-205 | O | H | Cl | H | Cl | H | H | G-86 |
| I.4-206 | O | CH₃ | H | H | H | H | H | G-86 |
| I.4-207 | O | H | H | H | Cl | H | H | G-86 |
| I.4-208 | O | Cl | H | H | H | H | H | G-93 |
| I4-209 | O | H | Cl | H | Cl | H | H | G-93 |
| I.4-210 | O | CH₃ | H | H | H | H | H | G-93 |
| I.4-211 | O | H | H | H | Cl | H | H | G-93 |
| I.4-212 | O | H | H | H | H | H | G-223 | G-86 |
| I.4-213 | O | H | H | H | H | H | G-223 | G-93 |
| I.4-214 | O | Cl | H | H | H | H | H | G-74 |
| I.4-215 | O | H | CH₃ | H | H | H | H | G-74 |
| I.4-216 | O | F | H | H | H | H | H | G-74 |
| I.4-217 | O | H | H | H | H | H | G-223 | G-74 |
| I.4-218 | O | H | Cl | H | Cl | H | H | G-74 |
| I.4-219 | O | CH₃ | H | H | H | H | H | G-74 |
| I.4-220 | O | H | H | H | Cl | H | H | G-74 |
| I.4-221 | O | H | H | H | H | H | G-223 | G-56 |
| I.4-222 | O | H | Cl | H | Cl | H | H | G-56 |
| I.4-223 | O | CH₃ | H | H | H | H | H | G-56 |
| I.4-224 | O | H | H | H | Cl | H | H | G-56 |
| I.4-225 | O | Cl | H | H | H | H | H | G-82 |
| I.4-226 | O | H | CH₃ | H | H | H | H | G-82 |
| I.4-227 | O | F | H | H | H | H | H | G-82 |
| I.4-228 | O | H | H | H | H | H | G-223 | G-82 |
| I.4-229 | O | H | Cl | H | Cl | H | H | G-82 |
| I.4-230 | O | CH₃ | H | H | H | H | H | G-82 |
| I.4-231 | O | H | H | H | Cl | H | H | G-82 |
| I.4-232 | O | Cl | H | H | H | H | H | G-101 |
| I.4-233 | O | H | CH₃ | H | H | H | H | G-101 |
| I.4-234 | O | F | H | H | H | H | H | G-101 |
| I.4-235 | O | H | H | H | H | H | G-223 | G-101 |
| I.4-236 | O | H | Cl | H | Cl | H | H | G-101 |
| I.4-237 | O | CH₃ | H | H | H | H | H | G-101 |
| I.4-238 | O | H | H | H | Cl | H | H | G-101 |
| I.4-239 | O | Cl | H | H | H | H | H | G-132 |
| I.4-240 | O | H | CH₃ | H | H | H | H | G-132 |
| I.4-241 | O | F | H | H | H | H | H | G-132 |
| I.4-242 | O | H | H | H | H | H | G-223 | G-132 |
| I.4-243 | O | H | Cl | H | Cl | H | H | G-132 |
| I.4-244 | O | CH₃ | H | H | H | H | H | G-132 |
| I.4-245 | O | H | H | H | Cl | H | H | G-132 |

TABLE 4-continued with base structure I.4 and the radical definitions specified hereinafter:

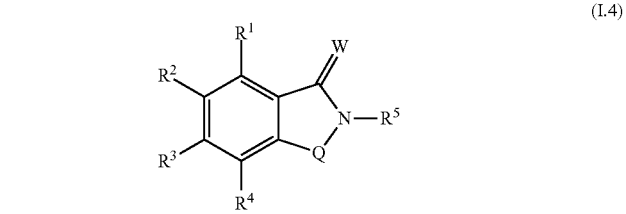
(I.4)

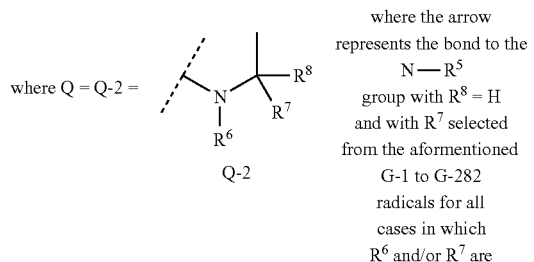

where Q = Q-2 = where the arrow represents the bond to the N—R⁵ group with $R^8$ = H and with $R^7$ selected from the aforementioned G-1 to G-282 radicals for all cases in which $R^6$ and/or $R^7$ are not H

| No. | W | $R^1$ | $R^2$ | $R^3$ | $R^4$ | $R^5$ | $R^6$ | $R^7$ |
|---|---|---|---|---|---|---|---|---|
| I.4-246 | O | Cl | H | H | H | H | H | G-83 |
| I.4-247 | O | H | CH₃ | H | H | H | H | G-83 |
| I.4-248 | O | F | H | H | H | H | H | G-83 |
| I.4-249 | O | H | H | H | H | H | G-223 | G-83 |
| I.4-250 | O | H | Cl | H | Cl | H | H | G-83 |
| I.4-251 | O | CH₃ | H | H | H | H | H | G-83 |
| I.4-252 | O | H | H | H | Cl | H | H | G-83 |
| I.4-253 | O | H | H | H | H | H | G-223 | G-85 |
| I.4-254 | O | H | Cl | H | Cl | H | H | G-85 |
| I.4-255 | O | CH₃ | H | H | H | H | H | G-85 |
| I.4-256 | O | H | H | H | Cl | H | H | G-85 |
| I.4-257 | O | H | H | H | H | H | G-1 | G-85 |
| I.4-258 | O | H | H | H | H | H | G-223 | G-128 |
| I.4-259 | O | H | Cl | H | Cl | H | H | G-128 |
| I.4-260 | O | CH₃ | H | H | H | H | H | G-128 |
| I.4-261 | O | H | H | H | Cl | H | H | G-128 |
| I.4-262 | O | H | H | H | CH₃ | H | H | G-84 |
| I.4-263 | O | H | H | H | H | H | G-1 | G-84 |
| I.4-264 | O | H | CH₃ | H | H | H | H | G-84 |
| I.4-265 | O | Cl | H | H | H | H | H | G-103 |
| I.4-266 | O | H | CH₃ | H | H | H | H | G-103 |
| I.4-267 | O | Cl | H | H | H | H | H | G-100 |
| I.4-268 | O | H | CH₃ | H | H | H | H | G-100 |
| I.4-269 | O | Cl | H | H | H | H | H | G-129 |
| I.4-270 | O | H | H | H | H | H | G-223 | G-129 |
| I.4-271 | O | Cl | H | H | H | H | H | G-84 |
| I.4-272 | O | H | H | H | H | H | G-223 | G-84 |
| I.4-273 | O | H | OCH₃ | OCH₃ | H | H | H | G-84 |
| I.4-274 | O | H | H | H | OCH₃ | H | H | G-84 |
| I.4-275 | O | H | CH₃ | H | H | H | H | G-99 |
| I.4-276 | O | H | H | H | H | H | G-223 | G-99 |
| I.4-277 | O | H | H | H | H | H | G-223 | G-100 |
| I.4-278 | O | H | Cl | H | Cl | H | H | G-100 |
| I.4-279 | O | CH₃ | H | H | H | H | H | G-100 |
| I.4-280 | O | H | H | H | Cl | H | H | G-99 |
| I.4-281 | O | Cl | H | H | H | H | H | G-99 |
| I.4-282 | O | F | H | H | H | H | H | G-100 |
| I.4-283 | O | F | H | H | H | H | H | G-99 |
| I.4-284 | O | F | H | H | H | H | H | G-103 |
| I.4-285 | O | H | H | H | H | H | G-223 | G-103 |
| I.4-286 | O | H | H | H | Cl | H | H | G-100 |
| I.4-287 | O | Cl | H | H | H | H | H | G-97 |
| I.4-288 | O | CH₃ | H | H | H | H | H | G-99 |
| I.4-289 | O | H | H | H | H | H | G-223 | G-97 |
| I.4-290 | O | H | Cl | H | Cl | H | H | G-97 |
| I.4-291 | O | CH₃ | H | H | H | H | H | G-97 |
| I.4-292 | O | H | H | H | Cl | H | H | G-97 |
| I.4-293 | O | F | H | H | H | H | H | G-84 |
| I.4-294 | O | CH₃ | H | H | H | H | H | G-84 |

TABLE 4-continued with base structure I.4 and the radical definitions specified hereinafter:

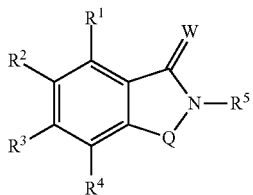
(I.4)

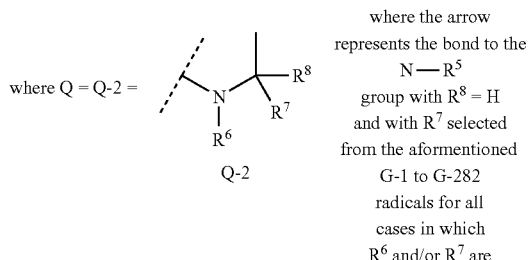

where Q = Q-2 = where the arrow represents the bond to the N—R⁵ group with $R^8$ = H and with $R^7$ selected from the aforementioned G-1 to G-282 radicals for all cases in which $R^6$ and/or $R^7$ are not H

| No. | W | R¹ | R² | R³ | R⁴ | R⁵ | R⁶ | R⁷ |
|---|---|---|---|---|---|---|---|---|
| I.4-295 | O | H | H | H | Cl | H | H | G-84 |
| I.4-296 | O | F | H | H | H | H | H | G-129 |
| I.4-297 | O | H | H | H | Cl | H | H | G-129 |
| I.4-298 | O | CH₃ | H | H | H | H | H | G-103 |
| I.4-299 | O | H | H | H | Cl | H | H | G-103 |
| I.4-300 | O | F | H | H | H | H | H | G-128 |
| I.4-301 | O | Cl | H | H | H | H | H | G-85 |
| I.4-302 | O | H | H | H | CH₃ | H | H | G-126 |
| I.4-303 | O | H | H | H | OCH₃ | H | H | G-211 |
| I.4-304 | O | F | H | H | H | H | H | G-211 |
| I.4-305 | O | H | H | H | CH₃ | H | H | G-211 |
| I.4-306 | O | Cl | H | H | H | H | H | G-211 |
| I.4-307 | O | H | H | H | H | H | G-223 | G-211 |
| I.4-308 | O | H | OCH₃ | OCH₃ | H | H | H | G-211 |
| I.4-309 | O | H | H | H | H | H | G-1 | G-211 |
| I.4-310 | O | H | H | H | OCH₃ | G-215 | H | G-13 |
| I.4-311 | O | H | H | H | OCH₃ | G-215 | H | G-19 |
| I.4-312 | O | H | H | H | OCH₃ | G-215 | H | G-55 |
| I.4-313 | O | H | H | H | OCH₃ | G-215 | H | G-37 |
| I.4-314 | O | H | H | H | OCH₃ | G-215 | H | G-18 |
| I.4-315 | O | H | H | H | OCH₃ | G-215 | H | G-74 |
| I.4-316 | O | H | H | H | OCH₃ | G-215 | H | G-80 |
| I.4-317 | O | H | H | H | OCH₃ | G-215 | H | G-82 |
| I.4-318 | O | H | H | H | OCH₃ | G-215 | H | G-83 |
| I.4-319 | O | H | H | H | OCH₃ | G-213 | H | G-13 |
| I.4-320 | O | H | H | H | OCH₃ | G-214 | H | G-13 |
| I.4-321 | O | H | H | H | OCH₃ | G-213 | H | G-19 |
| I.4-322 | O | H | H | H | OCH₃ | G-213 | H | G-55 |
| I.4-323 | O | H | H | H | OCH₃ | G-213 | H | G-37 |
| I.4-324 | O | H | H | H | OCH₃ | G-215 | H | G-81 |
| I.4-325 | O | H | H | H | OCH₃ | G-215 | H | G-85 |
| I.4-326 | O | H | H | H | OCH₃ | G-215 | H | G-96 |
| I.4-327 | O | H | H | H | OCH₃ | G-215 | H | G-56 |
| I.4-328 | O | H | H | H | OCH₃ | G-215 | H | G-132 |
| I.4-329 | O | H | H | H | OCH₃ | G-215 | H | G-100 |
| I.4-330 | O | H | H | H | OCH₃ | G-215 | H | G-99 |
| I.4-331 | O | H | H | H | OCH₃ | G-215 | H | G-103 |
| I.4-332 | O | H | H | H | OCH₃ | G-215 | H | G-35 |
| I.4-333 | O | H | H | H | OCH₃ | G-213 | H | G-18 |
| I.4-334 | O | H | H | H | OCH₃ | G-213 | H | G-74 |
| I.4-335 | O | H | H | H | OCH₃ | G-215 | H | G-111 |
| I.4-336 | O | H | H | H | OCH₃ | G-215 | H | G-84 |
| I.4-337 | O | H | H | H | OCH₃ | G-215 | H | G-102 |
| I.4-338 | O | H | H | H | OCH₃ | G-215 | H | G-127 |
| I.4-339 | O | H | H | H | OCH₃ | G-213 | H | G-80 |
| I.4-340 | O | H | H | F | OCH₃ | G-213 | H | G-82 |
| I.4-341 | O | H | H | H | Cl | H | H | G-95 |
| I.4-342 | O | H | Cl | H | CH₃ | H | H | G-95 |
| I.4-343 | O | H | Cl | H | H | H | H | G-63 |

TABLE 4-continued with base structure I.4 and the radical definitions specified hereinafter:

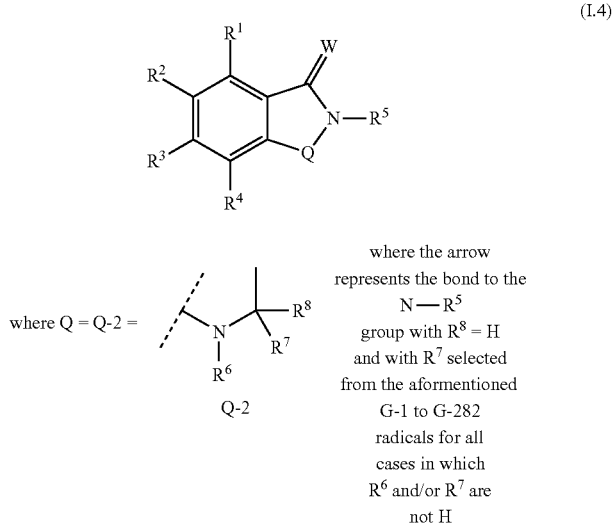

(I.4)

where Q = Q-2 = where the arrow represents the bond to the N—$R^5$ group with $R^8$ = H and with $R^7$ selected from the aforementioned G-1 to G-282 radicals for all cases in which $R^6$ and/or $R^7$ are not H

| No. | W | $R^1$ | $R^2$ | $R^3$ | $R^4$ | $R^5$ | $R^6$ | $R^7$ |
|---|---|---|---|---|---|---|---|---|
| I.4-344 | O | H | H | Cl | H | H | H | G-62 |
| I.4-345 | O | H | H | Cl | H | H | H | G-66 |
| I.4-346 | O | H | H | Cl | H | H | H | G-65 |
| I.4-347 | O | F | H | H | H | H | H | G-66 |
| I.4-348 | O | F | H | H | H | H | H | G-65 |
| I.4-349 | O | H | H | Cl | H | H | H | G-152 |
| I.4-350 | O | H | H | Cl | H | H | H | G-153 |
| I.4-351 | O | H | H | Cl | H | H | H | G-61 |
| I.4-352 | O | H | H | H | $OCH_3$ | H | H | G-56 |
| I.4-353 | O | H | H | H | $OCH_3$ | H | H | G-56 |
| I.4-354 | O | H | H | H | $CH_3$ | H | H | G-241 |
| I.4-355 | O | H | H | H | $CH_3$ | H | H | G-242 |
| I.4-356 | O | H | H | H | $CH_3$ | G-213 | H | G-8 |
| I.4-357 | O | H | H | H | $CH_3$ | G-213 | H | G-9 |
| I.4-358 | O | H | H | H | $CH_3$ | G-213 | H | G-10 |
| I.4-359 | O | H | H | H | $CH_3$ | G-213 | H | G-12 |
| I.4-360 | O | H | H | H | $CH_3$ | G-213 | H | G-13 |
| I.4-361 | O | H | H | H | $CH_3$ | G-213 | H | G-18 |
| I.4-362 | O | H | H | H | $CH_3$ | G-213 | H | G-19 |
| I.4-363 | O | H | H | H | $CH_3$ | G-213 | H | G-20 |
| I.4-364 | O | H | H | H | $CH_3$ | G-213 | H | G-25 |
| I.4-365 | O | H | H | H | $CH_3$ | G-213 | H | G-35 |
| I.4-366 | O | H | H | H | $CH_3$ | G-213 | H | G-37 |
| I.4-367 | O | H | H | H | $CH_3$ | G-213 | H | G-55 |
| I.4-368 | O | H | H | H | $CH_3$ | G-213 | H | G-56 |
| I.4-369 | O | H | H | H | $CH_3$ | G-213 | H | G-74 |
| I.4-370 | O | H | H | H | $CH_3$ | G-213 | H | G-80 |
| I.4-371 | O | H | H | H | $CH_3$ | G-213 | H | G-81 |
| I.4-372 | O | H | H | H | $CH_3$ | G-213 | H | G-82 |
| I.4-373 | O | H | H | H | $CH_3$ | G-213 | H | G-83 |
| I.4-374 | O | H | H | H | $CH_3$ | G-213 | H | G-84 |
| I.4-375 | O | H | H | H | $CH_3$ | G-213 | H | G-96 |
| I.4-376 | O | H | H | H | $CH_3$ | G-213 | H | G-99 |
| I.4-377 | O | H | H | H | $CH_3$ | G-213 | H | G-100 |
| I.4-378 | O | H | H | H | $CH_3$ | G-213 | H | G-101 |
| I.4-379 | O | H | H | H | $CH_3$ | G-213 | H | G-102 |
| I.4-380 | O | H | H | H | $CH_3$ | G-213 | H | G-127 |
| I.4-381 | O | H | H | H | $CH_3$ | G-213 | H | G-128 |
| I.4-382 | O | H | H | H | $CH_3$ | G-213 | H | G-132 |
| I.4-383 | O | H | H | H | $CH_3$ | G-213 | H | G-121 |
| I.4-384 | O | H | H | H | $CH_3$ | G-213 | H | G-126 |
| I.4-385 | O | H | H | H | $CH_3$ | G-213 | H | G-129 |
| I.4-386 | O | H | H | H | $CH_3$ | G-213 | H | G-131 |
| I.4-387 | O | H | H | H | $CH_3$ | G-213 | H | G-124 |
| I.4-388 | O | H | H | H | $CH_3$ | G-213 | H | G-247 |
| I.4-389 | O | H | H | H | $CH_3$ | G-213 | H | G-250 |
| I.4-390 | O | H | H | H | $CH_3$ | G-213 | H | G-254 |
| I.4-391 | O | H | H | H | $CH_3$ | G-215 | H | G-8 |
| I.4-392 | O | H | H | H | $CH_3$ | G-215 | H | G-9 |

TABLE 4-continued with base structure I.4 and the radical definitions specified hereinafter:

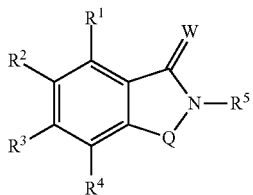
(I.4)

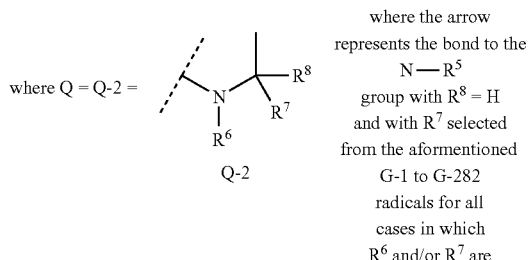

where Q = Q-2 =

Q-2 where the arrow represents the bond to the N—R$^5$ group with R$^8$ = H and with R$^7$ selected from the aformentioned G-1 to G-282 radicals for all cases in which R$^6$ and/or R$^7$ are not H

| No. | W | R$^1$ | R$^2$ | R$^3$ | R$^4$ | R$^5$ | R$^6$ | R$^7$ |
|---|---|---|---|---|---|---|---|---|
| I.4-393 | O | H | H | H | CH$_3$ | G-215 | H | G-10 |
| I.4-394 | O | H | H | H | CH$_3$ | G-215 | H | G-12 |
| I.4-395 | O | H | H | H | CH$_3$ | G-215 | H | G-13 |
| I.4-396 | O | H | H | H | CH$_3$ | G-215 | H | G-18 |
| I.4-397 | O | H | H | H | CH$_3$ | G-215 | H | G-19 |
| I.4-398 | O | H | H | H | CH$_3$ | G-215 | H | G-20 |
| I.4-399 | O | H | H | H | CH$_3$ | G-215 | H | G-25 |
| I.4-400 | O | H | H | H | CH$_3$ | G-215 | H | G-35 |
| I.4-401 | O | H | H | H | CH$_3$ | G-215 | H | G-37 |
| I.4-402 | O | H | H | H | CH$_3$ | G-215 | H | G-55 |
| I.4-403 | O | H | H | H | CH$_3$ | G-215 | H | G-56 |
| I.4-404 | O | H | H | H | CH$_3$ | G-215 | H | G-74 |
| I.4-405 | O | H | H | H | CH$_3$ | G-215 | H | G-80 |
| I.4-406 | O | H | H | H | CH$_3$ | G-215 | H | G-81 |
| I.4-407 | O | H | H | H | CH$_3$ | G-215 | H | G-82 |
| I.4-408 | O | H | H | H | CH$_3$ | G-215 | H | G-83 |
| I.4-409 | O | H | H | H | CH$_3$ | G-215 | H | G-84 |
| I.4-410 | O | H | H | H | CH$_3$ | G-215 | H | G-96 |
| I.4-411 | O | H | H | H | CH$_3$ | G-215 | H | G-99 |
| I.4-412 | O | H | H | H | CH$_3$ | G-215 | H | G-100 |
| I.4-413 | O | H | H | H | CH$_3$ | G-215 | H | G-101 |
| I.4-414 | O | H | H | H | CH$_3$ | G-215 | H | G-102 |
| I.4-415 | O | H | H | H | CH$_3$ | G-215 | H | G-127 |
| I.4-416 | O | H | H | H | CH$_3$ | G-215 | H | G-128 |
| I.4-417 | O | H | H | H | CH$_3$ | G-215 | H | G-132 |
| I.4-418 | O | H | H | H | CH$_3$ | G-215 | H | G-121 |
| I.4-419 | O | H | H | H | CH$_3$ | G-215 | H | G-126 |
| I.4-420 | O | H | H | H | CH$_3$ | G-215 | H | G-129 |
| I.4-421 | O | H | H | H | CH$_3$ | G-215 | H | G-131 |
| I.4-422 | O | H | H | H | CH$_3$ | G-215 | H | G-124 |
| I.4-423 | O | H | H | H | CH$_3$ | G-215 | H | G-247 |
| I.4-424 | O | H | H | H | CH$_3$ | G-215 | H | G-250 |
| I.4-425 | O | H | H | H | CH$_3$ | G-215 | H | G-254 |
| I.4-426 | O | H | H | H | Cl | G-213 | H | G-8 |
| I.4-427 | O | H | H | H | Cl | G-213 | H | G-9 |
| I.4-428 | O | H | H | H | Cl | G-213 | H | G-10 |
| I.4-429 | O | H | H | H | Cl | G-213 | H | G-12 |
| I.4-430 | O | H | H | H | Cl | G-213 | H | G-13 |
| I.4-431 | O | H | H | H | Cl | G-213 | H | G-18 |
| I.4-432 | O | H | H | H | Cl | G-213 | H | G-19 |
| I.4-433 | O | H | H | H | Cl | G-213 | H | G-20 |
| I.4-434 | O | H | H | H | Cl | G-213 | H | G-25 |
| I.4-435 | O | H | H | H | Cl | G-213 | H | G-35 |
| I.4-436 | O | H | H | H | Cl | G-213 | H | G-37 |
| I.4-437 | O | H | H | H | Cl | G-213 | H | G-55 |
| I.4-438 | O | H | H | H | Cl | G-213 | H | G-56 |
| I.4-439 | O | H | H | H | Cl | G-213 | H | G-74 |
| I.4-440 | O | H | H | H | Cl | G-213 | H | G-80 |
| I.4-441 | O | H | H | H | Cl | G-213 | H | G-81 |

TABLE 4-continued with base structure I.4 and the radical definitions specified hereinafter:

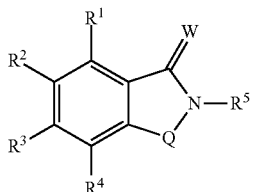
(I.4)

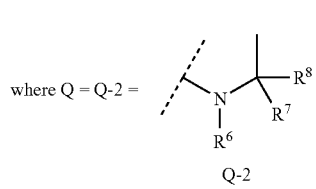

where Q = Q-2 = where the arrow represents the bond to the N—R⁵ group with $R^8$ = H and with $R^7$ selected from the aforementioned G-1 to G-282 radicals for all cases in which $R^6$ and/or $R^7$ are not H

| No. | W | $R^1$ | $R^2$ | $R^3$ | $R^4$ | $R^5$ | $R^6$ | $R^7$ |
|---|---|---|---|---|---|---|---|---|
| I.4-442 | O | H | H | H | Cl | G-213 | H | G-82 |
| I.4-443 | O | H | H | H | Cl | G-213 | H | G-83 |
| I.4-444 | O | H | H | H | Cl | G-213 | H | G-84 |
| I.4-445 | O | H | H | H | Cl | G-213 | H | G-96 |
| I.4-446 | O | H | H | H | Cl | G-213 | H | G-99 |
| I.4-447 | O | H | H | H | Cl | G-213 | H | G-100 |
| I.4-448 | O | H | H | H | Cl | G-213 | H | G-101 |
| I.4-449 | O | H | H | H | Cl | G-213 | H | G-102 |
| I.4-450 | O | H | H | H | Cl | G-213 | H | G-127 |
| I.4-451 | O | H | H | H | Cl | G-213 | H | G-128 |
| I.4-452 | O | H | H | H | Cl | G-213 | H | G-132 |
| I.4-453 | O | H | H | H | Cl | G-213 | H | G-121 |
| I.4-454 | O | H | H | H | Cl | G-213 | H | G-126 |
| I.4-455 | O | H | H | H | Cl | G-213 | H | G-129 |
| I.4-456 | O | H | H | H | Cl | G-213 | H | G-131 |
| I.4-457 | O | H | H | H | Cl | G-213 | H | G-124 |
| I.4-458 | O | H | H | H | Cl | G-213 | H | G-247 |
| I.4-459 | O | H | H | H | Cl | G-213 | H | G-250 |
| I.4-460 | O | H | H | H | Cl | G-213 | H | G-254 |
| I.4-461 | O | H | H | H | Cl | G-215 | H | G-8 |
| I.4-462 | O | H | H | H | Cl | G-215 | H | G-9 |
| I.4-463 | O | H | H | H | Cl | G-215 | H | G-10 |
| I.4-464 | O | H | H | H | Cl | G-215 | H | G-12 |
| I.4-465 | O | H | H | H | Cl | G-215 | H | G-13 |
| I.4-466 | O | H | H | H | Cl | G-215 | H | G-18 |
| I.4-467 | O | H | H | H | Cl | G-215 | H | G-19 |
| I.4-468 | O | H | H | H | Cl | G-215 | H | G-20 |
| I.4-469 | O | H | H | H | Cl | G-215 | H | G-25 |
| I.4-470 | O | H | H | H | Cl | G-215 | H | G-35 |
| I.4-471 | O | H | H | H | Cl | G-215 | H | G-37 |
| I.4-472 | O | H | H | H | Cl | G-215 | H | G-55 |
| I.4-473 | O | H | H | H | Cl | G-215 | H | G-56 |
| I.4-474 | O | H | H | H | Cl | G-215 | H | G-74 |
| I.4-475 | O | H | H | H | Cl | G-215 | H | G-80 |
| I.4-476 | O | H | H | H | Cl | G-215 | H | G-81 |
| I.4-477 | O | H | H | H | Cl | G-215 | H | G-82 |
| I.4-478 | O | H | H | H | Cl | G-215 | H | G-83 |
| I.4-479 | O | H | H | H | Cl | G-215 | H | G-84 |
| I.4-480 | O | H | H | H | Cl | G-215 | H | G-96 |
| I.4-481 | O | H | H | H | Cl | G-215 | H | G-99 |
| I.4-482 | O | H | H | H | Cl | G-215 | H | G-100 |
| I.4-483 | O | H | H | H | Cl | G-215 | H | G-101 |
| I.4-484 | O | H | H | H | Cl | G-215 | H | G-102 |
| I.4-485 | O | H | H | H | Cl | G-215 | H | G-127 |
| I.4-486 | O | H | H | H | Cl | G-215 | H | G-128 |
| I.4-487 | O | H | H | H | Cl | G-215 | H | G-132 |
| I.4-488 | O | H | H | H | Cl | G-215 | H | G-121 |
| I.4-489 | O | H | H | H | Cl | G-215 | H | G-126 |
| I.4-490 | O | H | H | H | Cl | G-215 | H | G-129 |

TABLE 4-continued with base structure I.4 and the radical definitions specified hereinafter:

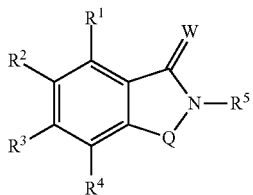
(I.4)

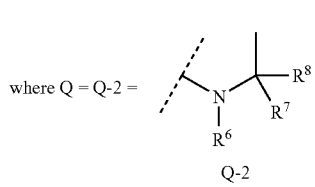

where Q = Q-2 = where the arrow represents the bond to the N—R⁵ group with $R^8$ = H and with $R^7$ selected from the aforementioned G-1 to G-282 radicals for all cases in which $R^6$ and/or $R^7$ are not H

| No. | W | $R^1$ | $R^2$ | $R^3$ | $R^4$ | $R^5$ | $R^6$ | $R^7$ |
|---|---|---|---|---|---|---|---|---|
| I.4-491 | O | H | H | H | Cl | G-215 | H | G-131 |
| I.4-492 | O | H | H | H | Cl | G-215 | H | G-124 |
| I.4-493 | O | H | H | H | Cl | G-215 | H | G-247 |
| I.4-494 | O | H | H | H | Cl | G-215 | H | G-250 |
| I.4-495 | O | H | H | H | Cl | G-215 | H | G-254 |
| I.4-496 | O | H | H | H | OH | G-213 | H | G-8 |
| I.4-497 | O | H | H | H | OH | G-213 | H | G-9 |
| I.4-498 | O | H | H | H | OH | G-213 | H | G-10 |
| I.4-499 | O | H | H | H | OH | G-213 | H | G-12 |
| I.4-500 | O | H | H | H | OH | G-213 | H | G-13 |
| I.4-501 | O | H | H | H | OH | G-213 | H | G-18 |
| I.4-502 | O | H | H | H | OH | G-213 | H | G-19 |
| I.4-503 | O | H | H | H | OH | G-213 | H | G-20 |
| I.4-504 | O | H | H | H | OH | G-213 | H | G-25 |
| I.4-505 | O | H | H | H | OH | G-213 | H | G-35 |
| I.4-506 | O | H | H | H | OH | G-213 | H | G-37 |
| I.4-507 | O | H | H | H | OH | G-213 | H | G-55 |
| I.4-508 | O | H | H | H | OH | G-213 | H | G-56 |
| I.4-509 | O | H | H | H | OH | G-213 | H | G-74 |
| I.4-510 | O | H | H | H | OH | G-213 | H | G-80 |
| I.4-511 | O | H | H | H | OH | G-213 | H | G-81 |
| I.4-512 | O | H | H | H | OH | G-213 | H | G-82 |
| I.4-513 | O | H | H | H | OH | G-213 | H | G-83 |
| I.4-514 | O | H | H | H | OH | G-213 | H | G-84 |
| I.4-515 | O | H | H | H | OH | G-213 | H | G-96 |
| I.4-516 | O | H | H | H | OH | G-213 | H | G-99 |
| I.4-517 | O | H | H | H | OH | G-213 | H | G-100 |
| I.4-518 | O | H | H | H | OH | G-213 | H | G-101 |
| I.4-519 | O | H | H | H | OH | G-213 | H | G-102 |
| I.4-520 | O | H | H | H | OH | G-213 | H | G-127 |
| I.4-521 | O | H | H | H | OH | G-213 | H | G-128 |
| I.4-522 | O | H | H | H | OH | G-213 | H | G-132 |
| I.4-523 | O | H | H | H | OH | G-213 | H | G-121 |
| I.4-524 | O | H | H | H | OH | G-213 | H | G-126 |
| I.4-525 | O | H | H | H | OH | G-213 | H | G-129 |
| I.4-526 | O | H | H | H | OH | G-213 | H | G-131 |
| I.4-527 | O | H | H | H | OH | G-213 | H | G-124 |
| I.4-528 | O | H | H | H | OH | G-213 | H | G-247 |
| I.4-529 | O | H | H | H | OH | G-213 | H | G-250 |
| I.4-530 | O | H | H | H | OH | G-213 | H | G-254 |
| I.4-531 | O | H | H | H | OH | G-215 | H | G-8 |
| I.4-532 | O | H | H | H | OH | G-215 | H | G-9 |
| I.4-533 | O | H | H | H | OH | G-215 | H | G-10 |
| I.4-534 | O | H | H | H | OH | G-215 | H | G-12 |
| I.4-535 | O | H | H | H | OH | G-215 | H | G-13 |
| I.4-536 | O | H | H | H | OH | G-215 | H | G-18 |
| I.4-537 | O | H | H | H | OH | G-215 | H | G-19 |
| I.4-538 | O | H | H | H | OH | G-215 | H | G-20 |
| I.4-539 | O | H | H | H | OH | G-215 | H | G-25 |

TABLE 4-continued with base structure I.4 and the radical definitions specified hereinafter:

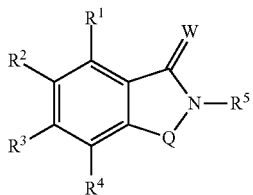
(I.4)

where Q = Q-2 = 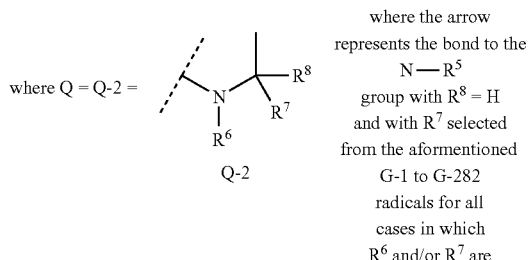

Q-2 where the arrow represents the bond to the N—R$^5$ group with R$^8$ = H and with R$^7$ selected from the aforementioned G-1 to G-282 radicals for all cases in which R$^6$ and/or R$^7$ are not H

| No. | W | R$^1$ | R$^2$ | R$^3$ | R$^4$ | R$^5$ | R$^6$ | R$^7$ |
|---|---|---|---|---|---|---|---|---|
| I.4-540 | O | H | H | H | OH | G-215 | H | G-35 |
| I.4-541 | O | H | H | H | OH | G-215 | H | G-37 |
| I.4-542 | O | H | H | H | OH | G-215 | H | G-55 |
| I.4-543 | O | H | H | H | OH | G-215 | H | G-56 |
| I.4-544 | O | H | H | H | OH | G-215 | H | G-74 |
| I.4-545 | O | H | H | H | OH | G-215 | H | G-80 |
| I.4-546 | O | H | H | H | OH | G-215 | H | G-81 |
| I.4-547 | O | H | H | H | OH | G-215 | H | G-82 |
| I.4-548 | O | H | H | H | OH | G-215 | H | G-83 |
| I.4-549 | O | H | H | H | OH | G-215 | H | G-84 |
| I.4-550 | O | H | H | H | OH | G-215 | H | G-96 |
| I.4-551 | O | H | H | H | OH | G-215 | H | G-99 |
| I.4-552 | O | H | H | H | OH | G-215 | H | G-100 |
| I.4-553 | O | H | H | H | OH | G-215 | H | G-101 |
| I.4-554 | O | H | H | H | OH | G-215 | H | G-102 |
| I.4-555 | O | H | H | H | OH | G-215 | H | G-127 |
| I.4-556 | O | H | H | H | OH | G-215 | H | G-128 |
| I.4-557 | O | H | H | H | OH | G-215 | H | G-132 |
| I.4-558 | O | H | H | H | OH | G-215 | H | G-121 |
| I.4-559 | O | H | H | H | OH | G-215 | H | G-126 |
| I.4-560 | O | H | H | H | OH | G-215 | H | G-129 |
| I.4-561 | O | H | H | H | OH | G-215 | H | G-131 |
| I.4-562 | O | H | H | H | OH | G-215 | H | G-124 |
| I.4-563 | O | H | H | H | OH | G-215 | H | G-247 |
| I.4-564 | O | H | H | H | OH | G-215 | H | G-250 |
| I.4-565 | O | H | H | H | OH | G-215 | H | G-254 |
| I.4-566 | O | H | H | H | OCH$_3$ | G-215 | H | G-84 |
| I.4-567 | O | H | H | H | OCH$_3$ | G-215 | H | G-131 |
| I.4-568 | O | H | H | H | OCH$_3$ | G-215 | H | G-129 |
| I.4-569 | O | H | H | H | OCH$_3$ | G-215 | H | G-128 |
| I.4-570 | O | H | H | H | OCH$_3$ | G-215 | H | G-124 |
| I.4-571 | O | H | H | H | OCH$_3$ | G-215 | H | G-126 |
| I.4-572 | O | H | H | H | OCH$_3$ | G-215 | H | G-247 |
| I.4-573 | O | H | H | H | OCH$_3$ | G-215 | H | G-248 |
| I.4-574 | O | H | H | H | OCH$_3$ | G-215 | H | G-254 |
| I.4-575 | O | H | H | H | OCH$_3$ | G-215 | H | G-263 |
| I.4-576 | O | H | H | H | OCH$_3$ | G-213 | H | G-84 |
| I.4-577 | O | H | H | H | OCH$_3$ | G-213 | H | G-131 |
| I.4-578 | O | H | H | H | OCH$_3$ | G-213 | H | G-129 |
| I.4-579 | O | H | H | H | OCH$_3$ | G-213 | H | G-128 |
| I.4-580 | O | H | H | H | OCH$_3$ | G-213 | H | G-124 |
| I.4-581 | O | H | H | H | OCH$_3$ | G-213 | H | G-126 |
| I.4-582 | O | H | H | H | OCH$_3$ | G-213 | H | G-247 |
| I.4-583 | O | H | H | H | OCH$_3$ | G-213 | H | G-248 |
| I.4-584 | O | H | H | H | OCH$_3$ | G-213 | H | G-254 |
| I.4-585 | O | H | H | H | OCH$_3$ | G-213 | H | G-263 |
| I.4-586 | O | H | H | H | OCH$_3$ | H | H | G-247 |
| I.4-587 | O | H | H | H | OCH$_3$ | H | H | G-248 |
| I.4-588 | O | H | H | H | OCH$_3$ | H | H | G-254 |

TABLE 4-continued with base structure I.4 and the radical definitions specified hereinafter:

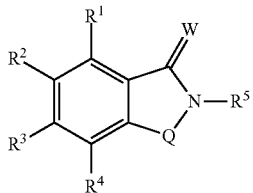
(I.4)

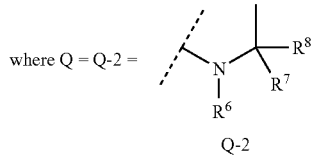

where Q = Q-2 = where the arrow represents the bond to the N—R⁵ group with $R^8$ = H and with $R^7$ selected from the aforementioned G-1 to G-282 radicals for all cases in which $R^6$ and/or $R^7$ are not H

| No. | W | $R^1$ | $R^2$ | $R^3$ | $R^4$ | $R^5$ | $R^6$ | $R^7$ |
|---|---|---|---|---|---|---|---|---|
| I.4-589 | O | H | H | H | OCH₃ | H | H | G-263 |
| I.4-590 | O | H | H | H | OCH₃ | H | H | G-250 |
| I.4-591 | O | H | H | H | CH₃ | H | H | G-247 |
| I.4-592 | O | H | H | H | CH₃ | H | H | G-248 |
| I.4-593 | O | H | H | H | CH₃ | H | H | G-254 |
| I.4-594 | O | H | H | H | CH₃ | H | H | G-263 |
| I.4-595 | O | H | H | H | CH₃ | H | H | G-250 |

TABLE 5 with base structure I.5 and the radical definitions specified hereinafter:

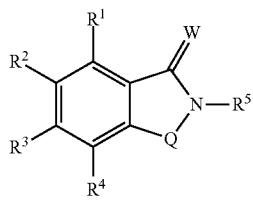
(I.5)

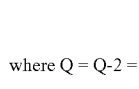

where Q = Q-2 = and with $R^7$ and $R^8$ selected from the aforementioned G-1 to G-282 radicals for all cases in which $R^7$ or $R^8$ corresponds to a G-1, G-2 or G-9 where the arrow represents the bond to the N—R⁵ group

TABLE 5-continued with base structure I.5 and the radical definitions specified hereinafter:

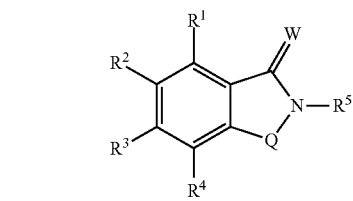
(I.5)

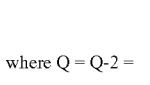

where Q = Q-2 = and with $R^7$ and $R^8$ selected from the aforementioned G-1 to G-282 radicals for all cases in which $R^7$ or $R^8$ corresponds to a G-1, G-2 or G-9 where the arrow represents the bond to the N—R⁵ group

| No. | W | $R^1$ | $R^2$ | $R^3$ | $R^4$ | $R^5$ | $R^6$ | $R^7$ | $R^8$ |
|---|---|---|---|---|---|---|---|---|---|
| I.5-1 | O | H | H | H | H | H | H | —(CH₂)₄— | |
| I.5-2 | O | H | Cl | H | H | H | H | G-9 | G-1 |
| I.5-3 | O | H | H | H | H | H | H | —(CH₂)₅— | |
| I.5-4 | O | H | Cl | H | H | H | H | G-2 | G-1 |
| I.5-5 | O | H | H | H | H | H | H | G-9 | G-1 |

| No. | W | $R^1$ | $R^2$ | $R^3$ | $R^4$ | $R^5$ | $R^6$ | $R^7$ | $R^8$ |
|---|---|---|---|---|---|---|---|---|---|
| I.5-6 | O | F | H | H | H | H | H | | 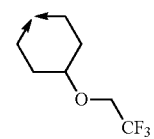 |

TABLE 5-continued with base structure I.5 and the radical definitions specified hereinafter:

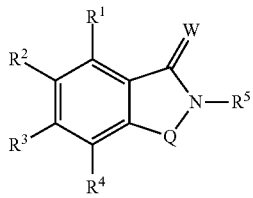

(I.5)

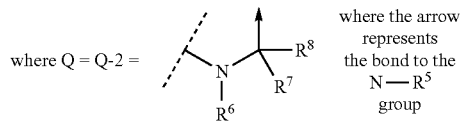

where Q = Q-2 =, where the arrow represents the bond to the N—R⁵ group and with $R^7$ and $R^8$ selected from the aformentioned G-1 to G-282 radicals for all cases in which $R^7$ or $R^8$ corresponds to a G-1, G-2 or G-9

| No. | W | R¹ | R² | R³ | R⁴ | R⁵ | R⁶ | R⁷ | R⁸ |
|---|---|---|---|---|---|---|---|---|---|
| I.5-7 | O | H | Cl | H | H | H | H | —(CH₂)₅— | |
| I.5-8 | O | H | CF₃ | H | H | H | OH | —(CH₂)₄— | |
| I.5-9 | O | H | H | CF₃ | H | H | OH | G-2 | G-1 |
| I.5-10 | O | H | H | CF₃ | H | H | OH | —(CH₂)₅— | |
| I.5-11 | O | H | CH₃ | H | H | H | H | —(CH₂)₅— | |
| I.5-12 | O | H | CH₃ | H | H | H | H | —(CH₂)₄— | |
| I.5-13 | O | H | H | H | H | H | H | cyclohexyl-CF₃ | |
| I.5-14 | O | H | Cl | H | H | H | H | cyclohexyl-CF₃ | |
| I.5-15 | O | H | Cl | H | H | H | H | —(CH₂)₄— | |
| I.5-16 | O | H | Cl | H | H | H | H | cyclohexyl-O-CH₂CF₃ | |
| I.5-17 | O | H | H | CF₃ | H | H | H | cyclohexyl-O-CH₂CF₃ | |
| I.5-18 | O | H | H | H | H | H | H | cyclohexyl-O-CH₂CF₃ | |

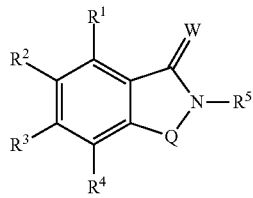

(I.5)

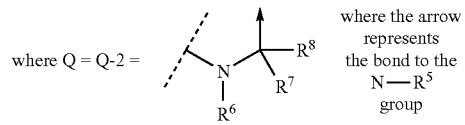

where Q = Q-2 =, where the arrow represents the bond to the N—R⁵ group and with $R^7$ and $R^8$ selected from the aformentioned G-1 to G-282 radicals for all cases in which $R^7$ or $R^8$ corresponds to a G-1, G-2 or G-9

| No. | W | R¹ | R² | R³ | R⁴ | R⁵ | R⁶ | R⁷ | R⁸ |
|---|---|---|---|---|---|---|---|---|---|
| I.5-19 | O | H | H | Cl | H | H | H | cyclohexyl-O-CH₂CF₃ | |
| I.5-20 | O | H | H | CF₃ | H | H | H | cyclohexyl-CF₃ | |
| I.5-21 | O | H | H | CH₃ | H | H | H | cyclohexyl-O-CH₂CF₃ | |
| I.5-22 | S | H | CH₃ | H | H | H | H | —(CH₂)₅— | |
| I.5-23 | S | H | CH₃ | H | H | H | H | —(CH₂)₄— | |
| I.5-24 | S | H | Cl | H | H | H | H | cyclohexyl-CF₃ | |

SPECTROSCOPIC DATA OF THE CHEMICAL EXAMPLES

Example No. I.1-1

¹H NMR (400 MHz, CDCl₃, δ, ppm) 10.30 (br. s, 1H, NH), 8.26 (d, 1H), 7.74 (dd, 1H), 7.68 (d, 1H), 7.46 (dd, 1H), 2.72 (t, 2H), 1.81 (quint, 2H), 1.48 (sext, 2H), 0.99 (t, 3H).

Example No. I.1-2

¹H NMR (400 MHz, CDCl₃, δ, ppm) 10.51 (br. s, 1H, NH), 8.19 (d, 1H), 7.68 (d, 1H), 7.42 (dd, 1H), 2.53 (s, 3H).

Example No. I.1-3

$^1$H NMR (400 MHz, d$_6$-DMSO δ, ppm) 12.44 (br. s. 1H, NH), 8.03 (d, 1H), 7.91 (d, 1H), 7.42 (dd, 1H), 2.39 (s, 3H).

Example No. I.1-4

$^1$H NMR (400 MHz, CDCl$_3$ δ, ppm) 9.88 (br. s, 1H, NH), 7.86 (d, 1H), 7.58 (dd, 1H), 7.47 (d, 1H), 2.68 (s, 3H), 2.32 (s, 3H).

Example No. I.1-5

$^1$H NMR (400 MHz. CDCl$_3$ δ, ppm) 9.51 (br. s, 1H, NH), 8.23 (d, 1H), 7.76 (dd, 1H), 7.66 (d, 1H), 7.47 (dd, 1H), 3.78 (m, 2H), 3.69-3.45 (m, 2H), 2.62 (m, 2H), 2.52 (s, 2H), 2.03 (m, 2H).

Example No. I.1-6

$^1$H NMR (400 MHz, d$_6$-DMSO δ, ppm) 12.52 (br. s, 1H, NH), 7.92 (d, 1H), 7.59 (d, 1H), 7.42 (dd, 1H), 2.73 (q, 2H), 2.44 (s, 3H), 1.38 (t, 3H).

Example No. I.1-7

$^1$H NMR (400 MHz, d$_6$-DMSO δ, ppm) 10.88 (br. s, 1H, NH), 8.08 (m, 1H), 7.61 (m, 1H), 7.48 (m, 1H), 2.23 (s, 3H).

Example No. I.1-8

$^1$H NMR (400 MHz, d$_6$-DMSO δ, ppm) 12.60 (br. s, 1H, NH), 8.19 (d, 2H), 8.07 (d, 1H), 7.84 (dd, 1H), 7.72 (d, 1H), 7.10 (d, 2H), 3.86 (s, 3H).

Example No. I.1-9

$^1$H NMR (400 MHz, d$_6$-DMSO δ, ppm) 12.57 (br. s, 1H, NH), 8.17 (d, 2H), 7.92 (d, 1H), 7.63 (dd, 1H), 7.59 (d, 1H), 7.08 (d, 2H), 3.86 (s, 3H), 2.45 (s, 3H).

Example No. I.1-10

$^1$H NMR (400 MHz, CDCl$_3$ δ, ppm) 12.28 (br. s, 1H, NH), 8.25 (d, 2H), 7.84 (dd, 1H), 7.69 (d, 1H), 7.53 (d, 1H), 7.49 (d, 2H).

Example No. I.1-11

$^1$H NMR (400 MHz, CDCl$_3$ δ, ppm) 9.52 (br. s, 1H, NH), 8.27 (d, 1H), 7.77 (dd, 1H), 7.69 (d, 1H), 7.47 (dd, 1H), 2.76 (q, 2H), 1.42 (t, 3H).

Example No. I.1-12

$^1$H NMR (400 MHz, CDCl$_3$ δ, ppm) 10.95 (br. s, 1H, NH), 8.61 (d, 1H), 7.47 (d, 1H), 7.44 (dd, 1H), 2.21 (a, 3H),

Example No. I.1-13

$^1$H NMR (400 MHz, CDCl$_3$ δ, ppm) 11.31 (br. s, 1H, NH), 8.32 (d, 1H), 8.04 (d, 1H), 7.79 (m, 2H), 7.60 (d, 1H), 7.48 (m, 1H), 7.22 (dd, 1H).

Example No. I.1-14

$^1$H NMR (400 MHz, d$_6$-DMSO δ, ppm) 12.30 (br. s, 1H, NH), 8.22 (d, 1H), 8.06 (d, 1H), 7.88 (d. 1H), 7.82 (dd, 1H), 7.67 (d, 1H), 7.24 (m, 1H).

Example No. I.1-15

$^1$H NMR (400 MHz, CDCl$_3$ δ, ppm) 9.24 (br. s, 1H, NH), 8.26 (dd, 1H), 7.73 (d, 1H), 7.69 (d, 1H), 7.44 (dd, 1H), 2.92 (sept, 1H), 1.39 (d, 6H).

Example No. I.1-16

$^1$H NMR (400 MHz, CDCl$_3$ δ, ppm) 9.97 (br. s, 1H, NH), 8.27 (d, 1H), 7.74 (dd, 1H), 7.69 (d, 1H), 7.46 (dd, 1H), 2.72 (t. 2H), 1.87 (sext, 2H), 1.08 (t, 3H).

Example No. I.1-17

$^1$H NMR (400 MHz, CDCl$_3$ δ, ppm) 12.32 (br. s, 1H, NH), 8.32 (m, 1H), 8.25 (d, 1H), 8.19 (d, 1H), 7.84 (dd, 1H), 7.70 (d, 1H), 7.54 (m, 2H), 7.45 (dd, 1H).

Example No. I.1-18

$^1$H NMR (400 MHz, CDCl$_3$ δ, ppm) 12.14 (br. s, 1H, NH), 8.81 (d, 1H), 7.57 (m, 2H). 7.53 (d, 1H), 7.22 (d, 1H), 7.11 (dd, 1H), 6.52 (m, 1H).

Example No. I.1-19

$^1$H NMR (400 MHz, CDCl$_3$ δ, ppm) 9.23 (br. s, 1H, NH), 8.22 (d, 1H), 7.34 (dd, 1H), 7.15 (d, 1H), 2.18 (s, 3H).

Example No. I.1-20

$^1$H NMR (400 MHz, CDCl$_3$ δ, ppm) 10.96 (br. s, 1H, NH), 8.54 (d, 1H), 7.60 (d, 1H), 7.57 (dd, 1H), 2.19 (s, 3H),

Example No. I.1-21

$^1$H NMR (400 MHz, CDCl$_3$ δ, ppm) 10.52 (br. s, 1H, NH), 8.49 (d, 1H), 8.38 (d, 1H), 8.20 (dd, 1H), 2.54 (s, 3H).

Example No. I.1-22

$^1$H NMR (400 MHz, CDCl$_3$ δ, ppm) 11.70 (br. s, 1H, NH), 8.53 (s, 1H), 6.92 (s, 1H). 3.97 (s, 3H), 3.88 (s, 3H), 1.32 (s, 9H).

Example No. I.1-23

$^1$H NMR (400 MHz, CDCl$_3$ δ, ppm) 9.42 (br. s, 1H, NH), 8.18 (d, 1H), 7.69 (d, 1H), 7.40 (dd, 1H), 2.72 (q, 2H), 1.40 (t, 3H).

Example No. I.1-24

$^1$H NMR (400 MHz, CDCl$_3$ δ, ppm) 11.30 (br. s, 1H, NH), 8.51 (d, 1H), 7.81 (d, 1H), 7.77 (dd, 1H), 1.32 (s, 9H).

Example No. I.1-25

$^1$H NMR (400 MHz, CDCl$_3$ δ, ppm) 10.05 (br. s, 1H, NH), 7.51 (s, 1H), 6.99 (s, 1H), 3.99 (s, 3H), 3.98 (s, 3H), 2.67 (t, 2H), 1.81 (m, 2H), 1.39 (m, 4H), 0.92 (t, 3H).

Example No. I.1-26

¹H NMR (400 MHz, CDCl₃ δ, ppm) 11.12 (br. s, 1H, NH), 8.66 (d, 1H), 7.49 (m, 2H), 7.17 (d, 2H), 7.08 (dd, 1H), 6.81 (d, 2H), 3.78 (s, 3H), 3.00 (m, 2H), 2.69 (m, 2H).

Example No. I.1-27

¹H NMR (400 MHz, CDCl₃ δ, ppm) 10.42 (br. s, 1H, NH), 7.89 (d, 1H), 7.60 (s, 1H), 7.53 (d, 1H), 7.45 (dd, 1H), 7.38 (dd, 1H), 7.13 (s, 1H), 4.02 (s, 3H), 4.01 (s, 3H).

Example No. I.1-28

¹H NMR (400 MHz, CDCl₃ δ, ppm) 11.10 (br. s, 1H, NH), 8.12 (d, 1H), 7.60 (d, 1H), 7.33 (dd, 1H), 2.61 (s, 3H), 2.59 (s, 3H).

Example No. I.1-29

¹H NMR (400 MHz, CDCl₃ δ, ppm) 10.65 (br. s, 1H, NH), 8.37 (m, 2H), 8.18 (d, 1H), 7.84 (d, 1H), 7.73 (dd, 1H), 7.09 (m, 2H).

Example No. I.1-30

¹H NMR (400 MHz, d₆-DMSO δ, ppm) 12.80 (br. s, 1H, NH), 8.63 (d, 1H), 8.28 (br. s, 1H, NH), 7.82 (d, 1H), 7.56 (dd, 1H), 7.19 (dd, 1H).

Example No. I.1-31

¹H NMR (400 MHz, d₆-DMSO δ, ppm) 12.20 (br. s, 1H, NH), 8.81 (d, 1H), 7.56 (d, 1H), 7.52 (dd, 1H), 7.39 (d, 1H), 7.09 (dd, 1H), 6.88 (d, 1H), 4.00 (s, 3H).

Example No. I.1-32

¹H NMR (400 MHz, d₆-DMSO δ, ppm) 11.10 (br. s, 1H, NH), 8.62 (d, 1H), 7.49 (d, 1H), 7.07 (dd, 1H), 2.12 (s, 3H).

Example No. I.1-33

¹H NMR (400 MHz, CDCl₃ δ, ppm) 10.38 (br. s, 1H, NH), 8.11 (d, 2H), 7.89 (d, 1H), 7.40 (dd, 1H), 7.22 (d, 1H), 7.05 (d, 2H), 4.05 (s, 3H), 3.90 (s, 3H).

Example No. I.1-34

¹H NMR (400 MHz, d₆-DMSO δ, ppm) 12.48 (br. s, 1H, NH), 9.60 (br. s, 1H, OH), 8.38 (d, 2H), 7.56 (d, 2H), 7.49 (d, 1H), 7.29 (dd, 1H), 7.17 (d, 1H).

Example No. I.1-35

¹H NMR (400 MHz, d₆-DMSO δ, ppm) 12.73 (br. s, 1H, NH), 8.08 (d, 1H), 7.58 (d, 1H), 7.42 (dd, 1H), 7.37 (d, 1H), 7.27 (d, 1H), 3.92 (s, 3H).

Example No. I.1-36

¹H NMR (400 MHz, d₆-DMSO δ, ppm) 12.82 (br. s. 1H, NH), 8.40 (d, 2H), 8.39 (d, 2H), 7.72 (d, 1H), 7.50 (dd, 1H), 7.42 (d, 1H), 3.97 (s, 3H).

Example No. I.1-38

¹H NMR (400 MHz, d₆-DMSO δ, ppm) 12.64 (br. s, 1H, NH), 9.68 (br. s, 1H, OH), 8.08 (d, 1H), 7.54 (d, 1H), 7.30 (dd, 1H), 7.26 (d, 1H), 7.23 (d, 1H).

Example No. I.1-40

¹H NMR (400 MHz, d₆-DMSO δ, ppm) 12.68 (br. s, 1H NH), 9.78 (br. s, 1H, OH), 8.19 (s, 1H), 7.55 (d, 1H), 7.32 (dd, 1H), 7.25 (d, 1H).

Example No. I.1-41

¹H NMR (400 MHz, d₆-DMSO δ, ppm) 12.74 (br. s, 1H, OH), 9.96 (br. s, 1H, NH), 8.67 (d, 2H), 8.36 (d, 2H), 7.59 (d, 1H), 7.38 (dd, 1H), 7.29 (d, 1H).

Example No. I.1-42

¹H NMR (400 MHz, d₆-DMSO δ, ppm) 12.21 (br. s, 1H, NH), 10.14 (br. s, 1H, OH), 9.42 (br. s, 1H, OH), 8.68 (d, 2H), 7.53 (d, 1H), 7.32 (dd, 1H), 7.18 (d, 1H), 6.88 (d. 2H).

Example No. I.1-43

¹H NMR (400 MHz. CDCl₃ δ, ppm) 9.88 (br. s, 1H, NH), 8.18 (d, 1H), 7.70 (dd, 1H), 7.65 (d, 1H), 7.42 (dd, 1H), 2.64 (d, 2H), 1.64 (m. 1H), 1.12 (d, 6H).

Example No. I.1-44

¹H NMR (400 MHz, CDCl₃ δ, ppm) 9.92 (br. s, 1H, NH), 8.26 (d, 1H), 7.72 (m, 2H), 7.43 (dd, 1H), 7.29 (d, 1H), 6.24 (d, 1H), 2.43 (s, 3H).

Example No. I.1-45

¹H NMR (400 MHz, CDCl₃ δ, ppm) 9.49 (br. s, 1H, NH), 8.26 (d. 1H), 7.71 (m, 2H), 7.42 (dd, 1H), 7.19 (s, 1H), 2.33 (s, 3H), 2.04 (s, 3H).

Example No. I.1-46

¹H NMR (400 MHz, CDCl₃ δ, ppm) 9.74 (br. s, 1H, NH), 8.28 (d, 1H), 7.75 (m, 2H), 7.48 (dd, 1H), 7.37 (d, 1H), 6.63 (d, 1H), 5.14 (s, 2H), 2.12 (s, 3H).

Example No. I.1-47

¹H NMR (400 MHz, CDCl₃ δ, ppm) 10.08 (br. s, 1H, NH), 8.27 (d, 1H), 7.78 (dd, 1H), 7.72 (d, 1H), 7.48 (dd, 1H), 7.31-7.21 (m, 5H), 3.18 (m, 2H), 3.04 (m, 2H).

Example No. I.1-48

¹H NMR (400 MHz, CDCl₃ δ, ppm) 10.43 (br. s, 1H, NH), 8.27 (d, 1H), 7.74 (dd, 1H), 7.69 (d, 1H), 7.46 (dd, 1H), 5.78 (m, 1H), 4.92 (m, 2H), 2.73 (m, 2H), 2.03 (m, 2H), 1.84 (m, 2H), 1.44 (m, 2H), 1.39-1.25 (m, 8H).

Example No. I.1-49

¹H NMR (400 MHz, CDCl₃ δ, ppm) 9.36 (br. s, 1H, NH), 8.08 (d, 1H), 7.74 (dd, 1H), 7.58 (d, 1H), 7.46 (dd, 1H), 6.48 (s, 1H), 3.51 (m, 2H), 3.37 (m, 2H), 2.58 (m, 2H), 2.52 (m, 2H), 1.95 (s, 6H), 1.80 (m, 1H), 1.59 (m, 1H).

Example No. I.1-50

$^1$H NMR (400 MHz, d$_6$-DMSO δ, ppm) 12.63 (br. s, 1H, NH), 8.21 (d, 1H), 7.96 (d, 1H), 7.85 (d. 1H), 7.67 (d, 1H), 7.37 (dd, 1H), 7.22 (dd, 1H), 2.58 (s, 3H).

Example No. I.1-51

$^1$H NMR (400 MHz, d$_6$-DMSO δ, ppm) 12.62 (br. s, 1H, NH), 8.11 (d, 1H), 8.02 (d, 1H), 7.72 (d, 1H), 7.66 (d, 1H), 7.50 (dd, 1H), 6.77 (m, 1H).

Example No. I.1-52

$^1$H NMR (400 MHz, d$_6$-DMSO δ, ppm) 12.49 (br. s, 1H, NH), 8.09 (d, 1H), 7.73 (d, 1H), 7.58 (d, 1H), 7.48 (dd, 1H), 6.39 (d, 1H), 2.42 (s, 3H).

Example No. I.1-53

$^1$H NMR (400 MHz, CDCl$_3$ ppm) 9.51 (br. s, 1H, NH), 8.36 (d, 1H), 8.14 (s, 1H), 7.66 (s, 1H), 7.51 (d, 1H), 6.68 (m, 1H).

Example No. I.1-54

$^1$H NMR (400 MHz, d$_6$-DMSO δ, ppm) 12.40 (br. s, 1H, NH), 8.08 (d, 1H), 7.69 (d, 1H), 7.47 (dd, 1H), 7.45 (s, 1H), 2.31 (s, 3H), 1.99 (s, 3H).

Example No. I.1-55

$^1$H NMR (400 MHz, d$_6$-DMSO δ, ppm) 12.78 (br. s, 1H, NH), 8.26 (d, 1H), (d, 1H), 7.90 (d, 1H), 7.71 (d, 1H), 7.50 (dd, 1H), 7.24 (m, 1H).

Example No. I.156

$^1$H NMR (400 MHz, d$_6$-DMSO δ, ppm) 12.39 (br. s, 1H, NH), 7.97 (d, 1H), 7.92 (d, 1H), 7.62 (dd, 1H), 7.59 (m, 2H), 6.73 (m, 1H), 2.45 (s, 3H).

Example No. I.1-57

$^1$H NMR (400 MHz, d$_6$-DMSO δ, ppm) 12.28 (br. s, 1H, NH), 7.90 (d, 1H), 7.62 (dd, 1H), 7.58 (d, 1H), 7.50 (d, 1H), 6.36 (d, 1H), 2.44 (s, 3H), 2.40 (s, 3H).

Example No. I.1-58

$^1$H NMR (400 MHz, d$_6$-DMSO δ, ppm) 12.20 (br. s, 1H, NH), 7.89 (d, 1H), 7.60 (dd, 1H), 7.56 (d. 1H), 7.38 (s, 1H), 2.42 (s, 3H), 2.31 (s, 3H), 1.98 (s, 3H).

Example No. I.1-59

$^1$H NMR (400 MHz, d$_6$-DMSO δ, ppm) 12.59 (br. s, 1H, NH), 8.20 (m, 1H), 7.93 (d, 1H), 7.84 (d, 1H), 7.62 (dd, 1H), 7.56 (d, 1H), 7.22 (m, 1H), 2.44 (s, 3H).

Example No. I.1-60

$^1$H NMR (400 MHz, d$_6$-DMSO δ, ppm) 12.61 (br. s, 1H, NH), 7.99 (d, 1H), 7.78 (m, 2H), 7.70 (m, 1H), 7.62 (d, 1H), 6.73 (m, 1H).

Example No. I.1-61

$^1$H NMR (400 MHz, d$_6$-DMSO δ, ppm) 12.54 (br. s, 1H, NH), 7.96 (d, 1H), 7.76 (m, 2H), 7.71 (m, 1H), 6.71 (m, 1H) 2.33 (s, 3H).

Example No. I.1-62

$^1$H NMR (400 MHz, CDCl$_3$ δ, ppm) 10.02 (br. s, 1H, NH), 7.93 (m, 1H), 7.75 (m, 1H), 7.50 (m, 1H), 7.37 (d, 1H), 6.64 (d, 1H), 5.16 (s, 2H), 2.12 (s, 3H).

Example No. I.1-63

$^1$H NMR (400 MHz, d$_6$-DMSO δ, ppm) 12.42 (br. s, 1H, NH), 7.74 (m, 2H), 7.67 (dd, 1H), 7.42 (d, 1H), 2.31 (s, 3H), 1.99 (s, 3H).

Example No. I.1-64

$^1$H NMR (400 MHz, d$_6$, DMSO δ, ppm) 12.78 (br. s, 1H, NH), 8.21 (d, 1H), 7.87 (d, 1H), 7.80 (dd, 1H), 7.71 (m, 1H), 7.68 (m, 1H), 7.22 (m, 1H).

Example No. I.1-65

$^1$H NMR (400 MHz, d$_6$-DMSO δ, ppm) 12.69 (br. s, 1H, NH), 8.05 (d, 1H), 8.01 (d, 1H), 7.83 (dd, 1H), 7.70 (d, 1H), 7.64 (d, 1H), 6.76 (m, 1H).

Example No. I.1-66

$^1$H NMR (400 MHz, d$_6$-DMSO δ, ppm) 12.55 (br. s, 1H, NH), 8.03 (d, 1H), 7.81 (dd, 1H), 7.70 (d. 1H), 7.57 (d, 1H), 6.39 (d, 1H), 2.41 (s, 3H).

Example No. I.1-67

$^1$H NMR (400 MHz, CDCl$_3$ (δ, ppm) 10.41 (br. s, 1H, NH), 8.27 (d, 1H), 7.70 (m, 2H), 7.42 (d, 1H), 6.67 (d, 1H), 5.18 (s, 2H), 2.13 (s, 3H).

Example No. I.1-68

$^1$H NMR (400 MHz, d$_6$-DMSO δ, ppm) 12.49 (br. s. 1H, NH), 8.02 (d, 1H), 7.80 (dd, 1H), 7.68 (d, 1H), 7.44 (s, 1H), 2.32 (s, 3H), 2.00 (s, 3H).

Example No. I.1-69

$^1$H NMR (400 MHz, d$_6$-DMSO δ, ppm) 12.52 (br. s, 1H, NH), 8.03 (d, 1H), 7.79 (m, 1H), 7.67 (d, 1H), 7.50 (d, 1H), 7.21 (dd, 1H), 6.74 (m, 1H).

Example No. I.1-70

$^1$H NMR (400 MHz, d$_6$-DMSO δ, ppm) 12.39 (br, s, 1H, NH), 7.76 (m, 1H), 7.58 (d, 1H), 7.48 (d, 1H), 7.19 (dd, 1H), 6.39 (d, 1H), 2.39 (s, 3H).

Example No. I.1-71

$^1$H NMR (400 MHz, d$_6$-DMSO δ, ppm) 12.52 (br. s, 1H, NH), 7.79 (m, 1H), 7.64 (d, 1H), 7.52 (d, 1H), 7.23 (dd, 1H), 6.79 (d, 1H), 5.13 (s, 2H), 2.09 (s, 3H).

Example No. I.1-72

$^1$H NMR (400 MHz, d$_6$-DMSO δ, ppm) 12.31 (br. s, 1H, NH), 7.74 (m, 1H), 7.47 (d, 1H), 7.46 (s, 1H), 7.18 (dd, 1H), 2.31 (s, 3H), 1.99 (s, 3H).

Example No. I.1-73

$^1$H NMR (400 MHz, d$_6$-DMSO δ, ppm) 12.67 (br. s, 1H, NH), 8.24 (d, 1H), 7.89 (d, 1H), 7.78 (m, 1H), 7.45 (d, 1H), 7.22 (m, 1H), 7.19 (m, 1H).

Example No. I.1-74

$^1$H NMR (400 MHz, CDCl$_3$ δ, ppm) 9.42 (br. s, 1H, NH), 8.12 (d, 1H), 7.61 (m, 2H), 7.32 (m, 2H), 6.63 (m, 1H), 2.65 (s, 3H).

Example No. I.1-75

$^1$H NMR (400 MHz, CDCl$_3$ δ, ppm) 9.40 (br. s, 1H, NH), 8.11 (d, 1H), 7.59 (d, 1H), 7.31 (dd, 1H), 7.28 (d, 1H), 6.23 (d, 1H), 2.63 (s, 3H), 2.42 (s, 3H).

Example No. I.1-76

$^1$H NMR (400 MHz, d$_6$-DMSO δ, ppm) 12.48 (br. s, 1H, NH), 7.97 (d, 1H), 7.68 (d, 1H), 7.58 (d, 1H), 7.39 (dd, 1H), 6.77 (d, 1H), 5.16 (s, 2H), 2.59 (s, 3H), 2.09 (s, 3H).

Example No. I.1-77

$^1$H NMR (400 MHz, CDCl$_3$ δ, ppm) 9.68 (br. s, 1H, NH), 8.09 (s, 1H), 7.64 (d, 1H), 7.59 (d, 1H), 7.31 (d, 1H), 6.62 (d, 1H), 5.14 (s, 2H), 2.50 (s, 3H), 2.13 (s, 3H).

Example No. I.1-78

$^1$H NMR (400 MHz, CDCl$_3$, ppm) 9.62 (br. s, 1H, NH), 8.36 (s, 1H), 8.13 (s, 1H), 7.48 (d, 1H), 6.66 (d, 1H), 5.15 (s, 2H), 2.11 (s, 3H).

Example No. I.1-95

$^1$H NMR (400 MHz, d$_6$-DMSO δ, ppm) 12.28 (br. s, 1H, NH), 7.73 (m, 1H), 7.66 (m, 2H), 2.62 (q, 2H), 1.24 (t, 3H).

Example No. I.1-99

$^1$H NMR (400 MHz, d$_6$-DMSO δ, ppm) 12.26 (br. s, 1H, NH), 8.01 (d, 1H), 7.80 (dd, 1H), 7.68 (d, 1H), 3.49 (quint, 1H), 2.40 (m, 2H), 2.26 (m, 2H), 2.01 (m, 1H), 1.83 (m, 1H).

Example No. I.1-114

$^1$H NMR (400 MHz, d$_6$-DMSO δ, ppm) 12.18 (br. s, 1H, NH), 11.14 (br. s, 1H, NH), 7.89 (m, 2H), 7.60 (dd, 1H), 7.52 (d, 1H), 2.68 (s, 3H), 2.42 (s, 3H).

Example No. I.1-115

$^1$H NMR (400 MHz, d$_6$-DMSO δ, ppm) 12.61 (br. s, 1H, NH), 11.10 (br. s, 1H, NH), 7.73 (m, 2H), 7.67 (m, 2H), 2.69 (s, 3H).

Example No. I.1-116

$^1$H NMR (400 MHz, d$_6$-DMSO δ, ppm) 12.62 (br. s, 1H, NH), 11.18 (br. s, 1H, NH), 8.01 (d, 1H), 7.78 (m, 2H), 7.62 (d, 1H), 2.68 (s, 3H),

Example No. I.1-117

$^1$H NMR (400 MHz, d$_6$-DMSO δ, ppm) 12.64 (br. s, 1H, NH), 10.90 (br. s, 1H, NH), 7.75 (s, 1H), 7.70 (m, 1H), 7.41 (d, 1H), 7.13 (m, 1H), 2.65 (s, 3H).

Example No. I.1-118

$^1$H NMR (400 MHz, d$_6$-DMSO δ, ppm) 12.67 (br. s, 1H, NH), 10.94 (br. s, 1H, NH), 7.92 (d, 1H), 7.78 (s, 1H), 7.63 (d, 1H), 7.29 (dd, 1H), 2.69 (s, 3H), 2.53 (s, 3H).

Example No. I.1-119

$^1$H NMR (400 MHz, d$_6$-DMSO δ, ppm) 12.30 (br. s, 1H, NH), 7.77 (m, 1H), 7.69 (m, 1H), 7.65 (m, 1H), 2.49 (m, 1H), 1.74 (m, 2H), 1.62 (m, 2H), 0.80 (t, 6H).

Example No. I.1-120

$^1$H NMR (400 MHz, d$_6$-DMSO δ, ppm) 12.22 (br. s, 1H, NH), 7.76 (m, 1H), 7.68 (m, 1H), 7.67 (m, 1H), 2.51 (s, 2H), 1.01 (s, 9H).

Example No. I.1-121

$^1$H NMR (400 MHz, d$_6$-DMSO δ, ppm) 12.57 (br. s, 1H, NH), 8.18 (d, 2H), 7.80 (m, 1H), 7.78 (d, 1H), 7.70 (m, 1H), 7.09 (d, 2H), 3.86 (s, 3H).

Example No. I.1-122

$^1$H NMR (400 MHz, d$_6$-DMSO δ, ppm) 12.35 (br. s, 1H, NH), 8.03 (d, 1H), 7.79 (dd, 1H), 7.65 (d. 1H), 2.48 (m, 1H), 1.73 (m, 2H), 1.61 (m, 2H), 0.79 (t, 6H).

Example No. I.1-123

$^1$H NMR (400 MHz, d$_6$-DMSO δ, ppm) 12.29 (br. s, 1H, NH), 8.03 (d, 1H), 7.80 (dd, 1H), 7.64 (d, 1H), 2.51 (s, 2H), 1.00 (s, 9H).

Example No. I.1-124

$^1$H NMR (400 MHz, d$_6$-DMSO δ, ppm) 12.20 (br. s, 1H, NH), 7.73 (m, 1H), 7.43 (d, 1H), 7.19 (m, 1H), 2.46 (m, 1H), 1.73 (m, 2H), 1.61 (m, 2H), 0.80 (t, 6H).

Example No. I.1-125

$^1$H NMR (400 MHz, d$_6$-DMSO δ, ppm) 12.12 (br. s, 1H, NH), 7.73 (m, 1H), 7.42 (d, 1H), 7.18 (m, 1H), 2.48 (s, 2H), 1.00 (s, 9H).

Example No. I.1-126

$^1$H NMR (400 MHz, d$_6$-DMSO δ, ppm) 12.42 (br. s, 1H, NH), 8.19 (d, 2H), 7.78 (m, 1H), 7.52 (d, 1H), 7.21 (m, 1H), 7.09 (d, 2H), 3.85 (s, 3H).

Example No. I.1-127

$^1$H NMR (400 MHz, d$_6$-DMSO δ, ppm) 12.68 (br. s, 1H, NH), 8.02 (d, 1H), 7.84 (s, 1H), 7.72 (m, 2H), 7.61 (d, 1H), 7.46 (dd, 1H), 2.52 (s, 3H).

Example No. I.1-128

$^1$H NMR (400 MHz, d$_6$-DMSO δ, ppm) 12.12 (br. s, 1H, NH), 7.92 (d, 1H), 7.63 (d, 1H), 7.32 (dd, 1H), 2.53 (m, 1H), 1.78 (m, 2H), 1.64 (m, 2H), 0.82 (t, 6H).

Example No. I.1-129

$^1$H NMR (400 MHz, d$_6$-DMSO δ, ppm) 12.09 (br. s, 1H, NH), 7.92 (d, 1H), 7.63 (d, 1H), 7.33 (dd, 1H), 2.51 (s, 2H), 1.02 (s, 9H).

Example No. I.1-130

$^1$H NMR (400 MHz, d$_6$-DMSO δ, ppm) 12.17 (br. s, 1H, NH), 8.08 (d, 1H), 7.77 (dd, 1H), 7.61 (d, 1H), 7.46 (dd, 1H), 2.48 (m, 1H), 1.76 (m, 2H), 1.62 (m, 2H), 0.80 (t, 6H).

Example No. I.1-131

$^1$H NMR (400 MHz, d$_6$-DMSO δ, ppm) 12.22 (br. s. 1H, NH), 8.06 (d, 1H), 7.75 (dd, 1H), 7.63 (d, 1H), 7.44 (dd, 1H), 2.94 (m, 2H), 2.73 (m, 2H), 2.62 (s, 3H).

Example No. I.1-132

$^1$H NMR (400 MHz, d$_6$-DMSO δ, ppm) 12.10 (br. s. 1H, NH), 8.09 (d, 1H), 7.78 (dd, 1H), 7.62 (d, 1H), 7.47 (dd, 1H), 2.49 (s, 2H), 1.01 (s, 9H).

Example No. I.1-133

$^1$H NMR (400 MHz, d$_6$-DMSO δ, ppm) 12.42 (br. s, 1H, NH), 8.20 (d, 2H), 8.13 (d, 1H), 7.82 (dd, 1H), 7.71 (d, 1H), 7.49 (dd, 1H), 7.10 (d, 2H), 3.86 (s, 3H).

Example No. I.1-134

$^1$H NMR (400 MHz, d$_6$-DMSO δ, ppm) 12.24 (br. s, 1H, NH), 8.08 (d, 1H), 7.67 (d, 1H), 7.50 (dd, 1H), 2.48 (s, 2H), 1.00 (s, 9H).

Example No. I.1-135

$^1$H NMR (400 MHz, d$_6$-DMSO δ, ppm) 12.57 (br. s, 1H, NH), 8.19 (d, 2H), 8.11 (d, 1H), 7.76 (d, 1H), 7.51 (dd, 1H), 7.10 (d, 2H), 3.86 (s, 3H).

Example No. I.1-136

$^1$H NMR (400 MHz, d$_6$-DMSO δ, ppm) 12.07 (br. s, 1H, NH), 7.88 (d, 1H), 7.69 (dd, 1H), 7.51 (d, 1H), 2.47 (m, 1H), 2.42 (s, 3H), 1.73 (m, 2H), 1.60 (m, 2H), 0.79 (t, 6H).

Example No. I.1-137

$^1$H NMR (400 MHz, d$_6$-DMSO δ, ppm) 12.01 (br. s, 1H, NH), 7.88 (d, 1H), 7.60 (dd, 1H), 7.51 (d, 1H), 2.49 (s, 2H), 2.42 (s, 3H), 1.00 (s, 9H).

Example No. I.1-138

$^1$H NMR (400 MHz, CDCl$_3$ δ, ppm) 10.28 (br. s, 1H, NH), 9.12 (br. s, 1H, NH), 8.29 (d, 1H), 7.69 (m, 2H), 7.57 (s, 1H), 7.40 (dd, 1H), 2.83 (s, 3H).

Example No. I.1-139

$^1$H NMR (400 MHz, d$_6$-DMSO δ, ppm) 12.67 (br. s, 1H, NH), 9.56 (br. s, 1H, NH), 8.09 (d, 1H), 7.79 (d, 1H), 7.67 (s, 1H), 7.43 (dd, 1H), 2.69 (s, 3H).

Example No. I.1-140

$^1$H NMR (400 MHz, d$_6$-DMSO δ, ppm) 13.91 (br. s, 1H, NH), 12.28 (br. s, 1H, NH), 8.22 (s, 1H), 8.09 (d, 1H), 7.86 (dd, 1H), 7.71 (d, 1H).

Example No. I.1-142

$^1$H NMR (400 MHz, CDCl$_3$ δ, ppm) 10.12 (br. s, 1H, NH), 9.43 (br. s, 1H, NH), 8.21 (d, 1H), 7.69 (dd, 1H), 7.60 (d, 1H), 3.92 (d, 2H), 2.69 (s, 3H).

Example No. I.1-143

$^1$H NMR (400 MHz, CDCl$_3$ δ, ppm) 9.72 (br. s, 1H, NH), 8.23 (d, 1H), 8.03 (br. s, 1H, NH), 7.76 (s, 1H), 7.49 (m, 1H), 5.29 (s, 2H), 1.55 (s, 9H).

Example No. I.1-144

$^1$H NMR (400 MHz, d$_6$-DMSO δ, ppm) 12.68 (br. s, 1H, NH), 11.38 (br. s, 1H, NH), 8.28 (d, 1H), 7.90 (s, 1H), 7.79 (s, 1H), 7.69 (d, 1H), 2.70 (s, 3H).

Example No. I.1-145

$^1$H NMR (400 MHz, d$_6$-DMSO δ, ppm) 12.21 (br. s, 1H, NH), 7.91 (d, 1H), 7.63 (d, 1H), 7.34 (dd, 1H), 7.29 (m, 4H), 7.19 (m, 1H), 3.08 (m, 2H), 2.91 (m, 2H), 2.53 (s, 3H).

Example No. I.1-146

$^1$H NMR (400 MHz, d$_6$-DMSO δ, ppm) 12.24 (br. s, 1H, NH), 9.42 (br. s, 1H, OH), 7.48 (d, 1H), 7.25 (dd, 1H), 7.17 (d, 1H), 2.62 (t, 1H), 1.73 (quint, 2H), 1.34 (sext, 2H), 0.91 (t, 3H).

Example No. I.1-147

$^1$H NMR (400 MHz, d$_6$-DMSO δ, ppm) 12.40 (br. s, 1H, NH), 9.09 (br. s, 1H, OH), 7.47 (d, 1H), 7.20 (dd, 1H), 7.12 (d, 1H), 1.96 (m, 1H), 1.25 (m, 2H), 1.00 (m, 2H).

Example No. I.1-148

$^1$H NMR (400 MHz, d$_6$-DMSO δ, ppm) 12.10 (br. s, 1H, NH), 9.18 (br. s, 1H, OH), 7.49 (d, 1H), 7.25 (dd, 1H), 7.17 (d, 1H), 3.02 (quint. 1H), 1.98 (m, 4H), 1.76 (m, 2H). 1.60 (m, 2H).

Example No. I.1-149

$^1$H NMR (400 MHz, d$_6$-DMSO δ, ppm) 12.05 (br. s, 1H, NH), 9.19 (br. s, 1H, OH), 7.48 (d, 1H), 7.24 (dd, 1H), 7.16 (d, 1H), 2.59 (m, 1H), 1.87 (m, 2H), 1.81 (m, 2H), 1.69 (m, 3H), 1.30 (m, 3H).

Example No. I.1-150

$^1$H NMR (40) MHz, d$_6$-DMSO δ, ppm) 12.15 (br. s, 1H, NH), 9.35 (br. s, 1H, OH), 7.49 (d, 1H), 7.28 (dd, 1H), 7.18 (d, 1H), 2.92 (sept, 1H), 1.29 (d, 6H).

Example No. I.1-151

$^1$H NMR (400 MHz, d$_6$-DMSO δ, ppm) 12.52 (br. s, 1H, NH), 9.69 (br. s, 1H, OH), 8.37 (d, 2H), 7.74 (d, 2H), 7.55 (d, 1H), 7.35 (dd, 1H), 7.22 (d, 1H).

Example No. I.1-152

$^1$H NMR (400 MHz, d$_6$-DMSO δ, ppm) 12.66 (br. s, 1H, NH), 8.19 (d, 1H), 7.84 (d, 1H), 7.68 (d, 1H), 7.41 (dd, 1H), 7.37 (d, 1H), 7.21 (m, 1H), 3.94 (s, 3H).

Example No. I.1-153

$^1$H NMR (400 MHz, d$_6$-DMSO δ, ppm) 12.20 (br. s, 1H, NH), 7.61 (d, 1H), 7.37 (dd, 1H), 7.30 (d, 1H), 3.89 (s, 3H), 2.59 (t, 1H), 1.69 (quint, 2H), 1.33 (sext, 2H), 0.92 (t, 3H).

Example No. I.1-154

$^1$H NMR (400 MHz, d$_6$-DMSO δ, ppm) 12.12 (br. s, 1H, NH), 7.62 (d, 1H), 7.36 (dd, 1H), 7.30 (d, 1H), 3.90 (s, 3H), 2.88 (sept, 1H), 1.25 (d, 6H).

Example No. I.1-155

$^1$H NMR (400 MHz, d$_6$-DMSO δ, ppm) 12.64 (br. s, 1H, NH), 8.12 (d, 2H), 7.77 (d, 2H), 7.69 (d, 1H), 7.46 (dd, 1H), 7.38 (d, 1H), 3.96 (s, 3H).

Example No. I.1-156

$^1$H NMR (400 MHz, d$_6$-DMSO δ, ppm) 12.09 (br. s, 1H, NH), 7.62 (d, 1H), 7.36 (dd, 1H), 7.29 (d, 1H), 3.88 (s, 3H), 2.56 (m, 1H), 1.88 (m, 2H), 1.79 (m, 2H), 1.65 (m, 2H), 1.57 (m, 2H), 1.25 (m, 2H).

Example No. I.1-157

$^1$H NMR (400 MHz, d$_6$-DMSO δ, ppm) 12.13 (br. s, 1H, NH), 7.61 (d, 1H), 7.36 (dd, 1H), 7.29 (d, 1H), 3.89 (s, 3H), 3.00 (quint, 1H), 1.94 (m, 2H), 1.87 (m, 2H), 1.75 (m, 2H), 1.59 (m, 2H).

Example No. I.1-158

$^1$H NMR (400 MHz, d$_6$-DMSO δ, ppm) 12.42 (br. s. 1H, NH), 7.59 (d, 1H), 7.29 (dd, 1H), 7.25 (d, 1H), 3.86 (s, 3H), 1.94 (m, 1H), 1.09 (m, 2H), 0.99 (m, 2H).

Example No. I.1-159

$^1$H NMR (400 MHz, d$_6$-DMSO δ, ppm) 12.68 (br. s, 1H, NH), 8.39 (m, 1H), 7.42 (d, 2H), 7.40 (d, 2H), 7.21 (d, 1H), 6.96 (d, 1H), 3.79 (s, 3H).

Example No. I.1-161

$^1$H NMR (400 MHz, d$_6$-DMSO δ, ppm) 12.01 (br. s, 1H, NH), 9.29 (br. s, 1H, OH), 7.48 (d, 1H), 7.26 (dd, 1H), 7.18 (d, 1H), 3.49 (quint, 1H), 2.52 (m, 2H), 2.20 (m, 2H), 1.98 (m, 1H), 1.85 (m, 1H).

Example No. I.1-162

$^1$H NMR (400 MHz, d$_6$-DMSO δ, ppm) 12.02 (br. s, 1H, NH), 7.61 (d, 1H), 7.33 (dd, 1H), 7.30 (d, 1H), 3.90 (s, 3H), 3.48 (quint, 1H), 2.40 (m, 2H), 2.22 (m, 2H), 1.95 (m, 1H), 1.82 (m, 1H).

Example No. I.1-163

$^1$H NMR (400 MHz, d$_6$-DMSO δ, ppm) 12.32 (br. s, 1H, NH), 7.88 (d, 1H), 7.63 (m, 3H), 7.47-7.33 (m, 5H), 7.00 (d, 1H), 3.92 (s, 3H).

Example No. I.1-164

$^1$H NMR (400 MHz, d$_6$-DMSO δ, ppm) 12.58 (br. s, 1H, NH), 9.57 (br. s, 1H, OH), 8.20 (d, 1H), 7.84 (d, 1H), 7.54 (d, 1H), 7.29 (dd, 1H), 7.22 (m, 2H).

Example No. I.1-165

$^1$H NMR (400 MHz, d$_6$-DMSO δ, ppm) 12.04 (br. s, 1H, NH), 8.22 (s, 1H), 7.48 (s, 1H), 7.13 (s, 1H), 6.52 (br. s, 1H, NH), 2.21 (s, 3H).

Example No. I.1-166

$^1$H NMR (400 MHz, d$_6$-DMSO δ, ppm) 12.89 (br. s, 1H, NH), 11.50 (br. s, 1H, NH), 11.32 (br. s, 1H, NH), 7.97 (d, 1H), 7.69 (d, 1H), 7.42 (dd, 1H), 4.33 (q, 2H), 2.68 (s, 3H), 1.32 (t, 3H).

Example No. I.1-167

$^1$H NMR (400 MHz, d$_6$-DMSO δ, ppm) 13.02 (br. s, 1H, NH), 11.98 (br. s, 1H, NH), 8.11 (s, 1H), 7.94 (d, 1H), 7.69 (d, 1H), 7.40 (dd, 1H), 2.63 (s, 3H).

Example No. I.1-168

$^1$H NMR (400 MHz, d$_6$-DMSO δ, ppm) 12.02 (br. s, 1H, NH), 9.88 (br. s, 1H, NH), 8.09 (d, 1H), 7.98 (dd, 1H), 7.95 (br. s, 1H, NH), 7.84 (d, 1H), 4.29 (q, 2H), 1.26 (t, 3H).

Example No. I.1-169

$^1$H NMR (400 MHz, d$_6$-DMSO δ, ppm) 9.88 (br. s, 1H, NH), 8.14 (s, 1H), 8.09 (d, 1H), 7.94 (d, 1H), 7.42 (dd, 1H), 6.70 (br. s, 1H, NH).

Example No. I.1-170

$^1$H NMR (400 MHz, d$_6$-DMSO δ, ppm) 10.35 (br. s, 1H, NH), 7.84 (s, 1H), 7.71 (s, 1H), 7.28 (m, 4H), 7.19 (m. 1H), 3.08 (m, 2H), 2.92 (m, 2H), 2.54 (s, 3H).

Example No. I.1-171

$^1$H NMR (400 MHz, d$_6$-DMSO δ, ppm) 12.12 (br. s, 1H, NH), 7.90 (d, 1H), 7.62 (d, 1H), 7.33 (dd, 1H), 2.73 (s, 3H), 2.22 (q, 2H), 1.27 (t, 3H).

Example No. I.1-172

$^1$H NMR (400 MHz, d$_6$-DMSO δ, ppm) 10.98 (br. s, 1H, NH), 8.05 (d, 1H), 7.93 (d, 1H), 7.44 (dd, 1H), 7.30 (m, 4H), 7.19 (m, 1H), 3.09 (m, 2H), 2.93 (m, 2H).

Example No. I.1-173

$^1$H NMR (400 MHz, d$_6$-DMSO δ, ppm) 12.58 (br. s, 1H. NH), 8.04 (d, 1H), 7.81 (dd, 1H), 7.70 (d, 1H), 7.55 (d, 1H), 6.40 (d, 1H), 2.77 (q, 2H), 1.27 (t, 3H).

Example No. I.1-174

$^1$H NMR (400 MHz, d$_6$-DMSO δ, ppm) 12.37 (br. s, 1H, NH), 7.74 (m, 1H), 7.56 (d, 1H), 7.48 (d, 1H), 7.19 (dd, 1H), 6.41 (d, 1H), 2.74 (q, 2H), 1.26 (t, 3H).

Example No. I.1-175

$^1$H NMR (400 MHz, d$_6$-DMSO δ, ppm) 12.36 (br. s, 1H, NH), 7.95 (d, 1H), 7.67 (d, 1H), 7.51 (d, 1H), 7.34 (dd, 1H), 6.39 (d, 1H), 2.78 (q, 2H), 2.58 (s, 3H), 1.26 (t, 3H).

Example No. I.1-176

$^1$H NMR (400 MHz, d$_6$-DMSO δ, ppm) 12.39 (br. s, 1H, NH), 8.46 (s, 1H), 8.02 (s, 1H), 7.77 (m, 1H), 7.48 (d, 1H), 7.20 (dd, 1H), 3.83 (s, 3H).

Example No. I.1-177

$^1$H NMR (400 MHz, d$_6$-DMSO δ, ppm) 12.50 (br. s, 1H, NH), 8.10 (d, 1H), 8.01 (s, 1H), 7.93 (s, 1H), 7.73 (d, 1H), 7.50 (dd, 1H), 4.02 (s, 3H).

Example No. I.1-178

$^1$H NMR (400 MHz, d$_6$-DMSO δ, ppm) 12.39 (br. s, 1H, NH), 8.03 (s, 1H), 7.96 (d, 1H), 7.94 (s, 1H), 7.68 (d, 1H), 7.37 (dd, 1H), 3.82 (s, 3H), 2.58 (s, 3H).

Example No. I.1-179

$^1$H NMR (400 MHz, d$_6$-DMSO δ, ppm) 12.78 (br. s, 1H, NH), 8.11 (d, 1H), 8.00 (s, 1H), 7.95 (d, 1H), 7.87 (d, 1H), 7.78 (d, 1H), 7.74 (d, 1H), 7.72 (d, 1H), 7.54 (dd, 1H). 7.22 (d, 1H).

Example No. I.1-180

$^1$H NMR (400 MHz, d$_6$-DMSO δ, ppm) 12.79 (br. s, 1H, NH), 8.12 (d, 1H), 7.81 (s, 1H), 7.77 (m, 2H), 7.66 (d, 1H), 7.53 (d, 1H), 7.51 (dd, 1H), 7.44 (dd, 1H), 7.23 (d, 1H).

Example No. I.1-181

$^1$H NMR (400 MHz, d$_6$-DMSO δ, ppm) 12.80 (br. s, 1H, NH), 8.11 (d, 1H), 7.81 (s, 1H), 7.75 (d, 1H), 7.71 (dd, 1H), 7.57 (m, 2H), 7.40 (dd, 1H), 7.33 (dd, 1H), 7.23 (d, 1H).

Example No. I.1-182

$^1$H NMR (400 MHz, d$_6$-DMSO δ, ppm) 12.52 (br. s, 1H, NH), 8.04 (d, 1H), 7.82 (dd, 1H), 7.70 (d, 1H), 7.56 (d, 1H), 6.40 (d, 1H), 2.74 (q, 2H), 1.25 (t, 3H).

Example No. I.1-183

$^1$H NMR (400 MHz, d$_6$-DMSO δ, ppm) 12.32 (br. s, 1H, NH), 8.10 (d, 1H), 7.96 (s, 1H), 7.73 (d, 1H), 7.62 (d, 1H), 7.51 (dd, 1H), 7.49 (d, 1H), 7.19-6.91 (t, 1H), 6.99-6.71 (t, 1H), 6.69 (dd, 1H), 5.68 (s, 2H).

Example No. I.1-184

$^1$H NMR (400 MHz, d$_6$-DMSO δ, ppm) 9.91 (br. s, 1H, NH), 8.05 (d, 1H), 7.73 (m, 1H), 7.41 (d, 1H), 7.18 (m, 1H), 6.93 (d, 1H), 6.63 (d, 1H), 2.78 (s, 3H).

Example No. I.1-185

$^1$H NMR (400 MHz, d$_6$-DMSO δ, ppm) 12.67 (br. s, 1H, NH), 7.73 (m, 3H), 7.57 (m, 2H), 7.42 (dd, 1H), 7.31 (dd, 1H), 7.23 (m, 2H).

Example No. I.1-186

$^1$H NMR (400 MHz, d$_6$-DMSO δ, ppm) 11.87 (br. s, 1H, NH), 8.62 (s, 1H), 7.72 (m, 1H), 7.40 (d, 1H), 7.14 (dd, 1H), 3.18 (s, 6H), 2.51 (s, 3H).

Example No. I.1-187

$^1$H NMR (400 MHz, d$_6$-DMSO δ, ppm) 12.66 (br. s, 1H, NH), 8.00 (m, 1H), 7.96 (d, 1H), 7.87 (d, 1H), 7.79 (m, 1H), 7.72 (m, 2H), 7.54 (d, 1H), 7.24 (m, 2H).

Example No. I.1-188

$^1$H NMR (400 MHz, d$_6$-DMSO δ, ppm) 12.69 (br. s, 1H, NH), 7.77 (m, 3H), 7.64 (d, 1H), 7.51 (m, 2H), 7.44 (dd, 1H), 7.22 (m, 2H).

Example No. I.1-189

$^1$H NMR (400 MHz, d$_6$-DMSO δ, ppm) 12.48 (br. s, 1H, NH), 7.99 (d, 1H), 7.89 (d, 1H), 7.60 (dd, 1H), 7.51 (d, 1H), 6.92 (d, 1H), 2.51 (s, 3H), 2.43 (s, 1H).

Example No. I.1-190

$^1$H NMR (400 MHz, d$_6$-DMSO δ, ppm) 12.40 (br. s, 1H, NH), 7.97 (d, 1H), 7.88 (d, 1H), 7.63 (dd, 1H), 7.55 (d, 1H), 6.40 (d, 1H), 2.74 (q, 2H), 2.47 (s, 3H), 1.26 (t, 3H).

Example No. I.1-191

$^1$H NMR (400 MHz, d$_6$-DMSO δ, ppm) 12.10 (br. s, 1H, NH), 7.92 (s, 1H), 7.69 (d, 1H), 7.64 (m, 1H), 7.58 (d, 1H), 7.05 (s, 1H), 2.52 (s, 3H), 2.46 (s, 3H).

Example No. I.1-192

$^1$H NMR (400 MHz, d$_6$-DMSO δ, ppm) 12.33 (br. s, 1H, NH), 8.60 (s, 1H), 7.91 (d, 1H), 7.86 (d, 1H), 7.61 (dd, 1H), 7.59 (d, 1H), 7.13 (s, 1H), 2.53 (s, 3H).

Example No. I.1-193

$^1$H NMR (400 MHz, d$_6$-DMSO δ, ppm) 12.28 (br. s, 1H, NH), 7.95 (s, 1H), 7.63 (m, 3H), 2.50 (s, 3H), 2.44 (s, 3H).

Example No. I.1-194

$^1$H NMR (400 MHz, d$_6$-DMSO δ, ppm) 11.86 (br. s, 1H, NH), 8.61 (s, 1H), 7.88 (s, 1H), 7.60 (d, 1H), 7.52 (d, 1H), 3.19 (s, 6H), 2.52 (s, 3H), 2.42 (s, 3H).

Example No. I.1-195

$^1$H NMR (400 MHz, d$_6$-DMSO δ, ppm) 11.98 (br. s, 1H, NH), 7.89 (d, 1H), 7.59 (dd, 1H), 7.53 (d, 1H), 7.19 (m, 1H), 7.08 (m, 1H), 6.13 (m, 1H), 4.06 (s, 3H), 2.43 (s, 3H).

Example No. I.1-196

$^1$H NMR (400 MHz, d$_6$-DMSO δ, ppm) 12.36 (br. s, 1H, NH), 7.91 (d, 1H), 7.62 (m, 2H), 7.56 (d, 1H), 6.56 (d, 1H), 5.48 (br. s, 1H, OH), 4.51 (s, 2H), 2.44 (s, 3H).

Example No. I.1-197

$^1$H NMR (400 MHz, d$_6$-DMSO δ, ppm) 12.19 (br. s, 1H, NH), 8.08 (d, 1H), 7.78 (d, 1H), 7.44 (dd, 1H), 7.27 (m, 1H), 7.12 (m, 1H), 6.17 (m, 1H), 4.06 (s, 3H).

Example No. I.1-198

$^1$H NMR (400 MHz, d$_6$-DMSO δ, ppm) 12.21 (br. s, 1H, NH), 8.03 (d, 1H), 7.79 (dd, 1H), 7.63 (d. 1H), 7.23 (m, 1H), 7.11 (m, 1H), 6.16 (m, 1H), 4.07 (s, 3H).

Example No. I.1-199

$^1$H NMR (400 MHz, d$_6$-DMSO δ, ppm) 12.80 (br. s, 1H, NH), 8.25 (d, 1H), 8.08 (d, 1H), 7.96 (d, 1H), 7.90 (d, 1H), 7.44 (dd, 1H), 7.23 (dd, 1H).

Example No. I.1-200

$^1$H NMR (400 MHz, d$_6$-DMSO δ, ppm) 12.54 (br. s, 1H, NH), 8.04 (d, 1H), 8.00 (s, 1H), 7.92 (s, 1H), 7.83 (dd, 1H), 7.69 (d. 1H), 4.03 (s, 3H).

Example No. I.1-201

$^1$H NMR (400 MHz, d$_6$-DMSO δ, ppm) 12.92 (br. s, 1H, NH), 8.25 (s, 1H), 8.08 (d, 1H), 8.02 (s, 1H), 7.97 (d, 1H), 7.46 (dd. 1H).

Example No. I.1-202

$^1$H NMR (400 MHz, d$_6$-DMSO δ, ppm) 12.78 (br. s, 1H, NH), 8.08 (m, 2H), 7.93 (d, 1H), 7.42 (dd, 1H), 6.96 (d, 1H), 2.57 (s, 3H).

Example No. I.1-203

$^1$H NMR (400 MHz, d$_6$-DMSO δ, ppm) 12.59 (br. s, 1H, NH), 8.08 (d, 1H), 7.95 (d, 1H), 7.60 (d. 1H), 7.42 (dd, 1H), 6.91 (d, 1H), 2.43 (s, 3H).

Example No. I.1-204

$^1$H NMR (400 MHz, d$_6$-DMSO δ, ppm) 12.82 (br. s, 1H, NH), 8.18 (d, 2H), 8.11 (d, 1H), 7.99 (d, 1H), 7.80 (d, 2H), 7.49 (dd, 1H).

Example No. I.1-205

$^1$H NMR (400 MHz, d$_6$-DMSO δ, ppm) 12.50 (br. s, 1H, NH), 8.04 (d, 1H), 7.97 (d, 1H), 7.83 (dd, 1H), 7.67 (m, 3H), 7.43 (m, 3H), 6.99 (d, 1H).

Example No. I.1-206

$^1$H NMR (400 MHz, d$_6$-DMSO δ, ppm) 12.31 (br. s, 1H, NH), 8.01 (d, 1H), 7.79 (dd, 1H), 7.61 (d, 1H), 3.04 (m, 1H), 2.12 (m, 1H), 1.99 (m, 1H), 1.88 (m, 2H), 1.72 (m, 2H), 1.63 (m, 2H).

Example No. I.1-207

$^1$H NMR (400 MHz, d$_6$-DMSO δ, ppm) 12.37 (br. s, 1H, NH), 8.42 (s, 1H), 8.10 (d, 1H), 7.93 (d, 1H), 7.60 (d, 1H), 7.44 (dd, 1H), 6.88 (m, 1H).

Example No. I.1-208

$^1$H NMR (400 MHz, d$_6$-DMSO δ, ppm) 12.48 (br. s, 1H, NH), 8.24 (d, 1H), 7.91 (d, 1H), 7.63 (d, 1H), 7.46 (dd, 1H), 6.98 (d, 1H), 2.43 (s, 3H).

Example No. I.1-209

$^1$H NMR (400 MHz, d$_6$-DMSO δ, ppm) 12.70 (br. s, 1H, NH), 8.09 (d, 1H), 7.94 (d, 1H), 7.61 (d, 1H), 7.44 (dd. 1H), 6.93 (d, 1H), 2.64 (q, 2H), 1.29 (t, 3H).

Example No. I.1-210

$^1$H NMR (400 MHz, d$_6$-DMSO δ, ppm) 12.42 (br. s, 1H, NH), 8.06 (d, 1H), 7.93 (d, 1H), 7.44 (dd, 1H), 2.73 (q, 2H), 1.39 (t, 3H).

Example No. I.1-211

$^1$H NMR (400 MHz, d$_6$-DMSO δ, ppm) 12.70 (br. s, 1H, NH), 7.79 (m, 1H), 7.64 (d, 1H), 7.47 (m, 1H), 7.28 (m, 4H), 7.22 (m, 1H), 3.10 (m, 2H), 2.95 (m, 2H).

Example No. I.1-212

$^1$H NMR (400 MHz, d$_6$-DMSO δ, ppm) 12.31 (br. s. 1H, NH), 8.01 (d, 1H), 7.79 (dd, 1H), 7.62 (d, 1H), 2.60 (t, 2H), 1.69 (quint, 2H), 1.33 (sext, 2H), 0.90 (t, 3H).

Example No. I.1-213

$^1$H NMR (400 MHz, d$_6$-DMSO δ, ppm) 12.33 (br. s, 1H, NH), 7.97 (d, 1H), 7.78 (m, 1H), 7.68 (m, 2H), 7.45 (m, 4H), 7.20 (m, 1H), 6.98 (d, 1H).

Example No. I.1-214

$^1$H NMR (400 MHz. CDCl$_3$ δ, ppm) 11.12 (br. s, 1H, NH), 8.29 (d, 1H), 7.97 (d, 1H), 7.59 (dd, 1H).

Example No. I.1-215

$^1$H NMR (400 MHz, d$_6$-DMSO δ, ppm) 12.75 (br. s, 1H, NH), 8.11 (d, 1H), 7.86 (d, 1H), 7.75 (m, 1H), 7.54 (d, 2H), 7.28 (d, 2H), 6.73 (d, 1H), 6.48 (d, 1H).

Example No. I.1-216

$^1$H NMR (400 MHz, d$_6$-DMSO δ, ppm) 12.29 (br. s, 1H, NH), 7.74 (m, 1H), 7.65 (m, 2H), 2.59 (t, 2H), 1.73 (sext, 2H), 0.93 (t, 3H).

Example No. I.1-221

$^1$H NMR (400 MHz, d$_6$-DMSO δ, ppm) 12.40 (br. s, 1H, NH), 8.05 (d, 1H), 7.92 (d, 1H), 7.41 (dd, 1H), 2.91 (sept, 2H), 1.28 (d, 6H).

Example No. I.1-222

$^1$H NMR (400 MHz, d$_6$-DMSO δ, ppm) 12.27 (br. s, 1H, NH), 8.04 (d, 1H), 7.90 (d, 1H), 7.42 (dd, 1H), 2.53 (m, 2H), 2.22 (m, 1H), 0.96 (d, 6H).

Example No. I.1-223

$^1$H NMR (400 MHz, d$_6$-DMSO δ, ppm) 12.09 (br. s, 1H, NH), 8.08 (d, 1H), 7.75 (dd, 1H), 7.59 (d, 1H), 7.43 (dd, 1H), 3.03 (quint, 1H), 2.00 (m, 2H), 1.90 (m, 2H), 1.76 (m, 2H), 1.61 (m, 2H).

Example No. I.1-224

$^1$H NMR (400 MHz, d$_6$-DMSO δ, ppm) 12.05 (br. s, 1H, NH), 8.09 (d, 1H), 7.74 (dd, 1H), 7.59 (d, 1H), 7.43 (dd, 1H), 2.60 (m, 1H), 1.90 (m, 2H), 1.80 (m, 2H), 1.69 (m, 1H), 1.60 (m, 2H), 1.25 (m, 3H).

Example No. I.1-228

$^1$H NMR (400 MHz, d$_6$-DMSO δ, ppm) 12.87 (br. s, 1H, NH), 8.32 (d, 1H), 8.28 (m, 2H), 8.03 (s, 1H), 7.79 (d, 1H), 7.41 (m, 2H).

Example No. I.1-229

$^1$H NMR (400 MHz, d$_6$-DMSO δ, ppm) 12.10 (br. s, 1H, NH), 8.22 (d, 1H), 7.78 (s, 1H), 7.69 (d, 1H), 2.00 (m, 1H), 1.12 (m, 2H), 1.09 (m, 2H).

Example No. I.1-230

$^1$H NMR (400 MHz, d$_6$-DMSO δ, ppm) 12.42 (br. s, 1H, NH), 8.29 (d, 1H), 7.91 (s, 1H), 7.73 (d, 1H), 2.92 (m, 1H), 1.29 (d, 6H).

Example No. I.1-231

$^1$H NMR (400 MHz, d$_6$-DMSO δ, ppm) 12.25 (br. s, 1H, NH), 8.28 (d, 1H), 7.91 (s, 1H), 7.74 (d, 1H), 2.54 (m, 2H), 2.20 (m, 1H), 0.94 (d, 6H).

Example No. I.1-232

$^1$H NMR (400 MHz, d$_6$-DMSO δ, ppm) 12.36 (br. s, 1H, NH), 8.26 (d, 1H), 7.89 (s, 1H), 7.72 (d. 1H), 3.09 (m, 1H), 2.01 (m, 2H), 1.95 (m, 2H), 1.78 (m, 2H), 1.62 (m, 2H).

Example No. I.1-233

$^1$H NMR (400 MHz, d$_6$-DMSO δ, ppm) 12.72 (br. s, 1H, NH), 8.25 (d, 1H), 7.88 (s, 1H), 7.72 (d, 1H), 2.61 (m, 1H), 1.92 (m, 2H), 1.80 (m, 2H), 1.69 (m, 1H), 1.60 (m, 1H), 1.27 (m, 4H).

Example No. I.1-234

$^1$H NMR (400 MHz, d$_6$-DMSO δ, ppm) 12.48 (br. s, 1H, NH), 8.27 (d, 1H), 7.89 (s, 1H), 7.72 (d, 1H), 2.62 (t, 2H), 1.72 (quint, 2H), 1.38 (sext, 2H), 0.91 (t, 3H).

Example No. I.1-236

$^1$H NMR (400 MHz, d$_6$-DMSO δ, ppm) 12.68 (br. s, 1H, NH), 8.30 (d, 1H), 8.19 (d, 2H), 7.99 (s, 1H), 7.72 (m, 3H).

Example No. I.1-237

$^1$H NMR (400 MHz, d$_6$-DMSO δ, ppm) 12.05 (br. s, 1H, NH), 8.30 (d, 1H), 8.24 (m, 2H), 7.99 (s, 1H), 7.71 (d, 1H), 7.55 (m, 3H).

Example No. I.1-238

$^1$H NMR (400 MHz, d$_6$-DMSO δ, ppm) 12.40 (br. s, 1H, NH), 8.28 (d, 1H), 8.02 (m, 1H), 7.99 (s, 1H), 7.73 (d, 1H), 7.62 (d, 1H), 6.77 (d, 1H),

Example No. I.1-239

$^1$H NMR (400 MHz, d$_6$-DMSO δ, ppm) 12.24 (br. s. 1H, NH), 8.30 (d, 1H), 8.24 (d, 2H), 7.97 (s, 1H), 7.71 (d, 1H), 7.10 (d, 2H), 3.86 (s, 3H).

Example No. I.1-240

$^1$H NMR (400 MHz, d$_6$-DMSO δ, ppm) 12.70 (br. s, 1H, NH), 8.25 (d, 1H), 7.90 (s, 1H), 7.72 (d, 1H), 7.39 (m, 1H), 7.31 (m, 3H), 7.22 (m, 1H), 3.97 (s, 2H).

Example No. I.1-246

$^1$H NMR (400 MHz, d$_6$-DMSO δ, ppm) 12.10 (br. s, 1H, NH), 8.11 (m, 1H), 7.40 (m, 1H), 7.29 (m, 1H), 3.49 (m, 1H), 2.42 (m, 2H), 2.25 (m, 2H), 1.99 (m, 1H), 1.85 (m, 1H).

Example No. I.1-248

$^1$H NMR (400 MHz, d$_6$-DMSO δ, ppm) 12.70 (br. s, 1H, NH), 8.10 (m, 1H), 7.31 (m, 1H), 7.27 (m, 1H), 2.58 (m, 1H), 1.90 (m, 2H), 1.81 (m, 2H), 1.59 (m, 2H), 1.29 (m, 4H).

Example No. I.1-249

$^1$H NMR (400 MHz, d$_6$-DMSO δ, ppm) 12.20 (br. s, 1H, NH), 8.11 (m, 1H), 7.32 (m, 1H), 7.29 (m, 1H), 2.56 (1, 2H), 1.72 (sext, 2H), 0.92 (t, 3H).

Example No. I.1-250

$^1$H NMR (400 MHz, d$_6$-DMSO δ, ppm) 12.79 (br. s, 1H, NH), 7.98 (m, 1H), 7.75 (d, 1H), 7.10 (m, 2H), 6.96 (m, 1H), 6.59 (m, 1H).

Example No. I.1-252

$^1$H NMR (400 MHz, d$_6$-DMSO δ, ppm) 12.02 (br. s. 1H, NH), 8.10 (m, 1H), 7.30 (m, 1H), 7.23 (m, 1H), 3.02 (quint, 1H), 1.96 (m, 2H), 1.88 (m, 2H), 1.71 (m, 2H), 1.59 (m, 2H).

Example No. I.1-255

$^1$H NMR (400 MHz, d$_6$-DMSO δ, ppm) 12.60 (br. s, 1H, NH), 7.92 (m, 1H), 7.51 (m, 1H), 1.98 (m, 1H), 1.08 (m, 4H).

Example No. I.1-256

¹H NMR (400 MHz, d₆-DMSO δ, ppm) 12.32 (br. s, 1H, NH), 7.96 (m, 1H), 7.62 (m, 1H), 2.59 (m, 1H), 1.90 (m, 2H), 1.79 (m, 2H), 1.68 (m, 1H), 1.54 (m, 2H), 1.24 (m, 3H).

Example No. I.1-257

¹H NMR (400 MHz, d₆-DMSO δ, ppm) 12.54 (br. s, 1H, NH), 7.91 (m, 1H), 7.59 (m, 1H), 4.28 (s, 2H), 3.90 (s, 3H).

Example No. I.1-259

¹H NMR (400 MHz, d₆-DMSO δ, ppm) 12.85 (br. s, 1H, NH), 8.16 (d, 1H), 7.99 (m, 1H), 7.83 (d, 1H), 7.67 (m, 1H), 7.21 (m, 1H).

Example No. I.1-260

¹H NMR (400 MHz, d₆-DMSO δ, ppm) 12.72 (br. s, 1H, NH), 8.02 (m, 2H), 7.75 (m, 1H), 7.63 (d, 1H), 6.74 (d, 1H).

Example No. I.1-261

¹H NMR (400 MHz, d₆-DMSO δ, ppm) 12.80 (br. s, 1H, NH), 8.08 (m, 1H), 7.78 (m, 1H), 7.62 (d, 1H), 7.59 (d, 1H), 7.55 (dd, 1H), 7.48 (dd, 1H).

Example No. I.1-262

¹H NMR (400 MHz, d₆-DMSO δ, ppm) 12.56 (br. s, 1H, NH), 7.97 (m, 1H), 7.68 (m, 1H), 7.30 (m, 4H), 7.22 (m, 1H), 3.92 (s, 2H).

Example No. I.1-263

¹H NMR (400 MHz, d₆-DMSO δ, ppm) 12.58 (br. s, 1H, NH), 7.98 (d, 1H), 7.73 (dd, 1H), 7.50 (d, 1H), 1.97 (m, 1H), 1.10 (m, 2H), 1.05 (m, 2H).

Example No. I.1-267

¹H NMR (400 MHz, d₆-DMSO δ, ppm) 12.05 (br. s, 1H, NH), 8.39 (s, 1H), 8.32 (m, 1H), 7.89 (s, 1H), 7.41 (m, 4H).

Example No. I.1-269

¹H NMR (400 MHz, d₆-DMSO δ, ppm) 12.85 (br. s, 1H, NH), 8.11 (s, 1H), 7.89 (d, 1H), 7.73 (d, 1H), 7.68 (d, 1H), 7.60 (m, 2H), 7.49 (m, 1H).

Example No. I.1-270

¹H NMR (400 MHz, d₆-DMSO δ, ppm) 12.26 (br. s, 1H, NH), 8.01 (d, 1H), 7.79 (dd, 1H), 7.62 (d, 1H), 7.35 (m, 2H), 7.31 (m, 2H), 7.24 (m, 1H), 3.95 (s, 2H).

Example No. I.1-271

¹H NMR (400 MHz, d₆-DMSO δ, ppm) 12.40 (br. s, 1H, NH), 8.02 (d, 1H), 7.76 (d, 1H), 7.63 (d, 1H), 7.30 (m, 2H), 7.04 (m, 2H), 6.94 (m, 1H), 4.96 (s, 2H).

Example No. I.1-272

¹H NMR (400 MHz, d₆-DMSO δ, ppm) 12.52 (br. s, 1H, NH), 8.04 (d, 1H), 7.52 (d, 1H), 7.41 (dd, 1H), 1.98 (m, 1H), 1.11 (m, 2H), 1.07 (m, 2H).

Example No. I.1-273

¹H NMR (400 MHz, d₆-DMSO δ, ppm) 12.79 (br. s, 1H, NH), 8.16 (d, 1H), 7.78 (d, 1H), 7.68 (d, 1H), 7.60 (d, 3H), 7.50 (dd, 1H).

Example No. I.1-274

¹H NMR (400 MHz, d₆-DMSO δ, ppm) 12.22 (br. s, 1H, NH), 8.07 (d, 1H), 7.63 (s, 1H), 7.47 (d, 1H), 3.03 (quint, 1H), 1.99 (m, 2H), 1.88 (m, 2H), 1.75 (m, 2H), 1.61 (m, 2H).

Example No. I.1-275

¹H NMR (400 MHz, d₆-DMSO δ, ppm) 12.62 (br. s, 1H, NH), 8.49 (d, 1H), 8.00 (s, 1H), 7.82 (s, 1H), 7.64 (m, 1H), 7.58 (m, 2H), 7.11 (d, 1H), 2.49 (s, 3H).

Example No. I.1-276

¹H NMR (400 MHz, d₆-DMSO δ, ppm) 12.28 (br. s, 1H, NH), 7.87 (d, 1H), 7.59 (dd, 1H), 7.50 (d, 1H), 7.35 (m, 2H), 7.31 (m, 2H), 7.23 (m, 1H), 2.91 (s, 2H), 2.44 (s, 3H).

Example No. I.1277

¹H NMR (400 MHz, d₆-DMSO δ, ppm) 12.32 (br. s, 1H, NH), 7.88 (d, 1H), 7.58 (dd, 1H), 7.49 (d, 1H), 7.30 (m, 2H), 7.04 (m, 2H), 6.95 (m, 1H), 4.92 (s, 2H), 2.44 (s, 3H).

Example No. I.1-278

¹H NMR (400 MHz, d₆-DMSO δ, ppm) 12.20 (br. s, 1H, NH), 7.71 (m, 2H), 7.65 (m, 1H), 3.49 (m, 1H), 2.40 (m, 2H), 2.27 (m, 2H), 1.99 (m, 1H), 1.83 (m, 1H).

Example No. I.1-279

¹H NMR (400 MHz, d₆-DMSO δ, ppm) 12.34 (br. s, 1H, NH), 7.69 m, 1H), 7.52 (m, 2H), 1.96 (m, 1H), 1.08 (m, 2H), 0.99 (m, 2H).

Example No. I.1-280

¹H NMR (400 MHz, d₆-DMSO δ, ppm) 12.22 (br. s, 1H, NH), 7.71 (m, 1H), 7.62 (m, 2H), 2.58 (m, 1H), 1.91 (m, 2H), 1.80 (m, 2H), 1.59 (m, 2H), 1.24 (m, 4H).

Example No. I.1-281:

¹H NMR (400 MHz, d₆-DMSO δ, ppm) 12.34 (br. s, 1H, NH), 7.72 (m, 1H), 7.69 (m, 2H), 4.32 (s, 2H), 3.91 (s, 3H).

Example No. I.1-282

¹H NMR (400 MHz, d₆-DMSO δ, ppm) 12.29 (br. s, 1H, NH), 7.73 (m, 1H), 7.66 (m, 2H), 2.59 (t, 2H), 1.73 (next, 2H), 0.92 (t, 3H).

Example No. I.1-283

¹H NMR (400 MHz, d₆-DMSO δ, ppm) 11.56 (br. s, 1H, NH), 8.48 m, 1H), 8.30 (m, 1H), 7.61 (dd, 1H), 7.55 (dd, 1H), 7.44 (m, 2H), 7.36 (m, 1H).

Example No. I.1-284

$^1$H NMR (400 MHz, d$_6$-DMSO δ, ppm) 12.50 (br. s, 1H NH), 8.39 (d, 2H), 7.59 (dd, 1H), 7.50 (m, 1H), 7.44 (d, 2H), 7.30 (m, 1H).

Example No. I.1-285

$^1$H NMR (400 MHz, d$_6$-DMSO δ, ppm) 12.39 (br. s, 1H, NH), 7.91 (d, 1H), 7.72 (m, 2H), 7.64 (m, 3H), 7.42 (m, 3H), 6.99 (d, 1H).

Example No. I.1-286

$^1$H NMR (400 MHz, d$_6$-DMSO δ, ppm) 12.20 (br. s, 1H, NH), 7.72 (m, 1H), 7.63 (m, 2H), 3.02 (quint, 1H), 2.00 (m, 2H), 1.89 (m, 2H), 1.75 (m, 2H), 1.60 (m, 2H).

Example No. I.1-288

$^1$H NMR (400 MHz, d$_6$-DMSO δ, ppm) 12.42 (br. s, 1H, NH), 7.78 (d, 1H), 7.69 (m, 2H), 7.30 (m, 2H), 7.06 (m, 2H), 6.99 (m, 1H), 5.00 (s, 2H).

Example No. I.1-289

$^1$H NMR (400 MHz, d$_6$-DMSO δ, ppm) 12.30 (br. s, 1H, NH), 8.10 (m, 1H), 7.28 (m, 1H), 7.22 (m, 1H), 4.28 (s, 2H), 3.38 (s, 3H).

Example No. I.1-291

$^1$H NMR (400 MHz, d$_6$-DMSO δ, ppm) 12.52 (br. s, 1H, NH), 7.97 (m, 1H), 7.68 (m, 1H), 3.48 (quint, 1H), 2.39 (m, 2H), 2.23 (m, 2H), 1.99 (m, 1H), 1.81 (m, 1H).

Example No. I.1-292

$^1$H NMR (400 MHz, d$_6$-DMSO δ, ppm) 12.34 (br. s, 1H, NH), 7.92 (m, 1H), 7.59 (m, 1H), 2.58 (m, 2H), 1.72 (m. 2H), 0.93 (t, 3H).

Example No. I.1-294

$^1$H NMR (400 MHz, d$_6$-DMSO δ, ppm) 12.35 (br. s, 1H, NH), 7.94 (m, 1H), 7.62 (m, 1H), 3.03 (quint, 1H), 1.96 (m, 2H), 1.87 (m, 2H), 1.72 (m, 2H), 1.60 (m, 2H).

Example No. I.1-295

$^1$H NMR (400 MHz, d$_6$-DMSO δ, ppm) 12.40 (br. s, 1H, NH), 7.98 (m, 1H), 7.67 (m, 1H), 7.29 (m, 2H), 7.02 (m, 2H), 6.98 (m, 1H), 4.98 (s, 2H).

Example No. I.1-296

$^1$H NMR (400 MHz, d$_6$-DMSO δ, ppm) 12.22 (br. s, 1H, NH), 8.08 (d, 1H), 7.69 (d, 1H), 7.48 (d, 1H), 3.50 (quint, 1H), 2.42 (m, 2H), 2.26 (m, 2H), 2.00 (m, 1H), 1.82 (m, 1H).

Example No. I.1-297

$^1$H NMR (400 MHz, d$_6$-DMSO δ, ppm) 12.28 (br. s, 1H, NH), 8.05 (d, 1H), 7.60 (d, 1H), 7.42 (dd, 1H), 2.60 (quint, 1H), 1.89 (m, 2H), 1.79 (m, 2H), 1.58 (m, 2H), 1.26 (m, 4H).

Example No. I.1-298

$^1$H NMR (400 MHz, d$_6$-DMSO δ, ppm) 12.31 (br. s, 1H, NH), 8.09 (d, 1H), 7.71 (d, 1H), 7.55 (dd, 1H), 4.34 (s, 2H), 3.42 (s, 3H).

Example No. I.1-299

$^1$H NMR (400 MHz, d$_6$-DMSO δ, ppm) 12.30 (br. s, 1H, NH), 8.08 (d, 1H), 7.64 (s, 1H), 7.48 (d, 1H), 2.59 (t, 2H), 1.73 (sext, 2H), 0.92 (t, 3H).

Example No. I.1-300

$^1$H NMR (400 MHz, d$_6$-DMSO δ, ppm) 12.04 (br. s, 1H, NH), 8.39 (s, 1H), 8.32 (m, 1H), 7.92 (d, 1H), 7.41 (m, 3H), 7.10 (d, 1H).

Example No. I.1-301

$^1$H NMR (400 MHz, d$_6$-DMSO δ, ppm) 12.41 (br. s, 1H, NH), 8.38 (d, 2H), 7.94 (d, 1H), 7.44 (m, 3H), 7.11 (d, 1H).

Example No. I.1-302

$^1$H NMR (400 MHz, d$_6$-DMSO δ, ppm) 12.05 (br. s, 1H, NH), 8.10 (d, 1H), 7.97 (d. 1H), 7.71 (d, 1H), 7.68 (s, 1H), 7.53-7.38 (m, 5H), 6.99 (d, 1H).

Example No. I.1-303

$^1$H NMR (400 MHz, d$_6$-DMSO δ, ppm) 12.46 (br. s, 1H, NH), 7.98 (d, 1H), 7.47 (s, 1H), 7.28 (m, 3H), 7.00 (m, 2H), 6.89 (m, 1H), 4.85 (s, 2H).

Example No. I.1-304

$^1$H NMR (400 MHz, d$_6$-DMSO δ, ppm) 11.96 (br. s, 1H, NH), 7.87 (d, 1H), 7.59 (dd, 1H), 7.53 (d, 1H), 3.48 (m, 1H), 2.39 (m, 2H), 2.23 (m, 2H), 1.99 (m, 1H), 1.84 (m, 1H).

Example No. I.1-305

$^1$H NMR (400 MHz, d$_6$-DMSO δ, ppm) 14.72 (br. s, 1H, NH), 7.82 (s, 1H), 7.51 (d, 1H), 7.38 (d. 1H), 2.40 (s, 3H), 1.94 (m, 1H), 1.07 (m, 2H), 0.99 (m, 2H).

Example No. I.1-306

$^1$H NMR (400 MHz, d$_6$-DMSO δ, ppm) 11.98 (br. s, 1H, NH), 7.88 (s, 1H), 7.59 (d, 1H), 7.50 (d, 1H), 2.55 (m, 1H), 2.44 (s, 3H), 1.90 (m, 2H), 1.79 (m, 2H), 1.70 (m, 1H), 1.56 (m, 2H), 1.22 (m, 3H).

Example No. I.1-307

$^1$H NMR (400 MHz, d$_6$-DMSO δ, ppm) 11.83 (br. s, 1H, NH), 7.89 (s, 1H), 7.59 (d, 1H), 7.50 (d, 1H), 4.30 (s, 2H), 3.90 (s, 3H), 2.42 (s, 3H).

Example No. I.1-308

$^1$H NMR (400 MHz, d$_6$-DMSO δ, ppm) 12.08 (br. s, 1H, NH), 7.86 (s, 1H), 7.58 (d, 1H), 7.47 (d, 1H), 2.56 (t, 2H), 2.42 (s, 3H), 1.74 (sext, 2H), 0.93 (t, 3H).

Example No. I.1-310

$^1$H NMR (400 MHz, d$_6$-DMSO δ, ppm) 11.84 (br. s, 1H, NH), 7.92 (d, 1H), 7.90 (s, 1H), 7.62 (m, 3H), 7.59 (d, 1H), 7.42 (m, 3H), 6.99 (d, 1H), 2.48 (s, 3H).

Example No. I.1-311

$^1$H NMR (400 MHz, d$_6$-DMSO δ, ppm) 12.01 (br. s, 1H, NH), 7.88 (s, 1H), 7.59 (d, 1H), 7.48 (d, 1H), 3.02 (quint, 1H), 2.42 (s, 3H), 1.98 (m, 2H), 1.88 (m, 2H), 1.73 (m, 2H), 1.60 (m, 2H).

Example No. I.1-312

$^1$H NMR (400 MHz, d$_6$-DMSO δ, ppm) 11.92 (br. s, 1H, NH), 7.96 (d, 1H), 7.46 (d, 1H), 7.28 (dd, 1H), 3.49 (m, 1H), 2.40 (m, 2H), 2.24 (m, 2H), 1.98 (m, 1H), 1.82 (m, 1H).

Example No. I.1-313

$^1$H NMR (400 MHz, d$_6$-DMSO δ, ppm) 12.33 (br. s, 1H, NH), 7.91 (d, 1H), 7.29 (s, 1H), 7.21 (d. 1H), 2.40 (s, 3H), 1.95 (m, 1H), 1.09 (m, 2H), 1.02 (m, 2H).

Example No. I.1-314

$^1$H NMR (400 MHz, d$_6$-DMSO δ, ppm) 11.99 (br. s, 1H, NH), 7.96 (d, 1H), 7.40 (s, 1H), 7.28 (d, 1H), 2.54 (m, 1H), 2.48 (s, 3H), 1.91 (m, 2H), 1.80 (m, 2H), 1.69 (m, 1H), 1.58 (m, 2H), 1.28 (m, 3H).

Example No. I.1-315

$^1$H NMR (400 MHz, d$_6$-DMSO δ, ppm) 12.03 (br. s, 1H, NH), 7.98 (d, 1H), 7.45 (s, 1H), 7.32 (d, 1H), 4.31 (s, 2H), 3.89 (s, 3H), 2.45 (s, 3H).

Example No. I.1-316

$^1$H NMR (400 MHz, d$_6$-DMSO δ, ppm) 12.03 (br. s, 1H, NH), 7.94 (d, 1H), 7.40 (s, 1H), 7.28 (d, 1H), 2.58 (t, 2H), 2.43 (s, 3H), 1.73 (sext, 2H), 0.92 (t, 3H).

Example No. I.1-317

$^1$H NMR (400 MHz, d$_6$-DMSO δ, ppm) 12.54 (br. s, 1H, NH), 8.29 (s, 1H), 8.20 (d, 1H), 7.98 (d, 1H), 7.56 (dd, 1H), 7.51 (d, 1H), 7.48 (s, 1H), 7.22 (d, 1H), 2.48 (s, 3H).

Example No. I.1-318

$^1$H NMR (400 MHz, d$_6$-DMSO δ, ppm) 12.54 (br. s, 1H, NH), 8.20 (d, 2H), 8.05 (d, 1H), 7.63 (d, 2H), 7.58 (s, 1H), 7.37 (d, 1H), 2.54 (s, 3H).

Example No. I.1-320

$^1$H NMR (400 MHz, d$_6$-DMSO δ, ppm) 12.32 (br. s, 1H, NH), 8.00 (d, 1H), 7.97 (d, 1H), 7.58 (d, 1H), 7.49 (s, 1H), 7.30 (d, 1H), 6.72 (m, 1H), 2.48 (s, 3H).

Example No. I.1-321

$^1$H NMR (400 MHz, d$_6$-DMSO δ, ppm) 12.50 (br. s, 1H, NH), 8.07 (d, 1H), 7.63 (d, 1H), 7.60 (m, 1H), 7.57 (m, 1H), 7.52 (m, 2H), 7.39 (dd, 3H).

Example No. I.1-322

$^1$H NMR (400 MHz, d$_6$-DMSO δ, ppm) 12.23 (br. s, 1H, NH), 8.00 (d, 1H), 7.93 (d, 1H), 7.66 (m, 2H), 7.42 (m, 4H), 7.31 (d, 1H), 6.99 (d, 1H), 2.47 (s, 3H).

Example No. I.1-323

$^1$H NMR (400 MHz, d$_6$-DMSO δ, ppm) 12.00 (br. s. 1H, NH), 7.95 (d, 1H), 7.40 (s, 1H), 7.27 (d, 1H), 3.02 (quint, 1H), 1.98 (m, 2H), 1.89 (m, 2H), 1.73 (m, 2H), 1.60 (m, 2H).

Example No. I.1-324

$^1$H NMR (400 MHz, d$_6$-DMSO δ, ppm) 12.28 (br. s, 1H, NH), 7.94 (d, 1H), 7.40 (s, 1H), 7.38 (d, 1H), 7.35-7.21 (m, 5H), 3.91 (s, 2H), 2.46 (s, 3H).

Example No. I.1-325

$^1$H NMR (400 MHz, d$_6$-DMSO δ, ppm) 12.66 (br. s, 1H, NH), 8.46 (s, 1H), 7.72 (d, 1H), 7.33 (m, 2H), 7.09 (m, 2H), 6.98 (m, 2H), 4.69 (s, 2H), 2.33 (s, 3H).

Example No. I.1-326

$^1$H NMR (400 MHz, d$_6$-DMSO δ, ppm) 11.99 (br. s, 1H, NH), 7.90 (d, 1H), 7.62 (d, 1H), 7.31 (dd, 1H), 2.56 (s, 3H), 2.94 (m, 1H), 2.05 (m, 1H), 1.98 (m, 2H), 1.83 (m, 2H), 1.72 (m, 1H).

Example No. I.1-327

$^1$H NMR (400 MHz, d$_6$-DMSO δ, ppm) 12.10 (br. s, 1H, NH), 7.91 (d, 1H), 7.61 (d, 1H), 7.30 (dd, 1H), 2.55 (s, 3H), 1.92 (m, 2H), 1.62 (m, 4H), 1.15 (m, 5H), 0.84 (m, 2H).

Example No. I.1-328

$^1$H NMR (400 MHz, d$_6$-DMSO δ, ppm) 12.05 (br. s, 1H, NH), 7.90 (d, 1H), 7.61 (d, 1H), 7.31 (dd, 1H), 2.69 (m, 1H), 2.54 (s, 3H), 2.11 (m, 1H), 1.82 (m, 1H), 1.26 (d, 3H), 0.82 (t, 3H).

Example No. I.1-329

$^1$H NMR (400 MHz, d$_6$-DMSO δ, ppm) 11.90 (br. s, 1H, NH), 7.92 (d, 1H), 7.63 (s, 1H), 7.34 (dd, 1H), 2.53 (s, 3H), 1.36 (s, 9H).

Example No. I.1-330

$^1$H NMR (400 MHz, d$_6$-DMSO δ, ppm) 10.21 (br. s. 1H, NH), 7.94 (d, 1H), 7.62 (d, 1H), 7.39 (dd, 1H), 4.13 (q, 2H), 2.53 (s, 3H).

Example No. I.1-331

$^1$H NMR (400 MHz, d$_6$-DMSO δ, ppm) 12.44 (br. s, 1H, NH), 7.97 (d, 1H), 7.69 (d. 1H), 7.41 (dd, 1H), 7.31 (m, 2H), 7.09 (m, 2H), 6.98 (m, 1H), 5.03 (s, 2H), 2.52 (s, 3H).

Example No. I.1-332

$^1$H NMR (400 MHz, d$_6$-DMSO δ, ppm) 12.32 (br. s, 1H, NH), 7.92 (d, 1H), 7.62 (d, 1H), 7.60 (s, 1H), 7.38 (m, 2H), 7.31 (d, 1H), 5.12 (s, 2H), 2.44 (s, 3H).

Example No. I.1-333

$^1$H NMR (400 MHz, d$_6$-DMSO δ, ppm) 12.40 (br. s, 1H, NH), 7.93 (d, 1H), 7.64 (d, 1H), 7.33 (m, 2H), 7.22 (s, 1H), 7.04 (m, 2H), 5.05 (s, 2H), 2.54 (s, 3H), Example No. I.1-334

$^1$H NMR (400 MHz, d$_6$-DMSO δ, ppm) 12.20 (br. s, 1H, NH), 7.92 (d, 1H), 7.62 (d, 1H), 7.40 (m, 2H), 7.33 (dd, 1H), 7.22 (m, 1H), 6.96 (d, 1H), 2.98 (m, 2H), 2.90 (m, 2H), 2.58 (s, 3H).

Example No. I.1-335

$^1$H NMR (400 MHz, d$_6$-DMSO δ, ppm) 12.40 (br. s, 1H, NH), 7.92 (d, 1H), 7.66 (d. 1H), 7.41 (m, 1H), 7.39 (dd, 1H), 7.28 (m, 4H), 5.32 (q, 1H), 2.54 (s, 3H), 1.68 (d, 3H).

Example No. I.1-337

$^1$H NMR (400 MHz, d$_6$-DMSO δ, ppm) 12.06 (br. s, 1H, NH), 7.90 (d, 1H), 7.78 (d, 2H), 7.70 (d, 1H), 7.52 (d, 1H), 7.45 (d, 2H), 7.40 (dd, 1H), 6.72 (d, 1H), 2.61 (s, 3H).

Example No. I.1-338

$^1$H NMR (400 MHz, d$_6$-DMSO ppm) 12.38 (br. s, 1H, NH), 8.76 (s, 1H), 8.55 (d, 1H), 7.98 (d, 1H), 7.69 (d, 1H), 7.60 (d, 1H), 7.45 (m, 2H), 7.40 (dd, 1H), 6.73 (d, 1H), 2.60 (s, 3H).

Example No. I.1-339

$^1$H NMR (400 MHz, d$_6$-DMSO δ, ppm) 12.20 (br. s, 1H, NH), 7.79 (d, 1H), 7.70 (d, 2H), 7.58 (m, 1H), 7.43 (d, 1H), 7.39 (d, 2H), 7.30 (dd, 1H), 6.62 (d, 1H), 2.60 (s, 3H).

Example No. I.1-340

$^1$H NMR (400 MHz, d$_6$-DMSO δ, ppm) 12.21 (br. s, 1H, NH), 8.32 (s, 1H), 8.28 (d, 1H), 8.09 (dd, 1H), 7.50 (m, 2H), 7.29 (dd, 1H), 7.10 (m, 1H).

Example No. I.1-343

$^1$H NMR (400 MHz, d$_6$-DMSO δ, ppm) 12.04 (br. s, 1H, NH), 7.91 (d, 1H), 7.62 (d. 1H), 7.32 (dd, 1H), 2.79 (m, 1H), 2.53 (s, 3H), 1.93 (m, 1H), 1.78 (m, 3H), 1.62-1.48 (m, 7H), 1.42 (m, 1H).

Example No. I.1-344

$^1$H NMR (400 MHz, d$_6$-DMSO δ, ppm) 12.56 (br. s, 1H, NH), 7.92 (d, 1H), 7.60 (d, 1H), 7.33 (dd, 1H), 7.31 (d, 2H), 7.09 (d, 2H), 5.02 (s, 2H), 2.49 (s, 3H).

Example No. I.1-345

$^1$H NMR (400 MHz, d$_6$-DMSO δ, ppm) 10.88 (br. s, 1H, NH), 7.72 (d, 1H), 7.61 (d, 1H), 7.32 (dd, 1H), 4.76 (m, 1H), 4.06 (m, 1H), 3.81 (m, 1H), 2.51 (s, 3H), 2.20 (m, 2H), 2.04 (m, 1H), 1.90 (m, 1H).

Example No. I.1-346

$^1$H NMR (400 MHz, d$_6$-DMSO δ, ppm) 12.15 (br. s, 1H, NH), 7.90 (d, 1H), 7.62 (d, 1H), 7.31 (d, 2H), 7.29 (m, 3H), 3.09 (m, 2H), 2.92 (m, 2H).

Example No. I.1-347

$^1$H NMR (400 MHz, d$_6$-DMSO δ, ppm) 12.16 (br. s, 1H, NH), 7.90 (d, 1H), 7.69 (s, 1H), 7.60 (m, 2H), 7.52 (m, 2H), 7.31 (dd, 1H), 3.20 (m, 2H), 2.99 (m, 2H), 2.54 (s, 3H).

Example No. I.1-348

$^1$H NMR (400 MHz, d$_6$-DMSO δ, ppm) 12.06 (br. s, 1H, NH), 7.88 (d, 1H), 7.59 (m, 2H), 7.27 (m, 4H), 7.14 (m, 1H), 3.42 (m, 1H), 2.89 (m, 2H), 2.52 (s, 3H), 1.28 (d, 3H).

Example No. I.1-349

$^1$H NMR (400 MHz, d$_6$-DMSO δ, ppm) 12.21 (br. s, 1H, NH), 8.00 (d, 1H), 7.96 (d, 1H), 7.86 (dd, 1H), 7.68 (d, 1H), 7.38 (m. 2H), 7.22 (m, 1H), 7.08 (d, 1H), 2.61 (s, 3H).

Example No. I.1-350

$^1$H NMR (400 MHz, d$_6$-DMSO δ, ppm) 12.01 (br. s, 1H, NH), 8.01 (d, 1H), 7.97 (dd, 1H), 7.71 (d, 1H), 7.68 (d, 1H), 7.64 (d, 1H), 7.35 (dd, 1H), 7.18 (d, 1H), 7.08 (d, 1H). 2.62 (s, 3H).

Example No. I.1-351

$^1$H NMR (400 MHz, d$_6$-DMSO δ, ppm) 10.62 (br. s, 1H, NH), 7.73 (m, 3H), 7.67 (d, 1H), 7.43 (m, 4H), 7.11-7.00 (d, 1H), 2.28 (s, 3H).

Example No. I.1-352

$^1$H NMR (400 MHz, d$_6$-DMSO δ, ppm) 11.82 (br. s, 1H, NH), 7.90 (d, 1H), 7.60 (d, 1H), 7.50 (m, 2H), 7.40 (m, 3H), 7.26 (dd, 1H), 2.62 (s, 3H), 2.30 (s, 3H).

Example No. I.1-353

$^1$H NMR (400 MHz, d$_6$-DMSO δ, ppm) 12.30 (br. s, 1H, NH), 7.89 (d, 1H), 7.58 (m, 2H), 7.48 (m, 3H), 7.27 (dd, 1H), 2.74 (s, 3H), 1.97 (s, 3H).

Example No. I.1-354

$^1$H NMR (400 MHz, d$_6$-DMSO δ, ppm) 12.05 (br. s, 1H, NH), 7.81 (d, 1H), 7.38 (m, 2H), 7.08 (dd, 1H), 6.92 (d, 1H), 2.68 (s, 3H), 1.82 (s, 3H).

Example No. I.1-355

$^1$H NMR (400 MHz, d$_6$-DMSO δ, ppm) 12.20 (br. s, 1H, NH), 7.94 (d, 1H), 7.63 (m, 2H), 7.32 (dd, 1H), 7.30 (d, 1H), 2.78 (s, 3H), 2.29 (s, 3H).

Example No. I.1-356

$^1$H NMR (400 MHz, d$_6$-DMSO δ, ppm) 12.14 (br. s, 1H, NH), 7.82 (d, 1H), 7.70 (d, 1H), 7.64 (d, 1H), 7.42 (dd, 1H), 6.61 (d, 1H), 2.32 (s, 3H), 2.25 (s, 3H).

Example No. I.1-357

$^1$H NMR (400 MHz, d$_6$-DMSO δ, ppm) 11.94 (br. s, 1H, NH), 8.57 (br. s, 1H, NH), 7.99 (d, 1H), 7.92 (d, 1H), 7.70 (d, 1H), 7.61 (dd, 1H), 7.40 (dd, 1H), 7.10 (d, 1H). 4.13 (q, 2H), 3.61 (m, 4H), 3.42 (m, 4H), 2.60 (s, 3H), 1.35 (t, 3H).

Example No. I.1-358

$^1$H NMR (400 MHz, d$_6$-DMSO δ, ppm) 12.03 (br. s, 1H, NH), 9.71 (br. s, 1H, NH), 8.14 (d, 1H), 8.03 (d, 1H), 7.81 (m, 1H), 7.77 (dd, 1H), 7.71 (d, 1H), 7.53 (dd, 1H), 7.13 (d, 1H), 4.12 (q, 2H), 2.53 (s, 2H), 2.48 (m, 4H), 1.59 (m, 4H), 1.40 (m, 2H), 1.33 (t, 3H).

Example No. I.1-374

$^1$H NMR (400 MHz, d$_6$-DMSO δ, ppm) 12.08 (br. s. 1H, NH), 7.91 (d, 1H), 7.62 (d, 1H), 7.31 (dd. 1H), 3.06 (quint, 1H), 2.55 (s, 3H), 1.94 (m, 4H), 1.78 (m, 2H), 1.64 (m, 2H).

Example No. I.1-375

$^1$H NMR (400 MHz, d$_6$-DMSO δ, ppm) 12.01 (br. s, 1H, NH), 7.90 (d, 1H), 7.61 (d, 1H), 7.30 (dd, 1H), 2.62 (m, 1H), 2.53 (s, 3H), 1.91 (m, 2H), 1.80 (m, 2H), 1.63 (m, 2H), 1.28 (m, 4H).

Example No. I.1377

$^1$H NMR (400 MHz, d$_6$-DMSO δ, ppm) 12.60 (br. s, 1H, NH), 7.32 (d, 2H), 7.93 (d, 1H), 7.59 (m, 3H), 7.29 (dd, 1H), 2.61 (s, 3H).

Example No. I.1-378

$^1$H NMR (400 MHz, d$_6$-DMSO ppm) 12.65 (br. s, 1H, NH), 8.31 (d, 2H), 7.94 (d, 1H), 7.59 (m, 3H), 7.28 (dd, 1H), 2.60 (s, 3H).

Example No. I.1-381

$^1$H NMR (400 MHz, d$_6$-DMSO δ, ppm) 12.34 (br. s, 1H, NH), 7.98 (d, 1H), 7.95 (d, 1H), 7.64 (m, 2H), 7.42 (m, 4H), 7.32 (dd, 1H), 7.01 (d, 1H), 2.62 (s, 3H).

Example No. I.1-382

$^1$H NMR (400 MHz, CDCl$_3$ δ, ppm) 11.49 (br. s, 1H, NH), 8.36 (d, 2H), 7.92 (d, 1H), 7.82 (d, 2H), 7.50 (dd, 1H), 7.29 (d, 1H), 4.08 (s, 3H).

Example No. I.1-383

$^1$H NMR (400 MHz, CDCl$_3$ δ, ppm) 8.22 (d, 1H), 7.71 (t, 1H), 7.63 (d, 1H), 7.72 (d, 1H), 7.45 (d, 2H), 7.41 (t, 1H), 7.32 (d, 2H), 6.10 (m, 1H), 3.32 (m, 2H), 2.90 (m, 4H), 2.80 (m, 2H), 2.70 (m, 2H), 2.06 (m, 2H).

Example No. I.1-384

$^1$H NMR (300 MHz, CDCl$_3$ δ, ppm) 8.29 (d, 1H), 7.72 (1, 1H), 7.63 (d, 1H), 7.64 (d, 1H), 7.15-7.48 (m, 4H), 7.05 (t, 2H), 3.26 (m, 2H), 2.95 (m, 2H), 2.65 (m, 3H), 2.31 (m, 4H), 2.04 (m, 2H), 1.88 (m, 2H).

Example No. I.1-385

$^1$H NMR (300 MHz, CDCl$_3$ δ, ppm) 8.29 (d, 1H), 7.71 (t, 1H), 7.63 (d, 1H), 7.48-7.28 (m, 5H), 3.20 (m, 2H), 2.95 (m, 2H), 2.60 (m, 3H), 2.30 (m, 4H), 2.00 (m, 2H), 1.85 (m, 2H).

Example No. I.1-386

$^1$H NMR (400 MHz, CDCl$_3$ δ, ppm) 8.30 (d, 1H), 7.71 (t, 1H), 7.63 (d, 1H), 7.44 (m, 3H), 7.35 (t, 1H), 7.24 (m, 2H), 3.20 (m, 2H), 2.94 (m, 2H), 2.60 (m, 3H), 2.29 (m, 4H), 2.00 (m, 2H), 1.89 (m, 2H).

Example No. I.1-387

$^1$H NMR (300 MHz, CDCl$_3$ δ, ppm) 8.24 (d, 1H), 7.70 (1, 1H), 7.63 (d, 1H), 7.45 (t, 1H), 7.34 (m, 5H) 6.10 (m, 1H), 3.35 (m, 2H), 2.90 (m, 4H), 2.84 (m, 2H), 2.48 (m, 2H), 2.06 (m, 2H).

Example No. I.1-388:

$^1$H NMR (400 MHz, CDCl$_3$ δ, ppm) 9.40 (m, 2H), 8.10 (m, 2H), 7.65 (d, 2H), 7.58 (m, 4H), 7.35 (d, 1H) 6.90 (t, 1H), 5.93 (m, 2H), 3.15 (m, 2H), 2.78 (m, 2H).

Example No. I.1-390

$^1$H NMR (400 MHz, CDCl$_3$ δ, ppm) 8.10 (d, 1H), 7.60 (d, 1H), 7.35 (m, 6H) 6.00 (m, 1H), 4.28 (m, 1H), 3.79 (m, 1H), 3.64 (m, 1H), 3.40 (m, 2H), 3.28 (m, 1H), 3.10 (t, 2H), 2.75 (m, 1H), 2.58 (s, 3H), 2.50 (t, 2H), 2.40 (m, 1H).

Example No. I.1-391

$^1$H NMR (400 MHz, CDCl$_3$ δ, ppm) 9.13 (d, 2H), 8.10 (d, 2H), 7.95 (d, 1H) 7.70 (d, 2H), 7.55 (m, 4H), 7.29 (m, 1H), 4.90 (t, 2H), 3.21 (t, 2H), 2.75 (t, 2H), 2.09 (s, 3H).

Example No. I.1-392

$^1$H NMR (400 MHz, CDCl$_3$ δ, ppm) 9.30 (d, 2H), 8.20 (d, 2H), 8.10 (d, 1H) 7.73 (d, 2H), 7.67 (t, 1H), 7.58 (m, 3H), 7.35 (t, 1H), 4.90 (t, 2H), 2.93 (t, 2H), 2.61 (t, 2H).

Example No. I.1-393

$^1$H NMR (400 MHz, CDCl$_3$ δ, ppm) 9.25 (d, 1H), 8.88 (d, 2H), 8.30 (t, 1H) 8.24 (d, 1H), 8.10 (d. 1H), 7.89 (t, 1H), 7.85 (t, 2H), 7.78 (dd, 1H), 7.59 (1, 1H), 7.32 (m, 1H), 4.95 (t, 2H), 3.48 (m, 2H), 2.90 (m, 2H).

Example No. I.1-394

$^1$H NMR (400 MHz, CDCl$_3$ δ, ppm) 8.10 (d, 1H), 7.60 (d, 1H), 7.85 (t, 1H) 7.80 (d, 2H), 7.66 (d, 2H), 3.82 (d, 2H), 3.26 (t, 2H), 2.95 (t, 2H), 2.75 (m, 3H), 2.59 (s, 3H), 2.45 (t, 2H), 2.32 (q, 2H), 2.02 (d, 2H).

Example No. I.1-395

$^1$H NMR (400 MHz, CDCl$_3$ δ, ppm) 9.20 (d, 2H), 8.03 (d, 2H), 7.70 (dd, 2H) 7.53 (t, 1H), 7.37 (d, 1H), 6.90 (t, 1H), 4.91 (t, 2H), 3.15 (m, 2H), 2.75 (m, 3H).

Example No. I.1-396

$^1$H NMR (400 MHz, CDCl$_3$ δ, ppm) 9.95 (br. s, 1H), 8.15 (d, 1H), 8.01 (d, 2H) 7.64 (d, 1H), 7.35 (m, 3H), 2.71 (s, 3H), 2.45 (s, 3H).

Example No. I.1-397

¹H NMR (400 MHz, CDCl₃ δ, ppm) 9.60 (br. s, 1H), 7.98 (d, 2H), 7.63 (s, 1H) 7.52 (d, 2H), 7.22 (s, 1H), 4.03 (s, 3H), 4.01 (s, 3H).

Example No. I.1-398

¹H NMR (400 MHz, CDCl₃ δ, ppm) 9.51 (br. s, 1H), 7.90 (d, 2H), 7.62 (s, 1H) 7.35 (d, 2H), 7.22 (s, 1H), 4.04 (s, 3H), 4.02 (s, 3H), 2.45 (s, 3H).

Example No. I.1-399

¹H NMR (400 MHz, CDCl₃ δ, ppm) 10.29 (br. s, 1H), 7.80 (m, 1H), 7.62 (s, 1H) 7.58 (d, 1H), 7.20 (s, 1H), 7.20 (d, 1H), 4.04 (s, 3H), 4.02 (s, 3H).

Example No. I.1-400

¹H NMR (400 MHz, CDCl₃ δ, ppm) 10.78 (br. s, 1H), 7.60 (s, 1H), 7.25 (m, 5H) 7.16 (s, 1H), 4.03 (s, 3H), 4.02 (s, 3H), 3.18 (m, 2H), 3.03 (m, 2H).

Example No. I.1-401

¹H NMR (400 MHz, d₆-DMSO δ, ppm) 7.80 (q, 1H), 7.47 (s, 1H), 7.44 (m, 1H) 7.24 (m, 1H), 7.20 (s, 1H), 4.03 (s, 3H), 4.02 (s, 3H).

Example No. I.1-402

¹H NMR (400 MHz, CDCl₃ δ, ppm) 9.20 (d, 2H), 8.05 (d, 2H), 7.71 (d, 2H) 7.54 (d, 2H), 7.35 (d. 1H), 6.91 (t, 1H), 4.91 (m, 2H), 3.11 (m, 2H), 2.75 (m, 2H).

Example No. I.1-403

¹H NMR (400 MHz, d₆-DMSO δ, ppm) 12.60 (br. s, 1H), 9.29 (d, 1H), 8.72 (d, 1H) 8.48 (m, 1H), 7.58 (dd, 1H), 7.50 (s, 1H), 7.25 (s, 1H), 3.84 (s, 3H), 3.80 (s, 3H).

Example No. I.1-404

¹H NMR (400 MHz, CDCl₃ δ, ppm) 10.50 (br. s, 1H), 9.37 (m, 1H), 8.82 (d, 1H) 8.50 (d, 1H), 7.94 (d, 1H), 7.53 (m, 1H), 7.50 (t, 1H), 7.30 (d, 1H), 4.05 (s, 3H).

Example No. I.1-405

¹H NMR (400 MHz, CDCl₃ δ, ppm) 9.96 (br. s, 1H), 8.17 (d, 1H), 8.07 (d, 1H) 7.81 (s, 1H), 7.72 (d. 1H), 7.69 (d, 1H), 7.45 (t. 1H), 2.66 (s, 3H).

Example No. I.1-406

¹H NMR (400 MHz, CDCl₃ δ, ppm) 9.19 (d, 2H), 8.02 (d, 2H), 7.94 (d, 1H) 7.70 (dd, 2H), 7.50 (d, 1H), 7.25 (m, 3H), 4.90 (t, 2H), 3.21 (t, 2H), 2.75 (t, 2H).

Example No. I.1-407

¹H NMR (400 MHz, CDCl₃ δ, ppm) 9.21 (d, 2H), 7.99 (m, 3H), 7.53 (m, 6H), 4.92 (t, 2H), 3.25 (t, 2H), 2.80 (t, 2H).

Example No. I.1-408

¹H NMR (400 MHz, CDCl₃ δ, ppm) 10.90 (br. s, 1H), 8.65 (d, 1H), 8.63 (d, 1H), 8.20 (d, 1H), 7.91 (1, 1H), 7.64 (d, 1H), 7.47 (dd, 1H), 7.40 (t, 1H), 2.73 (s, 3H).

Example No. I.1-409

¹H NMR (400 MHz, CDCl₃ δ, ppm) 10.90 (br. s, 1H), 8.66 (d, 1H), 8.53 (d, 1H), 7.90 (t, 1H), 7.70 (s, 1H), 7.47 (dd, 1H), 7.24 (s, 1H), 4.05 (s, 3H), 4.03 (s, 3H).

Example No. I.1-410

¹H NMR (400 MHz, CDCl₃ δ, ppm) 11.10 (br. s, 1H), 8.80 (m, 1H), 7.84 (d, 1H), 7.64 (s, 1H), 7.48 (m, 1H), 7.2 (s, 1H), 4.04 (s, 6H).

Example No. I.1-411

¹H NMR (300 MHz, CDCl₃ δ, ppm) 7.62 (m, 3H), 7.39 (m, 3H), 7.00 (t, 1H), 3.80 (m, 2H), 3.20 (m, 2H), 2.94 (t, 2H), 2.88 (m, 3H), 2.48 (m, 4H), 2.02 (m, 2H).

Example No. I.1-413

¹H NMR (400 MHz, CDCl₃ δ, ppm) 11.32 (br. s, 1H), 8.41 (m, 1H), 7.92 (m, 1H), 7.91 (d, 1H), 7.49 (m, 1H), 745 (1, 1H), 7.24 (d, 1H), 4.05 (s, 3H).

Example No. I.1-414

¹H NMR (400 MHz, CDCl₃ δ, ppm) 11.38 (br. s, 1H), 8.41 (m, 1H), 8.18 (d, 1H), 7.94 (d, 1H), 7.65 (d, 1H), 7.48 (m, 1H), 7.39 (t, 1H), 2.70 (s, 3H).

Example No. I.1-415

¹H NMR (400 MHz, CDCl₃ δ, ppm) 9.30 (br. s, 1H), 7.83 (d, 1H), 7.65 (s, 1H), 7.55 (d, 1H), 7.44 (dd, 1H), 7.21 (s, 1H), 4.03 (s, 3H), 4.02 (s, 3H).

Example No. I.1-416

¹H NMR (40) MHz, CDCl₃δ, ppm) 11.35 (br. s, 1H), 8.88 (m, 2H), 8.20 (d, 1H), 8.17 (m, 2H), 7.71 (d, 1H), 7.47 (t, 1H), 2.75 (s, 3H).

Example No. I.1-417

¹H NMR (400 MHz, CDCl₃ δ, ppm) 11.60 (br. s, 1H), 8.53 (s, 1H), 7.92 (d, 1H), 7.57 (m, 1H), 7.44 (t, 1H), 7.25 (d, 1H), 7.20 (d, 1H), 4.04 (s, 3H).

Example No. I.1-418

¹H NMR (400 MHz, CDCl₃ δ, ppm) 10.00 (br. s, 1H), 7.89 (d, 1H), 7.39 (t, 1H), 7.20 (d, 1H), 6.89 (s, 1H), 4.02 (s, 3H), 3.83 (s, 3H), 2.32 (s, 3H).

Example No. I.1-420

¹H NMR (400 MHz, CDCl₃ δ, ppm) 7.85 (d, 1H), 7.41 (t, 1H), 7.35-7.20 (m, 6H). 4.04 (s, 3H), 3.18 (m, 2H), 3.10 (m, 2H).

Example No. I.1-421

¹H NMR (400 MHz, CDCl₃ δ, ppm) 10.00 (br. s, 1H), 7.64 (s, 1H), 7.22 (s, 1H), 6.79 (s, 1H), 4.03 (s, 3H), 4.01 (s, 3H), 3.85 (s, 3H), 2.45 (s, 3H).

Example No. I.1-422

¹H NMR (400 MHz, CDCl₃ δ, ppm) 10.00 (br. s, 1H), 8.02 (d, 2H), 7.79 (d, 1H), 7.58 (d, 2H), 7.46 (s, 1H), 7.41 (t, 1H), 7.33 (d, 1H).

Example No. I.1-423

¹H NMR (400 MHz, d₆-DMSO δ, ppm) 7.84 (s, 1H), 7.72 (d, 1H), 7.43 (s, 1H), 7.11 (s, 1H), 6.85 (d, 1H), 6.72 (d, 1H), 6.63 (m, 1H), 3.91 (s, 3H), 3.88 (s, 3H).

Example No. I.1-424

¹H NMR (400 MHz, CDCl₃ δ, ppm) 11.18 (br. s, 1H), 8.42 (s, 1H) 7.62 (s, 1H), 7.57 (m, 1H), 7.18 (s, 1H), 7.09 (s, 1H), 4.03 (s, 3H).

Example No. I.1-425

¹H NMR (400 MHz, CDCl₃ δ, ppm) 11.23 (br. s, 1H), 8.89 (m, 2H), 8.21 (d, 1H), 8.15 (m, 2H), 7.70 (d, 1H), 7.48 (t, 1H), 2.75 (s, 3H).

Example No. I.1-426

¹H NMR (400 MHz, CDCl₃ δ, ppm) 10.20 (br. s, 1H), 8.16 (s, 1H), 8.11 (s, 1H), 7.60 (s, 1H), 7.22 (s, 1H), 4.03 (s, 3H), 4.02 (s, 6H).

Example No. I.1-427

¹H NMR (400 MHz, CDCl₃ δ, ppm) 10.95 (br. s, 1H), 7.63 (s, 1H), 7.18 (s, 1H), 6.75 (s, 1H), 4.01 (s, 3H), 4.00 (s, 3H), 3.85 (s, 3H), 2.35 (s, 3H).

Example No. I.1-428

¹H NMR (400 MHz, CDCl₃ δ, ppm) 9.90 (br. s, 1H), 8.12 (d, 1H), 7.64 (d, 1H), 7.60 (d, 1H), 7.52 (m, 1H), 7.33 (t, 1H), 6.75 (d, 1H), 6.67 (m, 1H), 6.52 (m, 1H), 2.68 (s, 3H).

Example No. I.1-429

¹H NMR (400 MHz, CDCl₃ δ, ppm) 9.25 (br. s, 1H), 7.61 (s, 1H), 7.52 (d, 1H), 7.15 (s, 1H), 6.85 (s, 2H), 6.74 (d, 1H), 5.76 (br. s, 1H), 4.02 (s, 3H), 4.00 (s, 3H), 3.95 (s, 6H).

Example No. I.1-430

¹H NMR (400 MHz, CDCl₃ δ, ppm) 10.65 (br. s, 1H), 8.15 (d, 1H), 7.79 (d, 1H), 7.62 (d, 1H), 7.60 (d, 2H), 7.35 (t, 1H), 6.98 (d, 2H), 6.81 (d, 1H), 3.88 (s, 3H), 2.69 (s, 3H).

Example No. I.1-431

¹H NMR (400 MHz, CDCl₃ δ, ppm) 7.58 (s, 1H), 7.24 (s, 1H), 7.29 (d, 2H), 6.81 (d, 2H), 4.03 (s, 3H), 4.01 (s, 3H), 3.78 (s, 3H), 3.12 (m, 2H), 3.05 (m, 2H).

Example No. I.1-432

¹H NMR (400 MHz, CDCl₃ δ, ppm) 10.00 (br. s, 1H), 7.65 (s, 1H), 7.50 (d, 1H), 7.20 (s, 1H), 7.00 (d, 1H), 4.72 (q, 2H), 4.03 (s, 3H), 4.01 (s, 3H), 1.55 (t, 3H).

Example No. I.1-433

¹H NMR (400 MHz, CDCl₃ δ, ppm) 7.84 (d, 1H), 7.74 (d, 1H), 7.55 (d, 2H), 7.40 (t, 1H), 7.23 (d, 1H), 6.99 (d, 1H), 6.93 (d, 2H), 4.05 (s, 3H), 3.85 (s, 3H).

Example No. I.1-434

¹H NMR (400 MHz, CDCl₃ δ, ppm) 9.05 (br. s, 1H), 7.55 (s, 1H), 7.13 (s, 1H), 6.46 (s, 2H), 5.41 (br. s, 1H), 4.01 (s, 3H), 3.99 (s, 3H), 3.82 (s, 6H), 3.07 (m, 2H), 2.97 (m, 2H).

Example No. I.1-435

¹H NMR (400 MHz, CDCl₃ δ, ppm) 10.55 (br. s, 1H), 7.64 (s, 1H), 7.59 (d, 1H), 7.18 (s, 1H), 6.97 (d, 1H), 4.39 (s, 3H), 4.05 (s, 3H), 4.03 (s, 3H).

Example No. I.1-436

¹H NMR (400 MHz, CDCl₃ δ, ppm) 12.20 (br. s, 1H), 8.91 (s, 1H), 8.63 (d, 1H), 8.02 (d, 1H), 8.00 (d, 1H), 7.95 (d, 1H), 7.50 (t, 1H), 7.40 (dd, 1H), 7.27 (d, 1H), 7.20 (d, 1H), 4.09 (s, 3H).

Example No. I.1-437

¹H NMR (400 MHz. CDCl₃ δ, ppm) 9.49 (br. s, 1H), 7.64 (s, 1H), 7.16 (s, 1H), 6.63 (s, 1H), 4.30 (s, 3H), 4.04 (s, 3H), 4.02 (s, 3H), 2.35 (s, 3H).

Example No. I.1-438

¹H NMR (400 MHz, CDCl₃ δ, ppm) 10.94 (br. s, 1H), 8.06 (dd, 2H), 7.62 (s, 1H), 7.25 (t, 2H), 7.22 (s, 1H), 4.04 (s, 3H), 4.03 (s, 3H).

Example No. I.1-439

¹H NMR (400 MHz, CDCl₃ δ, ppm) 10.80 (br. s, 1H), 8.15 (d, 1H), 7.81 (d, 1H), 7.65 (m, 3H), 7.48 (t. 1H), 7.15 (t, 2H), 6.88 (d. 1H), 2.69 (s, 3H).

Example No. I.1-440

¹H NMR (400 MHz, CDCl₃ δ, ppm) 8.50 (m, 1H), 8.30 (d, 1H), 7.82 (d, 1H), 7.69 (t, 1H), 7.68 (s, 1H), 4.06 (s, 3H), 4.05 (s, 3H).

Example No. I.1-441

¹H NMR (400 MHz, CDCl₃ δ, ppm) 10.58 (br. s, 1H), 8.25 (m, 1H), 8.10 (m, 1H), 7.83 (d, 1H), 7.70 (d, 1H), 7.61 (d, 1H), 7.50 (m, 1H), 2.52 (s, 3H).

Example No. I.1-442

¹H NMR (400 MHz, CDCl₃ δ, ppm) 8.3 (m, 1H), 7.95 (dd, 1H), 7.84 (d, 1H), 7.80 (dd, 1H), 7.50 (m, 1H).

Example No. I.1-443

$^1$H NMR (400 MHz, d$_6$-DMSO δ, ppm) 13.00 (br. s, 1H), 8.49 (d, 1H), 8.32 (d, 1H), 8.17 (d, 2H), 7.68 (d, 2H), 7.67 (t, 1H).

Example No. I.1-444;

$^1$H NMR (400 MHz, CDCl$_3$ δ, ppm) 9.91 (br. s, 1H), 8.50 (d, 1H), 8.10 (d, 1H), 8.01 (d, 2H), 7.53 (t, 1H), 7.39 (d, 2H), 2.48 (s, 3H).

Example No. I.1-445

$^1$H NMR (400 MHz, CDCl$_3$ δ, ppm) 10.83 (br. s, 1H), 8.42 (m, 1H), 7.88 (d, 1H), 7.70 (d, 1H), 7.62 (t, 1H), 7.48 (m, 2H).

Example No. I.1-446

$^1$H NMR (400 MHz, CDCl$_3$ δ, ppm) 9.22 (br. s, 1H), 7.93 (d, 2H), 7.91 (m, 1H), 7.81 (dd, 1H), 7.51 (dt, 1H), 7.38 (d, 2H), 2.46 (s, 3H).

Example No. I.1-447

$^1$H NMR (400 MHz, CDCl$_3$ δ, ppm) 10.80 (br. s, 1H), 8.10 (m, 1H), 7.65 (d, 1H), 7.55 (m, 1H), 6.78 (s, 1H), 3.85 (s, 3H), 2.49 (s, 3H), 2.35 (s, 3H).

Example No. I.1-448

$^1$H NMR (400 MHz, CDCl$_3$ δ, ppm) 10.99 (br. s, 1H), 7.91 (dd, 1H), 7.75 (dd, 1H), 7.46 (dt, 1H), 6.76 (s, 1H), 3.85 (s, 3H), 2.35 (s, 3H).

Example No. I.1-449

$^1$H NMR (400 MHz, CDCl$_3$ δ, ppm) 10.35 (br. s, 1H), 8.06 (d, 2H). 7.71 (d, 1H), 7.63 (t, 1H), 7.47 (d, 1H), 7.37 (d, 2H), 2.47 (s, 3H).

Example No. I.1-450

$^1$H NMR (400 MHz, CDCl$_3$ δ, ppm) 11.00 (br. s, 1H), 8.54 (m, 1H), 8.38 (d, 1H), 8.15 (m, 1H), 7.84 (m, 1H), 7.75 (d, 1H), 7.71 (t, 1H), 7.65 (m, 1H), 2.55 (s, 3H).

Example No. I.1451

$^1$H NMR (400 MHz, CDCl$_3$ δ, ppm) 10.80 (br. s, 1H), 7.85 (d, 1H), 7.65 (m, 4H), 7.44 (m, 4H), 6.91 (d, 1H).

Example No. I.1-452

$^1$H NMR (400 MHz, CDCl$_3$ δ, ppm) 11.38 (br. s, 1H), 8.05 (s, 1H), 7.60 (m, 2H), 7.30 (m, 4H), 7.21 (m, 1H), 3.18 (m, 2H), 3.01 (m, 2H), 2.50 (s, 3H).

Example No. I.1-453

$^1$H NMR (400 MHz, CDCl$_3$ δ, ppm) 10.96 (br. s, 1H), 7.95 (dd, 1H), 7.85 (d. 1H), 7.78 (dd, 1H), 7.65 (d, 2H), 7.56-7.40 (m, 4H), 6.92 (d. 1H).

Example No. I.1-454

$^1$H NMR (400 MHz, CDCl$_3$ δ, ppm) 9.45 (br. s, 1H), 8.48 (d, 1H), 8.10 (d, 1H), 8.05 (d, 2H), 7.52 (t, 1H), 7.05 (d, 2H), 3.91 (s, 3H).

Example No. I.1-455

$^1$H NMR (400 MHz, CDCl$_3$ δ, ppm) 11.16 (br. s, 1H), 8.46 (s, 1H), 8.10 (m. 1H), 7.68 (d, 1H), 7.60 (m, 1H), 7.59 (m, 1H), 7.11 (m, 1H).

Example No. I.1-456

$^1$H NMR (400 MHz, CDCl$_3$ δ, ppm) 10.98 (br. s, 1H), 8.11 (s, 1H), 7.84 (d, 1H), 7.65 (m, 4H), 7.44 (m, 3H), 6.95 (d, 1H), 2.52 (s, 3H).

Example No. I.1-457

$^1$H NMR (400 MHz, CDCl$_3$ δ, ppm) 10.84 (br. s, 1H), 8.79 (m, 1H), 8.55 (dd, 1H), 7.92 (dt, 1H), 7.72 (d, 1H), 7.62 (t, 1H), 7.50 (m, 2H).

Example No. I.1-458

$^1$H NMR (400 MHz, CDCl$_3$ δ, ppm) 10.92 (br. s, 1H), 8.65 (m, 1H), 8.56 (dd, 1H), 8.15 (m, 1H), 7.90 (dt, 1H), 7.72 (d. 1H), 7.60 (dd, 1H), 7.47 (m, 1H), 2.51 (s, 3H).

Example No. I.1-459

$^1$H NMR (400 MHz, CDCl$_3$ δ, ppm) 10.90 (br. s, 1H), 8.68 (m, 1H), 8.57 (d, 1H), 7.91 (dt, 1H), 7.70 (m, 1H), 7.61 (d, 1H), 7.50 (m, 1H), 7.14 (dd, 1H), Example No. I.1-460

$^1$H NMR (400 MHz, CDCl$_3$ δ, ppm) 10.72 (br. s, 1H), 7.75 (d, 1H), 7.60 (m, 2H), 7.52 (m, 1H), 7.43 (m, 1H), 6.76 (d, 1H), 6.69 (d, 1H), 6.50 (m, 1H).

Example No. I.1-461

$^1$H NMR (400 MHz, CDCl$_3$ δ, ppm) 10.60 (br. s, 1H), 8.10 (m, 1H), 7.68 (d, 1H), 7.62 (d, 1H), 7.59 (dd, 1H), 7.52 (m, 1H), 6.78 (d, 1H), 6.65 (d, 1H), 6.51 (m, 1H), 2.50 (s, 3H).

Example No. I.1-462

$^1$H NMR (400 MHz, d$_6$-DMSO δ, ppm) 12.45 (br. s, 1H), 7.85 (s, 1H), 7.76 (m, 2H), 7.70 (m, 2H), 6.90 (d, 1H), 6.75 (d, 1H), 6.65 (m, 1H).

Example No. I.1-463

$^1$H NMR (400 MHz, CDCl$_3$ δ, ppm) 10.46 (br. s, 1H), 8.06 (m, 1H), 7.60 (m, 2H), 7.20 (d, 2H), 6.82 (m, 2H), 3.78 (s, 3H), 3.11 (m, 2H), 3.00 (m, 2H), 2.50 (s, 3H).

Example No. I.1-464

$^1$H NMR (400 MHz, CDCl$_3$ δ, ppm) 8.99 (br. s, 1H), 8.03 (m, 1H), 7.58 (s, 2H), 7.35 (m, 1H), 6.30 (m, 1H), 6.08 (m, 1H), 3.19 (t, 2H), 3.01 (t, 2H), 2.48 (s, 3H).

Example No. I.1-465

$^1$H NMR (400 MHz, CDCl$_3$ δ, ppm) 9.29 (br. s, 1H), 8.12 (d, 1H), 7.62 (d, 1H), 7.60 (m, 1H), 7.51 (m, 1H), 7.34 (1, 1H), 6.75 (d, 1H), 6.65 (d, 1H), 6.51 (m, 1H), 2.67 (s, 3H).

Example No. I.1-466

$^1$H NMR (400 MHz, CDCl$_3$ δ, ppm) 11.00 (br. s, 1H), 8.71 (d, 1H), 8.69 (m, 1H), 8.27 (d, 1H), 7.95 (dt, 1H), 7.88 (d, 1H), 7.50 (m, 1H), 7.42 (t, 1H).

Example No. I.1-467

$^1$H NMR (400 MHz, CDCl$_3$ δ, ppm) 8.30 (m, 1H), 7.92 (dd, 1H), 7.75 (dd, 1H), 7.58 (m, 1H), 7.50 (m, 1H), 7.02 (m, 1H).

Example No. I.1-468

$^1$H NMR (400 MHz, CDCl$_3$ δ, ppm) 12.05 (br. s, 1H), 8.40 (d, 2H), 8.10 (m, 1H), 7.60 (m, 2H), 4.04 (s, 3H), 2.51 (s, 3H).

Example No. I.1-470

$^1$H NMR (400 MHz, CDCl$_3$ δ, ppm) 9.35 (br. s, 1H), 7.63 (d, 1H), 7.57 (t, 1H), 7.41 (d, 1H), 6.77 (s, 1H), 3.85 (s, 3H), 2.35 (s, 3H).

Example No. I.1-471

$^1$H NMR (400 MHz, CDCl$_3$ δ, ppm) 9.20 (br. s, 1H), 8.46 (dt, 1H), 7.90 (d, 1H), 7.46 (t, 1H), 7.26 (d, 1H), 7.10 (m, 1H), 6.98 (m, 1H), 4.04 (s, 3H).

Example No. I.1-472

$^1$H NMR (400 MHz, CDCl$_3$ δ, ppm) 7.90 (t, 2H), 7.47 (m, 4H), 7.26 (d, 1H), 4.02 (s, 3H).

Example No. I.1-473

$^1$H NMR (400 MHz, d$_6$-DMSO δ, ppm) 12.79 (br. s, 1H), 8.52 (m, 1H), 8.48 (d, 1H), 7.95 (d, 1H), 7.80 (t, 1H), 7.71 (d, 1H), 7.49 (t, 1H), 7.41 (d, 1H), 3.96 (s, 3H).

Example No. I.1-474

$^1$H NMR (400 MHz, CDCl$_3$ δ, ppm) 9.23 (br. s, 1H), 7.89 (d, 1H), 7.62 (m, 1H), 7.48 (d, 1H), 7.41 (t, 1H), 7.23 (d, 1H), 6.64 (m, 1H), 4.03 (s, 3H), Example No. I.1-475

$^1$H NMR (400 MHz, CDCl$_3$ δ, ppm) 9.23 (br. s, 1H), 7.90 (d, 1H), 7.46 (t, 2H), 7.31 (m, 2H), 7.28 (m, 1H), 4.00 (s, 3H), 2.50 (s, 3H).

Example No. I.1-476

$^1$H NMR (400 MHz, d$_6$-DMSO δ, ppm) 12.76 (br. s, 1H), 8.39 (d, 2H), 7.93 (d, 2H), 7.72 (d, 1H), 7.50 (t, 1H), 7.41 (d, 1H), 3.95 (s, 3H).

Example No. I.1-477

$^1$H NMR (400 MHz, d$_6$-DMSO δ, ppm) 12.45 (br. s, 1H), 8.10 (d, 2H), 7.70 (d, 1H), 7.43 (t, 1H), 7.37 (d, 1H), 7.35 (d, 2H), 3.94 (s, 3H), 2.40 (s, 3H).

Example No. I.1-479

$^1$H NMR (400 MHz, d$_6$-DMSO δ, ppm) 12.85 (br. s, 1H), 8.75 (m, 1H), 8.45 (d, 1H). 8.09 (t, 1H), 7.73 (d, 1H), 7.65 (dd, 1H), 7.50 (t, 1H), 7.43 (d, 1H), 3.98 (s, 3H).

Example No. I.1-480

$^1$H NMR (400 MHz, d$_6$-DMSO δ, ppm) 12.50 (br. s, 1H), 7.90 (d, 1H), 7.57 (d, 1H), 7.48 (t, 1H), 7.40 (d, 1H), 7.25 (d, 1H), 4.30 (s, 3H), 3.94 (s, 3H).

Example No. I.1-481

$^1$H NMR (400 MHz, d$_6$-DMSO δ, ppm) 12.40 (br. s, 1H), 7.69 (d, 1H), 7.46 (t, 1H), 7.40 (d, 1H), 7.00 (s, 1H), 4.21 (s, 3H), 3.93 (s, 3H).

Example No. I.1-483

$^1$H NMR (400 MHz, d$_6$-DMSO δ, ppm) 12.48 (br. s, 1H), 7.70 (d, 1H), 7.59 (d, 1H), 7.48 (t, 1H), 7.40 (d, 1H), 7.22 (d, 1H), 4.78 (q, 2H), 3.94 (s, 3H), 1.41 (t, 3H).

Example No. I.1-484

$^1$H NMR (400 MHz, d$_6$-DMSO δ, ppm) 7.88 (d, 1H), 7.70 (d, 2H), 7.67 (d, 1H), 7.52 (d, 2H), 7.42 (t, 1H), 7.37 (d, 1H), 7.04 (d, 1H), 3.93 (s, 3H).

Example No. I.1-485

$^1$H NMR (400 MHz, d$_6$-DMSO δ, ppm) 7.77 (d, 1H), 7.70 (m, 2H), 7.60 (d, 1H), 7.50 (t, 1H), 7.40 (d, 1H), 3.90 (s, 3H).

Example No. I.1-486

$^1$H NMR (400 MHz, CDCl$_3$ δ, ppm) 7.90 (d, 1H), 7.82 (d, 1H), 7.50 (t, 1H), 7.30 (m, 1H), 7.24 (d, 1H), 4.92 (s, 3H), 2.40 (s, 3H).

Example No. I.1-487

$^1$H NMR (400 MHz, CDCl$_3$ δ, ppm) 9.50 (br. s, 1H), 8.68 (d, 1H), 7.95 (dd, 1H), 7.65 (d, 1H), 7.51 (m, 1H), 7.45 (m. 2H), 7.41 (d, 1H), 2.67 (s, 3H).

Example No. I.1-488

$^1$H NMR (400 MHz, d$_6$-DMSO δ, ppm) 12.52 (br. s, 1H), 8.00 (d, 1H), 7.99 (m, 1H), 7.71 (d, 1H), 7.45 (m, 2H), 7.28 (m, 1H), 2.55 (s, 3H).

Example No. I.1-489

$^1$H NMR (400 MHz, d$_6$-DMSO δ, ppm) 12.70 (br. s, 1H), 8.40 (d, 2H), 8.01 (d, 1H), 7.95 (d, 2H), 7.74 (d, 1H), 7.45 (t, 1H), 2.55 (s, 3H).

Example No. I.1-490

$^1$H NMR (400 MHz, d$_6$-DMSO δ, ppm) 12.45 (br. s, 1H), 8.00 (d, 1H), 7.70 (d, 1H), 7.56 (d, 1H), 7.48 (m, 1H), 7.41 (t, 1H), 2.51 (s, 3H), 2.44 (s, 3H).

Example No. I.1-491

$^1$H NMR (400 MHz, CDCl$_3$ δ, ppm) 8.49 (m, 1H), 8.04 (m, 1H), 7.89 (d, 1H), 7.46-7.32 (m, 4H), 7.22 (m, 1H), 4.07 (s, 3H), 4.02 (s, 3H).

Example No. I.1-492

$^1$H NMR (400 MHz, d$_6$-DMSO δ, ppm) 12.71 (br. s, 1H), 8.08 (s, 1H), 7.90 (m, 2H), 7.73 (d, 1H), 7.52 (t, 1H), 7.41 (d, 1H), 3.90 (s, 3H).

Example No. I.1493

$^1$H NMR (400 MHz, d$_6$-DMSO δ, ppm) 12.65 (br. s, 1H), 7.80 (d, 1H), 7.71 (d, 1H), 7.68 (d, 1H), 7.60 (dd, 1H), 7.50 (t, 1H), 7.40 (t, 1H), 3.90 (s, 3H).

Example No. I.1-494

$^1$H NMR (400 MHz, CDCl$_3$ δ, ppm) 9.99 (br. s, 1H), 8.15 (d, 1H), 7.60 (d, 1H), 7.49 (d, 1H), 7.33 (t, 1H), 7.03 (d, 1H), 4.22 (q, 2H), 2.68 (s, 3H), 1.55 (t, 3H).

Example No. I.1-495

$^1$H NMR (400 MHz, CDCl$_3$ δ, ppm) 11.25 (br. s, 1H), 9.51 (d, 1H), 8.83 (d, 1H), 8.60 (m, 1H), 8.21 (d. 1H), 7.69 (d, 1H), 7.55 (m, 1H), 7.43 (t, 1H), 2.72 (s, 3H).

Example No. I.1-496

$^1$H NMR (400 MHz, CDCl$_3$ δ, ppm) 9.70 (br. s, 1H), 8.36 (t, 1H), 8.15 (d, 1H), 7.64 (d, 1H), 7.51 (d, 1H), 7.44 (d, 1H), 7.40 (t, 1H), 2.69 (s, 3H).

Example No. I.1-498

$^1$H NMR (400 MHz, CDCl$_3$ δ, ppm) 11.02 (br. s, 1H), 8.30 (s, 1H), 8.25 (s, 1H), 8.15 (d, 1H), 7.61 (d, 1H), 7.43 (t, 1H), 4.03 (s, 3H), 2.57 (s, 3H).

Example No. I.1-500

$^1$H NMR (400 MHz, d$_6$-DMSO δ, ppm) 12.20 (br. s, 1H), 7.94 (d, 1H), 7.87 (d, 1H), 7.65 (d. 1H), 7.34 (t, 1H), 7.29 (m, 1H), 7.13 (d, 1H), 7.00 (d, 1H), 6.84 (d, 1H), 6.10 (s, 2H), 2.52 (s, 3H).

Example No. I.1-501

$^1$H NMR (400 MHz, CDCl$_3$ δ, ppm) 10.52 (br. s, 1H), 8.16 (d, 1H), 7.66 (d, 1H), 7.40 (t, 1H), 6.85 (s, 1H), 4.36 (s, 3H), 2.65 (s, 3H), 2.37 (s, 3H).

Example No. I.1-502

$^1$H NMR (400 MHz, CDCl$_3$ δ, ppm) 10.60 (br. s, 1H), 8.20 (d, 1H), 7.67 (d, 1H), 7.64 (d, 1H), 7.42 (t, 1H), 7.06 (d, 1H), 4.91 (q, 2H), 2.66 (s, 3H), 1.59 (t, 3H).

Example No. I.1-503

$^1$H NMR (40) MHz, d$_6$-DMSO δ, ppm) 12.30 (br. s, 1H), 7.95 (d, 1H), 7.94 (d, 1H), 7.70 (d, 2H), 7.68 (d. 1H), 7.51 (d, 2H), 7.35 (t. 1H), 7.00 (d, 1H), 2.60 (s, 3H).

Example No. I.1-504

$^1$H NMR (400 MHz, d$_6$-DMSO δ, ppm) 12.75 (br. s, 1H), 8.59 (m, 1H), 8.53 (d, 1H), 8.00 (d, 1H), 7.97 (d, 1H), 7.80 (t, 1H), 7.72 (d, 1H), 7.44 (t, 1H), 2.53 (s, 3H).

Example No. I.1-505

$^1$H NMR (400 MHz, d$_6$-DMSO δ, ppm) 12.54 (br. s, 1H), 8.00 (d, 1H), 7.70 (d, 1H), 7.56 (d, 1H), 7.45 (m, 1H), 7.44 (t, 1H), 7.30 (d, 1H), 2.50 (s, 3H), 2.40 (s, 3H).

Example No. I.1-506

$^1$H NMR (400 MHz, d$_6$-DMSO (3, ppm) 8.20 (d, 1H), 7.96 (d, 1H), 7.87 (d, 1H), 7.75 (m, 1H), 7.69 (d, 1H), 7.55 (dd, 1H), 7.39 (t, 1H), 7.06 (d, 1H), 2.60 (s, 3H).

Example No. I.1-507

$^1$H NMR (400 MHz, CDCl$_3$ δ, ppm) 9.60 (br. s, 1H), 8.10 (d, 1H), 7.60 (d, 1H), 7.33 (t, 1H), 7.30-7.18 (m, 5H), 2.80 (t, 2H), 2.72 (t, 2H), 2.62 (s, 3H), 2.20 (m, 2H).

Example No. I.1-508

$^1$H NMR (400 MHz, CDCl$_3$ δ, ppm) 7.90 (d, 1H), 7.55 (d, 1H), 7.33 (t, 1H), 7.54 (d, 2H), 7.25 (d, 2H), 7.22 (d, 1H), 4.65 (s, 2H), 4.00 (s, 3H), 3.75 (s, 3H), 2.41 (s, 3H).

Example No. I.1-510

$^1$H NMR (400 MHz, CDCl$_3$ δ, ppm) 9.90 (br. s, 1H), 7.68 (m, 1H), 7.47 (d, 1H), 7.32-7.15 (m, 5H), 7.10 (dd, 1H), 2.78 (1, 2H), 2.72 (t, 2H), 2.20 (m, 2H).

Example No. I.1-511

$^1$H NMR (40) MHz, CDCl$_3$ δ, ppm) 9.74 (br. s, 1H), 7.58 (m, 2H), 7.43 (dd, 1H), 7.32-7.15 (m, 5H), 2.77 (t, 2H), 2.70 (t, 2H), 2.18 (m, 2H).

Example No. I.1-513

$^1$H NMR (400 MHz, CDCl$_3$ δ, ppm) 7.92 (d, 1H), 7.53-7.35 (m, 6H), 5.15 (d, 1H), 4.10 (d, 1H), 4.00 (s, 3H), 3.65 (s, 3H).

Example No. I.1-514

$^1$H NMR (400 MHz, CDCl$_3$ δ, ppm) 7.89 (m, 2H), 7.50 (m, 1H), 7.45 (t, 1H), 7.22 (d, 1H), 6.65 (m, 1H), 4.81 (s, 2H), 4.00 (s, 3H), 3.80 (s, 3H).

Example No. I.1-516

$^1$H NMR (400 MHz, d$_6$-DMSO δ, ppm) 12.00 (br. s, 1H), 7.40 (s, 1H), 7.29 (t, 2H), 7.25-7.15 (m, 3H), 7.08 (s, 1H), 3.89 (s, 3H), 3.85 (s, 3H), 2.65 (t, 2H), 2.59 (t, 2H), 2.03 (m, 2H).

Example No. I.1-517

$^1$H NMR (400 MHz, d$_6$-DMSO δ, ppm) 12.20 (br. s, 1H, NH), 7.92 (d, 1H), 7.63 (d, 1H), 7.32 (dd, 1H), 7.29 (d, 2H), 7.19 (d, 2H), 3.04 (m, 2H), 2.89 (m, 2H), 2.52 (s, 3H), 1.24 (s, 9H).

Example No. I.1-518

$^1$H NMR (400 MHz, d$_6$-DMSO δ, ppm) 12.11 (br. s, 1H, NH), 7.89 (d, 1H), 7.61 (d, 1H), 7.31 (dd, 1H), 7.26 (d, 2H), 7.12 (d, 2H), 2.69 (m, 2H), 2.62 (m, 2H), 2.51 (s, 3H), 2.46 (m, 1H), 1.23 (s, 9H), 0.89 (d, 3H).

Example No. I.1-519

$^1$H NMR (400 MHz, d$_6$-DMSO δ, ppm) 12.32 (br. s, 1H, NH), 8.08 (d, 1H), 7.68 (d, 1H), 7.50 (dd, 1H), 2.49 (m, 1H), 1.74 (m, 2H), 1.62 (m, 2H), 0.80 (t, 6H).

Example No. I.2-1

$^1$H NMR (400 MHz, CDCl$_3$ δ, ppm) 9.73 (br. s, 1H, NH), 8.99 (d, 1H), 8.48 (d, 1H), 7.41 (dd, 1H), 1.50 (s, 9H), Example No. I.2-2

$^1$H NMR (400 MHz, CDCl$_3$ δ, ppm) 9.78 (br. s, 1H, NH), 9.02 (dd, 1H), 8.59 (d, 1H), 7.42 (dd, 1H), 2.74 (s, 3H).

Example No. I.2-3

$^1$H NMR (400 MHz, CDCl$_3$ δ, ppm) 9.83 (br. s, 1H, NH), 8.78 (d, 1H), 7.77 (d, 1H), 2.63 (s, 3H).

Example No. I.2-4

$^1$H NMR (400 MHz, CDCl$_3$ δ, ppm) 9.65 (br. s, 1H, NH), 8.99 (d, 1H), 7.58 (d, 1H), 2.40 (s, 3H).

Example No. I.2-5

$^1$H NMR (400 MHz, CDCl$_3$ δ, ppm) 9.24 (br. s, 1H, NH), 8.70 (d, 1H), 7.57 (d, 1H), 2.02 (m, 1H), 1.53 (m, 2H), 1.21 (m, 2H).

Example No. I.2-6

$^1$H NMR (400 MHz, CDCl$_3$ δ, ppm) 10.22 (br. s, 1H, NH), 8.78 (d, 1H), 7.78 (d, 1H), 1.51 (s, 9H).

Example No. I.2-7

$^1$H NMR (400 MHz, CDCl$_3$ δ, ppm) 9.31 (br. s, 1H, NH), 8.78 (d, 1H), 7.77 (d, 1H), 2.79 (t, 1H), 1.96 (sext, 2H), 1.09 (t, 3H).

Example No. I.2-8

$^1$H NMR (400 MHz, CDCl$_3$ δ, ppm) 10.09 (br. s, 1H, NH), 8.79 (d, 1H), 7.78 (d, 1H), 3.60 (m, 1H), 2.62 (m, 2H), 2.47 (m, 2H), 2.17 (m, 1H), 2.06 (m, 1H).

Example No. I.2-9

$^1$H NMR (400 MHz, CDCl$_3$ δ, ppm) 9.58 (br. s, 1H, NH), 9.00 (d, 1H), 8.68 (d, 1H), 7.68 (d, 1H), 7.61 (d, 1H), 6.70 (m, 1H).

Example No. I.2-12

$^1$H NMR (400 MHz, d$_6$-DMSO δ, ppm) 12.38 (br. s, 1H, NH), 8.12 (d, 1H), 7.86 (m, 1H), 7.72 (m, 1H, NH), 7.58 (dd, 1H), 3.99 (s, 2H), 3.28 (m, 4H), 3.19 (m, 4H).

Example No. I.2-13

$^1$H NMR (400 MHz, d$_6$-DMSO δ, ppm) 12.24 (br. s, 1H, NH), 8.07 (d, 1H), 7.91 (d, 1H), 7.32 (m, 1H), 7.19 (s, 2H), 3.81 (s, 6H), 3.70 (s, 3H).

Example No. I.2-14

$^1$H NMR (400 MHz, d$_6$-DMSO δ, ppm) 11.46 (br. s, 1H, NH), 8.91 (d, 1H), 8.46 (d, 1H), 7.50 (dd, 1H), 2.69 (q, 2H), 1.28 (1, 3H).

Example No. I.2-15

$^1$H NMR (400 MHz, d$_6$-DMSO δ, ppm) 11.72 (br. s, 1H, NH), 8.21 (d, 1H), 7.68 (d, 1H), 7.42 (d, 1H), 7.37 (m, 1H, NH), 2.27 (s, 3H).

Example No. I.3-1

$^1$H NMR (400 MHz, d$_6$-DMSO δ, ppm) 11.98 (br. s. 1H, NH), 8.12 (d, 1H), 8.08 (d, 1H), 7.87 (dd, 1H), 7.43 (m, 5H), 7.32 (m, 1H), 2.31 (s, 3H).

Example No. I.3-2

$^1$H NMR (400 MHz, d$_6$-DMSO δ, ppm) 12.12 (br. s, 1H, NH), 8.11 (d, 1H), 7.82 (m, 1H), 7.77 (m, 1H), 7.41 (m, 4H), 7.33 (m, 1H), 2.30 (s, 3H).

Example No. I.3-3

$^1$H NMR (400 MHz, d$_6$-DMSO δ, ppm) 12.08 (br. s, 1H, NH), 8.10 (d, 1H), 8.01 (d, 1H), 7.50 (dd, 1H), 7.39 (m, 4H), 7.32 (m, 1H), 2.29 (s, 3H).

Example No. I.3-4

$^1$H NMR (400 MHz, d$_6$-DMSO δ, ppm) 12.19 (br. s, 1H, NH), 8.08 (d, 1H), 7.96 (d, 1H), 7.47 (dd, 1H), 5.78 (s, 1H), 2.29 (s, 3H).

Example No. I.3-5

$^1$H NMR (400 MHz, d$_6$-DMSO δ, ppm) 12.13 (br. s, 1H, NH), 8.09 (m, 1H), 7.82 (m, 1H), 7.75 (m, 1H), 7.40 (m, 2H), 7.26 (m, 2H), 2.27 (s, 3H).

Example No. I.3-6

$^1$H NMR (400 MHz, d$_6$-DMSO δ, ppm) 11.99 (br. s, 1H, NH), 8.11 (d, 1H), 8.07 (d. 1H), 7.87 (dd, 1H), 7.43 (m, 3H), 7.25 (m, 2H), 2.28 (s, 3H).

Example No. I.3-7

$^1$H NMR (400 MHz, d$_6$-DMSO δ, ppm) 12.17 (br. s, 1H, NH), 8.08 (d, 1H), 8.06 (d, 1H), 7.90 (dd, 1H), 7.41 (m, 2H), 7.26 (m, 2H), 2.26 (s, 3H).

Example No. I.3-8

$^1$H NMR (400 MHz, d$_6$-DMSO δ, ppm) 12.08 (br. s, 1H, NH), 8.12 (d, 1H), 8.07 (d, 1H), 7.89 (dd, 1H), 7.57 (m, 1H), 7.48 (m, 2H), 7.29 (m, 1H), 2.15 (s, 3H).

Example No. I.3-9

$^1$H NMR (400 MHz, d$_6$-DMSO δ, ppm) 12.17 (br. s, 1H, NH), 8.10 (d, 1H), 8.03 (d, 1H), 7.57 (dd, 1H), 7.50 (m, 1H), 7.48 (m, 1H), 7.28 (m, 1H), 2.14 (s, 3H).

Example No. I.3-10

$^1$H NMR (400 MHz, d$_6$-DMSO δ, ppm) 12.21 (br. s, 1H, NH), 8.08 (d, 1H), 8.06 (d. 1H), 7.91 (m, 1H), 7.58 (m, 1H), 7.47 (dd, 1H), 7.29 (m, 1H), 2.14 (s, 3H).

Example No. I.3-11

$^1$H NMR (400 MHz, d$_6$-DMSO δ, ppm) 12.09 (br. s, 1H, NH), 8.11 (d, 1H), 7.99 (d, 1H), 7.49 (dd, 1H), 7.42 (m, 2H), 7.27 (m, 2H), 2.27 (s, 3H).

Example No. I.3-12

$^1$H NMR (400 MHz, d$_6$-DMSO δ, ppm) 12.53 (br. s, 1H, NH), 8.19 (m, 2H), 7.97 (m, 1H), 7.62 (dd, 1H), 7.48 (dd, 1H), 7.39 (m, 1H), 7.20 (m, 1H).

Example No. I.3-13

$^1$H NMR (400 MHz, d$_6$-DMSO δ, ppm) 11.22 (br. s, 1H, NH), 8.19 (d, 1H), 8.07 (d, 1H), 7.91 (dd, 1H), 7.53 (dd, 1H), 4.31 (q, 2H), 2.46 (s, 3H), 1.31 (1, 3H).

Example No. I.3-14

$^1$H NMR (400 MHz, d$_6$-DMSO δ, ppm) 12.51 (br. s, 1H, NH), 8.21 (dd, 1H), 7.88 (dd, 1H), 7.82 (m, 1H), 7.52 (d, 2H), 7.39 (d, 2H).

Example No. I.3-15

$^1$H NMR (400 MHz, d$_6$-DMSO δ, ppm) 12.67 (br. s, 1H, NH), 8.23 (dd, 1H), 7.90 (dd. 1H), 7.84 (m, 1H), 7.60 (d. 1H), 7.58 (m, 1H), 7.41 (m, 2H).

Example No. I.3-16

$^1$H NMR (400 MHz, d$_6$-DMSO δ, ppm) 11.94 (br. s, 1H, NH), 8.13 (d, 1H), 8.07 (d, 1H), 7.87 (dd, 1H), 7.47 (dd, 1H), 7.25 (d, 1H), 7.22 (d, 1H), 7.14 (s, 1H), 7.10 (d, 1H), 6.93 (d, 1H), 6.81 (s, 1H), 6.72 (d, 1H), 6.03 (s, 2H), 4.02 (s, 2H).

Example No. I.3-17

$^1$H NMR (400 MHz, d$_6$-DMSO δ, ppm) 12.38 (br. s, 1H, NH), 8.19 (m, 2H), 7.97 (dd, 1H), 7.61 (dd, 1H), 7.54 (m, 2H), 7.40 (d, 2H).

Example No. I.3-18

$^1$H NMR (400 MHz, d$_6$-DMSO δ, ppm) 12.52 (br. s, 1H, NH), 8.21 (dd, 1H), 8.18 (d, 2H), 7.98 (d, 1H), 7.88 (dd, 1H), 7.53 (d, 2H).

Example No. I.3-19

$^1$H NMR (400 MHz, d$_6$-DMSO δ, ppm) 12.20 (br. s, 1H, NH), 8.07 (d, 1H), 8.05 (d, 1H), 7.92 (dd, 1H), 7.72 (s, 1H), 7.47 (d, 1H), 7.43 (d, 1H), 2.16 (s, 3H).

Example No. I.3-20

$^1$H NMR (400 MHz, d$_6$-DMSO δ, ppm) 12.52 (br. s, 1H, NH), 8.20 (m, 2H), 7.96 (dd, 1H), 7.62 (dd, 1H), 7.59 (d, 1H), 7.57 (m, 1H), 7.42 (m, 2H).

Example No. I.3-21

$^1$H NMR (400 MHz, d$_6$-DMSO δ, ppm) 12.68 (br. s, 1H, NH), 8.23 (dd, 1H), 7.87 (dd, 1H), 7.83 (d, 1H), 7.59 (d, 1H), 7.47 (m 1H), 7.42 (m, 2H).

Example No. I.3-22

$^1$H NMR (400 MHz, d$_6$-DMSO δ, ppm) 12.22 (br. s, 1H, NH), 8.11 (m, 1H), 7.81 (m, 1H), 7.77 (dd, 1H), 7.75 (s, 1H), 7.48 (d, 1H), 7.44 (d, 1H), 2.16 (s, 3H).

Example No. I.3-23

$^1$H NMR (400 MHz, d$_6$-DMSO δ, ppm) 12.08 (br. s, 1H, NH), 8.13 (d, 1H), 8.07 (d, 1H), 7.88 (dd, 1H), 7.73 (s, 1H), 7.47 (m, 3H), 2.16 (s, 3H).

Example No. I.3-24;

$^1$H NMR (400 MHz, d$_6$-DMSO δ, ppm) 12.68 (br. s, 1H, NH), 8.22 (m, 1H), 7.8 (m, 1H), 7.83 (m, 1H), 7.48 (m, 1H), 7.40 (m, 1H), 7.19 (m, 1H).

Example No. I.3-25

$^1$H NMR (400 MHz, d$_6$-DMSO δ, ppm) 12.21 (br. s, 1H, NH), 8.02 (d, 1H), 7.99 (d, 1H), 7.88 (dd, 1H), 5.78 (s, 1H), 2.28 (s, 3H).

Example No. I.3-26

$^1$H NMR (400 MHz, d$_6$-DMSO δ, ppm) 12.21 (br. s, 1H, NH), 8.04 (m, 1H), 7.81 (d, 1H), 7.73 (m, 1H), 5.77 (s, 1H), 2.27 (s, 3H).

Example No. I.3-27

$^1$H NMR (400 MHz, d$_6$-DMSO δ, ppm) 12.13 (br. s, 1H, NH), 8.10 (d, 1H), 8.02 (s, 1H), 7.73 (s, 1H), 7.50 (d, 1H), 7.47 (d, 1H), 7.44 (d, 1H), 2.17 (s, 3H).

Example No. I.3-28

$^1$H NMR (400 MHz, d$_6$-DMSO δ, ppm) 12.69 (br. s, 1H, NH), 8.21 (m, 1H), 8.18 (d, 1H), 8.12 (d, 1H), 7.99 (dd, 1H), 7.42 (m, 1H), 7.19 (m, 1H).

Example No. I.3-30

$^1$H NMR (400 MHz, d$_6$-DMSO δ, ppm) 12.75 (br. s, 1H), 11.10 (br. s, 1H), 8.18 (d, 1H), 8.15-8.10 (m, 2H), 7.93 (dd, 1H), 7.56 (dd, 1H).

Example No. I.3-31

$^1$H NMR (400 MHz, d$_6$-DMSO δ, ppm) 10.61 (br. s, 1H, NH), 8.30 (s, 1H), 8.18 (dd, 1H), 8.13 (m, 1H), 7.94 (dd, 1H), 7.86 (br. s, 1H, NH), 7.57 (dd, 1H), 7.32 (br. s, 1H, NH).

Example No. I.3-32

$^1$H NMR (400 MHz, d$_6$-DMSO δ, ppm) 13.48 (br. s. 1H, NH), 8.21 (dd. 1H), 8.16 (d, 1H), 7.98 (dd, 1H), 7.66 (dd, 1H), 4.42 (q, 2H), 1.35 (t, 3H).

Example No. I.3-33

$^1$H NMR (400 MHz, d$_6$-DMSO δ, ppm) 11.54 (br. s, 1H, NH), 8.21-8.18 (m, 2H), 8.12 (d, 1H), 7.95 (dd, 1H), 7.59 (dd, 1H), 4.30 (q, 2H), 1.31 (t, 3H).

Example No. I.3-34

$^1$H NMR (400 MHz, d$_6$-DMSO δ, ppm) 10.69 (br. s, 1H, NH), 8.34 (s, 1H), 8.19 (d, 1H), 8.10 (d, 1H), 7.94 (dd, 1H), 7.82 (br. s, 1H, NH), 7.57 (dd, 1H), 2.81 (m, 1H), 0.71 (m, 2H), 0.58 (m, 2H).

Example No. I.3-35

$^1$H NMR (400 MHz, d$_6$-DMSO δ, ppm) 10.67 (br. s, 1H, NH), 8.38 (s, 1H), 8.21-8.15 (m, 2H), 8.11 (d, 1H), 7.94 (dd, 1H), 7.56 (dd, 1H), 4.10 (sept, 1H), 1.18 (d, 6H).

Example No. I.3-36

$^1$H NMR (400 MHz, d$_6$-DMSO δ, ppm) 10.70 (br. s, 1H, NH), 8.81 (br. t, 1H, NH), 8.36 (s, 1H), 8.19 (d, 1H), 8.12 (d, 1H), 7.94 (dd, 1H), 7.58 (dd, 1H), 4.07 (d, 2H), 2.08 (s, 1H).

Example No. I.3-37

$^1$H NMR (400 MHz, d$_6$-DMSO δ, ppm) 10.62 (br. s, 1H, NH), 8.18 (d, 1H), 8.12 (d, 1H), 8.08 (s, 1H), 7.94 (dd, 1H), 7.57 (dd, 1H), 3.64 (m, 4H), 3.35 (m, 4H).

Example No. I.3-38

$^1$H NMR (400 MHz, d$_6$-DMSO δ, ppm) 10.67 (br. s, 1H, NH), 8.44 (br. t, 1H, NH), 8.34 (s, 1H), 8.18 (d, 1H), 8.11 (d, 1H), 7.94 (dd, 1H), 7.57 (dd, 1H), 3.14 (dd, 2H), 1.01 (m, 1H), 0.48 (m, 2H), 0.25 (m, 2H).

Example No. I.3-39

$^1$H NMR (400 MHz, d$_6$-DMSO δ, ppm) 9.58 (br. s, 1H, NH), 8.33 (d, 1H), 8.19 (d, 1H), 8.08 (s, 1H), 7.85 (dd, 1H), 7.52 (dd, 1H), 6.04 (m, 1H), 5.45 (m, 2H), 4.82 (dd, 2H).

Example No. I.3-40

$^1$H NMR (400 MHz, d$_6$-DMSO δ, ppm) 9.60 (br. s, 1H, NH), 8.35 (d, 1H), 8.19 (d, 1H), 8.10 (s, 1H), 7.86 (dd, 1H), 7.53 (dd, 1H), 4.15 (d, 2H), 1.14 (m, 1H), 0.68 (m, 2H). 0.40 (m, 2H).

Example No. I.3-41

$^1$H NMR (400 MHz, d$_6$-DMSO δ, ppm) 12.10 (br. s, 1H, NH), 8.29 (m, 1H), 8.18 (m, 1H), 7.82 (m, 1H), 7.46 (m, 2H), 7.39 (m, 3H), 2.30 (s, 3H).

Example No. I.4-1

$^1$H NMR (400 MHz, CDCl$_3$ δ, ppm) 7.84 (d, 1H), 7.57 (d, 2H), 7.44 (d, 2H), 7.23 (d, 1H), 6.85 (t, 1H), 5.90 (s, 1H), 5.82 (br. s, 1H), 4.20 (br. s, 1H), 2.13 (s, 3H).

Example No. I.4-2

$^1$H NMR (400 MHz, CDCl$_3$ δ, ppm) 7.84 (d, 1H), 7.50 (d, 2H), 7.27 (d, 2H), 7.22 (d, 1H), 6.83 (t, 1H), 5.85 (s, 1H), 5.82 (br. s, 1H), 4.20 (br. s, 1H), 2.40 (s, 3H), 2.13 (s, 3H).

Example No. I.4-3

$^1$H NMR (400 MHz, CDCl$_3$ δ, ppm) 7.98 (d, 1H), 7.41 (t, 1H), 7.35 (s, 4H), 6.90 (t, 1H), 6.69 (d, 1H), 5.97 (br. s, 1H), 5.58 (s, 1H), 2.69 (s, 3H).

Example No. I.4-4

$^1$H NMR (400 MHz, CDCl$_3$ δ, ppm) 7.98 (d, 1H), 7.43 (t, 1H), 7.31 (d, 2H), 7.19 (d, 2H), 6.88 (t, 1H), 6.70 (d, 1H), 5.90 (br. s, 1H), 5.04 (s, 1H), 2.65 (s, 3H), 2.36 (s, 3H).

Example No. I.4-5

$^1$H NMR (400 MHz, CDCl$_3$ δ, ppm) 7.58 (m, 3H), 7.42 (m, 2H), 6.92 (d, 1H), 6.84 (t, 1H), 5.88 (s, 1H), 5.70 (br. s, 1H), 4.85 (br. s, 1H), 3.85 (s, 3H).

Example No. I.4-6

$^1$H NMR (400 MHz, CDCl$_3$ δ, ppm) 7.55 (d, 1H), 7.50 (d, 2H), 7.25 (d, 2H), 6.90 (d, 1H), 6.82 (1, 1H), 5.85 (s, 1H), 5.71 (br. s, 1H), 4.86 (br. s, 1H), 3.82 (s, 3H), 2.40 (s, 3H).

Example No. I.4-7

$^1$H NMR (400 MHz, CDCl$_3$ δ, ppm) 7.82 (d, 1H), 7.41 (m, 1H), 7.21 (d, 1H), 6.82 (t, 1H), 6.45 (m, 1H), 6.36 (m, 1H), 5.96 (s, 1H), 5.87 (br. s, 1H), 4.50 (br. s. 1H), 2.18 (s, 3H).

Example No. I.4-8

$^1$H NMR (400 MHz, CDCl$_3$ δ, ppm) 7.95 (d, 1H), 7.40 (t, 1H), 7.33 (m, 1H), 6.87 (t, 1H), 6.65 (d, 1H), 6.35 (s, 1H), 6.35 (br. s, 1H), 6.20 (m, 1H), 5.63 (m, 1H), 2.96 (s, 3H).

Example No. I.4-9

$^1$H NMR (400 MHz, CDCl$_3$ δ, ppm) 7.79 (d, 1H), 7.31 (m, 2H), 7.25 (m, 3H), 7.16 (d, 1H), 6.77 (t, 1H), 6.25 (br. s, 1H), 4.90 (1, 1H), 3.95 (br. s, 1H), 2.90 (m, 1H), 2.78 (m, 1H), 2.17 (m, 2H), 2.00 (s, 3H).

Example No. I.4-10

$^1$H NMR (400 MHz, CDCl$_3$ δ, ppm) 7.93 (d, 1H), 7.40 (t, 1H), 7.28 (m, 2H), 7.19 (m, 3H), 6.83 (t, 1H), 6.70 (br. s, 1H), 6.62 (d, 1H), 4.55 (m, 1H), 2.91 (s, 3H), 2.77 (m, 1H), 2.64 (m, 1H), 2.10 (m, 1H), 1.95 (m, 1H).

Example No. I.4-12

$^1$H NMR (400 MHz, CDCl$_3$ δ, ppm) 7.53 (d, 1H), 7.42 (m, 1H), 6.90 (d, 1H), 6.82 (t, 1H), 6.45 (m, 1H), 6.36 (m, 1H), 6.23 (br. s, 1H), 5.95 (s, 1H), 5.10 (br. s, 1H), 3.85 (s, 3H).

Example No. I.4-13;

$^1$H NMR (400 MHz, CDCl$_3$ δ, ppm) 7.85 (d, 1H), 7.41 (m, 1H), 7.24 (m, 2H), 7.04 (m, 1H), 6.85 (t, 1H), 6.20 (s, 1H), 6.00 (br. s, 1H), 4.43 (br. s, 1H), 2.17 (s, 3H).

Example No. I.4-14

¹H NMR (400 MHz, CDCl₃ δ, ppm) 8.00 (d, 1H), 7.44 (t, 1H), 7.25 (m, 1H), 7.05 (m, 1H), 6.93 (m, 1H), 6.91 (t, 1H), 6.65 (d, 1H), 6.30 (br. s, 1H), 5.85 (s, 1H) 2.83 (s, 3H).

Example No. I.4-15

¹H NMR (400 MHz, CDCl₃ δ, ppm) 7.54 (d, 1H), 7.40 (m, 1H), 7.22 (d, 1H), 7.02 (dd, 1H), 6.93 (d, 1H), 6.85 (t, 1H), 6.28 (s, 1H), 5.90 (br. s, 1H), 5.05 (br. s, 1H), 3.85 (s, 3H).

Example No. I.4-16

¹H NMR (400 MHz, CDCl₃ δ, ppm) 7.49 (d, 1H), 7.30 (m, 2H), 7.22 (m, 3H), 6.86 (d, 1H), 6.77 (t. 1H), 6.32 (br. s, 1H), 4.92 (1, 1H), 4.66 (br. s, 1H), 3.84 (s, 3H), 2.82 (m. 2H), 2.14 (m, 2H).

Example No. I.4-17:

¹H NMR (400 MHz, CDCl₃ δ, ppm) 7.84 (d, 1H), 7.73 (m, 1H), 7.43 (m, 1H), 7.32 (m, 2H), 7.32 (d, 1H), 6.81 (t, 1H), 6.35 (s, 1H), 5.91 (br. s, 1H), 4.56 (br. s, 1H), 2.15 (s, 3H).

Example No. I.4-18

¹H NMR (400 MHz, CDCl₃ δ, ppm) 7.95 (dd, 1H), 7.46 (dt, 1H), 7.40 (d, 1H), 7.25 (m, 2H), 7.17 (t, 1H), 6.87 (t, 1H), 6.74 (d, 1H), 6.26 (br. s, 1H), 6.13 (s, 1H), 2.90 (s, 3H).

Example No. I.4-19

¹H NMR (400 MHz. CDCl₃ δ, ppm) 7.73 (m, 1H), 7.40 (m, 1H), 7.39 (s, 1H), 7.32 (m, 2H), 6.28 (s, 1H), 6.19 (s, 1H), 6.00 (br. s, 1H), 4.50 (br. s, 1H), 3.86 (s, 3H), 3.85 (s, 3H).

Example No. I.4-20

¹H NMR (400 MHz, CDCl₃ δ, ppm) 7.78 (m, 1H), 7.55 (d, 1H), 7.41 (m, 1H), 7.33 (m, 2H), 6.90 (d, 1H), 6.81 (t, 1H), 6.38 (s, 1H), 5.84 (br. s, 1H), 5.07 (br. s. 1H), 3.85 (s, 3H).

Example No. I.4-21

¹H NMR (400 MHz, CDCl₃ δ, ppm) 7.83 (d, 1H), 7.74 (m, 4H), 7.24 (d, 1H), 6.85 (t, 1H), 6.14 (br. s, 1H), 5.97 (s, 1H), 4.24 (br. s, 1H), 2.15 (s, 3H).

Example No. I.4-22

¹H NMR (400 MHz, CDCl₃ δ, ppm) 7.95 (d, 1H), 7.61 (d, 2H), 7.50 (d, 2H), 7.44 (t, 1H), 6.90 (t, 1H), 6.70 (br. s, 1H), 6.69 (d, 1H), 5.67 (br. s, 1H), 2.75 (s, 3H).

Example No. I.4-23:

¹H NMR (400 MHz, CDCl₃ δ, ppm) 7.63 (d, 2H), 7.56 (d, 2H), 7.50 (m, 4H), 7.44 (s, 1H), 6.53 (br. s, 1H), 6.21 (s, 1H), 5.63 (d, 1H), 4.55 (d, 1H), 4.31 (d, 1H), 3.87 (s. 3H), 3.73 (s, 3H).

Example No. I.4-24

¹H NMR (400 MHz, CDCl₃ δ, ppm) 7.75 (d, 2H), 7.70 (d, 2H), 7.55 (d, 1H), 6.93 (d, 1H), 6.85 (t, 1H), 5.96 (br. s, 1H), 5.96 (s, 1H), 4.90 (br. s, 1H), 3.85 (s, 3H).

Example No. I.4-25

¹H NMR (400 MHz, CDCl₃ δ, ppm) 7.81 (d, 1H), 7.65 (d, 1H), 7.45 (d, 1H), 7.30 (dd, 1H), 7.21 (d, 1H), 6.81 (t, 1H), 6.30 (s, 1H), 6.10 (br. s. 1H), 4.55 (br, s, 1H), 2.14 (s, 3H).

Example No. I.4-26

¹H NMR (400 MHz, CDCl₃ δ, ppm) 7.94 (d, 1H), 7.46 (dt, 1H), 7.43 (d, 1H), 7.19 (t, 1H), 7.15 (dd, 1H), 6.89 (t, 1H), 6.72 (d, 1H), 6.22 (br. s, 1H), 6.08 (d, 1H), 2.89 (s, 3H).

Example No. I.4-27

¹H NMR (400 MHz, CDCl₃ δ, ppm) 7.68 (d, 1H), 7.44 (d, 1H), 7.40 (s, 1H), 7.30 (dd, 1H), 6.23 (d, 1H), 6.18 (s, 1H), 5.75 (br. s, 1H), 4.40 (br. s, 1H), 3.88 (s, 3H), 3.87 (s, 3H).

Example No. I.4-28

¹H NMR (400 MHz, CDCl₃ δ, ppm) 7.70 (d, 1H), 7.50 (d, 1H), 7.44 (d, 1H), 7.30 (dd, 1H), 6.90 (d, 1H), 6.82 (t, 1H), 6.32 (a, 1H), 5.91 (br. s, 1H), 5.04 (br. s, 1H), 3.85 (s, 3H).

Example No. I.4-29;

¹H NMR (400 MHz, CDCl₃ δ, ppm) 7.71 (dt. 1H), 7.53 (d, 1H), 6.90 (m, 2H), 6.84 (m, 2H), 6.26 (s, 1H), 5.92 (br. s, 1H), 4.90 (br. s, 1H), 3.85 (s, 3H).

Example No. I.4-30

¹H NMR (400 MHz, CDCl₃ δ, ppm) 7.83 (d, 1H), 7.67 (dt, 1H), 7.22 (d, 1H), 6.98-6.86 (m, 2H), 6.82 (t, 1H), 6.25 (s, 1H), 5.95 (br. s, 1H), 4.32 (br. s, 1H), 2.15 (s, 3H).

Example No. I.4-31

¹H NMR (400 MHz, CDCl₃ δ, ppm) 7.95 (d, 1H), 7.44 (t, 1H), 7.25 (t, 1H), 6.91-6.86 (m, 3H), 6.68 (d, 1H), 6.20 (br. s, 1H), 6.00 (d, 1H), 2.86 (s, 3H).

Example No. I.4-32

¹H NMR (400 MHz, CDCl₃ δ, ppm) 7.82 (d, 1H), 7.53 (t, 1H), 7.33 (dt, 2H), 7.23 (d, 1H), 6.82 (t, 1H), 6.23 (s, 1H), 5.95 (br. s, 1H), 4.36 (br. s, 1H), 2.15 (s, 3H).

Example No. I.4-33

¹H NMR (400 MHz, CDCl₃ δ, ppm) 7.95 (d, 1H), 7.44 (t, 1H), 7.29 (d, 1H), 7.20 (d, 1H), 7.12 (t, 1H), 6.89 (t, 1H), 6.68 (d, 1H), 6.13 (br. s, 1H), 5.99 (d, 1H), 2.89 (s, 3H).

Example No. I.4-34

¹H NMR (400 MHz, CDCl₃ δ, ppm) 7.54 (t, 1H), 7.39 (s, 1H), 7.35 (d, 1H), 7.30 (dd, 1H), 6.20 (s, 1H), 6.17 (d, 1H), 5.80 (br. s, 1H), 4.30 (br. s, 1H), 3.87 (s, 3H), 3.86 (s, 3H).

Example No. I.4-35

¹H NMR (400 MHz, CDCl₃ δ, ppm) 7.56 (t, 1H), 7.52 (d, 1H), 7.35 (d, 1H), 7.30 (d, 1H), 6.90 (d, 1H), 6.82 (t, 1H), 6.25 (s, 1H), 5.88 (br. s, 1H), 4.94 (br. s, 1H), 3.85 (s, 3H).

Example No. I.4-36

¹H NMR (400 MHz, CDCl₃ δ, ppm) 7.85 (d, 1H), 7.70 (d, 1H), 7.30 (d, 1H), 7.25 (m, 2H), 6.85 (d, 1H), 6.11 (s, 1H), 5.71 (br. s, 1H), 4.10 (br. s, 1H), 2.47 (s, 3H), 2.15 (s, 3H).

Example No. I.4-37

¹H NMR (400 MHz, CDCl₃ δ, ppm) 7.98 (dd, 1H), 7.45 (dt, 1H), 7.41 (d, 1H), 7.24 (m, 2H), 6.92 (t, 1H), 6.77 (d, 1H), 5.84 (s, 1H), 5.80 (br. s, 1H), 2.61 (s, 3H), 2.45 (s, 3H).

Example No. I.4-38

¹H NMR (400 MHz, CDCl₃ δ, ppm) 7.65 (d, 1H), 7.41 (s, 1H), 7.26 (m, 1H), 7.23 (m, 1H), 6.22 (s, 1H), 6.06 (s, 1H), 5.61 (br. s, 1H), 4.05 (br. s, 1H), 3.89 (s, 3H), 3.87 (s, 3H), 2.45 (s, 3H).

Example No. I.4-39

¹H NMR (400 MHz, CDCl₃ δ, ppm) 7.70 (d, 1H), 7.55 (d, 1H), 7.27 (m, 1H), 7.23 (m, 1H), 6.92 (d, 1H), 6.85 (t, 1H), 6.11 (s, 1H), 5.66 (br. s, 1H), 4.78 (br. s, 1H), 3.85 (s, 3H), 2.45 (s, 1H).

Example No. I.4-40

¹H NMR (400 MHz, CDCl₃ δ, ppm) 7.80 (m, 2H), 7.70 (s, 1H), 7.56 (d, 1H), 7.22 (d, 1H), 6.82 (t, 1H), 6.54 (br. s, 1H), 6.35 (s, 1H), 4.68 (br. s, 1H), 2.15 (s, 3H).

Example No. I.4-41

¹H NMR (400 MHz. CDCl₃ δ, ppm) 7.94 (d, 1H), 7.69 (s, 1H), 7.49 (dt, 1H), 7.43 (d, 1H), 7.34 (d. 1H), 6.90 (t, 1H), 6.75 (d, 1H), 6.40 (br. s, 1H), 6.13 (d, 1H), 2.95 (s, 3H).

Example No. I.4-43

¹H NMR (400 MHz, CDCl₃ δ, ppm) 7.86 (d, 1H), 7.69 (s, 1H), 7.57 (d, 1H), 7.54 (d, 1H), 6.91 (d, 1H), 6.82 (t, 1H), 6.38 (s, 1H), 6.10 (br. s, 1H), 5.15 (br. s, 1H), 3.85 (s, 3H).

Example No. I.4-44:

¹H NMR (400 MHz, CDCl₃ δ, ppm) 9.07 (s, 1H), 8.70 (d, 1H), 8.40 (d, 1H), 7.75 (d, 1H), 7.70 (dd, 1H), 7.63 (br. s, 1H), 7.24 (d, 1H), 6.84 (t, 1H), 6.14 (s, 1H), 5.35 (br. s, 1H), 2.17 (s, 3H).

Example No. I.4-45

¹H NMR (400 MHz, CDCl₃ δ, ppm) 8.63 (m, 2H), 7.99 (d, 1H), 7.77 (dt, 1H), 7.45 (dt, 1H), 7.31 (dd, 1H), 6.91 (t, 1H), 6.70 (d, 1H), 6.20 (br. s, 1H), 5.66 (d, 1H), 2.76 (s, 3H).

Example No. I.4-46

¹H NMR (400 MHz, CDCl₃ δ, ppm) 7.50 (s, 1H), 7.33 (d, 1H), 7.15 (m, 5H), 6.02 (s, 1H), 5.88 (d, 1H), 5.82 (br. s, 1H), 4.44 (d, 1H), 4.03 (d, 1H), 3.90 (s, 3H), 3.67 (s, 3H), 2.25 (s, 3H), 2.12 (s, 3H).

Example No. I.4-48

¹H NMR (400 MHz, CDCl₃ δ, ppm) 7.45 (s, 1H), 7.28 (m, 1H), 7.20 (d, 1H), 6.97 (m, 3H), 6.89 (dd, 1H), 6.45 (s, 1H), 6.23 (br. s, 1H), 5.85 (d, 1H), 4.70 (d, 1H), 4.40 (d, 1H), 3.87 (s, 3H), 3.83 (s, 3H).

Example No. I.4-49

¹H NMR (400 MHz, CDCl₃ δ, ppm) 7.73 (m, 1H), 7.54 (d, 1H), 7.43 (m, 1H), 7.35 (m, 2H), 6.85 (d, 1H), 6.35 (s, 1H), 5.89 (br. s, 1H), 5.04 (br. s, 1H), 3.85 (s, 3H).

Example No. I.4-50

¹H NMR (400 MHz, CDCl₃ δ, ppm) 7.42 (s, 1H), 7.30 (m, 1H), 7.23 (m, 1H), 6.77-6.70 (m, 3H), 6.83 (t, 1H), 6.30 (s, 1H), 6.09 (br. s, 1H), 5.95 (d, 1H), 4.60 (d, 1H), 4.36 (d, 1H), 3.87 (s, 3H), 3.82 (s, 3H).

Example No. I.4-54

¹H NMR (400 MHz, CDCl₃ δ, ppm) 7.60 (s, 1H), 7.54 (d, 1H), 7.47 (m, 1H), 6.91 (d, 1H), 6.84 (t, 1H), 6.65 (d, 1H), 5.91 (s, 1H), 5.90 (br. s, 1H), 4.85 (br. s. 1H), 3.85 (s. 3H).

Example No. I.4-55

¹H NMR (400 MHz, CDCl₃ δ, ppm) 7.84 (d, 1H), 7.51 (d, 1H), 7.42 (m, 1H), 7.34 (m, 1H), 7.23 (d, 1H), 6.83 (t, 1H), 6.07 (br. s, 1H), 6.01 (s, 1H), 4.30 (br. s, 1H), 2.15 (s, 3H).

Example No. I.4-56

¹H NMR (400 MHz, CDCl₃ δ, ppm) 7.97 (d, 1H), 7.42 (t, 1H), 7.30 (m, 1H), 7.27 (m, 1H), 7.08 (d, 1H), 6.90 (t, 1H), 6.67 (d, 1H), 6.33 (br. s, 1H), 5.69 (s, 1H), 2.76 (s, 3H).

Example No. I.4-57

¹H NMR (400 MHz, CDCl₃ δ, ppm) 7.55 (d, 1H), 7.50 (m, 1H), 7.40 (m, 1H), 7.33 (d, 1H), 6.91 (d, 1H), 6.83 (t, 1H), 6.00 (s, 1H), 5.95 (br. s, 1H), 4.93 (br. s, 1H), 3.85 (s, 3H).

Example No. I.4-58

¹H NMR (400 MHz, CDCl₃ δ, ppm) 8.70 (s, 1H), 7.52 (s, 1H), 7.49 (t, 1H), 7.16 (d, 1H), 7.03 (t, 1H), 6.83 (t, 1H), 6.66 (s, 1H), 6.56 (br. s, 1H), 3.97 (s, 3H), 3.92 (s, 3H).

Example No. I.4-59

¹H NMR (400 MHz, CDCl₃ δ, ppm) 8.72 (s, 1H), 7.55 (s, 1H), 7.28 (d, 1H), 7.20 (d, 1H), 6.89 (dd, 1H), 6.61 (s, 1H), 6.00 (br, a, 1H), 3.94 (s, 6H).

Example No. I.4-60

¹H NMR (400 MHz, CDCl₃ δ, ppm) 7.56 (d, 1H), 7.37 (m, 2H), 7.29 (m, 1H), 7.12-7.05 (m, 3H), 7.00 (d, 1H), 6.90 (d, 1H), 6.62 (br. s, 1H), 5.45 (d, 1H), 4.35 (d, 2H), 3.92 (s, 3H).

Example No. I.4-61

¹H NMR (400 MHz, CDCl₃ δ, ppm) 7.45 (s, 1H), 7.32 (m, 1H), 7.26 (m, 1H), 7.19 (m, 1H), 7.15 (m, 1H), 7.04 (m, 2H), 6.29 (s, 1H), 6.18 (br. s, 1H), 5.70 (d, 1H), 4.50 (d, 1H), 4.20 (d, 1H), 3.88 (s, 3H), 3.76 (s, 3H).

Example No. I.4-63

$^1$H NMR (400 MHz, CDCl$_3$ δ, ppm) 7.97 (d, 1H), 7.41 (t, 1H), 7.30 (s, 1H), 6.88 (d, 1H), 6.78 (br. s, 1H), 6.64 (d, 1H), 5.60 (s, 1H), 3.82 (s, 3H), 2.80 (s, 3H).

Example No. I.4-66

$^1$H NMR (400 MHz, CDCl$_3$ δ, ppm) 7.97 (d, 1H), 7.40 (t, 1H), 6.86 (t, 1H), 6.65 (d, 1H), 6.20 (br. s, 1H), 5.80 (s, 1H), 5.56 (d, 1H), 3.71 (s, 3H), 2.80 (s, 3H), 2.17 (s, 3H).

Example No. I.4-68

$^1$H NMR (400 MHz, CDCl$_3$ δ, ppm) 7.97 (d, 1H), 7.41 (t, 1H), 7.37-7.23 (m, 5H), 6.87 (t, 1H), 6.65 (d, 1H), 6.61 (d, 1H), 6.40 (br. s, 1H), 6.31 (dd, 1H), 5.08 (dd, 1H), 2.88 (s, 3H).

Example No. I.4-71

$^1$H NMR (400 MHz, CDCl$_3$ δ, ppm) 7.95 (d, 1H), 7.55 (d, 2H), 7.42 (d, 2H), 7.34 (t, 1H), 6.91 (t, 1H), 6.68 (d, 1H), 5.90 (s, 1H), 5.75 (br. s, 1H), 4.35 (br. s, 1H).

Example No. I.4-72

$^1$H NMR (400 MHz, CDCl$_3$ δ, ppm) 7.54 (d, 1H), 6.90 (d, 1H), 6.80 (t, 1H), 6.19 (s, 1H), 6.07 (br. s, 1H), 5.90 (s, 1H), 5.75 (br. s, 1H), 4.95 (br. s, 1H), 3.84 (s, 3H), 3.76 (s, 3H), 2.27 (s, 3H).

Example No. I.4-73

$^1$H NMR (400 MHz, CDCl$_3$ δ, ppm) 7.81 (d, 1H), 7.22 (d, 1H), 6.81 (t, 1H), 6.69 (br. s, 1H), 6.19 (s, 1H), 5.92 (s, 1H), 4.56 (br. s, 1H), 3.77 (s, 3H), 2.28 (s, 3H), 2.15 (s, 3H).

Example No. I.4-74

$^1$H NMR (400 MHz, CDCl$_3$ δ, ppm) 7.82 (d, 1H), 7.43 (m, 2H), 7.35 (m, 3H), 7.21 (d, 1H), 6.80 (t, 1H), 6.76 (d, 1H), 6.40 (dd, 1H) 5.87 (br, s, 1H), 5.48 (d, 1H), 4.19 (br. s, 1H), 2.17 (s, 3H).

Example No. I.4-75

$^1$H NMR (400 MHz, CDCl$_3$ δ, ppm) 7.53 (d, 1H), 7.40 (m, 2H), 7.34 (m, 3H), 6.90 (d, 1H), 6.80 (t, 1H), 6.73 (d, 1H), 6.39 (dd, 1H) 5.90 (br. s, 1H), 5.48 (d, 1H), 4.32 (br. s, 1H), 3.85 (s, 3H).

Example No. I.4-76

$^1$H NMR (400 MHz, CDCl$_3$ δ, ppm) 7.81 (d, 1H), 7.40 (m, 1H), 7.21 (d, 1H), 6.80 (t, 1H), 6.57 (d, 1H), 6.40 (m, 1H), 6.38 (m, 1H), 6.30 (dd, 1H), 5.90 (br. s, 1H), 5.44 (d, 1H), 4.16 (br. s, 1H), 2.16 (s, 3H).

Example No. I.4-77

$^1$H NMR (400 MHz, CDCl$_3$ δ, ppm) 7.95 (d, 1H), 7.40 (dt, 1H), 7.33 (s, 1H), 6.85 (t, 1H), 6.65 (d, 1H), 6.43 (d, 1H), 6.36 (br. s, 1H), 6.36 (m, 1H), 6.30 (m, 1H), 6.22 (dd, 1H), 5.04 (dd, 1H), 2.89 (s, 3H).

Example No. I.4-78;

$^1$H NMR (400 MHz, CDCl$_3$ δ, ppm) 7.52 (d, 1H), 7.39 (m, 1H), 6.90 (d, 1H), 6.80 (t, 1H), 6.55 (d, 1H), 6.40 (m, 1H), 6.37 (m, 1H), 6.30 (dd, 1H) 5.74 (br. s, 1H), 5.43 (d, 1H), 4.80 (br. s, 1H), 3.85 (s, 3H).

Example No. I.4-80

$^1$H NMR (400 MHz, CDCl$_3$ δ, ppm) 7.54 (d, 2H), 7.42 (d, 2H), 7.41 (s, 1H), 6.20 (s, 1H), 5.85 (s, 1H), 5.64 (br. s, 1H), 4.15 (br. s, 1H), 3.89 (s, 3H), 3.86 (s, 3H).

Example No. I.4-81

$^1$H NMR (400 MHz, CDCl$_3$ δ, ppm) 7.47 (d, 2H), 7.42 (s, 1H), 7.25 (d, 2H), 6.19 (s, 1H), 5.80 (s, 1H), 5.65 (br. s, 1H), 4.15 (br. s, 1H), 3.89 (s, 3H), 3.86 (s, 3H), 2.40 (s, 3H).

Example No. I.4-84

$^1$H NMR (400 MHz, CDCl$_3$, ppm) 7.61 (s, 1H), 7.52 (d, 1H), 7.46 (m, 1H), 6.93 (d, 1H), 6.82 (t, 1H), 6.67 (d, 1H), 5.90 (s, 1H), 5.87 (br. s, 1H), 4.82 (br. s, 1H), 2.27 (s, 3H).

Example No. I.4-85

$^1$H NMR (400 MHz, CDCl$_3$ δ, ppm) 7.97 (d, 1H), 7.45 (m, 1H), 7.41 (d, 1H), 7.37 (m, 1H), 6.90 (t, 1H), 6.68 (d, 1H), 6.59 (br. s, 1H), 6.34 (m, 1H), 5.59 (d, 1H), 2.80 (s, 3H).

Example No. I.4-89

$^1$H NMR (400 MHz, CDCl$_3$ δ, ppm) 7.83 (d, 1H), 7.65 (s, 1H), 7.60 (s, 1H), 7.23 (d, 1H), 6.84 (t, 1H), 5.97 (br. s, 1H), 5.90 (s, 1H), 4.23 (br. s, 1H), 3.94 (s, 3H), 2.15 (s, 3H).

Example No. I.4-90

$^1$H NMR (400 MHz. CDCl$_3$ δ, ppm) 7.98 (dd, 1H), 7.42 (dt, 1H), 6.88 (t, 1H), 6.67 (d, 1H), 6.59 (s, 2H), 6.51 (d. 1H), 6.18 (dd, 1H), 6.10 (br. s, 1H), 5.60 (br. s, 1H), 5.07 (dd, 1H), 3.89 (s, 6H), 2.90 (s, 3H).

Example No. I.4-92

$^1$H NMR (400 MHz, CDCl$_3$ δ, ppm) 7.96 (dd, 1H), 7.41 (dt, 1H), 7.29 (d, 2H), 6.86 (t, 1H), 6.83 (d, 2H), 6.65 (d, 1H), 6.55 (d, 1H), 6.24 (br. s, 1H), 6.18 (dd, 1H), 5.60 (br. s, 1H), 5.05 (dd, 1H), 3.80 (s, 3H), 2.89 (s, 3H).

Example No. I.4-93

$^1$H NMR (400 MHz, CDCl$_3$ δ, ppm) 7.53 (d, 1H), 7.36 (d, 2H), 6.90 (d, 1H), 6.88 (d, 2H), 6.80 (t, 1H), 6.68 (d, 1H), 6.25 (dd, 1H) 5.75 (br. s, 1H), 5.45 (d, 1H), 4.80 (br. s, 1H), 3.85 (s, 3H), 3.82 (s, 3H).

Example No. I.4-94

$^1$H NMR (400 MHz, CDCl$_3$ δ, ppm) 7.45 (s, 1H), 7.28 (d, 2H), 7.20 (d, 2H), 7.12 (d, 4H), 6.20 (s, 1H), 6.05 (br. s, 1H), 6.64 (d, 1H), 4.41 (d, 1H), 4.10 (d, 1H), 3.87 (s, 3H), 3.68 (s, 3H), 2.32 (s, 3H), 2.31 (s, 3H).

Example No. I.4-95

$^1$H NMR (400 MHz, CDCl$_3$ δ, ppm) 7.84 (d, 1H), 7.41 (d, 1H), 7.60 (s, 1H), 7.22 (d, 1H), 6.83 (t, 1H), 6.42 (d, 1H), 6.08 (br. s, 1H), 5.99 (s, 1H), 4.43 (br. s, 1H), 4.17 (q, 2H), 2.16 (s, 3H), 1.50 (t, 3H).

Example No. I.4-96

$^1$H NMR (400 MHz, CDCl$_3$ δ, ppm) 7.97 (dd, 1H), 7.40 (dt, 1H), 6.86 (t, 1H), 6.65 (d, 1H), 6.23 (br. s, 1H), 6.03 (d, 1H), 5.65 (d, 1H), 4.12 (q, 2H), 2.81 (s, 3H), 1.45 (t, 3H).

Example No. I.4-97;

$^1$H NMR (400 MHz, CDCl$_3$ δ, ppm) 7.55 (d, 1H), 7.40 (d, 1H), 6.90 (d, 1H), 6.82 (d, 2H), 6.44 (d, 1H), 6.01 (br. s, 1H), 5.99 (s. 1H), 5.03 (br. s, 1H), 4.17 (q, 2H), 3.85 (s, 3H), 1.50 (t, 3H).

Example No. I.4-98

$^1$H NMR (400 MHz, CDCl$_3$ δ, ppm) 7.82 (d, 1H), 7.40 (dd, 2H), 7.22 (d, 1H), 7.05 (t, 2H), 6.82 (t, 1H), 6.72 (d, 1H), 6.31 (dd, 1H), 5.73 (br. s, 1H), 5.47 (d, 1H), 4.16 (br. s, 1H), 2.16 (s, 3H).

Example No. I.4-99

$^1$H NMR (400 MHz, CDCl$_3$ δ, ppm) 7.97 (dd, 1H), 7.42 (dt, 1H), 7.32 (dd, 2H), 7.00 (t, 2H), 6.88 (t, 1H), 6.65 (d, 1H), 6.57 (d, 1H), 6.40 (br. s, 1H), 6.23 (dd, 1H), 5.07 (dd, 1H), 2.90 (s, 3H).

Example No. I.4-100

$^1$H NMR (400 MHz, CDCl$_3$ δ, ppm) 7.82 (d, 1H), 7.21 (d, 1H), 6.96 (d, 1H), 6.85 (t, 1H), 6.79 (m, 2H), 6.66 (d, 1H), 6.21 (dd, 1H), 5.98 (s, 2H), 5.90 (br. s, 1H), 5.45 (d, 1H), 4.15 (br. s, 1H), 2.16 (s, 3H).

Example No. I.4-101

$^1$H NMR (400 MHz, CDCl$_3$ δ, ppm) 7.97 (dd, 1H), 7.41 (dt, 1H), 6.87 (m, 2H), 6.80 (d, 1H), 6.74 (d, 1H), 6.65 (d, 1H), 6.52 (d, 1H), 6.14 (dd, 1H), 5.95 (s, 2H), 5.91 (br. s, 1H), 5.04 (dd, 1H), 2.87 (s, 3H).

Example No. I.4-102

$^1$H NMR (400 MHz, CDCl$_3$ δ, ppm) 7.53 (d, 1H), 6.95 (m, 1H), 6.90 (d, 1H), 6.85 (d, 1H), 6.80 (d, 1H), 6.77 (d, 1H), 6.64 (d, 1H), 6.20 (dd, 1H), 5.97 (s, 2H), 5.70 (br. s, 1H), 5.44 (d, 1H), 4.79 (br. s, 1H), 3.85 (s, 3H).

Example No. I.4-103

$^1$H NMR (400 MHz, CDCl$_3$ δ, ppm) 7.85 (d, 1H), 7.26 (d, 1H), 6.89 (t, 1H), 6.19 (s, 1H), 6.05 (s, 1H), 5.95 (br. s, 1H), 4.18 (br. s, 1H), 4.00 (s, 3H), 2.26 (s, 3H), 2.16 (s, 3H).

Example No. I.4-104

$^1$H NMR (400 MHz, CDCl$_3$ δ, ppm) 7.97 (dd, 1H), 7.46 (dt, 1H), 6.95 (t, 2H), 6.80 (d, 1H), 6.40 (br. s, 1H), 5.98 (s, 1H), 5.75 (s, 1H), 3.93 (s, 3H), 2.71 (s, 3H), 2.21 (s, 3H).

Example No. I.4-105

$^1$H NMR (400 MHz. CDCl$_3$ δ, ppm) 7.54 (d, 1H), 6.93 (d, 1H), 6.87 (t, 1H), 6.16 (s, 1H), 6.05 (s, 1H), 5.65 (br. s, 1H), 4.85 (br. s, 1H), 4.00 (s, 3H), 3.85 (s, 3H), 2.25 (s, 3H).

Example No. I.4-106

$^1$H NMR (400 MHz, CDCl$_3$ δ, ppm) 7.42 (s, 1H), 6.25 (s, 1H), 6.15 (s, 1H), 6.00 (s, 1H), 5.65 (br. s, 1H), 4.11 (br. s, 1H), 3.99 (s, 3H), 3.90 (s, 3H), 3.89 (s, 3H), 2.25 (s, 3H).

Example No. I.4-107

$^1$H NMR (400 MHz, CDCl$_3$ δ, ppm) 7.86 (d, 1H), 7.50 (d, 1H), 7.27 (d, 1H), 6.90 (t, 1H), 6.40 (d, 1H), 6.14 (s, 1H), 5.80 (br. s, 1H), 4.16 (br. s, 1H), 4.10 (s, 3H), 2.17 (s, 3H).

Example No. I.4-108

$^1$H NMR (400 MHz, CDCl$_3$ δ, ppm) 7.98 (dd, 1H), 7.46 (dt, 1H), 7.41 (d, 1H), 6.96 (t, 2H), 6.80 (d, 1H), 6.44 (br. s, 1H), 6.20 (d, 1H), 5.83 (s, 1H), 4.02 (s, 3H), 2.70 (s, 3H).

Example No. I.4-109

$^1$H NMR (400 MHz, CDCl$_3$ δ, ppm) 7.56 (d, 1H), 7.47 (d, 1H), 6.95 (d, 1H), 6.88 (t, 1H), 6.40 (d, 1H), 6.14 (s, 1H), 5.72 (br. s, 1H), 4.86 (br. s, 1H), 4.10 (s, 3H), 3.86 (s, 3H).

Example No. I.4-110

$^1$H NMR (400 MHz, CDCl$_3$ δ, ppm) 8.14 (d, 1H), 8.05 (dd, 1H), 7.84 (d, 1H), 7.76 (dt, 1H), 7.30 (m, 1H), 7.24 (d, 1H), 6.83 (t, 1H), 6.75 (d, 1H), 6.48 (dd, 1H), 6.07 (br. s, 1H), 5.52 (d, 1H), 4.20 (br. s, 1H), 2.18 (s, 3H).

Example No. I.4-111

$^1$H NMR (400 MHz. CDCl$_3$ δ, ppm) 8.56 (d, 1H), 8.50 (dd, 1H), 7.97 (dd, 1H), 7.68 (dt, 1H), 7.42 (dt, 1H), 7.23 (m, 1H), 6.90 (1, 1H), 6.65 (d, 1H), 6.00 (d. 1H), 6.40 (dd, 1H), 6.26 (br. s, 1H), 5.10 (s, 1H), 2.90 (s, 3H).

Example No. I.4-112

$^1$H NMR (400 MHz, CDCl$_3$ δ, ppm) 7.53 (d, 1H), 7.40 (m, 2H), 7.04 (t, 2H), 6.90 (d, 1H), 6.81 (t, 1H), 6.70 (d, 1H), 6.30 (dd, 1H), 5.73 (br. s, 1H), 5.46 (d, 1H), 4.80 (br. s, 1H), 3.85 (s, 3H).

Example No. I.4-115

$^1$H NMR (400 MHz, CDCl$_3$ δ, ppm) 7.86 (d, 1H), 7.53 (d, 1H), 7.27 (d, 1H), 6.90 (t, 1H), 6.40 (d, 1H), 6.12 (s, 1H), 5.86 (br. s, 1H), 4.44 (q, 2H), 4.17 (br. s, 1H), 2.17 (s, 3H), 1.50 (t, 3H).

Example No. I.4-116

¹H NMR (400 MHz, CDCl₃ δ, ppm) 8.00 (dd, 1H), 7.47 (d, 1H), 7.47 (dt, 1H), 6.97 (t, 1H), 6.80 (d, 1H), 6.22 (d, 1H), 6.17 (br. s, 1H), 5.83 (s, 1H), 4.46 (q, 2H), 2.70 (s, 3H), 1.47 (t, 3H).

Example No. I.4-117

¹H NMR (400 MHz, CDCl₃ δ, ppm) 7.55 (d, 1H), 7.50 (d, 1H), 6.95 (d, 1H), 6.88 (t, 1H), 6.39 (d, 1H), 6.14 (s, 1H), 5.82 (br. s, 1H), 4.88 (br. s, 1H), 4.45 (q, 2H), 3.85 (s, 3H), 1.49 (t, 3H).

Example No. I.4-118

¹H NMR (400 MHz, CDCl₃ δ, ppm) 7.50 (d, 1H), 7.43 (s, 1H), 6.49 (d, 1H), 6.25 (s, 1H), 6.07 (d, 1H), 5.70 (br. s, 1H), 4.42 (q, 2H), 4.14 (br. s, 1H), 3.89 (s, 3H), 3.88 (s, 3H), 1.50 (t, 3H).

Example No. I.4-119

¹H NMR (400 MHz, CDCl₃ δ, ppm) 7.83 (d, 1H), 7.34 (m, 4H), 7.22 (d, 1H), 6.81 (t, 1H), 6.70 (d, 1H), 6.37 (dd, 1H), 5.77 (br. s, 1H), 4.17 (br. s, 1H), 2.16 (s, 3H).

Example No. I.4-120

¹H NMR (400 MHz, CDCl₃ δ, ppm) 7.97 (dd, 1H), 7.41 (d, 1H), 7.26 (s, 4H), 6.88 (t, 1H), 6.65 (d, 1H), 6.55 (d, 1H), 6.30 (dd, 1H), 6.27 (br. s, 1H), 5.07 (dd, 1H), 2.89 (s, 3H).

Example No. I.4-121

¹H NMR (400 MHz, CDCl₃ δ, ppm) 7.53 (d, 1H), 7.32 (m, 4H), 6.90 (d, 1H), 6.81 (t, 1H), 6.69 (d, 1H), 6.47 (dd, 1H), 5.78 (br. s, 1H), 5.48 (d. 1H), 4.80 (br. s, 1H), 3.85 (s, 3H).

Example No. I.4-122

¹H NMR (400 MHz. CDCl₃ δ, ppm) 7.47 (s, 1H), 7.28 (s, 4H), 6.52 (d, 1H), 6.33 (s, 1H), 6.30 (dd, 1H), 6.13 (br. s, 1H), 5.20 (dd, 1H), 4.18 (br. s, 1H), 3.90 (s, 3H), 3.87 (s, 3H).

Example No. I.4-123

¹H NMR (400 MHz, CDCl₃ δ, ppm) 7.84 (d, 1H), 7.62 (m, 2H), 7.24 (d, 1H), 7.15 (t, 2H), 6.85 (t, 1H), 5.90 (s, 1H), 5.78 (br. s, 1H), 4.20 (br. s, 1H), 2.15 (s, 3H).

Example No. I.4-124

¹H NMR (400 MHz, CDCl₃ δ, ppm) 7.99 (dd, 1H), 7.43 (m, 3H), 7.09 (t, 2H), 6.90 (t, 1H), 6.70 (d, 1H), 5.95 (br. s. 1H), 5.59 (d, 1H), 2.67 (s, 3H).

Example No. I.4-125

¹H NMR (400 MHz, CDCl₃ δ, ppm) 7.61 (m, 2H), 7.55 (d, 1H), 7.15 (t, 2H), 6.92 (d, 1H), 6.85 (t, 1H), 5.89 (s, 1H), 5.67 (br. s, 1H), 4.85 (br. s, 1H), 3.85 (s, 3H).

Example No. I.4-126

¹H NMR (400 MHz, CDCl₃ δ, ppm) 7.60 (m, 2H), 7.41 (s, 1H), 7.14 (t, 2H), 6.20 (s, 1H), 5.85 (s, 1H), 5.57 (br. s, 1H), 4.15 (br. s, 1H), 3.90 (s, 3H), 3.87 (s, 3H).

Example No. I.4-127

¹H NMR (400 MHz, CDCl₃ δ, ppm) 7.90 (m, 1H), 7.84 (d, 2H), 7.74 (d, 1H), 7.60 (t, 1H), 7.25 (d, 1H), 6.85 (t, 1H), 5.97 (s, 1H), 5.95 (br. s, 1H), 4.25 (br. s, 1H), 2.15 (s, 3H).

Example No. I.4-128

¹H NMR (400 MHz, CDCl₃ δ, ppm) 7.99 (dd, 1H), 7.65 (m, 3H), 7.51 (t, 1H), 7.45 (dt, 1H), 6.91 (t, 1H), 6.67 (d, 1H), 6.12 (br. s, 1H), 5.66 (d, 1H), 2.73 (s, 3H).

Example No. I.4-129

¹H NMR (400 MHz, d₆-DMSO δ, ppm) 8.47 (br. s, 1H), 7.80 (m, 1H), 7.73 (d, 1H), 7.67 (d, 1H), 7.60 (t, 1H), 7.22 (d, 1H), 6.99 (d. 1H), 6.76 (br. s, 1H), 6.65 (t, 1H), 5.80 (s, 1H), 3.80 (s, 3H).

Example No. I.4-130

¹H NMR (400 MHz, CDCl₃ δ, ppm) 7.89 (m, 1H), 7.81 (d, 1H), 7.72 (d. 1H), 7.58 (t, 1H), 7.41 (s, 1H), 6.21 (s, 1H), 5.94 (s, 1H), 5.70 (br. s, 1H), 4.20 (br. s, 1H), 3.90 (s, 3H), 3.87 (s, 3H).

Example No. I.4-132

¹H NMR (400 MHz, CDCl₃ δ, ppm) 8.04 (dd, 1H), 7.80 (d, 1H), 7.45 (dt, 1H), 7.35 (d, 1H), 7.29 (t, 1H), 7.25 (t, 1H), 7.24 (s, 1H), 6.92 (1, 1H), 6.87 (d, 1H), 5.94 (br. s, 1H), 5.86 (d, 1H), 3.80 (s, 3H), 2.70 (s, 3H).

Example No. I.4-133

¹H NMR (400 MHz, CDCl₃ δ, ppm) 7.90 (d, 1H), 7.60 (d, 1H), 7.36 (d, 1H), 7.30 (t, 1H), 7.28 (s, 1H), 7.18 (t, 1H), 6.91 (d, 1H), 6.84 (t, 1H), 6.19 (s, 1H), 5.85 (br. s, 1H), 4.98 (br. s, 1H), 3.81 (s, 6H).

Example No. I.4-135

¹H NMR (400 MHz, CDCl₃ δ, ppm) 7.85 (d, 1H), 7.70 (s, 1H), 7.60 (d, 1H), 7.18 (t, 1H), 6.92 (d, 1H), 6.60 (d, 1H), 6.25 (d, 1H), 6.03 (br. s, 1H), 4.80 (br. s, 1H).

Example No. I.4-136

¹H NMR (400 MHz, CDCl₃ δ, ppm) 7.84 (d, 1H), 7.74 (m, 1H), 7.69 (m, 1H), 7.55 (d, 1H), 7.15 (dd, 1H), 6.60 (d, 1H), 6.30 (m, 1H), 6.14 (br. s, 1H), 4.08 (br. s, 1H), 2.28 (s, 3H).

Example No. I.4-137

¹H NMR (400 MHz, CDCl₃ δ, ppm) 7.84 (d, 1H), 7.70 (s, 1H), 7.60 (m, 2H), 7.08 (d t, 1H), 6.65 (dd, 1H), 6.33 (s, 1H), 6.16 (br. s, 1H), 4.60 (br. s, 1H).

Example No. I.4-138

¹H NMR (400 MHz, CDCl₃ δ, ppm) 7.94 (d, 1H), 7.65 (s, 1H), 7.45 (t, 1H), 7.40 (d, 1H), 7.35 (d, 1H), 6.89 (1, 1H), 6.84

Example No. I.4-139

¹H NMR (400 MHz, CDCl₃ δ, ppm) 7.41 (d, 1H), 7.23 (m, 1H), 7.19 (t, 1H), 7.03 (dd, 1H), 6.95 (d, 1H), 6.62 (d, 1H), 6.10 (s, 1H), 5.98 (br. s, 1H), 4.67 (br. s, 1H).

Example No. I.4-140

¹H NMR (400 MHz, CDCl₃ δ, ppm) 7.76 (m, 1H), 7.40 (d, 1H), 7.21 (m, 1H), 7.18 (dd, 1H), 6.62 (d. 1H), 6.15 (s, 1H), 5.84 (br. s, 1H), 4.43 (br. s, 1H), 2.30 (s, 3H).

Example No. I.4-141

¹H NMR (400 MHz, CDCl₃ δ, ppm) 7.64 (dd, 1H), 7.40 (d, 1H), 7.22 (m, 1H), 7.10 (dt, 1H), 7.02 (m, 1H), 6.68 (dd, 1H), 6.16 (s, 1H), 5.95 (br. s, 1H), 4.50 (br. s, 1H).

Example No. I.4-143

¹H NMR (400 MHz, CDCl₃ δ, ppm) 7.42 (s, 1H), 7.27 (t, 1H), 6.90 (d, 1H), 6.61 (d, 1H), 6.47 (d, 1H), 6.38 (m, 1H), 6.16 (br. s, 1H), 5.84 (s, 1H), 4.70 (br. s, 1H).

Example No. I.4-145

¹H NMR (400 MHz. CDCl₃ δ, ppm) 7.85 (dd. 1H), 7.40 (m. 2H), 6.81 (t, 1H), 6.45 (d, 1H), 6.36 (m, 1H), 6.27 (br. s. 1H), 6.00 (s, 1H), 5.16 (br. s, 1H).

Example No. I.4-146

¹H NMR (400 MHz, CDCl₃ δ, ppm) 7.86 (d, 1H), 7.71 (m, 1H), 7.47-7.31 (m, 4H), 6.81 (t, 1H), 6.40 (d, 1H), 6.05 (br. s, 1H), 5.20 (br. s, 1H).

Example No. I.4-147

¹H NMR (40) MHz, CDCl₃ δ, ppm) 7.87 (d, 1H), 7.75 (m, 4H), 7.4 (d, 1H), 6.85 (t, 1H), 6.01 (s, 1H), 6.00 (br. s, 1H), 4.93 (br. s, 1H).

Example No. I.4-148

¹H NMR (400 MHz, CDCl₃ δ, ppm) 7.75 (m, 1H), 7.42 (m, 1H), 7.35 (m, 2H), 7.17 (t, 1H), 6.90 (d, 1H), 6.60 (d, 1H), 6.25 (s, 1H, 5.97 (br. s, 1H), 4.70 (br. s, 1H).

Example No. I.4-149

¹H NMR (400 MHz, CDCl₃ δ, ppm) 7.74 (m, 2H), 7.41 (m, 1H). 7.32 (m, 2H), 7.15 (dd, 1H), 6.60/d. 1H), 6.30 (d, 1H), 5.97 (br. s, 1H), 4.50 (br. s, 1H), 2.29 (s, 3H),

Example No. I.4-150

¹H NMR (400 MHz, CDCl₃ δ, ppm) 7.73 (m, 1H), 7.62 (dd, 1H), 7.44 (m 1H), 7.34 (m, 2H), 7.05 (dt, 1H), 6.65 (dd, 1H), 6.32 (s, 1H, 6.05 (br. s, 1H), 4.55 (br. s, 1H).

Example No. I.4-151

¹H NMR (400 MHz, CDCl₃ δ, ppm) 7.94 (d, 1H), 7.41 (m, 2H), 7.25 (m, 2H), 7.15 (t, 1H), 6.85 (t, 1H), 6.80 (d, 1H), 6.30 (br. s, 1H), 6.15 (d. 1H), 5.83 (m, 1H), 5.26 (d, 1H), 5.23 (d, 1H), 4.10 (m, 1H), 3.63 (m, 1H).

Example No. I.4-152

¹H NMR (400 MHz, CDCl₃ δ, ppm) 7.85 (d, 1H), 7.67 (m, 1H), 7.49-7.31 (m 4H), 6.38 (s, 1H), 6.05 (br. s, 1H), 5.20 (br. s, 1H).

Example No. I.4-153

¹H NMR (400 MHz, d₆-DMSO δ, ppm) 8.23 (br. s, H), 7.57 (m, 2H), 7.48 (m, 1H), 7.36 (m 2H), 7.18 (d, 1H), 6.68 (t, 1H), 6.35 (br. s, 1H), 6.10 (m, 1H), 2.10 (s, 3H).

Example No. I.4-154

¹H NMR (400 MHz, CDCl₃ δ, ppm) 7.73 (s, 4H), 7.20 (t, 1H), 6.95 (d, 1H), 6.61 (d. 1H), 5.91 (br. s, 1H), 5.88 (s, 1H), 4.50 (br. s. 1H).

Example No. I.4-155

¹H NMR (400 MHz, CDCl₃ δ, ppm) 7.77 (m, 1H), 7.72 (m, 4H), 7.18 (dd, 1H), 6.61 (d, 1H), 5.94 (d, 1H), 5.80 (br. s, 1H), 4.25 (br. s, 1H), 2.30 (s, 3H).

Example No. I.4-156

¹H NMR (400 MHz, CDCl₃ δ, ppm) 7.73 (m, 4H), 7.64 (dd, 1H), 7.10 (dt, 1H), 6.68 (dd, 1H), 5.95 (s, 1H), 5.95 (br. s, 1H), 4.31 (br. s, 1H).

Example No. I.4-157

¹H NMR (400 MHz, CDCl₃ δ, ppm) 7.74 (m, 1H), 7.40 (m, 1H), 7.15 (dd, 1H), 6.63 (d, 1H), 6.43 (d, 1H), 6.35 (m, 1H), 6.04 (br. s, 1H), 5.88 (d, 1H), 4.48 (br. s, 1H), 2.28 (s, 3H).

Example No. I.4-158

¹H NMR (400 MHz, CDCl₃ δ, ppm) 7.62 (dd, 1H), 7.41 (s, 1H), 7.07 (dt, 1H), 6.70 (dd, 1H), 6.44 (d, 1H), 6.37 (m, 1H), 6.03 (br. s, 1H), 5.90 (d, 1H), 4.51 (br. s, 1H).

Example No. I.4-159

¹H NMR (400 MHz, CDCl₃ δ, ppm) 7.83 (d, 1H), 7.43 (d, 1H), 7.40 (d, 1H), 6.44 (d, 1H), 6.37 (m, 1H), 6.30 (br. s, 1H), 5.98 (m, 1H), 5.65 (br. s, 1H).

Example No. I.4-160

¹H NMR (400 MHz, CDCl₃ δ, ppm) 7.81 (d, 1H), 7.41 (s, 1H), 7.21 (d, 1H), 6.82 (t, 1H), 6.45 (d, 1H), 6.42 (br. s, 1H), 6.36 (m, 1H), 5.95 (m, 1H), 4.50 (br. s, 1H), 2.17 (s, 3H).

Example No. I.4-161

¹H NMR (400 MHz, CDCl₃ δ, ppm) 7.85 (d, 1H), 7.41 (d, 1H), 7.25 (m, 2H), 7.04 (dd, 1H), 6.85 (t, 1H), 6.20 (s, 1H), 5.90 (br. s, 1H), 4.42 (br. s, 1H), 2.17 (s, 3H).

Example No. I.4-162

¹H NMR (400 MHz, CDCl₃ δ, ppm) 7.83 (d, 1H), 7.74 (m, 4H), 7.25 (d, 1H), 6.85 (t, 1H), 6.06 (br. s, 1H), 5.97 (s, 1H), 4.25 (br. s, 1H), 2.15 (s, 3H).

Example No. I.4-163

$^1$H NMR (400 MHz, CDCl$_3$ δ, ppm) 7.53 (d, 2H), 7.42 (d, 2H), 7.19 (t, 1H), 6.92 (d, 1H), 6.60 (d, 1H), 5.90 (br. s, 1H), 5.78 (s, 1H), 4.55 (br. s, 1H).

Example No. I.4-164

$^1$H NMR (400 MHz, CDCl$_3$ δ, ppm) 7.75 (m, 1H), 7.54 (d, 2H), 7.41 (d, 2H), 7.16 (dd, 1H), 6.60 (d, 1H), 5.85 (s, 1H), 5.70 (br. s, 1H), 4.20 (br. s, 1H), 2.30 (s, 3H).

Example No. I.4-165

$^1$H NMR (400 MHz, CDCl$_3$ δ, ppm) 7.63 (dd, 1H), 7.54 (d, 2H), 7.42 (d, 2H), 7.08 (dt, 1H), 6.65 (dd, 1H), 5.86 (s, 1H), 5.82 (br. s, 1H), 4.28 (br. s, 1H).

Example No. I.4-166

$^1$H NMR (400 MHz, CDCl$_3$ δ, ppm) 7.97 (dd, 1H), 7.42-7.30 (m, 5H), 6.89 (t, 1H), 6.76 (d, 1H), 6.65 (br. s, 1H), 5.78 (m, 1H), 5.74 (d, 1H), 5.20 (m, 2H), 3.95 (m, 1H), 3.55 (m, 1H).

Example No. I.4-167

$^1$H NMR (400 MHz, CDCl$_3$, ppm) 7.85 (d, 1H), 7.55 (d, 2H), 7.45 (d, 2H), 7.42 (d, 1H), 5.92 (s, 1H), 5.81 (br. s, 1H), 4.87 (br. s, 1H).

Example No. I.4-168

$^1$H NMR (400 MHz, CDCl$_3$, ppm) 7.85 (d, 1H), 7.57 (d, 2H), 7.45 (d, 2H), 7.25 (d, 1H), 6.85 (t, 1H), 5.89 (s, 1H), 5.77 (br. s, 1H), 4.22 (br. s, 1H), 2.15 (s, 3H).

Example No. I.4-169

$^1$H NMR (400 MHz, CDCl$_3$ δ, ppm) 7.87 (d, 1H), 7.56 (d, 2H), 7.45 (d, 2H), 7.43 (d, 1H), 6.85 (t, 1H), 5.94 (s, 1H), 5.82 (br. s, 1H), 4.90 (br. s, 1H).

Example No. I.4-170

$^1$H NMR (400 MHz, CDCl$_3$ δ, ppm) 7.69 (dt, 1H), 7.17 (t, 1H), 7.00-6.84 (m, 3H), 6.60 (d, 1H), 6.14 (d, 1H), 5.91 (br. s, 1H), 4.54 (br. s, 1H).

Example No. I.4-171

$^1$H NMR (400 MHz, CDCl$_3$ δ, ppm) 7.74 (m, 1H), 7.69 (dt, 1H), 7.15 (dd, 1H), 6.93 (dt, 1H), 6.87 (m, 1H), 6.60 (d, 1H), 6.20 (s, 1H), 5.86 (br. s, 1H), 4.31 (br. s, 1H), 2.30 (s, 3H).

Example No. I.4-172

$^1$H NMR (400 MHz, CDCl$_3$, ppm) 7.70-7.60 (m, 2H), 7.08 (dt, 1H), 7.00-6.84 (m, 2H), 6.65 (dd, 1H), 6.20 (s, 1H), 5.89 (br. s, 1H), 4.35 (br. s, 1H).

Example No. I.4-174

$^1$H NMR (400 MHz, CDCl$_3$ δ, ppm) 7.83 (d, 1H), 7.68 (dt, 1H), 7.22 (d, 1H), 6.95 (dt, 1H), 6.89 (m, 1H), 6.83 (t, 1H), 6.75 (s, 1H), 5.84 (br. s, 1H), 4.32 (br. s, 1H), 2.15 (s, 3H).

Example No. I.4-175

$^1$H NMR (400 MHz. CDCl$_3$ δ, ppm) 7.85 (d, 1H), 7.65 (dt, 1H), 7.41 (d, 1H), 7.00-6.85 (m, 2H), 6.83 (t, 1H), 6.30 (s, 1H), 6.10 (br. s, 1H), 5.00 (br. s, 1H).

Example No. I.4-176

$^1$H NMR (400 MHz, CDCl$_3$ δ, ppm) 7.50 (d, 1H), 7.40 (m, 1H), 7.30 (m, 1H), 7.18 (t, 1H), 6.91 (d, 1H), 6.60 (d, 1H), 6.10 (br. s, 1H), 5.90 (d, 1H), 4.60 (br. s, 1H).

Example No. I.4-177

$^1$H NMR (400 MHz, CDCl$_3$ δ, ppm) 7.64 (dd, 1H), 7.50 (m, 1H), 7.40 (m, 1H), 7.29 (m, 1H), 7.08 (dt, 1H), 6.65 (dd, 1H), 5.99 (s, 1H), 5.89 (br. s, 1H), 4.32 (br. s, 1H).

Example No. I.4-179

$^1$H NMR (400 MHz, CDCl$_3$ δ, ppm) 7.84 (d, 1H), 7.51 (m, 1H), 7.42 (m, 2H), 7.30 (m, 1H), 6.15 (br. s, 1H), 6.04 (s, 1H), 4.95 (br. s, 1H).

Example No. I.4-180

$^1$H NMR (400 MHz, CDCl$_3$, ppm) 7.82 (d, 1H), 7.53 (d, 1H), 7.41 (m, 1H), 7.36 (m, 1H), 7.25 (d, 1H), 6.81 (t, 1H), 6.05 (br. s, 1H), 6.02 (s, 1H), 4.36 (br. s, 1H), 2.19 (s, 3H).

Example No. I.4-181

$^1$H NMR (400 MHz, CDCl$_3$ δ, ppm) 7.86 (d, 1H), 7.51 (m, 1H), 7.42 (m, 2H), 7.31 (m, 1H), 6.83 (t, 1H), 6.05 (s, 1H), 6.00 (br. s, 1H), 4.97 (br. s, 1H).

Example No. I.4-182

$^1$H NMR (400 MHz, CDCl$_3$ δ, ppm) 7.36-719 (m, 5H), 7.12 (t, 1H), 6.86 (d, 1H), 6.47 (d, 1H), 5.90 (br. s, 1H), 4.79 (m, 1H), 4.17 (br. s, 1H), 2.85 (m, 1H), 2.74 (m, 1H), 2.10 (m, 2H).

Example No. I.4-183

$^1$H NMR (400 MHz. CDCl$_3$ δ, ppm) 7.68 (m, 1H), 7.30 (t, 2H), 7.22 (m, 3H), 7.10 (dd, 1H), 6.53 (d. 1H), 6.17 (br. s, 1H), 4.90 (1, 1H), 3.99 (br. s, 1H), 2.70 (m, 2H), 2.10 (m, 2H).

Example No. I.4-184

$^1$H NMR (400 MHz, CDCl$_3$ δ, ppm) 7.58 (dd, 1H), 7.36-7.19 (m, 5H), 7.03 (dt, 1H), 6.55 (dd, 1H), 6.10 (br. s, 1H), 4.86 (t, 1H), 4.00 (br. s, 1H), 2.80 (m, 2H), 2.11 (m, 2H).

Example No. I.4-186

$^1$H NMR (400 MHz, CDCl$_3$ δ, ppm) 7.80 (d, 1H), 7.35 (d, 1H), 7.35-7.20 (m, 5H), 6.70 (br. s, 1H), 4.95 (t, 1H), 4.68 (br. s, 1H), 2.84 (m, 2H), 2.17 (m, 2H).

Example No. I.4-187

$^1$H NMR (400 MHz, CDCl$_3$ δ, ppm) 7.71 (d, 1H), 7.32 (t, 2H), 7.26 (m, 3H), 7.15 (d, 1H), 6.76 (m, 1H), 6.20 (br. s, 1H), 5.00 (t, 1H), 3.96 (br. s, 1H), 2.92 (m, 1H), 2.80 (m, 1H), 2.20 (m, 2H).

Example No. I.4-188

¹H NMR (400 MHz, CDCl₃ δ, ppm) 7.80 (d, 1H), 7.35 (d, 1H), 7.30 (t, 2H), 7.25 (m, 3H), 6.78 (t, 1H), 6.67 (br. s, 1H), 4.97 (t, 1H), 4.72 (br. s, 1H), 2.85 (m, 2H), 2.19 (m, 2H).

Example No. I.4-189

¹H NMR (400 MHz, CDCl₃ δ, ppm) 7.45 (d, 2H), 7.25 (d, 2H), 7.18 (t, 1H), 6.91 (d, 1H), 6.59 (d, 1H), 5.82 (br. s, 1H), 5.75 (s, 1H), 4.45 (br. s, 1H), 2.40 (s, 3H).

Example No. I.4-190

¹H NMR (400 MHz, CDCl₃ δ, ppm) 7.65 (dd, 1H), 7.46 (d, 2H), 7.24 (d, 2H), 7.07 (dt, 1H), 6.63 (dd, 1H), 5.82 (s, 1H), 5.77 (br. s, 1H), 4.25 (br. s, 1H), 2.40 (s, 3H).

Example No. I.4-191

¹H NMR (400 MHz. CDCl₃ δ, ppm) 7.75 (m, 1H), 7.47 (d, 2H), 7.24 (d, 2H), 7.15 (dd, 1H), 6.59 (d. 1H), 5.81 (s, 1H), 5.70 (br. s, 1H), 4.21 (br. s, 1H), 2.40 (s, 3H), 2.30 (s, 3H).

Example No. I.4-192

¹H NMR (400 MHz, CDCl₃ δ, ppm) 7.85 (d, 1H), 7.48 (d, 2H), 7.41 (d, 1H), 7.29 (d, 2H), 5.89 (s, 1H), 5.80 (br. s, 1H), 4.85 (br. s, 1H), 2.40 (s, 3H).

Example No. I.4-193

¹H NMR (400 MHz, CDCl₃ δ, ppm) 7.85 (d, 1H), 7.50 (d, 2H), 7.27 (d, 2H), 7.22 (d, 1H), 6.82 (t, 1H), 5.85 (s, 1H), 5.76 (br. s, 1H), 4.21 (br. s, 1H), 2.40 (s, 3H), 2.12 (s, 3H).

Example No. I.4-194

¹H NMR (400 MHz, CDCl₃ δ, ppm) 7.88 (d, 1H), 7.50 (d, 2H), 7.41 (d, 1H), 7.28 (d, 2H), 6.82 (t, 1H), 5.90 (s, 1H), 5.81 (br. s, 1H), 4.90 (br. s, 1H), 2.40 (s, 3H).

Example No. I.4-195

¹H NMR (400 MHz, CDCl₃ δ, ppm) 7.87 (s, 1H), 7.80 (d, 1H), 7.75 (d, 1H), 7.60 (t, 1H), 7.20 (t, 1H), 6.96 (d, 1H), 6.62 (d, 1H), 5.89 (s, 1H), 5.89 (br. s, 1H), 4.50 (br. s, 1H).

Example No. I.4-196

¹H NMR (400 MHz, CDCl₃ δ, ppm) 7.87 (s, 1H), 7.81 (d, 1H), 7.75 (m, 1H), 7.71 (d, 1H), 7.58 (t, 1H), 7.18 (dd, 1H), 6.62 (d, 1H), 5.95 (s, 1H), 5.93 (br. s, 1H), 4.30 (br. s, 1H), 2.30 (s, 3H).

Example No. I.4-197

¹H NMR (400 MHz, CDCl₃ δ, ppm) 7.88 (s, 1H), 7.80 (d, 1H), 7.74 (d, 1H), 7.64 (m, 1H), 7.59 (t, 1H), 7.10 (dt, 1H), 6.68 (dd, 1H), 5.96 (s, 1H), 5.96 (br. s, 1H), 4.33 (br. s, 1H).

Example No. I.4-199

¹H NMR (400 MHz, CDCl₃ δ, ppm) 7.90 (s, 1H), 7.84 (d, 2H), 7.74 (d, 1H), 7.60 (t, 1H), 7.25 (d, 1H), 6.85 (t, 1H), 6.03 (br. s, 1H), 5.97 (s, 1H), 4.25 (br. s, 1H), 2.15 (s, 3H).

Example No. I.4-200

¹H NMR (400 MHz, CDCl₃ δ, ppm) 7.90 (s, 1H), 7.87 (d, 1H), 7.84 (d, 1H), 7.75 (d, 1H), 7.62 (t, 1H), 7.44 (d, 1H), 6.86 (t, 1H), 6.06 (br. s, 1H), 6.04 (s, 1H), 4.93 (br. s, 1H).

Example No. I.4-201

¹H NMR (400 MHz, CDCl₃ δ, ppm) 7.75 (m, 1H), 7.49 (d, 1H), 7.40 (m, 1H), 7.30 (m, 1H), 7.16 (dd, 1H), 6.60 (d, 1H), 5.97 (s, 1H), 5.85 (br. s, 1H), 4.30 (br. s, 1H), 2.30 (s, 3H).

Example No. I.4-203

¹H NMR (400 MHz, CDCl₃ δ, ppm) 8.77 (d, 1H), 8.71 (dd, 1H), 8.03 (dt, 1H), 7.77 (m, 1H), 7.40 (dd, 1H), 7.19 (dd, 1H), 6.62 (d, 1H), 5.94 (s, 1H), 5.81 (br. s, 1H), 4.26 (br. s, 1H), 2.30 (s, 3H).

Example No. I.4-204

¹H NMR (400 MHz, CDCl₃ δ, ppm) 8.78 (d, 1H), 8.72 (dd, 1H), 8.01 (dt, 1H), 7.65 (dd, 1H), 7.41 (dd, 1H), 7.10 (dt, 1H), 6.68 (dd, 1H), 5.95 (s, 1H), 5.90 (br. s, 1H), 4.30 (br. s, 1H).

Example No. I.4-206

¹H NMR (400 MHz, CDCl₃ δ, ppm) 8.80 (d, 1H), 8.71 (dd, 1H), 8.04 (dt, 1H), 7.84 (d, 1H), 7.41 (dd, 1H), 7.25 (d, 1H), 6.86 (t, 1H), 6.00 (br. s, 1H), 5.97 (s, 1H), 4.25 (br. s, 1H), 2.15 (s, 3H).

Example No. I.4-207

¹H NMR (400 MHz. CDCl₃ δ, ppm) 8.80 (d, 1H), 8.74 (dd, 1H), 8.04 (dt, 1H), 7.89 (d, 1H), 7.44 (m, 2H), 6.87 (1, 1H), 6.02 (s, 1H), 5.93 (br. s, 1H), 4.92 (br. s, 1H).

Example No. I.4-208

¹H NMR (400 MHz, CDCl₃ δ, ppm) 7.15 (t, 1H), 6.90 (d, 1H), 6.61 (d, 1H), 6.20 (br. 1H), 6.16 (s, 1H), 5.79 (s, 1H), 4.70 (br. s, 1H), 3.76 (s, 3H), 2.27 (s, 3H).

Example No. I.4-209

¹H NMR (400 MHz, CDCl₃ δ, ppm) 7.85 (d, 1H), 7.40 (d, 1H), 6.15 (s, 1H), 6.05 (br, s, 1H), 5.92 (s, 1H), 5.03 (br. s, 1H), 3.77 (s, 3H), 2.28 (s, 3H).

Example No. I.4-210

¹H NMR (400 MHz, CDCl₃ δ, ppm) 7.83 (d, 1H), 7.20 (d, 1H), 6.81 (t, 1H), 6.18 (s, 1H), 6.00 (br. s, 1H), 5.90 (s, 1H), 4.40 (br. s, 1H), 3.77 (s, 3H), 2.28 (s, 3H), 2.15 (s, 3H).

Example No. I.4-211

¹H NMR (400 MHz, CDCl₃ δ, ppm) 7.85 (d, 1H), 7.40 (d, 1H), 6.80 (t, 1H), 6.18 (s, 1H), 6.07 (br. s, 1H), 5.95 (s, 1H), 5.05 (br. s, 1H), 3.77 (s, 3H), 2.28 (s, 3H).

Example No. I.4-213

¹H NMR (400 MHz, CDCl₃ δ, ppm) 7.97 (dd, 1H), 7.35 (dt, 1H), 6.84 (t, 1H), 6.70 (d, 1H), 6.15 (br. s, 1H), 5.84 (s, 1H), 5.82 (m, 1H), 5.68 (d, 1H), 5.29 (m, 1H), 5.20 (m, 1H), 3.96 (m, 1H), 3.74 (m, 1H), 3.70 (s, 3H), Example No. I.4-214

$^1$H NMR (400 MHz, CDCl$_3$ δ, ppm) 7.67 (d, 1H), 7.45 (d, 1H), 7.32 (dd, 1H), 7.17 (t, 1H), 6.90 (d, 1H), 6.60 (d, 1H), 6.20 (s, 1H), 6.06 (br. s, 1H), 4.70 (br. s, 1H).

Example No. I.4-215

$^1$H NMR (400 MHz, CDCl$_3$ δ, ppm) 7.74 (m, 1H), 7.67 (d, 1H), 7.43 (d, 1H), 7.30 (dd, 1H), 7.15 (dd, 1H), 6.60 (d, 1H), 6.25 (s, 1H), 5.94 (br. s, 1H), 4.47 (br. s, 1H), 2.28 (s, 3H).

Example No. I.4-216

$^1$H NMR (400 MHz, CDCl$_3$ δ, ppm) 7.66 (d, 1H), 7.61 (dd, 1H), 7.45 (d, 1H), 7.32 (dd, 1H), 7.07 (dt, 1H), 6.65 (dd, 1H), 6.28 (s, 1H), 6.05 (br. s, 1H), 4.50 (br. s, 1H).

Example No. I.4-219

$^1$H NMR (400 MHz, CDCl$_3$ δ, ppm) 7.81 (d, 1H), 7.65 (d, 1H), 745/d. 1H), 7.30 (dd, 1H), 7.22 (d, 1H), 6.81 (1, 1H), 6.29 (d, 1H), 6.10 (br. s, 1H), 4.55 (br. s, 1H), 2.15 (s, 3H).

Example No. I.4-220

$^1$H NMR (400 MHz, CDCl$_3$ δ, ppm) 7.85 (d, 1H), 7.65 (d, 1H), 7.46 (d, 1H), 7.41 (dd, 1H), 7.32 (dd, 1H), 6.83 (t, 1H), 6.35 (m, 1H), 5.98 (br. s, 1H), 5.17 (br. s, 1H).

Example No. I.4-221

$^1$H NMR (400 MHz. CDCl$_3$ δ, ppm) 7.97 (dd. 1H), 7.43-7.24 (m. 8H), 6.85 (t, 1H), 6.70 (d, 1H), 6.58 (d, 1H), 6.30 (dd, 1H), 6.22 (br. s, 1H), 5.89 (m, 1H), 5.33 (d. 1H), 5.25 (m, 2H), 4.09 (m, 1H), 3.78 (m, 1H).

Example No. I.4-222

$^1$H NMR (400 MHz, CDCl$_3$ δ, ppm) 7.84 (d, 1H), 7.46-7.30 (m. 6H), 6.77 (d, 1H), 6.34 (dd. 1H), 5.90 (br. s, 1H), 5.52 (d, 1H), 4.85 (br. s, 1H).

Example No. I.4-223

$^1$H NMR (400 MHz, CDCl$_3$ δ, ppm) 7.82 (d, 1H), 7.42 (d, 2H), 7.40-7.30 (m, 3H), 7.21 (d, 1H), 6.81 (t, 1H), 6.76 (d, 1H), 6.40 (dd, 1H), 5.90 (br. s, 1H), 5.49 (d, 1H), 4.18 (br. s, 1H), 2.16 (s, 3H).

Example No. I.4-224

$^1$H NMR (400 MHz. CDCl$_3$ δ, ppm) 7.85 (d, 1H), 7.46-7.30 (m, 6H), 6.80 (t, 1H), 6.77 (d, 1H), 6.37 (dd, 1H), 5.90 (br. s, 1H), 5.53 (d, 1H), 4.87 (br. s, 1H).

Example No. I.4-225

$^1$H NMR (400 MHz, CDCl$_3$ δ, ppm) 7.54 (dd, 1H), 7.36 (dd, 1H), 7.30 (dd, 1H), 7.27 (t, 1H), 6.91 (d, 1H), 6.60 (d, 1H), 6.12 (s, 1H), 5.95 (br. s, 1H), 4.57 (br. s, 1H).

Example No. I.4-226

$^1$H NMR (400 MHz, CDCl$_3$ δ, ppm) 7.74 (m, 1H), 7.54 (dd, 1H), 7.34 (dd, 1H), 7.30 (dd, 1H), 7.15 (dd, 1H), 6.60 (d, 1H), 6.18 (m, 1H), 5.80 (br. s, 1H), 4.43 (br. s, 1H), 2.29 (s, 3H).

Example No. I.4-227

$^1$H NMR (400 MHz, CDCl$_3$ δ, ppm) 7.62 (dd, 1H), 7.52 (dd, 1H), 7.36 (dd, 1H), 7.30 (dd, 1H), 7.08 (dt, 1H), 6.66 (d, 1H), 6.20 (s, 1H), 5.91 (br. s, 1H), 4.39 (br. s, 1H).

Example No. I.4-228

$^1$H NMR (400 MHz, CDCl$_3$ δ, ppm) 7.95 (dd, 1H), 7.41 (dt, 1H), 7.26 (m, 1H), 7.18 (d, 1H), 7.13 (t, 1H), 6.88 (t, 1H), 6.80 (d, 1H), 6.14 (br. s, 1H), 6.01 (d, 1H), 5.83 (m, 1H), 5.27 (d, 1H), 5.20 (m, 1H), 4.10 (m, 1H), 3.70 (m, 1H).

Example No. I.4-229

$^1$H NMR (400 MHz, CDCl$_3$ δ, ppm) 7.85 (d, 1H), 7.49 (dd, 1H), 7.41 (d, 1H), 7.38 (dd, 1H), 7.34 (dd, 1H), 6.27 (s, 1H), 5.94 (br. s, 1H), 5.00 (br. s, 1H).

Example No. I.4-230

$^1$H NMR (400 MHz, CDCl$_3$ δ, ppm) 7.81 (d, 1H), 7.53 (t, 1H), 7.34 (dd, 1H), 7.30 (dd, 1H), 7.21 (d, 1H), 6.81 (t, 1H), 6.22 (m, 1H), 6.05 (br. s, 1H), 4.35 (br. s, 1H), 2.14 (s, 3H).#

Example No. I.4-231

$^1$H NMR (400 MHz, CDCl$_3$ δ, ppm) 7.85 (d, 1H), 7.51 (t, 1H), 7.41 (d, 1H), 7.36 (dd, 1H), 7.33 (dd, 1H), 6.83 (t, 1H), 6.29 (s, 1H), 6.01 (br. s, 1H), 5.03 (br. s, 1H).

Example No. I.4-232

$^1$H NMR (400 MHz, CDCl$_3$ δ, ppm) 7.60 (s, 1H), 7.48 (m, 1H), 7.18 (t, 1H), 6.91 (d, 1H), 6.61 (s, 1H), 6.60 (d, 1H), 6.03 s, 1H), 5.80 (s, 1H), 4.48 (br. s, 1H).

Example No. I.4-233

$^1$H NMR (400 MHz, CDCl$_3$ δ, ppm) 7.75 (m, 1H), 7.60 (s, 1H), 7.47 (m, 1H), 7.16 (dd, 1H), 6.61 (s, 1H), 6.60 (d, 1H), 5.88 (s, 1H), 5.75 (br. s, 1H), 4.20 (br. s, 1H), 2.30 (s, 3H).

Example No. I.4-234

$^1$H NMR (400 MHz, CDCl$_3$ δ, ppm) 7.64 (dd, 1H), 7.60 (s, 1H), 7.48 (m, 1H), 7.08 (dt, 1H), 6.67 (dd, 1H), 6.61 (m, 1H), 5.89 (s, 1H), 5.85 (br. s, 1H), 4.25 (br. s, 1H).

Example No. I.4-235

$^1$H NMR (400 MHz, CDCl$_3$ δ, ppm) 7.97 (dd, 1H), 7.40 (s, 1H), 7.35 (m, 2H), 6.89 (t, 1H), 6.74 (d, 1H), 6.47 (br. s, 1H), 6.35 (d, 1H), 5.85 (m, 1H), 5.72 (d, 1H), 5.28 (d, 1H), 5.24 (m, 1H), 4.03 (m, 1H), 3.65 (m, 1H).

Example No. I.4-236

$^1$H NMR (400 MHz, CDCl$_3$ δ, ppm) 7.85 (d, 1H), 7.62 (s, 1H), 7.50 (m, 1H), 7.41 (d, 1H), 6.63 (m, 1H), 6.15 (br. s, 1H), 5.95 (s, 1H), 4.86 (br. s, 1H), Example No. I.4-237

$^1$H NMR (400 MHz, d$_6$-DMSO δ, ppm) 8.38 (br. s, 1H), 7.57 (m, 1H), 7.50 (m, 1H), 7.49 (d 1H), 7.13 (d, 1H), 6.61 (t, 1H), 6.50 (m, 1H), 6.40 (br. s, 1H), 5.65 (t, 1H). 2.10 (s, 3H).

Example No. I.4-238

¹H NMR (400 MHz. CDCl₃ δ, ppm) 7.87 (d, 1H), 7.62 (s, 1H), 7.50 (m, 1H), 7.40 (dd, 1H), 6.85 (t, 1H), 6.65 (m, 1H), 5.96 (s, 1H), 5.76 (br. s, 1H), 4.89 (br. s, 1H).

Example No. I.4-242

¹H NMR (400 MHz, CDCl₃ δ, ppm) 7.97 (d, 1H), 7.48 (dt, 1H), 7.38-7.19 (m, 5H), 6.49 (d, 1H), 6.12 (dd, 1H), 6.08 (br. s, 1H), 5.95 (s, 2H), 5.89 (m, 1H), 5.32 (m, 1H), 5.27 (m, 1H), 5.20 (dd, 1H), 4.07 (m, 1H), 3.77 (m, 1H).

Example No. I.4-243

¹H NMR (400 MHz, CDCl₃ δ, ppm) 7.83 (d, 1H), 7.40 (d, 1H), 6.95 (d, 1H), 6.86 (d, 1H), 6.79 (d, 1H), 6.66 (d, 1H), 6.15 (dd, 1H), 5.99 (s, 2H), 5.79 (br. s, 1H), 5.49 (d, 1H), 4.80 (br. s, 1H).

Example No. I.4-244

¹H NMR (400 MHz. CDCl₃ δ, ppm) 7.81 (d, 1H), 7.21 (d, 1H), 6.95 (s, 1H), 6.85 (d, 1H), 6.80 (t, 1H), 6.78 (d, 1H), 6.65 (d, 1H), 6.20 (dd, 1H), 5.98 (s, 2H), 5.80 (br. s, 1H), 5.45 (d, 1H), 4.15 (br. s, 1H), 2.16 (s, 3H).

Example No. I.4-245

¹H NMR (400 MHz, CDCl₃ δ, ppm) 7.85 (d, 1H), 7.40 (d, 1H), 6.95 (s, 1H), 6.86 (dd, 1H), 6.80 (m, 2H), 6.66 (d, 1H), 6.18 (dd, 1H), 5.98 (s, 2H), 5.88 (br. s, 1H), 5.50 (d, 1H), 4.84 (br. s, 1H).

Example No. I.4-246

¹H NMR (400 MHz, CDCl₃ δ, ppm) 7.65 (d, 1H), 7.27 (dd, 1H), 7.23 (m, 1H), 7.20 (t, 1H), 6.94 (d, 1H), 6.63 (dd, 1H), 6.00 (s, 1H), 5.80 (br. s, 1H), 4.45 (br. s, 1H), 2.43 (s, 3H).

Example No. I.4-247

¹H NMR (400 MHz, CDCl₃ δ, ppm) 7.75 (m, 1H), 7.67 (d, 1H), 7.26 (m, 1H), 7.23 (m, 1H), 7.17 (dd, 1H), 6.62 (d, 1H), 6.08 (s, 1H), 5.73 (br. s, 1H), 4.16 (br. s, 1H), 2.44 (s, 3H), 2.30 (s, 3H).

Example No. I.4-248

¹H NMR (400 MHz, CDCl₃ δ, ppm) 7.75 (d, 1H), 7.74 (dd, 1H), 7.27 (m, 1H), 7.24 (m, 1H), 7.08 (dt, 1H), 6.68 (dd, 1H), 6.09 (s, 1H), 5.75 (br. s, 1H), 4.20 (br. s, 1H), 2.45 (s, 3H).

Example No. I.4-250

¹H NMR (400 MHz, CDCl₃ δ, ppm) 7.85 (d, 1H), 7.65 (d, 1H), 7.42 (d, 1H), 7.30 (dd, 1H), 7.26 (m, 1H), 6.64 (s, 1H), 5.71 (br. s, 1H), 4.78 (br. s, 1H), 2.46 (s, 3H).

Example No. I.4-251

¹H NMR (400 MHz, CDCl₃ δ, ppm) 7.85 (d, 1H), 7.70 (d, 1H), 7.30 (dd, 1H), 7.25 (m, 2H), 6.85 (t, 1H), 6.10 (s, 1H), 5.68 (br. s, 1H), 4.10 (br. s, 1H), 2.46 (s, 3H), 2.15 (s, 3H).

Example No. I.4-252

¹H NMR (400 MHz, CDCl₃ δ, ppm) 7.88 (d, 1H), 7.67 (d, 1H), 7.44 (dd, 1H), 7.30 (dd, 1H), 7.27 (m, 1H), 6.85 (t, 1H), 6.15 (s, 1H), 5.83 (br. s, 1H), 4.81 (br. s, 1H), 2.46 (s, 3H).

Example No. I.4-253

¹H NMR (400 MHz, CDCl₃ δ, ppm) 8.56 (m, 1H), 7.95 (dd, 1H), 7.61 (dt, 1H), 7.39 (dt, 1H), 7.32 (d, 1H), 7.22 (m, 1H), 6.85 (t, 1H), 6.77 (d, 1H), 6.35 (br. s, 1H), 5.82 (m, 1H), 5.78 (d, 1H), 5.39 (m, 1H), 5.30 (m, 1H), 4.10 (m, 1H), 3.85 (m, 1H).

Example No. I.4-254

¹H NMR (400 MHz. CDCl₃ δ, ppm) 8.64 (m, 1H), 7.83 (d, 1H), 7.80 (dt, 1H), 7.54 (d, 1H), 7.40 (d. 1H), 7.33 (m, 1H), 6.50 (br. s, 1H), 5.97 (m, 1H), 5.45 (br. s, 1H).

Example No. I.4-256

¹H NMR (400 MHz, CDCl₃ δ, ppm) 8.64 (m, 1H), 7.85 (d, 1H), 7.80 (d, 1H), 7.58 (d, 1H), 7.40 (dd, 1H), 7.32 (m, 1H), 6.80 (t, 1H), 6.44 (br. s, 1H), 6.00 (m, 1H), 5.44 (br. s, 1H).

Example No. I.4-257

¹H NMR (40) MHz, CDCl₃ δ, ppm) 8.58 (m, 1H), 7.95 (dd, 1H), 7.63 (t. 1H), 7.42 (dt. 1H), 7.2 (m. 1H), 7.24 (m, 1H), 6.85 (1, 1H), 6.68 (d, 1H), 6.40 (br. s, 1H), 5.71 (m, 1H), 2.94 (s, 3H).

Example No. I.4-258

¹H NMR (400 MHz. CDCl₃ δ, ppm) 7.96 (dd, 1H), 7.35 (dt, 1H), 7.32 (s, 1H), 6.85 (t, 1H), 6.71 (d. 1H), 6.40 (d, 1H), 6.36 (m, 1H), 6.29 (m, 1H), 6.24 (br. s, 1H), 6.20 (dd, 1H), 5.90 (m, 1H), 5.33 (m, 1H), 5.27 (m, 1H), 5.18 (dd. 1H), 4.10 (m. 1H), 3.77 (m. 1H).

Example No. I.4-259

¹H NMR (40) MHz, CDCl₃ δ, ppm) 7.82 (d, 1H), 7.42 (m. 1H), 7.40 (d, 1H), 6.58 (d, 1H), 6.4 (m, 2H), 6.25 (dd, 1H), 5.90 (br. s. 1H), 5.46 (d, 1H), 4.83 (br. s, 1H).

Example No. I.4-260

¹H NMR (400 MHz, CDCl₃ δ, ppm) 7.81 (d, 1H), 7.40 (m, 1H), 7.20 (d, 1H), 6.81 (t, 1H), 6.57 (d, 1H), 6.40 (m, 1H), 6.38 (m, 1H), 6.30 (dd, 1H), 5.90 (br. s, 1H), 5.43 (d, 1H), 4.15 (br. s, 1H).

Example No. I.4-261

¹H NMR (400 MHz, CDCl₃ δ, ppm) 7.85 (d, 1H), 7.40 (m, 1H), 7.39 (d, 1H), 6.80 (t, 1H), 6.58 (d, 1H), 6.40 (m, 2H), 6.28 (dd, 1H), 5.90 (br. s, 1H), 5.49 (d, 1H), 4.85 (br. s, 1H).

Example No. I.4-262

¹H NMR (400 MHz, CDCl₃ δ, ppm) 7.83 (d, 1H), 7.60 (d, 1H), 7.25 (m, 1H), 7.20 (d, 1H), 7.13 (d, 1H), 6.80 (t, 1H), 6.30 (m, 1H), 5.97 (br. s, 1H), 4.52 (br. s, 1H), 2.34 (s, 3H), 2.12 (s, 3H).

Example No. I.4-263

$^1$H NMR (400 MHz, CDCl$_3$ δ, ppm) 7.94 (dd, 1H), 7.45 (dt, 1H), 7.22 (m, 1H), 7.16 (d, 1H), 6.98 (d, 1H), 6.86 (t, 1H), 6.72 (d, 1H), 6.20 (br. s, 1H), 6.10 (d, 1H), 2.85 (s, 3H), 2.30 (s, 3H).

Example No. I.4-264

$^1$H NMR (400 MHz, CDCl$_3$ δ, ppm) 7.75 (m, 1H), 7.61 (d, 1H), 7.22 (m, 1H), 7.14 (dd, 1H), 7.11 (d, 1H), 6.59 (d, 1H), 6.26 (m, 1H), 5.90 (br. s, 1H), 4.44 (br. s, 1H), 2.34 (s, 3H), 2.28 (s, 3H).

Example No. I.4-266

$^1$H NMR (400 MHz, CDCl$_3$ δ, ppm) 7.78 (m, 1H), 7.50 (d, 1H), 7.20 (dd, 1H), 6.65 (d, 1H), 6.38 (d, 1H), 6.10 (s, 1H), 5.86 (br. s, 1H), 4.42 (q, 2H), 4.25 (br. s, 1H), 2.30 (s, 3H), 1.49 (t, 3H).

Example No. I.4-267

$^1$H NMR (400 MHz, CDCl$_3$ δ, ppm) 7.21 (t, 1H), 6.98 (d, 1H), 6.64 (d, 1H), 6.19 (s, 1H), 5.96 (s, 1H), 5.83 (br. s, 1H), 4.45 (br. s, 1H), 3.97 (s, 3H), 2.25 (s, 3H).

Example No. I.4-268

$^1$H NMR (400 MHz, CDCl$_3$ δ, ppm) 7.75 (m, 1H), 7.19 (dd, 1H), 6.64 (d, 1H), 6.15 (s, 1H), 6.09 (br. s, 1H), 6.00 (s, 1H), 4.25 (br. s, 1H), 3.97 (s, 3H), 2.30 (s, 3H), 2.23 (s, 3H).

Example No. I.4-270

$^1$H NMR (400 MHz, CDCl$_3$ δ, ppm) 7.97 (dd, 1H), 7.36 (dt, 1H), 7.28 (d, 2H), 6.85 (t, 1H), 6.83 (d, 2H), 6.70 (d, 1H), 6.52 (d, 1H), 6.16 (dd, 1H), 6.14 (br. s, 1H), 5.89 (m, 1H), 5.32 (m, 1H), 5.25 (m, 1H), 5.20 (dd, 1H), 4.07 (m, 1H), 3.80 (s, 3H), 3.78 (m, 1H).

Example No. I.4-271

$^1$H NMR (400 MHz, CDCl$_3$ δ, ppm) 7.60 (d, 1H), 7.24 (m, 1H), 7.15 (t, 1H), 7.14 (d, 1H), 6.90 (d, 1H), 6.58 (d, 1H), 6.20 (m, 1H), 5.90 (br. s, 1H), 4.65 (br. s, 1H), 2.35 (s, 3H).

Example No. I.4-272

$^1$H NMR (400 MHz, CDCl$_3$ δ, ppm) 7.93 (dd, 1H), 7.41 (dt, 1H), 7.20 (m, 1H), 7.18 (d, 1H), 6.95 (d, 1H), 6.85 (t, 1H), 6.77 (d, 1H), 6.25 (br. s, 1H), 6.13 (d, 1H), 5.81 (m, 1H), 5.36 (m, 1H), 5.30 (m, 1H), 4.07 (m, 1H), 3.63 (m, 1H), 2.30 (s, 3H).

Example No. I.4-273

$^1$H NMR (400 MHz, CDCl$_3$ δ, ppm) 7.60 (d, 1H), 7.40 (s, 1H), 7.22 (m, 1H), 7.12 (d, 1H), 6.74 (m, 1H), 6.68 (s, 1H), 5.82 (br. s, 1H), 4.41 (br. s. 1H), 3.86 (s, 3H), 3.85 (s, 3H), 2.34 (s, 3H).

Example No. I.4-274

$^1$H NMR (400 MHz, CDCl$_3$ δ, ppm) 7.65 (d, 1H), 7.54 (d, 1H), 7.23 (m, 1H), 7.13 (d, 1H), 6.90 (d, 1H), 6.80 (t, 1H), 6.32 (m, 1H), 5.84 (br. s, 1H), 5.03 (br. s, 1H), 3.85 (s, 3H), 2.35 (s, 3H).

Example No. I.4-275

$^1$H NMR (400 MHz. CDCl$_3$ δ, ppm) 7.77 (m, 1H), 7.45 (d, 1H), 7.20 (dd, 1H), 6.65 (d, 1H), 6.37 (d. 1H), 6.10 (d, 1H), 5.90 (br. s, 1H), 4.24 (br. s, 1H), 4.07 (s, 3H), 2.30 (s, 3H).

Example No. I.4-276

$^1$H NMR (400 MHz, CDCl$_3$ δ, ppm) 8.00 (dd, 1H), 7.43 (dt, 1H), 7.40 (s, 1H), 6.96 (t, 1H), 6.85 (d, 1H), 6.20 (d, 1H), 6.07 (br. s, 1H), 5.97 (d, 1H), 5.83 (m, 1H), 5.24 (m, 1H), 5.14 (m, 1H), 4.00 (m, 1H), 3.98 (s, 3H), 3.54 (m, 1H).

Example No. I.4-278

$^1$H NMR (400 MHz, CDCl$_3$ δ, ppm) 7.86 (d, 1H), 7.45 (d, 1H), 6.19 (s, 1H), 6.10 (s, 1H), 6.01 (br. s, 1H), 4.87 (br. s, 1H), 3.98 (s, 3H), 2.25 (s, 3H).

Example No. I.4-279

$^1$H NMR (400 MHz, CDCl$_3$ δ, ppm) 7.86 (d, 1H), 7.25 (d, 1H), 6.89 (t, 1H), 6.20 (s, 1H), 6.05 (d. 1H), 5.76 (br. s, 1H), 4.15 (br. s, 1H), 4.00 (s, 3H), 2.27 (s, 3H), 2.17 (s, 3H).

Example No. I.4-280

$^1$H NMR (400 MHz, CDCl$_3$ δ, ppm) 7.90 (d, 1H), 7.50 (d, 1H), 7.45 (d, 1H), 6.90 (t, 1H), 6.42 (d, 1H), 6.20 (s, 1H), 5.86 (br. s, 1H), 4.90 (br. s, 1H), 4.10 (s, 3H).

Example No. I.4-281

$^1$H NMR (400 MHz, CDCl$_3$ δ, ppm) 7.48 (d, 1H), 7.23 (t, 1H), 6.99 (d, 1H), 6.65 (d, 1H), 6.41 (d, 1H), 6.05 (s, 1H), 5.85 (br. s, 1H), 4.47 (br. s, 1H), 4.06 (s, 3H).

Example No. I.4-282

$^1$H NMR (400 MHz, CDCl$_3$ δ, ppm) 7.30 (dt, 1H), 6.62 (dd, 1H), 6.51 (d. 1H), 6.17 (s, 1H), 6.00 (s, 1H), 5.72 (br. s, 1H), 4.50 (br. s, 1H), 3.97 (s, 3H), 2.25 (s, 3H).

Example No. I.4-284

$^1$H NMR (400 MHz, CDCl$_3$ δ, ppm) 7.51 (d, 1H), 7.30 (dt, 1H), 6.65 (dd, 1H), 6.52 (d, 1H), 6.40 (d, 1H), 6.09 (s, 1H), 5.75 (br. s, 1H), 4.51 (br. s, 1H), 4.40 (q, 2H), 1.50 (t, 3H).

Example No. I.4-287

$^1$H NMR (400 MHz, CDCl$_3$ δ, ppm) 7.62 (s, 1H), 7.60 (s, 1H), 7.18 (t, 1H), 6.92 (d, 1H), 6.60 (d, 1H), 6.08 s, 1H), 5.80 (s, 1H), 4.49 (br. s, 1H), 3.93 (s, 3H).

Example No. I.4-288

$^1$H NMR (600 MHz, CDCl$_3$ δ, ppm) 7.86 (d, 1H), 7.50 (d, 1H), 7.27 (d, 1H), 6.90 (t, 1H), 6.41 (d, 1H), 6.14 (s, 1H), 5.79 (br. s, 1H), 4.18 (br. s, 1H), 4.10 (s, 3H), 2.18 (s, 3H).

Example No. I.4-289

¹H NMR (600 MHz, CDCl₃ δ, ppm) 7.99 (d, 1H), 7.44 (s, 1H), 7.39 (t, 1H), 7.32 (s, 1H), 6.89 (t, 1H), 6.73 (d, 1H), 6.15 (br. s, 1H), 5.85 (m, 1H), 5.75 (d, 1H), 5.26 (m, 2H), 4.00 (m, 1H), 3.85 (s, 3H), 3.65 (m, 1H).

Example No. I.4-290

¹H NMR (600 MHz, CDCl₃ δ, ppm) 7.85 (s, 1H), 7.66 (s, 1H), 7.61 (s, 1H), 7.41 (s, 1H), 5.95 (s, 1H), 5.87 (br. s, 1H), 4.87 (br. s, 1H), 3.96 (s, 3H).

Example No. I.4-291

¹H NMR (600 MHz, CDCl₃ δ, ppm) 7.84 (d, 1H), 7.67 (s, 1H), 7.61 (s, 1H), 7.30 (d, 1H), 6.85 (t, 1H), 5.91 (s, 1H), 5.77 (br. s, 1H), 4.21 (br. s, 1H), 3.95 (s, 3H), 2.15 (s, 3H).

Example No. I.4-292

¹H NMR (400 MHz, CDCl₃ δ, ppm) 7.86 (d, 1H), 7.66 (s, 1H), 7.60 (s, 1H), 7.41 (d, 1H), 6.84 (t, 1H), 5.95 (s, 1H), 5.81 (br. s, 1H), 4.90 (br. s, 1H), 3.95 (s, 3H).

Example No. I.4-293

¹H NMR (400 MHz, CDCl₃ δ, ppm) 7.60 (d, 1H), 7.24 (m, 2H), 7.13 (d, 1H), 6.54 (dd, 1H), 6.45 (d, 1H), 6.24 (s, 1H), 5.93 (br. s, 1H), 4.73 (br. s, 1H), 2.35 (s, 3H).

Example No. I.4-294

¹H NMR (600 MHz, CDCl₃ δ, ppm) 7.83 (d, 1H), 7.60 (d, 1H), 7.25 (m, 1H), 7.20 (d, 1H), 7.14 (d, 1H), 6.80 (t, 1H), 6.30 (s, 1H), 5.90 (br. s, 1H), 4.53 (br. s, 1H), 2.35 (s, 3H), 2.15 (s, 3H).

Example No. I.4-295

¹H NMR (400 MHz, CDCl₃ δ, ppm) 7.85 (d, 1H), 7.60 (d, 1H), 7.40 (d, 1H), 7.26 (m, 1H), 7.14 (d, 1H), 6.80 (1, 1H), 6.35 (d, 1H), 5.98 (br. s, 1H), 5.15 (br. s, 1H), 2.35 (s, 3H).

Example No. I.4-297

¹H NMR (600 MHz, CDCl₃ δ, ppm) 7.85 (d, 1H), 7.40 (d, 1H), 7.37 (d, 2H), 6.90 (d, 2H), 6.80 (t, 1H), 6.71 (d, 1H), 6.33 (dd, 1H), 5.79 (br. s, 1H), 5.51 (d, 1H), 4.85 (br. s, 1H), 3.84 (s, 3H).

Example No. I.4-298

¹H NMR (400 MHz, CDCl₃ δ, ppm) 7.85 (d, 1H), 7.52 (d, 1H), 7.26 (d, 1H), 6.90 (t, 1H), 6.40 (d, 1H), 6.12 (s, 1H), 5.94 (br. s, 1H), 4.45 (q, 2H), 4.19 (br. s, 1H), 2.16 (s, 3H), 1.50 (t, 3H).

Example No. I.4-300

¹H NMR (400 MHz, CDCl₃ δ, ppm) 7.40 (d, 1H), 7.25 (m, 1H), 6.55 (m, 2H), 6.45 (d, 1H), 6.40 (d, 1H), 6.38 (m, 1H), 6.22 (dd, 1H), 5.70 (br. s, 1H), 5.36 (d, 1H), 4.42 (br. s, 1H).

Example No. I.4-301

¹H NMR (400 MHz, d₆-DMSO δ, ppm) 8.56 (dd, 1H), 8.47 (br. d, 1H), 7.85 (dt, 1H), 7.58 (br. s, 1H) 7.49 (d, 1H), 7.36 (m, 1H), 7.14 (t, 1H) 6.75 (d, 1H), 6.65 (d, 1H), 5.62 d, 1H).

Example No. I.4-303

¹H NMR (400 MHz, CDCl₃ δ, ppm) 7.49 (d, 1H), 7.30 (m, 2H), 7.20 (m, 3H), 6.87 (d, 1H), 6.68 (t, 1H), 5.75 (br. s, 1H), 4.90 (m, 1H), 4.65 (br. s, 1H), 3.85 (s, 3H), 2.69 (m, 2H), 1.80 (m, 4H).

Example No. I.4-304

¹H NMR (400 MHz, CDCl₃ δ, ppm) 7.30 (m, 2H), 7.19 (m, 4H), 6.52 (dd, 1H), 6.41 (d, 1H), 5.75 (br. s, 1H), 4.80 (m, 1H), 4.25 (br. s, 1H), 2.70 (m, 2H), 1.79 (m, 4H).

Example No. I.4-305

¹H NMR (400 MHz, CDCl₃ δ, ppm) 7.78 (d, 1H), 7.30 (m, 2H), 7.20 (m, 4H), 6.79 (t, 1H), 6.15 (br. s, 1H), 4.88 (m, 1H), 3.98 (br. s, 1H), 2.70 (m, 2H), 2.14 (s, 3H), 1.82 (m, 4H).

Example No. I.4-307

¹H NMR (400 MHz, CDCl₃ δ, ppm) 7.92 (dd, 1H), 7.35 (dt, 1H), 7.25 (m, 2H), 7.16 (d, 1H), 7.10 (d, 2H), 6.85 (t, 1H), 6.85 (br. s, 1H), 6.70 (d, 1H), 5.85 (m, 1H), 5.25 (m, 1H), 5.20 (m, 1H), 4.60 (m, 1H), 4.03 (dd, 1H), 3.70 (dd, 1H), 2.57 (m, 2H), 1.85-1.57 (m, 4H).

Example No. I.4-308

¹H NMR (400 MHz, CDCl₃ δ, ppm) 7.31 (s, 1H), 7.30 (m, 2H), 7.20 (m, 3H), 6.85 (br. s, 1H), 6.16 (s, 1H), 4.83 (m, 1H), 4.64 (br. s, 1H), 3.86 (s, 3H), 3.85 (s, 3H), 2.70 (m, 2H), 1.80 (m, 4H).

Example No. I.4-309

¹H NMR (400 MHz, CDCl₃ δ, ppm) 7.90 (dd, 1H), 7.48 (dt, 1H), 7.25 (m, 2H), 7.16 (m, 1H), 7.11 (d, 2H), 6.82 (1, 1H), 6.60 (d, 1H), 6.48 (br. s, 1H), 4.55 (m, 1H), 2.89 (s, 3H), 2.60 (t, 2H), 1.85-1.57 (m, 4H).

Example No. I.4-310

¹H NMR (400 MHz, CDCl₃ δ, ppm) 7.48 (d, 1H), 7.30 (d, 2H), 7.16 (d, 2H), 6.85 (d, 1H), 6.76 (t, 1H), 5.92 (s, 1H), 4.97 (br. s, 1H), 3.88 (m, 1H), 3.79 (s, 3H), 3.47 (m, 1H), 3.30 (m, 1H), 3.15 (m, 2H), 3.05 (m, 3H), 2.33 (s, 3H), 1.30 (t, 3H), 1.25 (t, 3H).

Example No. I.4-311

¹H NMR (400 MHz, CDCl₃ δ, ppm) 7.54 (d, 1H), 7.42 (m, 1H), 7.33 (m, 1H), 6.85 (d, 1H), 6.79 (t, 1H), 6.34 (m, 1H), 5.94 (s, 1H), 4.83 (br. s, 1H), 3.95 (m, 1H), 3.80 (s, 3H), 3.05 (m, 1H), 2.72 (m, 1H), 2.55 (m, 5H), 1.00 (t, 6H).

Example No. I.4-313

¹H NMR (400 MHz, CDCl₃ δ, ppm) 7.57 (d, 1H), 7.40 (d, 1H), 7.27 (d, 1H), 7.25 (t, 1H), 7.17 (t, 1H), 6.77 (d, 1H), 6.72

(t, 1H), 6.43 (s, 1H), 5.44 (br. s, 1H), 4.15 (m, 1H), 3.75 (s, 3H), 2.88-2.46 (m, 7H), 1.04 (t, 6H).

Example No. I.4-314

$^1$H NMR (400 MHz, CDCl$_3$ δ, ppm) 7.57 (d, 2H), 7.50 (d, 2H), 7.48 (d, 1H), 6.85 (d, 1H), 6.78 (t, 1H), 6.15 (s, 1H), 5.11 (br. s, 1H), 4.15 (m, 1H), 3.79 (s, 3H), 3.40 (m, 2H), 3.15 (m, 5H), 1.30 (t, 6H).

Example No. I.4-315

$^1$H NMR (400 MHz, CDCl$_3$ δ, ppm) 7.46 (d, 1H), 7.43 (d, 1H), 7.15 (dd. 1H), 7.06 (d, 1H), 6.81 (d, 1H), 6.75 (1, 1H), 6.32 (s, 1H), 5.54 (br. s, 1H), 4.26 (m, 1H), 3.78 (s, 3H), 3.47 (m, 1H), 3.35-3.10 (m, 6H), 1.30 (m, 6H).

Example No. I.4-316

$^1$H NMR (400 MHz, CDCl$_3$ δ, ppm) 7.47 (d, 1H), 7.16 (dd, 1H), 6.85 (m, 2H), 6.77 (t, 2H), 6.30 (s, 1H), 4.75 (br. s, 1H), 4.21 (m, 1H), 3.80 (s, 3H), 3.43 (m, 1H), 3.37-3.10 (m, 6H), 1.35 (m, 6H).

Example No. I.4-317

$^1$H NMR (400 MHz, CDCl$_3$ δ, ppm) 7.47 (d, 1H), 7.29 (dd, 1H), 7.20 (dd, 1H), 7.01 (t, 1H), 6.83 (d, 1H), 6.75 (t, 1H), 6.32 (s, 1H), 5.20 (br. s, 1H), 4.25 (m, 1H), 3.80 (s, 3H), 3.45 (m, 1H), 3.35-3.10 (m, 6H), 1.35 (m, 6H).

Example No. I.4-318

$^1$H NMR (400 MHz, CDCl$_3$ δ, ppm) 7.49 (d, 1H), 7.22 (m, 1H), 7.17 (d, 1H), 7.10 (dd, 1H), 6.83 (d, 1H), 6.75 (t, 1H), 6.38 (s, 1H), 4.94 (br. s, 1H), 3.97 (m, 1H), 3.77 (s, 3H), 3.35 (m, 2H), 3.25-3.00 (m, 5H), 1.30 (m, 6H).

Example No. I.4-319

$^1$H NMR (400 MHz, CDCl$_3$ δ, ppm) 7.58 (d, 1H), 7.42 (d, 2H), 7.22 (d, 2H), 6.88 (d, 1H), 6.80 (t, 1H), 6.04 (s, 1H), 4.85 (br. s, 1H), 4.61 (d, 1H), 3.80 (s, 3H), 3.65 (s, 3H), 3.31 (d. 1H), 2.40 (s, 3H).

Example No. I.4-321

$^1$H NMR (400 MHz, CDCl$_3$ δ, ppm) 7.56 (d, 1H), 7.54 (m, 1H), 7.47 (m, 1H), 6.90 (d, 1H), 6.73 (t, 1H), 6.56 (m, 1H), 6.07 (s, 1H), 4.84 (br. s, 1H), 4.72 (d, 1H), 3.85 (s, 3H), 3.70 (s, 3H), 3.55 (d, 1H).

Example No. I.4-322

$^1$H NMR (400 MHz, CDCl$_3$ δ, ppm) 7.50 (d, 1H), 7.38 (m, 2H), 7.20 (m, 1H), 7.14 (d, 2H), 6.86 (d, 1H), 6.76 (1, 1H), 4.80 (dd, 1H), 4.60 (br. s, 1H), 4.59 (d, 1H), 3.90 (d, 1H), 3.85 (s, 3H), 3.75 (s, 3H), 2.79-2.60 (m, 2H), 2.25 (m, 1H), 2.05 (m, 1H).

Example No. I.4-323

$^1$H NMR (400 MHz, CDCl$_3$ δ, ppm) 7.55 (d, 1H), 7.50 (dd, 1H), 7.40 (dd, 1H), 7.28 (m, 2H), 6.84 (d, 1H), 6.75 (t, 1H), 6.41 (s, 1H), 5.76 (br. s, 1H), 4.80 (d, 1H), 3.79 (s, 3H), 3.71 (s, 3H), 3.45 (d, 1H).

Example No. I.4-324

$^1$H NMR (400 MHz. CDCl$_3$ δ, ppm) 7.67 (m, 1H), 7.55 (d, 1H), 7.43 (d, 1H), 7.35 (d, 1H), 6.80 (d, 1H), 6.75 (t, 1H), 6.53 (d. 1H), 5.48 (br. s, 1H), 4.21 (m, 1H), 3.75 (s, 3H), 2.85 (m, 1H), 2.80-2.45 (m, 6H), 1.04 (m, 6H).

Example No. I.4-325

$^1$H NMR (400 MHz, CDCl$_3$ δ, ppm) 8.55 (m, 1H), 7.64 (dt, 1H), 7.45 (d, 1H), 7.25 (d, 1H), 7.21 (dd, 1H), 6.83 (d, 1H), 6.75 (t, 1H), 6.00 (s, 1H), 5.50 (br. s, 1H), 4.30 (m, 1H), 3.80 (s, 3H), 3.53 (m, 1H), 3.44 (m, 1H), 3.28 (m, 1H), 3.20 (m, 4H), 1.45 (t, 6H).

Example No. I.4-326

$^1$H NMR (400 MHz, CDCl$_3$ δ, ppm) 7.47 (d, 1H), 7.30 (d, 1H), 6.87 (d, 1H), 6.79 (t, 1H), 6.15 (d, 1H), 5.95 (s, 1H), 5.60 (br. s, 1H), 4.11 (q, 2H), 3.95 (m, 1H), 3.82 (s, 3H), 3.65 (m, 1H), 3.30 (m, 1H), 3.15 (m, 5H), 1.45 (t. 3H), 1.32 (t, 6H).

Example No. I.4-327

$^1$H NMR (400 MHz, CDCl$_3$ δ, ppm) 7.50 (d, 1H), 7.33 (m, 2H), 7.28 (m, 3H), 6.87 (d, 1H), 6.79 (t, 1H), 6.68 (d, 1H), 6.37 (dd, 1H), 5.48 (dd, 1H), 4.90 (br. s, 1H), 4.13 (m, 1H), 3.84 (s, 3H), 3.35 (m, 1H), 3.25 (m, 1H), 3.04 (m, 1H), 2.94 (m, 4H), 1.21 (t, 6H).

Example No. I.4-328

$^1$H NMR (400 MHz, CDCl$_3$ δ, ppm) 7.54 (d, 1H), 6.86 (m, 1H), 6.85 (d, 1H), 6.79 (m, 2H), 6.75 (t, 1H), 6.49 (d, 1H), 6.21 (dd, 1H), 5.94 (s, 2H), 5.39 (dd, 1H), 4.79 (br. s, 1H), 4.00 (m, 1H), 3.83 (s, 3H), 3.10 (m, 1H), 2.81-2.50 (m, 6H), 1.05 (t, 6H).

Example No. I.4-329

$^1$H NMR (400 MHz, CDCl$_3$ δ, ppm) 7.49 (d, 1H), 6.85 (d, 1H), 6.80 (t, 1H), 6.33 (s, 1H), 5.82 (s, 1H), 5.07 (br. s, 1H), 4.15 (m, 1H), 3.90 (s, 3H), 3.80 (s, 3H), 3.46 (m, 1H), 3.36 (m, 1H), 3.17 (m, 5H), 2.12 (s, 3H), 1.32 (t, 6H).

Example No. I.4-330

$^1$H NMR (400 MHz. CDCl$_3$ δ, ppm) 7.49 (d, 1H), 6.85 (d, 1H), 6.80 (t, 1H), 6.41 (s, 1H), 6.06 (d. 1H), 5.10 (br. s, 1H), 4.15 (m, 1H), 3.98 (s, 3H), 3.80 (s, 3H), 3.42 (m, 2H), 3.25 (m, 5H), 1.32 (1, 6H).

Example No. I.4-331

$^1$H NMR (400 MHz, CDCl$_3$ δ, ppm) 7.50 (d, 1H), 7.33 (d, 1H), 6.85 (d, 1H), 6.80 (t, 1H), 6.43 (d, 1H), 6.03 (d, 1H), 5.09 (br. s, 1H), 4.25 (m, 2H), 4.15 (m, 1H), 3.80 (s, 3H), 3.48 (m, 1H), 3.37 (m, 1H), 3.17 (m, 5H), 1.49 (t, 3H), 1.32 (1, 6H).

Example No. I.4-332

$^1$H NMR (400 MHz, d$_6$-DMSO δ, ppm) 7.75 (m, 1H), 7.65 (d, 1H), 7.58 (m, 2H), 7.28 (d, 1H), 7.03 (br. s, 1H), 6.91 (d, 1H), 6.63 (t, 1H), 6.09 (d, 1H), 3.93 (m, 1H), 3.85 (s, 3H), 2.93 (m, 1H), 2.64 (m, 1H), 2.50 (m, 5H), 0.94 (m, 6H).

Example No. I.4-333

$^1$H NMR (400 MHz, CDCl$_3$ δ, ppm) 7.68 (m, 4H), 7.58 (d, 1H), 6.90 (d, 1H), 6.83 (t, 1H), 6.15 (s, 1H), 4.88 (br. s, 1H), 4.68 (d, 1H), 3.82 (s, 3H), 3.68 (s, 3H), 3.30 (d, 1H).

Example No. I.4-334

$^1$H NMR (400 MHz, CDCl$_3$ δ, ppm) 7.54 (d, 1H), 7.44 (d, 1H), 7.43 (m, 1H), 7.22 (dd. 1H), 6.85 (d, 1H), 6.78 (1, 1H), 6.35 (s, 1H), 5.74 (br. s, 1H), 4.76 (d, 1H), 3.80 (s, 3H), 3.71 (s, 3H), 3.47 (d, 1H).

Example No. I.4-336

$^1$H NMR (400 MHz, CDCl$_3$ δ, ppm) 7.50 (d, 1H), 7.23 (m, 1H), 7.10 (d, 1H), 6.97 (d, 1H), 6.80 (d, 1H), 6.74 (t, 1H), 6.32 (d, 1H), 5.45 (br. s, 1H), 4.18 (m, 1H), 3.77 (s, 3H), 3.25 (m, 1H), 3.20-2.90 (m, 6H), 2.30 (s, 3H), 1.25 (t, 6H).

Example No. I.4-339

$^1$H NMR (400 MHz. CDCl$_3$ δ, ppm) 7.55 (d, 1H), 7.50 (m, 1H), 6.86 (m, 3H), 6.80 (1, 1H), 6.32 (s, 1H), 4.99 (br. s, 1H), 4.75 (d, 1H), 3.81 (s, 3H), 3.70 (s, 3H), 3.52 (d, 1H).

Example No. I.4-340

$^1$H NMR (400 MHz, CDCl$_3$ δ, ppm) 7.55 (d, 1H), 7.35 (t, 1H), 7.29 (m, 2H), 6.86 (m, 3H), 6.79 (t, 1H), 6.30 (s, 1H), 5.02 (br. s, 1H), 4.76 (d, 1H), 3.80 (s, 3H), 3.70 (s, 3H), 3.52 (d, 1H).

Example No. I.4-341

$^1$H NMR (400 MHz, CDCl$_3$ δ, ppm) 10.96 (br. s, 1H, NH), 9.82 (br. s, 1H, NH), 7.90 (d, 1H), 7.83 (s, 1H), 7.48 (d, 1H), 6.89 (dd, 1H), 6.10 (s, 1H), 5.65 (br. s, 1H, NH).

Example No. I.4-342

$^1$H NMR (400 MHz, CDCl$_3$ δ, ppm) 10.54 (br. s, 1H, NH), 9.44 (br. s, 1H, NH), 8.11 (s, 1H), 7.83 (s, 1H), 7.72 (d, 1H), 5.99 (s, 1H), 4.92 (br. s, 1H, NH), 2.24 (s, 3H).

Example No. I.4-343

$^1$H NMR (400 MHz, d$_6$-DMSO δ, ppm) 8.06 (d, 1H), 7.85 (dd, 1H), 7.82 (br. s, 1H, NH), 7.71 (d, 1H), 7.59 (d, 1H), 7.19 (br. s, 1H, NH), 7.14 (m, 1H), 6.69 (d, 1H), 2.73 (q, 2H), 1.23 (t, 3H).

Example No. I.4-344

$^1$H NMR (400 MHz, d$_6$-DMSO δ, ppm) 8.62 (br. d, 1H, NH), 7.90 (s, 1H), 7.83 (d, 1H), 7.80 (d, 1H), 7.68 (dd, 1H), 7.62 (s, 1H), 7.60 (m, 1H), 6.89 (d, 1H), 6.83 (d, 1H), 6.71 (dd, 1H), 6.41 (d, 1H), 5.88 (br. m, 1H, NH).

Example No. I.4-345

$^1$H NMR (400 MHz, d$_6$-DMSO δ, ppm) 8.63 (br. d, 1H, NH), 7.78 (d, 1H), 7.62 (m, 3H), 7.48 (m, 1H), 7.40 (dd, 1H), 6.90 (d, 1H), 6.83 (d, 1H), 6.70 (dd, 1H), 6.40 (d, 1H), 5.88 (br. m, 1H, NH).

Example No. I.4-346

$^1$H NMR (400 MHz, d$_6$-DMSO δ, ppm) 8.64 (br. d, 1H, NH), 7.62 (m, 3H), 7.50 (m, 1H), 7.36 (dd, 1H), 7.27 (dd, 1H), 6.89 (d, 1H), 6.82 (d, 1H), 6.72 (dd, 1H), 6.40 (d, 1H), 5.89 (br. m, 1H, NH).

Example No. I.4-347

$^1$H NMR (400 MHz, d$_6$-DMSO δ, ppm) 8.56 (br. d, 1H, NH), 7.67 (m, 2H), 7.60 (d, 1H), 7.45 (m. 1H), 7.39 (dd, 1H), 7.22 (dd, 1H), 6.90 (d, 1H), 6.61 (d, 1H), 6.41 (m, 2H), 5.78 (br. m, 1H, NH).

Example No. I.4-348

$^1$H NMR (400 MHz, d$_6$-DMSO δ, ppm) 8.57 (br. d, 1H, NH), 7.70 (s, 1H), 7.61 (dd, 1H), 7.52 (m, 1H), 7.36 (dd, 1H), 7.29 (d, 1H), 7.23 (m, 1H), 6.90 (d, 1H), 6.62 (d, 1H), 6.42 (m, 2H), 5.78 (br. m, 1H, NH).

Example No. I.4-349

$^1$H NMR (400 MHz, d$_6$-DMSO δ, ppm) 9.09 (br. m, 1H, NH), 7.88 (m, 1H), 7.61 (d, 2H), 7.58 (dd, 1H), 7.50 (d, 2H), 6.83 (d, 1H), 6.78 (s, 1H), 6.55 (d, 1H), 6.46 (d, 1H), 5.33 (br. d, 1H, NH).

Example No. I.4-350

$^1$H NMR (400 MHz, d$_6$-DMSO δ, ppm) 9.12 (br. d, 1H, NH), 7.88 (m, 1H), 7.79 (m, 3H), 7.59 (d. 1H), 7.24 (m, 1H), 6.91 (d, 1H), 6.80 (d. 1H), 6.57 (dd, 1H), 6.49 (d, 1H), 5.37 (br. d, 1H, NH), 2.32 (s, 3H).

Example No. I.4-351

$^1$H NMR (400 MHz, d$_6$-DMSO δ, ppm) 8.62 (br. d, 1H, NH), 7.60 (d, 2H), 7.33 (s, 1H), 7.31 (d, 2H), 7.28 (d, 1H), 6.82 (d, 1H), 6.80 (d, 1H), 6.71 (dd, 1H), 6.38 (d, 1H), 5.86 (br. d, 1H, NH).

Example No. I.4-354

$^1$H NMR (400 MHz, d$_6$-DMSO δ, ppm) 8.05 (br. s, 1H, NH), 7.50 (d, 1H), 7.30 (d, 2H). 7.18 (d, 2H), 7.12 (d, 1H), 6.62 (dd, 1H), 5.84 (br. s, 1H, NH), 4.71 (m, 1H), 2.68 (m, 2H), 2.11 (s, 3H), 1.98 (m, 2H), 1.25 (s, 9H).

Example No. I.4-355

$^1$H NMR (400 MHz, d$_6$-DMSO δ, ppm) 7.94 (br. s, 1H, NH), 7.46 (d, 1H), 7.23 (d, 2H), 7.10 (d, 1H), 7.05 (d, 2H), 6.59 (dd, 1H), 5.89 (br. s, 1H, NH), 4.72 (m, 1H), 2.59 (m, 1H), 2.28 (m, 1H), 2.10 (s, 3H), 1.73 (m, 1H), 1.42 (m, 1H), 1.24 (s, 9H), 0.82 (d, 3H).

Example No. I.5-1

$^1$H NMR (400 MHz, d$_6$-DMSO δ, ppm) 8.08 (br. s, 1H, NH), 7.78 (d, 1H), 7.60 (dd, 1H), 6.71 (br. s, 1H, NH), 6.69 (d, 1H), 6.62 (dd, 1H), 1.79 (m, 4H), 1.64 (m, 4H).

Example No. I.5-2

$^1$H NMR (400 MHz, d$_6$-DMSO δ, ppm) 8.98 (br. s, 1H, NH), 7.88 (br. s, 1H, NH) 7.47 (d, 2H), 7.40 (d, 1H), 7.37 (d, 2H), 7.25 (d, 1H), 6.79 (d, 1H), 1.63 (s, 3H).

Example No. I.5-3

$^1$H NMR (400 MHz, d$_6$-DMSO δ, ppm) 8.29 (br. s, 1H, NH), 7.63 (d, 1H), 7.42 (dd, 1H), 7.13 (d, 1H), 6.91 (dd, 1H), 6.60 (br. s, 1H, NH), 1.82 (m, 2H), 1.66 (m, 4H), 1.57 (m, 4H).

Example No. I.5-4

$^1$H NMR (400 MHz, d$_6$-DMSO δ, ppm) 8.76 (br. s, 1H, NH), 7.73 (m, 1H), 7.18 (m, 2H), 6.91 (br. s, 1H, NH), 6.62 (d, 1H), 1.78 (q, 2H), 1.48 (s, 3H), 1.00 (t, 3H).

Example No. I.5-5

$^1$H NMR (400 MHz, d$_6$-DMSO δ, ppm) 8.79 (br. s, 1H, NH), 7.66 (br. s, 1H, NH), 7.48 (d, 2H), 7.36 (d, 2H), 7.21 (m, 1H), 6.76 (d, 1H), 6.59 (m, 1H), 1.63 (s, 3H).

Example No. I.5-6

$^1$H NMR (400 MHz, d$_6$-DMSO δ, ppm) 8.58 (br. s, 1H, NH), 8.21 (s, 1H), 7.20 (m, 1H), 7.17 (s, 1H), 7.08 (m, 1H), 6.64 (d, 1H), 6.15 (br. s, 1H, NH), 3.61 (m, 4H), 1.93 (m, 4H).

Example No. I.5-7

$^1$H NMR (400 MHz, d$_6$-DMSO δ, ppm) 8.10 (br. s, 1H, NH), 7.58 (d, 1H), 7.23 (dd, 1H), 6.82 (d, 1H), 6.69 (br. s, 1H, NH), 1.75 (m, 2H), 1.59 (m, 6H), 1.46 (m, 1H), 1.26 (m, 1H).

Example No. I.5-8

$^1$H NMR (400 MHz, d$_6$-DMSO δ, ppm) 9.70 (br. s, 1H, OH), 8.89 (br. s, 1H, NH), 7.82 (d, 1H), 7.36 (s, 1H), 7.25 (d, 1H), 2.16 (m, 2H), 1.70 (m, 2H), 1.63 (m, 4H).

Example No. I.5-9

$^1$H NMR (400 MHz, d$_6$-DMSO δ, ppm) 9.52 (br. s, 1H, OH), 8.59 (br. s, 1H, NH), 7.82 (d, 1H), 7.32 (s, 1H), 6.21 (d, 1H), 1.85 (q, 1H), 1.64 (q, 1H), 1.32 (s, 3H), 0.94 (t, 3H).

Example No. I.5-10

$^1$H NMR (400 MHz, d$_6$-DMSO δ, ppm) 9.60 (br. s, 1H, OH), 8.63 (br. s, 1H, NH), 7.82 (d, 1H), 7.34 (s, 1H), 7.23 (d, 1H), 1.88 (m, 2H), 1.68 (m, 2H), 1.59 (m, 6H).

Example No. I.5-11

$^1$H NMR (400 MHz, d$_6$-DMSO δ, ppm) 7.81 (br. s, 1H, NH), 7.37 (d, 1H), 7.03 (dd, 1H), 6.71 (d, 1H), 6.39 (br. s, 1H, NH), 2.16 (s, 3H), 1.72 (m, 2H), 1.53 (m, 6H), 1.40 (m, 1H), 1.22 (m, 1H).

Example No. I.5-12

$^1$H NMR (400 MHz, d$_6$-DMSO δ, ppm) 8.00 (br. s, 1H, NH), 7.38 (d, 1H), 7.04 (dd, 1H), 6.61 (d, 1H), 6.51 (br. s, 1H, NH), 2.18 (s, 3H), 1.78 (m, 4H), 1.64 (m, 4H).

Example No. I.5-13

$^1$H NMR (400 MHz, d$_6$-DMSO δ, ppm) 8.23 (br. s, 1H, NH), 7.50 (d, 1H), 7.11 (dd. 1H), 6.67 (d, 1H), 6.52 (br. s, 1H, NH), 6.48 (dd, 1H), 2.21 (m, 1H), 2.02 (m, 2H), 1.71 (m, 4H), 1.59-1.47 (m, 2H).

Example No. I.5-14

$^1$H NMR (400 MHz, d$_6$-DMSO δ, ppm) 8.13 (br. s, 1H, NH), 7.51 (d, 1H), 7.28 (m, 1H), 7.03 (br. s, 1H, NH), 6.92 (d, 1H), 2.23 (m, 1H), 2.04 (m, 2H), 1.70 (m, 3H), 1.68-1.47 (m, 3H).

Example No. I.5-15

$^1$H NMR (400 MHz, d$_6$-DMSO δ, ppm) 8.26 (br. s, 1H, NH), 7.50 (d, 1H), 7.23 (dd, 1H), 6.97 (br. s, 1H, NH), 6.72 (d, 1H), 1.79 (m, 4H), 1.67 (m, 4H).

Example No. I.5-16

$^1$H NMR (400 MHz, d$_6$-DMSO δ, ppm) 8.13 (br. s, 1H, NH), 7.49 (d, 1H), 7.26 (dd. 1H), 6.98 (br. s, 1H, NH), 6.86 (d, 1H), 4.06 (q, 2H), 3.50 (m, 1H), 1.82 (m, 3H), 1.78 (m, 1H), 1.60 (m, 4H).

Example No. I.5-17

$^1$H NMR (400 MHz, d$_6$-DMSO δ, ppm) 8.20 (br. s, 1H, NH), 7.74 (d, 1H), 7.21 (s, 1H), 7.19 (br. s, 1H, NH), 6.90 (d, 1H), 4.08 (q, 2H), 3.51 (m, 1H), 1.90 (m, 4H), 1.62 (m, 4H).

Example No. I.5-18

$^1$H NMR (400 MHz, d$_6$-DMSO δ, ppm) 7.91 (br. s, 1H, NH), 7.57 (d, 1H), 7.21 (dd, 1H), 6.82 (d, 1H), 6.78 (br. s, 1H, NH), 4.07 (q, 2H), 3.50 (m, 1H), 1.85 (m. 4H), 1.61 (m, 4H).

Example No. I.5-19

$^1$H NMR (400 MHz, d$_6$-DMSO δ, ppm) 8.08 (br. s, 1H, NH), 7.55 (d, 1H), 7.03 (br. s. 1H, NH), 6.81 (d. 1H), 6.63 (dd, 1H), 4.05 (q, 2H), 3.49 (m, 1H), 1.87 (m, 3H), 1.78 (m, 1H), 1.62 (m, 4H).

Example No. I.5-20

$^1$H NMR (400 MHz, d$_6$-DMSO δ, ppm) 8.58 (br. s, 1H, NH), 7.76 (d, 1H), 7.10 (br. s, 1H, NH), 6.99 (s, 1H), 6.92 (d, 1H), 2.29 (m, 1H), 2.06 (m, 2H), 1.75 (m, 3H), 1.66-1.49 (m, 3H).

Example No. I.5-21

$^1$H NMR (400 MHz, d$_6$-DMSO δ, ppm) 7.99 (br. s, 1H, NH), 7.50 (d, 1H), 7.12 (d, 1H), 6.62 (dd, 1H), 5.61 (br. s, 1H, NH), 4.04 (q, 2H), 3.56 (m, 1H), 2.13 (s, 3H), 1.88 (m, 4H), 1.67 (m, 4H).

Example No. I.5-22

$^1$H NMR (400 MHz, d$_6$-DMSO δ, ppm) 9.94 (br. s, 1H, NH), 7.85 (br. s, 1H, NH), 7.08 (dd, 1H), 6.75 (d. 1H), 6.73 (s, 1H), 2.18 (s, 3H), 1.82 (m, 2H), 1.61 (m, 2H), 1.52 (m, 5H), 1.19 (m, 1H).

Example No. I.5-24;

$^1$H NMR (400 MHz, d$_6$-DMSO δ, ppm) 10.30 (br. s, 1H, NH), 8.00 (br. m, 1H, NH), 7.30 (m. 1H), 6.92 (d. 1H), 6.74 (d, 1H), 2.32 (m. 1H), 2.12 (m, 1H), 2.07 (m, 1H), 1.82 (m, 1H), 1.72 (m, 3H), 1.63 (m, 1H), 1.52 (m, 1H).

The present invention accordingly provides for the inventive use of at least one compound selected from the group consisting of substituted fused pyrimidinones and dihydropyrimidinones of the formula (I), and of any desired mixtures of these inventive fused pyrimidinones and dihydropyrimidinones of the formula (I), with active agrochemical ingredients in accordance with the definition below, for enhancement of the resistance of plants to abiotic stress factors, preferably cold or drought stress (stress caused by drought and/or lack of water), most preferably drought stress, especially for invigoration of plant growth and/or for increasing the plant yield.

The present invention further provides a spray solution for treatment of plants, comprising an amount, effective for enhancement of the resistance of plants to abiotic stress factors, of at least one compound selected from the group consisting of substituted fused pyrimidinones and dihydropyrimidinones of the formula (I). Abiotic stress conditions which can be relativized may include, for example, drought, cold and hot conditions, drought stress (stress caused by drought and/or lack of water), osmotic stress, waterlogging, elevated soil salinity, elevated exposure to minerals, ozone conditions, strong light conditions, limited availability of nitrogen nutrients, limited availability of phosphorus nutrients.

In one embodiment, it is possible, for example, that the compounds envisaged in accordance with the invention, i.e. the corresponding substituted fused pyrimidinones and dihydropyrimidinones, are applied by spray application to appropriate plants or plant parts to be treated. The inventive compounds (I) are used as envisaged in accordance with the invention preferably with a dosage between 0.00005 and 3 kg/ha, more preferably between 0.0001 and 2 kg/ha, especially preferably between 0.0005 and 1 kg/ha. If, in the context of the present invention, abscisic acid is used simultaneously with substituted fused pyrimidinones and dihydropyrimidinones, for example in the context of a combined preparation or formulation, abscisic acid is preferably added in a dosage between 0.001 and 3 kg/ha, more preferably between 0.005 and 2 kg/ha, especially preferably between 0.01 and 1 kg/ha.

The term "resistance to abiotic stress" is understood in the context of the present invention to mean various kinds of advantages for plants. Such advantageous properties are manifested, for example, in the following improved plant characteristics: improved root growth with regard to surface area and depth, increased stolon and tiller formation, stronger and more productive stolons and tillers, improvement in shoot growth, increased lodging resistance, increased shoot base diameter, increased leaf area, higher yields of nutrients and constituents, for example carbohydrates, fats, oils, proteins, vitamins, minerals, essential oils, dyes, fibers, better fiber quality, earlier flowering, increased number of flowers, reduced content of toxic products such as mycotoxins, reduced content of residues or disadvantageous constituents of any kind, or better digestibility, improved storage stability of the harvested material, improved tolerance to disadvantageous temperatures, improved tolerance to drought and aridity, and also oxygen deficiency as a result of waterlogging, improved tolerance to elevated salt contents in soil and water, enhanced tolerance to ozone stress, improved compatibility with respect to herbicides and other plant treatment compositions, improved water absorption and photosynthesis performance, advantageous plant properties, for example acceleration of ripening, more homogeneous ripening, greater attractiveness to beneficial animals, improved pollination, or other advantages well known to a person skilled in the art.

More particularly, the inventive use exhibits the advantages described in spray application to plants and plant parts. Combinations of the corresponding substituted fused pyrimidinones and dihydropyrimidinones of the formula (I) with substances including insecticides, attractants, acaricides, fungicides, nematicides, herbicides, growth regulators, safeners, substances which influence plant maturity, and bactericides can likewise be employed in the control of plant disorders in the context of the present invention. In addition, the combined use of corresponding substituted fused pyrimidinones and dihydropyrimidinones of the formula (I) with genetically modified cultivars with a view to increased tolerance to abiotic stress is likewise possible.

As is known, some of the various kinds of advantages for plants, which have been mentioned above, can be combined, and generally applicable terms can be used to describe them. Such terms are, for example, the following names: phytotonic effect, resistance to stress factors, less plant stress, plant health, healthy plants, plant fitness, plant wellness, plant concept, vigor effect, stress shield, protective shield, crop health, crop health properties, crop health products, crop health management, crop health therapy, plant health properties, plant health products, plant health management, plant health therapy, greening effect or regreening effect, freshness, or other terms with which a person skilled in the art is quite familiar.

In the context of the present invention, a good effect on resistance to abiotic stress is understood to mean, without limitation, at least an emergence improved by generally 3%, especially more than 5%, preferably more than 10%,
at least a yield enhanced by generally 3%, especially more than 5%, preferably more than 10%,
at least a root development improved by generally 3%, especially more than preferably more than 10%,
at least a shoot size rising by generally 3%, especially more than 5%, preferably more than 10%,
at least a leaf area increased by generally 3%, especially more than 5%, preferably more than 10%,
at least a photosynthesis performance improved by generally 3%, especially more than 5%, preferably more than 10%, and/or
at least a flower formation improved by generally 3%, especially more than 5%, preferably more than 10%, and the effects may occur individually or else in any combination of two or more effects.

The present invention further provides a spray solution for treatment of plants, comprising an amount, effective for enhancement of the resistance of plants to abiotic stress factors, of at least one compound of the formula (I). The spray solution may comprise other customary constituents, such as solvents, formulation aids, especially water. Further constituents may include active agrochemical ingredients described in detail below.

The present invention further provides for the use of corresponding spray solutions for increasing the resistance of plants to abiotic stress factors. The remarks which follow apply both to the inventive use of the compounds of the formula (I) per se and to the corresponding spray solutions.

In accordance with the invention, it has additionally been found that the application, to plants or in their environment, of the compounds of the formula (I) in combination with at least one fertilizer as defined below is possible.

Fertilizers which can be used in accordance with the invention together with the compounds of the formula (I) elucidated in detail above are generally organic and inorganic nitrogen-containing compounds, for example ureas, urea/formaldehyde condensation products, amino acids, ammonium salts and ammonium nitrates, potassium salts (preferably chlorides, sulfates, nitrates), salts of phosphoric acid and/or salts of phosphorous acid (preferably potassium salts and ammonium salts). In this context, particular mention should be made of the NPK fertilizers, i.e. fertilizers which contain nitrogen, phosphorus and potassium, calcium ammonium nitrate, i.e. fertilizers which additionally contain calcium, or ammonium nitrate sulfate (formula $(NH_4)_2SO_4 \cdot NH_4NO_3$), ammonium phosphate and ammonium sulfate.

These fertilizers are common knowledge to those skilled in the art; see also, for example, Ullmann's Encyclopedia of Industrial Chemistry, 5th edition, Vol. A 10, pages 323 to 431, Verlagsgesellschaft, Weinheim, 1987.

The fertilizers may also contain salts of micronutrients (preferably calcium, sulfur, boron, manganese, magnesium, iron, boron, copper, zinc, molybdenum and cobalt) and phytohormones (for example vitamin B1 and indole-3-acetic acid) or mixtures thereof. Fertilizers used in accordance with the invention may also contain other salts such as monoammonium phosphate (MAP), diammonium phosphate (DAP), potassium sulfate, potassium chloride, magnesium sulfate. Suitable amounts for the secondary nutrients, or trace elements, are amounts of 0.5 to 5% by weight, based on the overall fertilizer. Further possible ingredients are crop protection compositions, insecticides or fungicides, growth regulators or mixtures thereof. This will be explained in more detail below.

The fertilizers can be used, for example, in the form of powders, granules, prills or compactates. However, the fertilizers can also be used in liquid form, dissolved in an aqueous medium. In this case, dilute aqueous ammonia can also be used as a nitrogen fertilizer. Further possible ingredients for fertilizers are described, for example, in Ullmann's Encyclopedia of Industrial Chemistry, 5th edition, 1987, volume A 10, pages 363 to 401, DE-A 41 28 828, DE-A 19 05 834 and DE-A 196 31 764. The general composition of the fertilizers which, within the context of the present invention, may take the form of straight and/or compound fertilizers, for example composed of nitrogen, potassium or phosphorus, may vary within a wide range. In general, a content of 1 to 30% by weight of nitrogen (preferably 5 to 20% by weight), 1 to 20% by weight of potassium (preferably 3 to 15% by weight) and a content of 1 to 20% by weight of phosphorus (preferably 3 to 10% by weight) is advantageous. The microelement content is usually in the ppm range, preferably in the range from 1 to 1000 ppm.

In the context of the present invention, the fertilizer and the compounds of the formula (I) may be administered simultaneously, i.e. synchronously. However, it is also possible first to apply the fertilizer and then a compound of the formula (I), or first to apply a compound of the formula (I) and then the fertilizer. In the case of nonsynchronous application of a compound of the formula (I) and the fertilizer, the application in the context of the present invention is, however, effected in a functional relationship, especially within a period of generally 24 hours, preferably 18 hours, more preferably 12 hours, specifically 6 hours, more specifically 4 hours, even more specifically within 2 hours, In very particular embodiments of the present invention, the inventive compound of the formula (I) and the fertilizer are applied within a time frame of less than 1 hour, preferably less than 30 minutes, more preferably less than 15 minutes.

The active ingredients of the formula (I) to be used in accordance with the invention, if appropriate in combination with fertilizers, can preferably be used on the following plants, though the enumeration which follows is not limiting.

Preferred plants are those from the group of the useful plants, ornamental plants, turfgrass types, commonly used trees which are employed as ornamentals in public and domestic areas, and forestry trees. Forestry trees include trees for the production of timber, cellulose, paper and products made from parts of the trees. The term "useful plants" as used here refers to crop plants which are employed as plants for obtaining foods, animal feeds, fuels or for industrial purposes.

The useful plants include, for example, the following types of plants: triticale, durum (hard wheat), turf, vines, cereals, for example wheat, barley, rye, oats, rice, corn and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao beans and peanuts; cucurbits, for example pumpkin/squash, cucumbers and melons; fiber plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; Lauraceae, for example avocado, *Cinnamomum*, camphor, or also plants such as tobacco; nuts, coffee, eggplant, sugarcane, tea, pepper, grapevines, hops, bananas, latex plants and ornamentals, for example flowers, shrubs, deciduous trees and coniferous trees. This enumeration does not constitute a restriction.

The following plants are considered to be particularly suitable target crops for the application of the method according to the invention: oats, rye, triticale, durum, cotton, eggplant, turf, pome fruit, stone fruit, soft fruit, corn, wheat, barley, cucumber, tobacco, vines, rice, cereals, pear, peppers, beans, soybeans, oilseed rape, tomato, bell pepper, melons, cabbage, potatoes and apples.

Examples of trees which can be improved in accordance with the method according to the invention include: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved by the method according to the invention include: from the tree species *Aesculus: A. hippocastanum, A. pariflora, A. carnea*; from the tree species *Platanus: P. aceriflora, P. occidentalis, P. racemosa*; from the tree species *Picea: P. abies*; from the tree species *Pinus: P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus: E. grandis, E. globulus, E. camadentis, E. nitens, E. obliqua, E. regnans, E. pilularus*.

Particularly preferred trees which can be improved by the method according to the invention include: from the tree species *Pinus: P. radiate, P. ponderosa, P. contorta, P. sylvestre, P. strobes*; from the tree species *Eucalyptus: E. grandis, E. globulus* and *E. camadentis*.

Particularly preferred trees which can be improved by the method according to the invention include: horse chestnut, Platanaceae, linden tree, maple tree.

The present invention can also be applied to any turfgrass types, including cool-season turfgrasses and warm-season turfgrasses. Examples of cool-season turfgrasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poe annua* L.), upland bluegrass (*Poe glaucantha* Gaudin), wood bluegrass (*Poe nemorelis* L) end bulbous bluegrass (*Poe bulbosa* L.); bentgresses (*Agrostis* spp.) such as creeping bentgrass (*Agrostis palustris* Huds.), colonial bentgrass (*Agrostis tenuis* Sibth.), velvet bentgrass (*Agrostis canine* L.), South German Mixed Bentgrass (*Agrostis* spp. including *Agrostis tenius* Sibth., *Agrostis canine* L., and *Agrostis palustris* Huds.), and redtop (*Agrostis alba* L.);

fescues (*Festuca* spp.), such as red fescue (*Festuca rubra* L. spp. rubra), creeping fescue (*Festuca rubra* L.), chewings fescue (*Festuce rubra* commutate Gaud.), sheep fescue (*Festuca ovina* L.), hard fescue (*Festuca longifolia* Thuill.), hair fescue (*Festucu capillata* Lam.), tail fescue (*Festuca arundinacea* Schreb.) and meadow fescue (*Festuca elanor* L.); ryegrasses (*Lolium* spp.), such as annual ryegrass (*Lolium multiflorum* Lam.), perennial ryegrass (*Lolium perenne* L.) and italian ryegrass (*Lolium multiflorum* Lam.); and wheatgrasses (*Agropyron* spp.), such as fairway wheatgrass (*Agropyron cristatum* (L.) Gaertn.), crested wheatgrass (*Agropyron desertorum* (Fisch.) Schuit.) and western wheatgrass (*Agropyron smithii* Rydb.).

Examples of further coot-season turfgrasses are beachgrass (*Ammophila breviligulata* Fern.), smooth bromegress (*Bromus inermis* Leyss.), cattails such as Timothy (*Phleum pretense* L.), sand cattail (*Phleum subulatum* L.), orchard grass (*Dactylis glomerata* L.), weeping alkaligrass (*Puccinellia distans* (L.) Parl.) and crested dog's-tail (*Cynosurus cristatus* L.).

Examples of warm-season turfgrasses are Bermuda grass (*Cynodon* spp. L. C. Rich), zoysia grass (*Zoysia* spp. Wild.), St. Augustine grass (*Stenotaphrum secundatum* Walt Kuntze), centipede grass (*Eremochloe ophiuroides* Munro Hack.), carpet grass (*Axonopus affinis* Chase), Bahia grass (*Paspalum notatum* Flugge), Kikuyu grass (*Pennisetum clandestinurn* Hochst. ex Chiov.), buffalo grass (*Buchloe dactyloids* (Nutt.) Engelm.), Blue gramma (*Bouteloua gracilis* (H.B.K.) Lag. ex Griffiths), seashore *paspalum* (*Paspalum vaginaturn* Swartz) and sideoats grarna (*Bouteloua curtipendula* (Michx.) Torr.). Cool-season turfgrasses are generally preferred for the use in accordance with the invention. Particular preference is given to bluegrass, bentgrass and redtop, fescues and ryegrasses. Bentgrass is especially preferred.

More preferably, plants of the plant cultivars which are commercially available or are in use are treated in accordance with the invention. Plant cultivars are understood to mean plants which have new properties ("traits") and which have been obtained by conventional breeding, by mutagenesis or with the aid of recombinant DNA techniques. Crop plants may accordingly be plants which can be obtained by conventional breeding and optimization methods or by biotechnological and genetic engineering methods or combinations of these methods, including the transgenic plants and including the plant cultivars which are protectable and non-protectable by plant breeders' rights.

The treatment method according to the invention can thus also be used for the treatment of genetically modified organisms (GMOs), for example plants or seeds. Genetically modified plants (or transgenic plants) are plants in which a heterologous gene has been integrated stably into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing (an)other gene(s) which is/are present in the plant (using for example antisense technology, cosuppression technology or RNAi technology [RNA interference]). A heterologous gene present in the genome is also called a transgene. A transgene that is defined by its specific presence in the plant genome is called a transformation or transgenic event.

Plants and plant cultivars which are preferably treated in accordance with the invention include all plants which have genetic material which imparts particularly advantageous, useful traits to these plants (whether obtained by breeding and/or biotechnological means).

Plants and plant cultivars which can likewise be treated in accordance with the invention are those plants which are resistant to one or more abiotic stress factors. The abiotic stress conditions may include, for example, drought, cold and hot conditions, osmotic stress, waterlogging, elevated soil salinity, elevated exposure to minerals, ozone conditions, strong light conditions, limited availability of nitrogen nutrients, limited availability of phosphorus nutrients or avoidance of shade.

Plants and plant cultivars which can likewise be treated in accordance with the invention are those plants which are characterized by enhanced yield characteristics. Enhanced yield in these plants may be the result of, for example, improved plant physiology, improved plant growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processibility and better storage stability.

Plants which can likewise be treated in accordance with the invention are hybrid plants that already express the characteristics of heterosis, or hybrid vigor, which generally results in higher yield, increased vigor, better health and better resistance toward biotic and abiotic stress factors. Such plants are typically produced by crossing an inbred male-sterile parent line (the female parent) with another inbred male-fertile parent line (the male parent). The hybrid seed is typically harvested from the male-sterile plants and sold to growers. Male-sterile plants can sometimes (for example in corn) be produced by detasseling (i.e. mechanical removal of the male reproductive organs or male flowers); however, it is more typical for male sterility to be the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmatic male sterility (CMS) have been described, for example, for *Brassica* species (WO 92/005251, WO 95/009910, WO 98/27806, WO 05/002324, WO 06/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396, in which, for example, a ribonuclease such as a barnase is selectively expressed in the tapetum cells in the stamens. Fertility can then be restored by expression in the tapetum cells of a ribonuclease inhibitor such as barstar (e.g. WO 91/002069).

Plants or plant cultivars (obtained by plant biotechnology methods such as genetic engineering) which can likewise be treated in accordance with the invention are herbicide-tolerant plants, i.e. plants which have been made tolerant to one or more given herbicides. Such plants can be obtained either by genetic transformation, or by selection of plants containing a mutation imparting such herbicide tolerance.

Herbicide-tolerant plants are, for example, glyphosate-tolerant plants, i.e. plants which have been made tolerant to the herbicide glyphosate or salts thereof. For example, glyphosate-tolerant plants can be obtained by transforming the plant with a gene which encodes the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an *Eleusine* EPSPS (WO 01/66704). The gene may also be a mutated EPSPS, as described, for example, in EP-A 0837944, WO 00/066746, WO 00/066747 or WO 02/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyltransferase enzyme as described, for example, in WO 02/036782, WO 03/092360, WO 05/012515 and WO 07/024,782. Glyphosate-tolerant plants can also be obtained by selecting plants containing naturally occurring mutations of the abovementioned genes, as described, for example, in WO 01/024615 or WO 03/013226.

Other herbicide-resistant plants are, for example, plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase are described, for example, in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated HPPD enzyme according to WO 96/038567, WO 99/024585 and WO 99/024586. Tolerance to HPPD inhibitors can also be obtained by transforming plants with genes encoding certain enzymes enabling the formation of homogentisate despite the inhibition of the native HPPD enzyme by the HPPD inhibitor. Such plants and genes are described in WO 99/034008 and WO 2002136787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Further herbicide-resistant plants are plants that have been made tolerant to acetolactate synthase (ALS) inhibitors. The known ALS inhibitors include, for example, sulfonylurea, imidazolinone, triazolopyrimidines, pyrimidinyl oxy(thio) benzoates and/or sulfonylaminocarbonyltriazolinone herbicides. It is known that different mutations in the ALS enzyme (also known as acetohydroxy acid synthase, AHAS) confer tolerance to different herbicides and groups of herbicides, as described, for example, in Tranel and Wright, Weed Science (2002), 50, 700-712, but also in U.S. Pat. No. 5,605,011, U.S. Pat. No. 5,378,824, U.S. Pat. No. 5,141,870 and U.S. Pat. No. 5,013,659. The production of sulfonylurea-tolerant plants and imidazolinone-tolerant plants has been described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and in the international publication WO 96/033270. Further imidazolinone-tolerant plants have also been described, for example, in WO 2004/040012, WO 2004/106529, WO 2005/020673, WO 2005/093093, WO 2006/007373, WO 2006/015376, WO 2006/024351 and WO 2006/060634. Further sulfonylurea- and imidazolinone-tolerant plants have also been described, for example in WO 2007/024782.

Further plants tolerant to imidazolinones, sulfonylureas and/or sulfamoylcarbonyltriazolinones can be obtained by induced mutagenesis, by selection in cell cultures in the presence of the herbicide or by mutation breeding, as described, for example, for soybeans in U.S. Pat. No. 5,084,082, for rice in WO 97/41218, for sugarbeet in U.S. Pat. No. 5,773,702 and WO 99/057965, for lettuce in U.S. Pat. No. 5,198,599 or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation which imparts such insect resistance.

In the present context, the term "insect-resistant transgenic plant" includes any plant containing at least one transgene comprising a coding sequence which encodes the following:
1) an insecticidal crystal protein from *Bacillus thuringiensis* or an insecticidal portion thereof, such as the insecticidal crystal proteins compiled by Crickmore at al., Microbiology and Molecular Biology Reviews (1998), 62, 807-813, updated by Crickmore et al. (2005) in the *Bacillus thuringiensis* toxin nomenclature, (online at: http://www.lifesci.sussex.ac.uk/Home/Neil_Crickmore/Bt/), or insecticidal portions thereof, for example proteins of the Cry protein classes Cry1Ab, Cry1Ac, Cry1F, Cry2Ab, Cry3Ae or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or
3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by corn event MON98034 (WO 2007/027777); or
4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in corn events MON863 or MON88017, or the Cry3A protein in corn event MR 604; or 5) an insecticidal secreted protein from *Bacillus thuringiensis* or *Bacillus cereus*, or an insecticidal portion thereof, such as the vegetative insecticidal proteins (VIPs) listed under the following link, for example proteins from the VIP3Aa protein class: http://www.lifesci.sussex.ac.uk/HomeiNeil_Crickmore/Bt/vip.html; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the abovementioned classes 1 to 8. In one embodiment, an insect-resistant plant contains more than one transgene encoding a protein of any one of the abovementioned classes 1 to 8, to expand the range of target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose)polymerase (PARP) gene in the plant cells or plants, as described in WO 2000/004173 or EP 04077984.5 or EP 06009836.5;

b. plants which contain a stress tolerance-enhancing transgene capable of reducing the expression and/or the activity of the PARG encoding genes of the plants or plant cells, as described, for example, in WO 2004/090140;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyl transferase, nicotinamide adenine dinucleotide synthetase or nicotinamide phosphoribosyltransferase, as described, for example, in EP 04077624.7 or WO 2006/133827 or PCT/EP07/002, 433.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behavior, the gel resistance, the grain size and/or grain morphology of the starch in comparison to the synthesized starch in wild-type plant cells or plants, such that this modified starch is better suited for certain applications. These transgenic plants synthesizing a modified starch are described, for example, in EP 0571427, WO 95/004826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 2000/008184, WO 2000/008185, WO 2000/28052, WO 2000/77229, WO 2001/12782, WO 2001/12826, WO 2002/101059, WO 2003/071860, WO 2004/056999, WO 20051030942, WO 2005/030941, WO 20051095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001114569, WO 2002/79410, WO 2003/33540, WO 2004/078983, WO 2001/19975, WO 95/26407, WO 96/34968, WO 98/20145, WO 99/12950, WO 99/66050, WO 99/53072, U.S. Pat. No. 6,734, 341, WO 2000/11192, WO 98/22604, WO 98/32326, WO 2001/98509, WO 2001/98509, WO 2005/002359, U.S. Pat. No. 5,824,790, U.S. Pat. No. 6,013,861, WO 94/004693, WO 94/009144, WO 94/11520, WO 95/35026 and WO 97/20936, 2) Transgenic plants which synthesize non-starch carbohydrate polymers or which synthesize non-starch carbohydrate polymers with altered properties in comparison to wild-type plants without genetic modification. Examples are plants producing polyfructose, especially of the inulin and levan type, as described in EP 0663956, WO 96/001904, WO 96/021023, WO 98/039460 and WO 99/024593, plants producing alpha-1,4-glucans, as described in WO 95/031553, US 2002/031826, U.S. Pat. No. 6,284,479, U.S. Pat. No. 5,712,107, WO 97/047806, WO 97/047807, WO 97/047808 and WO 2000/14249, plants producing alpha-1,6-branched alpha-1,4-glucans, as described in WO 2000/73422, and plants producing alternan, as described in WO 2000/047727, EP 06077301.7, U.S. Pat. No. 5,908,975 and EP 0728213.

3) Transgenic plants which produce hyaluronan, as for example described in WO 06/032538, WO 2007/039314, WO 2007/039315, WO 2007/039316, JP 2006/304779 and WO 2005/012529.

Plants or plant cultivars (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, which contain an altered form of cellulose synthase genes, as described in WO 98/000549;

b) plants, such as cotton plants, which contain an altered form of rsw2 or rsw3 homologous nucleic acids, as described in WO 2004/053219;

c) plants, such as cotton plants, with an increased expression of sucrose phosphate synthase, as described in WO 2001/017333;

d) plants, such as cotton plants, with an increased expression of sucrose synthase, as described in WO 02/45485;

e) plants, such as cotton plants, wherein the timing of the plasmodesmatal gating at the basis of the fiber cell is altered, for example through downregulation of fiber-selective 13-1, 3-glucanase as described in WO 2005/017157;

f) plants, such as cotton plants, which have fibers with altered reactivity, for example through the expression of the N-acetylglucosaminetransferase gene including nodC and chitin synthase genes, as described in WO 2006/136351.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics and include:

a) plants, such as oilseed rape plants, which produce oil having a high oleic acid content, as described, for example, in U.S. Pat. No. 5,969,169, U.S. Pat. No. 5,840,946 or U.S. Pat. No. 6,323,392 or U.S. Pat. No. 6,063,947;

b) plants, such as oilseed rape plants, which produce oil having a low linolenic acid content, as described in U.S. Pat. No. 6,270,828, U.S. Pat. No. 6,169,190 or U.S. Pat. No. 5,965,755;

c) plants, such as oilseed rape plants, which produce oil having a low level of saturated fatty acids, as described, for example, in U.S. Pat. No. 5,434,283.

Particularly useful transgenic plants which may be treated according to the invention are plants which comprise one or more genes which encode one or more toxins are the transgenic plants and which are sold under the following trade names: YIELD GARD® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants which should be mentioned are corn varieties, cotton varieties and soybean varieties which are available under the following trade names: Roundup Ready® (tolerance to glyphosate, for example corn, cotton, soybeans), Liberty Link® (tolerance to phosphinothricin, for example oilseed rape), IMI® (tolerance to imidazolinone) and SCS® (tolerance to sulfonylurea, for example corn). Herbicide-resistant plants (plants bred in a conventional manner for herbicide tolerance) which should be mentioned include the varieties sold under the Clearfield® name (for example corn).

Particularly useful transgenic plants which may be treated according to the invention are plants containing transformation events, or a combination of transformation events, and that are listed for example in the databases for various national or regional regulatory agencies.

The compounds of the formula (I) to be used in accordance with the invention can be converted to customary formulations, such as solutions, emulsions, wettable powders, water and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers, and also microencapsulations in polymeric substances. In the context of the present invention, it is especially preferred when the compounds of the formula (I) are used in the form of a spray formulation.

The present invention therefore additionally also relates to a spray formulation for enhancing the resistance of plants to abiotic stress. A spray formulation is described in detail hereinafter:

The formulations for spray application are produced in a known manner, for example by mixing the compounds of the formula (I) for use in accordance with the invention with extenders, i.e. liquid solvents and/or solid carriers, optionally with use of surfactants, i.e. emulsifiers and/or dispersants and/or foam formers. Further customary additives, for example customary extenders and solvents or diluents, dyes, wetting agents, dispersants, emulsifiers, antifoams, preservatives, secondary thickeners, stickers, gibberellins and also water, can optionally also be used. The formulations are prepared either in suitable facilities or else before or during application.

The auxiliaries used may be those substances which are suitable for imparting, to the composition itself and/or to preparations derived therefrom (for example spray liquors), particular properties such as particular technical properties and/or else special biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender utilized is water, it is also possible to use, for example, organic solvents as auxiliary solvents. Useful liquid solvents essentially include: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethyl sulfoxide, and also water.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Useful wetting agents which may be present in the formulations usable in accordance with the invention are all substances which promote wetting and which are conventionally used for the formulation of active agrochemical ingredients. Preference is given to using alkyl naphthalenesulfonates, such as diisopropyl or diisobutyl naphthalenesulfonates.

Useful dispersants and/or emulsifiers which may be present in the formulations usable in accordance with the invention are all nonionic, anionic and cationic dispersants conventionally used for the formulation of active agrochemical ingredients. Usable with preference are nonionic or anionic dispersants or mixtu of nonionic or anionic dispersants. Suitable nonionic dispersants are especially ethylene oxide/propylene oxide block polymers, alkylphenol polyglycol ethers and tristyrylphenol polyglycol ether, and the phosphated or sulfated derivatives thereof. Suitable anionic dispersants are especially lignosulfonates, polyacrylic acid salts and arylsulfonatelformaldehyde condensates.

Antifoams which may be present in the formulations usable in accordance with the invention are all foam-inhibiting substances conventionally used for the formulation of active agrochemical ingredients, Silicone antifoams and magnesium stearate can be used with preference.

Preservatives which may be present in the formulations usable in accordance with the invention are all substances usable for such purposes in agrochemical compositions. Examples include dichlorophene and benzyl alcohol hemiformal.

Secondary thickeners which may be present in the formulations usable in accordance with the invention are all substances usable for such purposes in agrochemical compositions. Preferred examples include cellulose derivatives, acrylic acid derivatives, xanthan, modified clays and finely divided silica.

Stickers which may be present in the formulations usable in accordance with the invention include all customary binders usable in seed-dressing products. Preferred examples include polyvinylpyrrolidone, polyvinyl acetate, polyvinyl alcohol and tylose. Gibberellins which may be present in the formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of the Crop Protection Compositions and Pesticides], vol. 2, Springer Verlag, 1970, p. 401-412).

Further additives may be fragrances, mineral or vegetable, optionally modified oils, waxes and nutrients (including trace nutrients), such as salts of iron, manganese, boron, copper, cobalt, molybdenum and zinc. Additionally present may be stabilizers, such as cold stabilizers, antioxidants, light stabilizers or other agents which improve chemical and/or physical stability.

The formulations contain generally between 0.01 and 98% by weight, preferably between 0.5 and 90%, of the compound of the formula (I).

The inventive active ingredient may be present in its commercially available formulations and in the use forms, prepared from these formulations, as a mixture with other active ingredients, such as insecticides, attractants, sterilants, bactericides, acaricides, nematicides, fungicides, growth regulators, herbicides, safeners, fertilizers or semiochemicals.

In addition, the described positive effect of the compounds of the formula (I) on the plants' own defenses can be supported by an additional treatment with active insecticidal, fungicidal or bactericidal ingredients.

Preferred times for the application of compounds of the formula (I) for enhancing resistance to abiotic stress are treatments of the soil, stems and/or leaves with the approved application rates.

The active ingredients of the formula (I) may generally additionally be present in their commercial formulations and in the use forms prepared from these formulations in mixtures with other active ingredients, such as insecticides, attractants, sterilants, acaricides, nematicides, fungicides, bactericides, growth regulators, substances which influence plant maturity, safeners or herbicides, Particularly favorable mixing partners are, for example, the active ingredients of the different classes, specified below in groups, without any preference resulting from the sequence thereof:

Fungicides:

F1) nucleic acid synthesis inhibitors, for example benalaxyl, benalaxyl-M, bupirimate, chiralaxyl, clozylacon, dimethirimol, ethirimol, furalaxyl, hymexazole, metalaxyl, metalaxyl-M, ofurace, oxadixyl, oxolinic acid;

F2) mitosis and cell division inhibitors, for example benomyl, carbendazim, diethofencarb, fuberidazole, fluopicolid, pencycuron, thiabendazole, thiophanate-methyl, zoxamide and chloro-7-(4-methylpiperidin-1-yl)-6-(2,4,6-trifluorophenyl) [1,2,4]triazolo[1,5-a]pyrimidine:

F3) respiratory chain complex NI inhibitors, for example diflumetorim, bixafen, boscalid, carboxin, diflumethorim, fenfuram, fluopyram, flutolanil, furametpyr, mepronil, oxycarboxin, penflufen, penthiopyrad, thifluzamid, N-[2-(1,3-dimethyl-butyl)phenyl]-5-fluoro-1,3-dimethyl-1H-pyrazole-4-carboxamide, isopyrazam, sedaxan, 3-(difluoromethyl)-1-methyl-N-(3',4',5-trifluorobiphenyl-2-yl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-0]-3-(difluoromethyl)-1-methyl-1H-pyrazole-4-carboxamide and corresponding salts;

F4) respiratory chain complex III inhibitors, for example amisulbrom, azoxystrobin, cyazofamid, dimoxystrobin, enestrobin, famoxadon, fenamidon, fluoxastrobin, kresoxim-methyl, metominostrobin, orysastrobin, pyraclostrobin, pyribencarb, picoxystrobin, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(ethoxyimino)-N-methyl-2-(2{[({(1E)-1-[3-(trifluoromethyl)phenyl]ethylidene}amino)oxy] methyl}phenyl)ethanamide and corresponding salts, (2E)-2-(methoxyimino)-N-methyl-2-{2-[(E)-({1-[3-(trifluoromethyl)phenyl]ethoxy}imino)methyl] phenyl}ethanamide, (2E)-2-{2-[({[(1E)-1-(3-{[(E)-1-fluoro-2-phenylethenyl]oxy}phenyl)ethylidene]amino}oxy) methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl] ethylidene}amino)oxy]methyl}phenyl)-2,4-dihydro-3H-1,2,4-triazol-3-one, 2-methyl {2-[({cyclopropyl[(4-methoxyphenyl)imino]methyl}sulfanyl)methyl]phenyl}-3-methoxyacrylate, N-(3-ethyl-3,5,5-trimethylcyclohexyl)-3-(formylamino)-2-hydroxybenzamide and corresponding salts;

F5) decouplers, for example dinocap, fluazinam;

F6) ATP production inhibitors, for example fentin acetate, fentin chloride, fentin hydroxide, silthiofam F7) amino acid and protein biosynthesis inhibitors, for example andoprim, blasticidin-S, cyprodinil, kasugamycin, kasugamycin hydrochloride hydrate, mepanipyrim, pyrimethanil F8) signal transduction inhibitors, for example fenpiclonil, fludioxonil, quinoxyfen F9) lipid and membrane synthesis inhibitors, for example chlozolinate, iprodione, procymidone, vinclozolin, ampropylfos, potassium-ampropylfos, edifenphos, iprobenfos (IBP), isoprothiolane, pyrazophos, tolciofos-methyl, biphenyl, iodocarb, propamocarb, propamocarb hydrochloride F10) ergosterol biosynthesis inhibitors, for example fenhexamid, azaconazole, bitertanol, bromuconazole, diclobutrazole, difenoconazole, diniconazole, diniconazole-M, etaconazoie, fenbuconazole, fluquinconazole, flusilazole, flutriafol, furconazole, furconazoie-cis, hexaconazole, imibenconazole, ipconazole, metconazole, myclobutanil, paclobutrazole, penconazole, propiconazole, prothioconazole, simeconazole, spiroxamine, tebuconazoie, triadimefon, triadimenol, triticonazole, uniconazoie, voriconazole, imazalil, imazalil sulfate, oxpoconazoie, fenarimol, flurprimidol, nuarimol, pyrifenox, triforin, pefurazoat, prochloraz, triflumizole, viniconazole, aldimorph, dodemorph, dodemorph acetate, fenpropimorph, tridemorph, fenpropidin, naftifin, pyributicarb, terbinafin, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidaformamide, N-ethyl-N-methyl-N'-{2-methyl-5-(trifluoromethyl)-4-[3-(trimethylsilyl)propoxy]phenyl}imidoformamide and O-{1-[(4-methoxyphenoxy)methyl]-2,2-dimethylpropyl}-1H-imidazole-1-carbothioate;

F11) cell wall synthesis inhibitors, for example benthiavalicarb, bialaphos, dimethomorph, fiumorph, iprovalicarb, polyoxins, polyoxorim, validamycin A F12) melanine biosynthesis inhibitors, for example capropamide, diciocymet, fenoxanil, phthalide, pyroquilon, tricyazole F13) resistance induction, for example acibenzolar-S-methyl, probenazole, tiadinil F14) multisite, for example captafol, captan, chlorothalonil, copper salts such as: copper hydroxide, copper naphthenate, copper oxychloride, copper sulfate, copper oxide, oxine-copper and Bordeaux mixture, dichlofluanid, dithianon, dodine, dodine free base, ferbam, folpet, fluorololpet, guazatine, guazatine acetate, iminociadine, iminactadine albesilate, iminoctadine triacetate, mancopper, mancozeb, maneb, metiram, metiram zinc, propineb, sulfur and sulfur preparations containing calcium polysulfide, thiram, tolylfluanid, zineb, ziram F15) unknown mechanism, for example amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulfate, diphenylamine, ethaboxam, ferimzone, flurnetover, flusulfamide, fluopicolide, fluoroimide, fosatyl-Al, hexachlorobenzene, 8-hydroxyquinoline sulfate, iprodione, irumamycin, isotianil, methasulfocarb, metrafenone, methyl isothiocyanate, mildiomycin, natamycin, nickel dimethyldithlocarbamate, nitrothal-isopropyl, octhilinone, oxamocarb, oxyfenthiln, pentachlorophenol and salts, 2-phenylphenol and salts, piperalin, propanosine-sodium, proquinazid, pyrroInitrin, quintozene, tecloftalam, tecnazene, triazoxide, trichlamide, zarilamid and 2,3,5,6-tetrachloro-4-(methylsulfonyl)pyridine, N-(4-chlor)-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4-]triazolo[1,5-a]pyrimidine, 5-chloro-6-(2,4,6-trifluorophenyl)-N-[(1R)-1,2,2-trimethylpropyl][1,2,4-]triazolo[1,5-a]pyrimidine-7-amine, 5-chloro-N-[(1R)-1,2-dimethylpropyl]-6-(2,4,6-trifluorophenyl)[1,2,4]triazolo[1,5-a]pyrimidine-7-amine, N-[1-(5-bromo-3-chloropyridin-2-yl)ethyl]-2,4-dichloronicotinamide, N-(5-bromo-3-Chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-fomlylamino-2-hydroxybenzamide, 2-[[[[1-[3-(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethy)benzamide, N-(3',4'-dichloro-5-fluorobiphenyl-2-yl)-3-(difluoromethy)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropy]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide.

Bactericides:

bronopol, dichlorophen, nitrapyrin, nickel dimethydithiocarbamate, kasugamy in, octhilinone, furancarboxylic acid, oxytetracyclin, probenazole, streptomycin, tecloftalam, copper sulfate and other copper preparations.

Insecticides/acaricides/nematicides:

I1) acetylcholine esterase (AChE) inhibitors, a) from the substance group of the carbamates, for example alanycarb, aldicarb, aldoxycarb, ailyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, fenoxycarb, formetanate, furathiocarb, isoprocarb, metam-sodium, methiocarb, methomyl, metolcarb, oxamyl, pirimicarb, promecarb, propoxur, thiodicarb, thiolanox, trimethacarb, XMC, xylylcarb, triazamate, b) from the group of the organophosphates, for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chiormephos, Chlorpyrifos(-methyl/-ethyl), coumaphos, cyanofenphos, cyanophos, chlorfenvinphos, demeton-S-methyl, demeton-S-methylsulfone, dialifos, diazinon, dichlofenthion, dichlorvosIDDVP, dicrotophos, dimethoate, dimethylvinphos, dioxabenzofos, disulfoton. EPN, ethion, ethoprophos, etrimfos, famphur, fenamiphos, fenitrothion, fensulfothion, fenthion, flupyrazolos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, ometpoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion I2) sodium channel modulators/voltage-dependent sodium channel blockers, a) from the group of the pyrethroids, for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, eflusilanate, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, pyrethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum), b) DDT, c) oxadiazines, for example indoxacarb, d) semicarbazones, for example metaflumizone (BAS3201)

I3) acetylcholine receptor agonists/antagonists, a) from the group of the chloronicotinyls, for example acetamiprid, AKD 1022, clothianidin, dinotefuran, imidacloprid, imidaclothiz, nitenpyram, nithiazine, thiacloprid, thiamethoxam, b) nicotine, bensultap, cartap; c) sulfoxaflor (N-[methyloxido[1-[6 (trifluoromethyl)-3-pyridinyl]ethyl]-λ4-sulfanydene]cyanamide)

I4) acetylcholine receptor modulators from the group of the spinosyns, for example spinosad I5) GABA-gated chloride channel antagonists, a) from the group of the organochlorines, for example camphechlor, chlordane, endosulfan, gamma-HCH, HCH, heptachlor, lindane, methoxychlor, b) fiproles, for example acetoprole, ethiprole, fipronil, pyrafluprole, pyriprole, vaniliprole;

I6) chloride channel activators, for example abamectin, emamectin, emamectin benzoate, ivermectin, lepimectin, milbemycin;

I7) juvenile hormone mimetics, for example diofenolan, epofenonane, fenoxycarb, hydroprene, kinoprene, methoprene, pyriproxifen, triprene;

I8) ecdysone agonists/disruptors, for example chromafenozide, halofenozide, methoxyfenozide, tebufenozide;

I9) chitin biosynthesis inhibitors, for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron, buprofezin, cyromazine;

I10) inhibitors of oxidative phosphorylation, a) ATP disruptors, for example diafenthiuron, b) organotin compounds, for example azocyclotin, cyhexatin, fenbutatin oxide;

I11) decouplers of oxidative phosphorylation by interruption of the H-proton gradient, a) from the group of the pyrroles, for example chlorfenapyr, b) from the class of the dinitrophenols, for example binapacryl, dinobuton, dinocap, DNOC, meptyldinocap;

I12) site I electron transport inhibitors, for example METIs, especially, as examples, fenazaquin, fenpyroximate, pyrimidifen, pyridaben, tebufenpyrad, tolfenpyrad or else hydramethylnon, dicofol, I13) site II electron transport inhibitors, for example rotenone;

I14) site III electron transport inhibitors, for example acequinocyl, fluacrypyrim;

I15) microbial disruptors of the insect gut membrane, for example *Bacillus thuringiensis* strains;

I16) lipid synthesis inhibitors, a) from the group of the tetronic acids, for example spirodiclofen, spiromesifen, b) from the class of the tetramic acids, for example spirotetramat, cis-3-(2,5-dimethylphenyl)-4-hydroxy-8-methoxy-1-azaspiro[4.5]dec-3-en-2-one;

I17) octopaminergic agonists, for example amitraz;

I18) inhibitors of magnesium-stimulated ATPase, for example propargite;

I19) nereistoxin analogs, for example thiocyclam hydrogen oxalate, thiosultap-sodium;

I20) ryanodine receptor agonists, a) from the group of the benzenedicarboxamides, for example fiubendiamide, b) from the group of the anthranilamides, for example rynaxypyr (3-bromo-N-{4-chloro-2-methyl-6-[(methylamino)carbonyl]phenyl}-1-(3-chloropyridin-2-yl)-1H-pyrazole-5-carboxamide), cyazypyr (ISO-proposed) (3-bromo-N-{4-cyano-2-methyl-6-[(methylamino)carbonyl]phenyl}-1-(3-chloropyridin-2-yl)-1H-pyrazole-5-carboxamide) (known from WO 2004067528);

I21) biologics, hormones or pheromones, for example azadirachtin, *Bacillus* spec., *Beauveria* spec., codlernone. *Metarrhizium* spec., *Paecilomyces* spec., thuringiensin, *Verticillium* spec.;

I22) active ingredients with unknown or nonspecific mechanisms of action, a) fumigants, for example aluminum phosphide, methyl bromide, sulfuryl fluoride, b) antifeedants, for example cryolite, flonicamide, pymetrozine, c) mite growth inhibitors, for example clofentezine, etoxazole, hexythiazox, d) amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnon, japonilure, metoxadiazone, petroleum, piperonyl butoxide, potassium oleate, pyridalyl, sulfluramid, tetradifon, tetrasul, triarathene, verbutin or lepimectin.

Safeners are preferably selected from the group consisting of:

S1) compounds of the formula (S1)

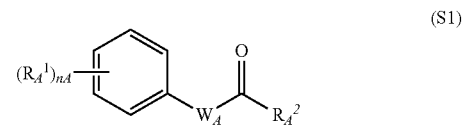

(S1)

where the symbols and indices are each defined as follows:
$n_A$ is a natural number from 0 to 5, preferably 0 to 3;
$R_A^1$ is halogen, $(C_1-C_4)$alkyl, $(C_1-C_4)$alkoxy, nitro or $(C_1-C_4)$haloalkyl:

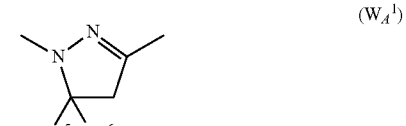

$(W_A^1)$

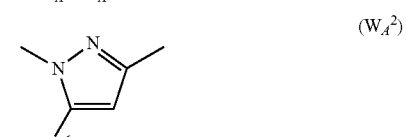

$(W_A^2)$

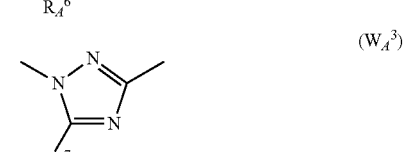

$(W_A^3)$

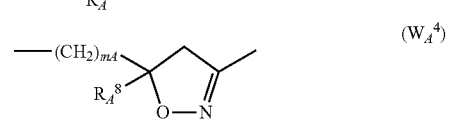

$(W_A^4)$ $W_A$ is an unsubstituted or substituted divalent heterocyclic radical from the group of the partially unsaturated or aromatic five-membered heterocycles having 1 to 3 ring heteroatoms of the N or O type, where at least one nitrogen atom and at most one oxygen atom is present in the ring, preferably a radical from the group of $(W_A^1)$ $(W_A^4)$, $m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group of 0 and 5, which is joined to the carbonyl group in (51) via the nitrogen atom and is unsubstituted or substituted by radicals from the group of $(C_1-C_4)$alkyl, $(C_1-C_4)$alkoxy or optionally substituted phenyl, preferably a radical of the formula $OR_A^3$, $NHR_A^4$ or $N(CH_3)_2$, especially of the formula $OR_A^3$;

$R_A^3$ is hydrogen or an unsubstituted or substituted aliphatic hydrocarbyl radical preferably having a total of 1 to 18 carbon atoms;

$R_A^4$ is hydrogen, $(C_1-C_6)$alkyl, $(C_1-C_6)$alkoxy or substituted or unsubstituted phenyl;

$R_A^5$ is H, $(C_1-C_8)$alkyl, $(C_1-C_8)$haloalkyl, $(C_1-C_4)$alkoxy$(C_1-C_8)$alkyl, cyano or $COOR_A^9$ in which $R_A^9$ is hydrogen, $(C_1-C_8)$alkyl, $(C_1-C_8)$haloalkyl, $(C_1-C_4)$alkoxy-$(C_1-C_4)$alkyl, $(C_1-C_6)$hydroxyalkyl, $(C_3-C_{12})$cycloalkyl or tri-$(C_1-C_4)$alkylsilyl;

$R_A^6$, $R_A^7$, $R_A^8$ are the same or different and are each hydrogen, $(C_1-C_8)$alkyl, $(C_1-C_8)$haloalkyl, $(C_3-C_{12})$cycloalkyl or substituted or unsubstituted phenyl;

preferably:

a) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described, for example, in EP-A-268554;

d) compounds of the triazolecarboxylic acid type (S1$^d$), preferably compounds such as fenchlorazole(-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;

e) compounds of the 5-benzyl- or 5-phenyl-2-isoxazoline-3-carboxylic acid or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazoline-3-carboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

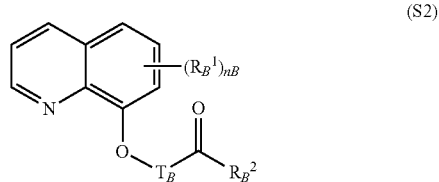

(S2)

where the symbols and indices are each defined as follows:

$R_B^1$ is halogen; $(C_1-C_4)$alkyl, $(C_1-C_4)$alkoxy, nitro or $(C_1-C_4)$haloalkyl;

$n_B$ is a natural number from 0 to 5, preferably 0 to 3;

$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group of O and S, which is joined to the carbonyl group in (S2) via the nitrogen atom and is unsubstituted or substituted by radicals from the group of $(C_1-C_4)$alkyl, $(C_1-C_4)$alkoxy or optionally substituted phenyl, preferably a radical of the formula $OR_B^3$, $NHR_B^4$ or $N(CH_3)_2$, especially of the formula $OR_B^3$;

$R_B^3$ is hydrogen or an unsubstituted or substituted aliphatic hydrocarbyl radical preferably having a total of 1 to 18 carbon atoms;

$R_B^4$ is hydrogen, $(C_1-C_6)$alkyl, $(C_1-C_6)$alkoxy or substituted or unsubstituted phenyl;

$T_B$ is a $(C_1$ or $C_2)$-alkanediyl chain which is unsubstituted or substituted by one or two $(C_1-C_4)$alkyl radicals or by [$(C_1-C_3)$alkoxy]carbonyl:

preferably:

a) compounds of the 8-quinolinoxyacetic acid type (S2$^a$), preferably 1-methylhexyl (5-chloro-8-quinolinoxy)acetate "cloquintocet-mexyl" (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (32-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

b) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

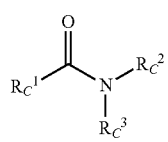

where the symbols and indices are each defined as follows:

$R_C^1$ is $(C_1-C_4)$alkyl, $(C_1-C_4)$haloalkyl, $(C_2-C_4)$alkenyl, $(C_2-C_4)$haloalkenyl, $(C_3-C_7)$cycloalkyl, preferably dichloromethyl;

$R_C^2$, $R_C^3$ are the same or different and are each hydrogen, $(C_1-C_4)$alkyl, $(C_2-C_4)$alkenyl,
$(C_2-C_4)$alkynyl, $(C_1-C_4)$haloalkyl, $(C_2-C_4)$haloalkenyl, $(C_1-C_4)$alkylcarbamoyl-$(C_1-C_4)$alkyl, $(C_2-C_4)$alkenylcarbamoyl-$(C_1-C_4)$alkyl, $(C_1-C_4)$alkoxy-$(C_1-C_4)$alkyl, dioxolanyl-$(C_1-C_4)$alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring; preferably: active ingredients of the dichloroacetamide type, which are frequently used as pre-emergence safeners (soil-acting safeners), for example "dichlormid" (N,N-diallyl-2,2-dichloroacetamide) (33-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (33-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4,5]decane) from Nitrokemia or Monsanto (33-7), "TI-35" (1-dichloroacetylazepane) from TRI-Chemical RT (S3-8), "diclonon" (dicyclonone) or "BAS145138" or "LAB145138" (S3-9) ((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-Acylsulfonamides of the formula (S4) and salts thereof

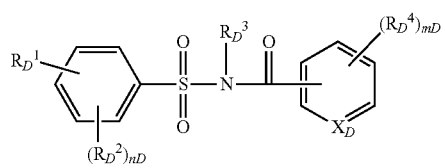

in which the symbols and indices are each defined as follows:
$X_D$ is CH or N;
$R_D^1$ is $CO-NR_D^5R_D^6$ or $NHCO-R_D^7$;
$R_D^2$ is halogen, $(C_1-C_4)$haloalkyl, $(C_1-C_4)$haloalkoxy, nitro, $(C_1-C_4)$alkyl, $(C_1-C_4)$alkoxy, $(C_1-C_4)$alkylsulfonyl, $(C_1-C_4)$alkoxycarbonyl or $(C_1-C_4)$alkylcarbonyl;
$R_D^3$ is hydrogen, $(C_1-C_4)$alkyl, $(C_2-C_4)$alkenyl or $(C_2-C_4)$alkynyl;
$R_D^4$ is halogen, nitro, $(C_1-C_4)$alkyl, $(C_1-C_4)$haloalkyl, $(C_1-C_4)$haloalkoxy, $(C_3-C_6)$cycloalkyl, phenyl, $(C_1-C_4)$alkoxy, cyano, $(C_1-C_4)$alkylthio, $(C_1-C_4)$alkylsulfinyl, $(C_1-C_4)$alkylsulfonyl, $(C_1-C_4)$alkoxycarbonyl or $(C_1-C_4)$alkylcarbonyl;
$R_D^5$ is hydrogen, $(C_1-C_6)$alkyl, $(C_3-C_6)$cycloalkyl, $(C_2-C_6)$alkenyl, $(C_2-C_6)$alkynyl, $(C_5-C_6)$cycloalkenyl, phenyl or 3- to 6-membered heterocyclyl containing $v_D$ heteroatoms from the group of nitrogen, oxygen and sulfur, where the seven latter radicals are each substituted by $v_D$ substituents from the group of halogen, $(C_1-C_6)$alkoxy, $(C_1-C_6)$haloalkoxy, $(C_1-C_2)$alkylsulfinyl, $(C_1-C_2)$alkylsulfonyl, $(C_3-C_6)$cycloalkyl, $(C_1-C_4)$alkoxycarbonyl, $(C_1-C_4)$alkylcarbonyl and phenyl, and in the case of cyclic radicals also $(C_1-C_4)$alkyl and $(C_1-C_4)$haloalkyl;
$R_D^6$ is hydrogen, $(C_1-C_6)$alkyl, $(C_2-C_6)$alkenyl or $(C_2-C_6)$alkynyl, where the three latter radicals are each substituted by $v_D$ radicals from the group of halogen, hydroxyl, $(C_1-C_4)$alkyl, $(C_1-C_4)$alkoxy and $(C_1-C_4)$alkylthio, or
$R_1^5$ and $R_D^6$ together with the nitrogen atom which bears them form a pyrrolidinyl or piperidinyl radical;
$R_D^7$ is hydrogen, $(C_1-C_4)$alkylamino, di-$(C_1-C_4)$alkylamino, $(C_1-C_6)$alkyl, $(C_3-C_6)$cycloalkyl, where the 2 latter radicals are substituted by $v_D$ substituents from the group of halogen, $(C_1-C_4)$alkoxy, $(C_1-C_6)$haloalkoxy and $(C_1-C_4)$alkylthio, and in the case of cyclic radicals also $(C_1-C_4)$alkyl and $(C_1-C_4)$haloalkyl;
$n_D$ is 0, 1 or 2;
$m_D$ is 1 or 2;
$v_D$ is 0, 1, 2 or 3;
among these, preference is given to compounds of the N-acylsulfonamide type, for example of the formula (S4$^a$) below, which are known, for example, from WO-A-97/45016

in which
$R_D^7$ is $(C_1-C_6)$alkyl, $(C_3-C_6)$cycloalkyl, where the 2 latter radicals are substituted by $v_D$ substituents from the group of halogen, $(C_1-C_4)$alkoxy, $(C_1-C_6)$haloalkoxy and $(C_1-C_{1i})$alkylthio, and in the case of cyclic radicals also $(C_1-C_4)$alkyl and $(C_1-C_4)$haloalkyl;
$R_D^4$ is halogen, $(C_1-C_4)$alkyl, $(C_1-C_4)$alkoxy, $CF_3$;
$m_D$ is 1 or 2;
$v_D$ is 0, 1, 2 or 3;
and also to acylsulfamoylbenzamides, for example of the formula (S4$^b$) below, which are known, for example, from WO-A-99/16744,

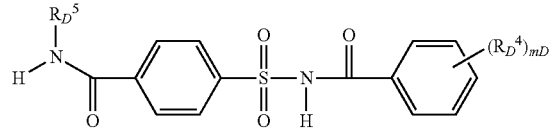

for example those in which $R_D{}^5$=cyclopropyl and $(R_D{}^4)$=2-OMe ist ("cyprosulfamide", S4-1),
$R_D{}^5$=cyclopropyl and $(R_D{}^4)$=5-Cl-2-OMe (S4-2),
$R_D{}^5$=ethyl and $(R_D{}^4)$=2-OMe (S4-3),
$R_D{}^5$=isopropyl and $(R_D{}^4)$=5-Cl-2-OMe (34-4) and
$R_D{}^5$=isopropyl and $(R_D{}^4)$=2-OMe (S4-5),
and to compounds of the N-acylsulfamoylphenylurea type, of the formula (S4$^c$), which are known, for example, from EP-A-365484,

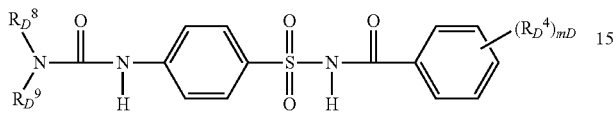

(S4$^c$)

in which
$R_D{}^8$ and $R_D{}^9$ are each independently hydrogen, $(C_1-C_8)$alkyl, $(C_3-C_8)$cycloalkyl, $(C_3-C_6)$alkenyl, $(C_3-C_6)$alkynyl,
$R_D{}^4$ is halogen, $(C_1-C_4)$alkyl, $(C_1-C_4)$alkoxy, $CF_3$
$m_D$ is 1 or 2;
for example
1-[4-(N-2-methoxybenzoylsulfamoyl)phenyl]-3-methylurea,
1-[4-(N-2-methoxybenzoylsulfamoyl)phenyl]-3,3-dimethylurea;
1-[4-(N-4,5-dimethylbenzoylsulfamoyl)phenyl]-3-methylurea.

S5) Active ingredients from the class of the hydroxyaromatics and the aromatic-aliphatic carboxylic acid derivatives (35), for example ethyl 3,4,5-triacetoxybenzoate, 3,5-dimethoxy-4-hydroxybenzoic acid, 3,5-dihydroxybenzoic acid, 4-hydroxysalicyic acid, 4-fluorosalicyclic acid, 2-hydroxycinnamic acid, 2,4-dichlorocinnamic acid, as described in WO-A 2004/084631, WO-A-2005/015994, WO-A-2005/016001.

S6) Active ingredients from the class of the 1,2-dihydroquinoxalin-2-ones (36), for example
1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

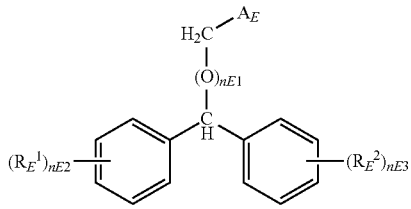

(S7)

in which the symbols and indices are each defined as follows:
$R_E{}^1$, $R_E{}^2$ are each independently halogen, $(C_1-C_4)$alkyl, $(C_1-C_4)$alkoxy, $(C_1-C_4)$haloalkyl, $(C_1-C_4)$alkylamino, di-$(C_1-C_4)$alkyamino, nitro;

$A_E$ is $COOR_E{}^3$ or $COSR_E{}^4$
$R_E{}^3$, $R_E{}^4$ are each independently hydrogen, $(C_1-C_4)$alkyl, $(C_2-C_6)$alkenyl, $(C_2-C_4)$alkynyl, cyanoalkyl, $(C_1-C_4)$haloalkyl, phenyl, nitrophenyl, benzyl, halobenzyl, pyridinylalkyl and alkylammonium,
$n_E{}^1$ is 0 or 1
$n_E{}^2$, $n_E{}^3$ are each independently 0, 1 or 2,
preferably diphenylmethoxyacetic acid, ethyl diphenymethoxyacetate, methyl diphenylmethoxyacetate (CAS reg. no. 41858-19-9) (S7-1).

S8) Compounds of the formula (S8), as described in WO-A-98/27049,

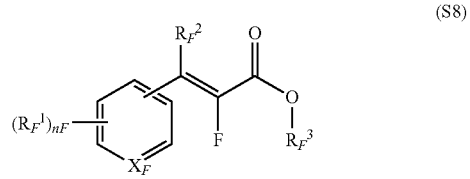

(S8)

in which
$X_F$ is CH or N,
$n_F$ in the case that $X_F$=N is an integer from 0 to 4 and in the case that $X_F$=CH is an integer from 0 to 5,
$R_F{}^1$ is halogen, $(C_1-C_4)$alkyl, $(C_1-C_4)$haloalkyl, $(C_1-C_4)$alkoxy, $(C_1-C_4)$haloalkoxy, nitro, $(C_1-C_4)$alkylthio, $(C_1-C_4)$alkylsulfonyl, $(C_1-C_4)$alkoxycarbonyl, optionally substituted phenyl, optionally substituted phenoxy,
$R_F{}^2$ is hydrogen or $(C_1-C_4)$alkyl
$R_F{}^3$ is hydrogen, $(C_1-C_8)$alkyl, $(C_2-C_4)$alkenyl, $(C_2-C_4)$alkynyl, or aryl, where each of the aforementioned carbon-containing radicals is unsubstituted or substituted by one or more, preferably up to three identical or different radicals from the group consisting of halogen and alkoxy; or salts thereof.

preferably compounds in which
$X_F$ is CH,
$n_F$ is an integer from 0 to 2,
$R_F{}^1$ is halogen, $(C_1-C_4)$alkyl, $(C_1-C_4)$haloalkyl, $(C_1-C_4)$alkoxy, $(C_1-C_4)$haloalkoxy,
$R_F{}^2$ is hydrogen or $(C_1-C_4)$alkyl,
$R_F$ is hydrogen, $(C_1-C_8)$alkyl, $(C_2-C_4)$alkenyl, $(C_2-C_4)$alkynyl, or aryl, where each of the aforementioned carbon-containing radicals is unsubstituted or substituted by one or more, preferably up to three identical or different radicals from the group consisting of halogen and alkoxy; or salts thereof.

S9) Active ingredients from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS reg. no.: 219479-18-2), 1,2-dihydro-4-hydroxy-1-methyl-3-(5-tetrazolylcarbonyl)-2-quinolone (CAS reg. no.: 95855-00-8), as described in WO-A-1999/000020.

S10) Compounds of the formula (S10$^a$) or (S10$^b$),
as described in WO-A-2007/023719 and WO-A-2007/023764,

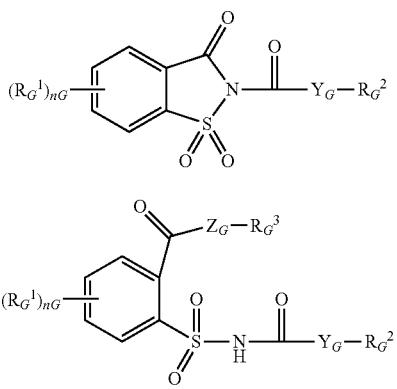

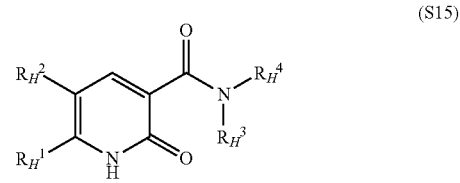

in which
R$_G^1$ is halogen, (C$_1$-C$_4$)alkyl, methoxy, nitro, cyano, CF$_3$, OCF$_3$,
Y$_G$, Z$_G$ are each independently O or S,
n$_G$ is an integer from 0 to 4,
R$_G^2$ is (C$_1$-C$_{16}$)alkyl, (C$_2$-C$_6$)alkenyl, (C$_3$-C$_6$)cycloalkyl, aryl; benzyl, halobenzyl,
R$_G^3$ is hydrogen or (C$_1$-C$_6$)alkyl.

S11) Active ingredients of the oxyimino compound type (S11), which are known as seed-dressing compositions, for example "oxabetrinil" ((Z)-1,3-dioxolan-2-yl-methoxy-imino(phenyl)acetonitrile) (S11-1), which is known as a seed-dressing safener for millet/sorghum, against damage by metolachlor, "fluxofenim" (1-(4-chlorophenyl)-2,2,2-trilluoro-1-ethanone O-(1,3-dioxolan-2-ylmethyl)oxime) (S11-2), which is known as a seed-dressing safener for millet/sorghum against damage by metolachlor, and "cyometrinil" or "CGA-43089" ((Z)-cyanomethoxylmino(phenyl)acetonitrile) (S11-3), which is known as a seed-dressing safener for millet/sorghum against damage by metolachlor.

S12) Active ingredients from the class of the isothiochromanones (S12), for example methyl [(3-oxo-1H-2-benzothiopyran-4(3H)-ylidene)methoxy]acetate (CAS reg. no. 205121-04-6) (312-1) and related compounds from WO-A-1998/13361.

S13) One or more compounds from group (S13): "naphthalic anhydride" (1,8-naphthalenedicarboxylic anhydride) (S13-1), which is known as a seed-dressing safener for corn against damage by thiocarbamate herbicides, "fenclorim" (4,6-dichloro-2-phenylpyrimidine) (S13-2), which is known as a safener for pretilachlor in sown rice, "flurazole" (benzyl 2-chloro-4-trifluoro-methyl-1,3-thiazole-5-carboxylate) (S13-3), which is known as a seed-dressing safener for millet/sorghum against damage by aiachlor and metolachlor, "CL 304415" (CAS reg. no. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS reg. no. 96420-72-3) (2-dichloromethyl-2-methyl-1,3-dioxolane) (S13-5) from Nitrokemia, which is known as a safener for corn, "MG-838" (CAS reg. no. 133993-74-5) (2-propenyl 1-oxa-4-azaspiro[4.5]decane-4-carbodithioate) (S13-6) from Nitrokemia, "disuifoton" (O,O-diethyl S-2-ethylthioethyl phosphorodithioate) (S13-7), "dietholate" (O,O-diethyl O-phenylphosphorothioate) (S13-8), "mephenate" (4-chlor)phenyl methylcarbamate) (313-9).

S14) Active ingredients which, in addition to herbicidal action against harmful plants, also have safener action on crop plants such as rice, for example "dirnepiperate" or "MY-93" (S-1-methyl-1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as a safener for rice against damage by the herbicide imazosulfuron, "cumyluron"="JC-940" (3-(2-chlorophenylmethyl)-1-(1-methyl-1-phenylethypurea, see JP-A-60087254), which is known as a safener for rice against damage by some herbicides, "methoxyphenone" or "NK 049" (3,3'-dimethyl-4-methoxybenzophenone), which is known as a safener for rice against damage by some herbicides, "CSB" (1-bromo-4-(chloromethylsulfonyl)benzene) from Kumiai, (CAS reg. no. 54091-06-4), which is known as a safener against damage by some herbicides in rice.

S15) Compounds of the formula (S15) or tautomers thereof as described in WO-A-2008/131861 and WO-A-2008/131860, in which R$_H^1$ is a (C$_1$-C$_6$)haloalkyl radical and
R$_H^2$ is hydrogen or halogen and
R$_H^3$, R$_H^4$ are each independently hydrogen, (C$_1$-C$_{16}$)alkyl, (C$_2$-C$_{16}$)alkenyl or (C$_2$-C$_{16}$)alkynyl, where each of the latter 3 radicals is unsubstituted or substituted by one or more radicals from the group of halogen, hydroxyl, cyano, (C$_1$-C$_4$)alkoxy, (C$_1$-C$_4$)haloalkoxy, (C$_1$-C$_4$)alkylthio, (C$_1$-C$_4$)alkylamino, di[(C$_1$-C$_4$)alkyl]amino, [(C$_1$-C$_4$)alkoxy]carbonyl, [(C$_1$-C$_4$)haloalkoxy]carbonyl, (C$_3$-C$_6$)cycloalkyl which is unsubstituted or substituted, phenyl which is unsubstituted or substituted, and heterocyclyl which is unsubstituted or substituted, or (C$_3$-C$_6$)cycloalkyl, (C$_4$-C$_6$)cycloalkenyl, (C$_3$-C$_6$)cycloalkyl which is fused on one side of the ring to a 4 to 6-membered saturated or unsaturated carbocyclic ring, or (C$_4$-C$_6$)cycloalkenyl which is fused on one side of the ring to a 4 to 6-membered saturated or unsaturated carbacyclic ring, where each of the latter 4 radicals are unsubstituted or substituted by one or more radicals from the group of halogen, hydroxyl, cyano, (C1-C4)alkyl, (C1-C4)haloalkyl, (C1-C4)alkoxy, (C1-C4)haloalkoxy, (C1-C4)alkylthio, (C1-C4)alkylamino, di[(C1-C4)alkyl]amino, [(C1-C4)alkoxy]carbonyl, [(C1-C4)haloalkoxy]carbonyl, (C3-C6)cycloalkyl which is unsubstituted or substituted, phenyl which is unsubstituted or substituted, and heterocyclyl which is unsubstituted or substituted,
or
R$_H^3$ is (C$_1$-C$_4$)alkoxy, (C$_2$-C$_4$)alkenyloxy, (C$_2$-C$_6$)alkynyloxy or (C$_2$-C$_4$)haloalkoxy and
R$_H^4$ is hydrogen or (C$_1$-C$_4$)-alkyl or
R$_H^3$ and R$_H^4$ together with the directly bonded nitrogen atom are a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$alkyl, $(C_1-C_4)$haloalkyl, $(C_1-C_4)$alkoxy, $(C_1-C_4)$haloalkoxy and $(C_1-C_4)$alkylthio.

S16) Active ingredients which are used primarily as herbicides but also have safener action on crop plants, for example (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy) butyric acid (2,4-DB), (4-chloro-o-tolyloxy)acetic acid (MCPA), 4-(4-chloro-o-tolyloxy)butyric acid, 4-(4-Chloro-phenoxy)butyrc acid, 3,6-dichloro-2-methoxybenzoic acid (dicamba), 1-(ethoxycarbonyl)ethyl 3,6-dichloro-2-methoxybenzoate (lactidichlor-ethyl).

Substances which Influence Plant Maturity:

Combination partners usable for the compounds of the formula (I) in mixture formulations or in tankmixes are, for example, known active ingredients based on inhibition of, for example, 1-aminocyclopropane-1-carboxylate synthase, 1-aminocyclopropane-1-carboxylate oxidase and the ethylene receptors, for example ETR1, ETR2, ERS1, ERS2 or EIN4, as described, for example, in Blotechn, Adv. 2006, 24, 357-367, Bot. Bull. Acad. Sin. 199, 40, 1-7 or Plant Growth Reg. 1993, 13, 41-46 and literature cited therein.

Examples of known substances which influence plant maturity and can be combined with the compounds of the formula (I) include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. In this list, one or else, in some cases, more than one application form is mentioned by way of example:
rhizobitoxine, 2-aminoethoxyvinylglycine (AVG), methoxyvinylglycine (MVG), vinylglycine, aminooxyacetic acid, sinefungin, S-adenosylhomocysteine, 2-keto-4-methyl thiobutyrate, 2-(methoxy)-2-oxoethyl (isopropylidene)aminooxyacetate, 2-(hexyloxy)-2-oxoethyl (isopropylidene)aminooxyacetate, 2-(isopropyloxy)-2-oxoethyl (cyclohexylidene)aminooxyacetate, putrescine, spermidine, spermine, 1,8-diamino-4-aminoethyloctane, L-canaline, daminozide, methyl 1-aminocyclopropyl-1-carboxylate, N-methyl-1-aminocyclopropyl-1-carboxylic acid, 1-aminocyclopropyl-1-carboxamide, substituted 1-aminocyclopropyl-1-carboxylic acid derivatives as described in DE3335514, EP30287, DE2906507 or U.S. Pat. No. 5,123,951, 1-aminocyclopropyl-1-hydroxamic acid, 1-methylcyclopropene, 3-methylcyclopropene, 1-ethylcyclopropene, 1-n-propylcyclopropene, 1-cyclopropenylmethanol, carvone, eugenol, sodium cycloprop-1-en-1-ylacetate, sodium cycloprop-2-en-1-ylacetate, sodium 3-(cycloprop-2-en-1-yl)propanoate, sodium 3-(cycloprop-1-en-1-yl)propanoate, jasmonic acid, jasmonic acid methyl ester, jasmonic acid ethyl ester.

Substances which Influence Plant Health and Germination:

Combination partners usable for the compounds of the formula (I) in mixture formulations or in tankmixes are, for example, known active ingredients which influence plant health (the compounds are designated by the "common name" according to the International Organization for Standardization (ISO) or by the chemical name or by the code number, and always include all use forms, such as acids, salts, esters and isomers such as stereoisomers and optical isomers): sarcosin, phenylalanine, tryptophan, N'-methyl-1-phenyl-1-N,N-diethylamino-methanesulfonamide, apio-galacturonans as described in WO2010017956, 4-oxo-4-[(2-phenylethyl)amino]butanoic acid, 4-{[2-(1H-indol-3-yl) ethyl]amino}-4-oxobutanoic acid, 4-[(3-methylpyridin-2-yl) amino]-4-oxobutanoic acid, allantoin, 5-aminolevulinic acid, (2S,3R)-2-(3,4-dihydroxyphenyl)-3,4-dihydro-2H-chromene-3,5,7-triol and structurally related catechols as described in WO2010122956, 2-hydroxy-4-(methyl-sulfanyl)butanoic acid, (3E,3αR,8βS)-3-({[(2R)-4-methyl-5-oxo-2,5-dihydrofuran-2-yl]oxy}methylene)-3,3α,4,8β-tetrahydro-2H-indeno[1,2-b]furan-2-one and analogous lactones as described in EP2248421, abscisic acid, (2Z,4E)-5-[(1R,6R)-6-ethynyl-1-hydroxy-2,6-dimethyl-4-oxocyclohex-2-en-1-yl]-3-methylpenta-2,4-dienoic acid, methyl-(2Z,4E)-5-[(1R, 6R)-6-ethynyl-1-hydroxy-2,6-dimethyl-4-oxocyclohex-2-en-1-yl]-3-methylpenta-2,4-dienoate, 4-phenylbutyric acid, sodium 4-phenylbutanoate, potassium 4-phenylbutanoate.

Herbicides or Plant Growth Regulators:

Combination partners usable for the compounds of the formula (I) in mixture formulations or in tankmixes are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem H, protoporphyrinogen oxidase, as described, for example, in Weed Research 26 (1986) 441-445 or "The Pesticide Manual", 14th edition, The British Crop Protection Council and the Royal Soc. of Chemistry, 2006 and literature cited therein.

Examples of known herbicides or plant growth regulators which can be combined with compounds of the formula (I) include the active ingredients which follow (the compounds are designated by the "common name" according to the International Organization for Standardization (ISO) or by the chemical name or by the code number) and always encompass all use forms, such as adds, salts, esters and isomers, such as stereoisomers and optical isomers. In this list, one or else, ill some cases, more than one application form is mentioned by way of example:
acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachior, aminopyralid, amitrole, ammonium sulfamate, ancymidol, anilofos, asulam, atrazine, azafeniclin, azimsulfuron, aziprotryne, beflubutamid, benazolin, benazolin-ethyl, bencarbazone, benflluralin, benfuresate, bensulide, bensulfuron, bensulfuronmethyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clornazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhaiofop-butyl, cyperquat, cyprazine, cyprazole, 2,4-D, 2,4-DB, daimuron/dymron, dalapon, daminozide, dazomet, n-decanoi, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatykethyl, difenoxuron, difenzoquat, diflufenican, diflufenzopyr, diflufenzopyr-sodium, dimefuron, dikegulac-sodium, dimefuron, dimepiperate, dimethachior, dirnethametryn, dimethenarnid, dimethenamid-P, dimethipin, dimetrasulfuron, dinitramine, dinoseb, dinoterb, diphenamid, dipropetryn, diquat, diquat-dibromide, dithlopyr, diuron. DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxylen-ethyl, ethoxysulfuron, etobenzanid. F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fiuroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibbereilic acid, glufosinate, glufosinate-ammonium, glufasinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haioxyfop-P-ethoxyethyl, haloxyrop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop. KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulluron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosuifocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribarnbenz, pyribarnbenz-isopropyl, pyribambenz-propyl, pyribenzoxirn, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalolop, quizalofop-ethyl, quizalofop-P, quizalofop-P-ethyl, quizalofop-P-tefuryl, rimsulfuron, safiufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesiurn), sulfosulfuron, SYN-523. SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr; tridiphane; trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, D-0862, i.e. 3,4-dichloro-N-{2-[(4,6-dimethoxypyrimidin-2-yl)oxy]benzyl}aniline, and the following compounds:

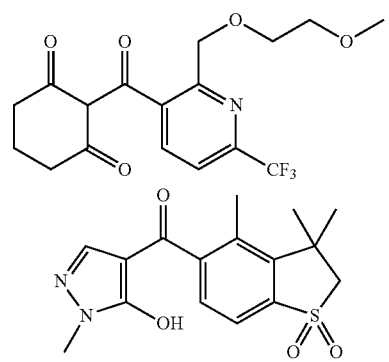

-continued

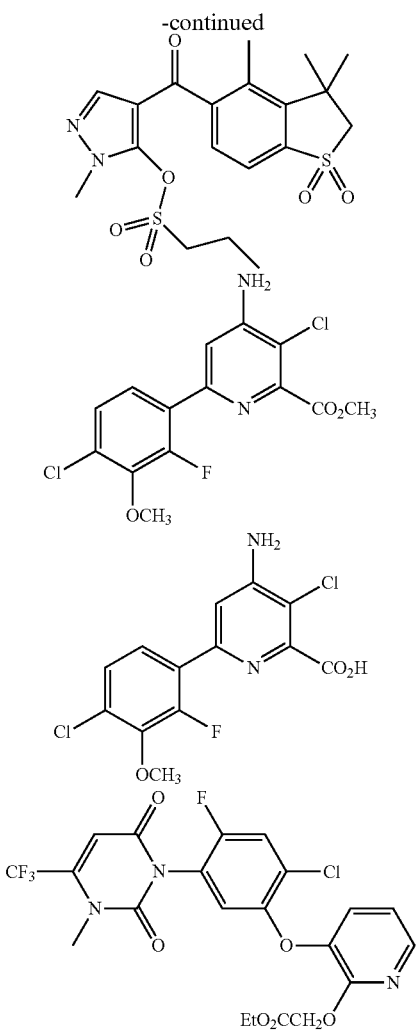

The invention is to be illustrated by the biological examples which follow, but without restricting it thereto.

Biological Examples

Seeds of monocotyledonous and dicotyledonous crop plants were laid out in sandy loam in wood-fiber pots, covered with soil and cultivated in a greenhouse under good growth conditions. The test plants were treated at the early leaf stage (BBCH10-BBCH13). To ensure uniform water supply before commencement of stress, the potted plants were supplied with the maximum amount of water immediately beforehand by dam irrigation and, after application, transferred in plastic inserts in order to prevent subsequent, excessively rapid drying. The inventive compounds, formulated in the form of wettable powders (WP), wettable granules (WG), suspension concentrates (SC) or emulsion concentrates (EC), were sprayed onto the green parts of the plants as an aqueous suspension at an equivalent water application rate of 600 l/ha with addition of 0.2% wetting agent (agrotin). Substance application is followed immediately by stress treatment of the plants (cold or drought stress). For cold stress treatment, the plants were kept under the following controlled conditions:
"day": 12 hours with illumination at 8° C.
"night": 12 hours without illumination at 1° C.
Drought stress was induced by gradual drying out under the following conditions:

"day": 14 hours with illumination at 26° C.
"night": 10 hours without illumination at 18° C.

The duration of the respective stress phases was guided mainly by the state of the untreated (=treated with blank formulation without test compound), stressed control plants and thus varied from crop to crop. It was ended (by re-irrigating or transfer to a greenhouse with good growth conditions) as soon as irreversible damage was observed on the untreated, stressed control plants. In the case of dicotyledonous crops, for example oilseed rape and soybeans, the duration of the drought stress phase varied between 3 and 5 days, in the case of monocotyledonous crops, for example wheat, barley or corn, between 6 and 10 days. The duration of the cold stress phase varied between 12 and 14 days.

The end of the stress phase was followed by an approx. 5-7-day recovery phase, during which the plants were once again kept under good growth conditions in a greenhouse. In order to rule out any influence of the effects observed by any fungicidal action of the test compounds, it was additionally ensured that the tests proceeded without fungal infection and without infection pressure.

After the recovery phase had ended, the intensities of damage were rated in visual comparison to untreated, unstressed controls of the same age (in the case of drought stress) or the same growth stage (in the case of cold stress). The intensity of damage was first assessed as a percentage (100%=plants have died, 0%=like control plants). These values were then used to calculate the efficacy of the test compounds (=percentage reduction in the intensity of damage as a result of substance application) by the following formula:

$$EF = \frac{(DV_{us} - DV_{ts}) \times 100}{DV_{us}}$$

EF: efficacy (%)
$DV_{us}$: damage value of the untreated, stressed control
$DV_{ts}$: damage value of the plants treated with test compound The tables A-1 and B-1 to B-4 below list mean values in each case from three results of the same test.

Efficacies of selected compounds of the formula (I) under cold stress using the example of ZEAMX:

TABLE A-1

| No. | Substance | Dosage | Unit | EF (ZEAMX) |
|---|---|---|---|---|
| 1 | I.1-36 | 25 | g/ha | >5 |
| 2 | I.1-172 | 25 | g/ha | >5 |
| 3 | I.1-204 | 25 | g/ha | >5 |
| 4 | I.1-429 | 250 | g/ha | >5 |
| 5 | I.1-440 | 25 | g/ha | >5 |
| 6 | I.3-31 | 250 | g/ha | >5 |
| 7 | I.4-51 | 250 | g/ha | >5 |
| 8 | I.4-63 | 50 | g/ha | >5 |
| 9 | I.4-183 | 25 | g/ha | >5 |
| 10 | I.4-184 | 250 | g/ha | >5 |

Efficacies of selected compounds of the formula (I) under drought stress using the examples of HORVS, BRSNS, ZEAMX und TRZAS:

TABLE B-1

| No. | Substance | Dosage | Unit | EF (HORVS) |
|---|---|---|---|---|
| 1 | I.1-32 | 500 | g/ha | >5 |

TABLE B-2

| No. | Substance | Dosage | Unit | EF (BRSNS) |
|---|---|---|---|---|
| 1 | I.1-145 | 50 | g/ha | >5 |
| 2 | I.1-153 | 500 | g/ha | >5 |
| 3 | I.1-165 | 250 | g/ha | >5 |
| 4 | I.1-181 | 250 | g/ha | >5 |
| 5 | I.1-267 | 250 | g/ha | >5 |
| 6 | I.1-281 | 250 | g/ha | >5 |
| 7 | I.1-283 | 250 | g/ha | >5 |
| 8 | I.1-338 | 100 | g/ha | >5 |
| 9 | I.3-1 | 250 | g/ha | >5 |
| 10 | I.3-17 | 250 | g/ha | >5 |
| 11 | I.3-31 | 25 | g/ha | >5 |
| 12 | I.4-16 | 250 | g/ha | >5 |
| 13 | I.4-75 | 250 | g/ha | >5 |
| 14 | I.4-90 | 250 | g/ha | >5 |
| 15 | I.4-115 | 250 | g/ha | >5 |
| 16 | I.4-181 | 250 | g/ha | >5 |
| 17 | I.4-232 | 250 | g/ha | >5 |
| 18 | I.5-22 | 2.5 | g/ha | >5 |

TABLE B-3

| No. | Substance | Dosage | Unit | EF (ZEAMX) |
|---|---|---|---|---|
| 1 | I.1-15 | 500 | g/ha | >5 |
| 2 | I.1-30 | 500 | g/ha | >5 |
| 3 | I.1-44 | 500 | g/ha | >5 |
| 4 | I.1-45 | 500 | g/ha | >5 |
| 5 | I.1-139 | 500 | g/ha | >5 |
| 6 | I.1-148 | 500 | g/ha | >5 |
| 7 | I.1-153 | 500 | g/ha | >5 |
| 8 | I.1-157 | 500 | g/ha | >5 |
| 9 | I.1-165 | 250 | g/ha | >5 |
| 10 | I.1-197 | 250 | g/ha | >5 |
| 11 | I.1-201 | 250 | g/ha | >5 |
| 12 | I.1-267 | 250 | g/ha | >5 |
| 13 | I.1-281 | 250 | g/ha | >5 |
| 14 | I.1-282 | 250 | g/ha | >5 |
| 15 | I.1-283 | 250 | g/ha | >5 |
| 16 | I.1-303 | 250 | g/ha | >5 |
| 17 | I.1-318 | 250 | g/ha | >5 |
| 18 | I.1-338 | 100 | g/ha | >5 |
| 19 | I.1-424 | 250 | g/ha | >5 |
| 20 | I.3-31 | 250 | g/ha | >5 |
| 21 | I.3-17 | 250 | g/ha | >5 |
| 22 | I.3-32 | 250 | g/ha | >5 |
| 23 | I.4-21 | 1000 | g/ha | >5 |
| 24 | I.4-85 | 250 | g/ha | >5 |
| 25 | I.4-84 | 250 | g/ha | >5 |
| 26 | I.4-97 | 250 | g/ha | >5 |
| 27 | I.4-165 | 250 | g/ha | >5 |
| 28 | I.4-175 | 250 | g/ha | >5 |
| 29 | I.4-177 | 250 | g/ha | >5 |
| 30 | I.4-180 | 250 | g/ha | >5 |
| 31 | I.4-181 | 250 | g/ha | >5 |
| 32 | I.4-196 | 250 | g/ha | >5 |
| 33 | I.4-295 | 250 | g/ha | >5 |
| 34 | I.4-324 | 250 | g/ha | >5 |
| 35 | I.4-330 | 250 | g/ha | >5 |
| 36 | I.4-340 | 25 | g/ha | >5 |
| 37 | I.5-22 | 250 | g/ha | >5 |

TABLE B-4

| No. | Substance | Dosage | Unit | EF (TRZAS) |
|---|---|---|---|---|
| 1 | I.1-165 | 250 | g/ha | >5 |
| 2 | I.1-197 | 250 | g/ha | >5 |
| 3 | I.1-281 | 250 | g/ha | >5 |
| 4 | I.1-338 | 100 | g/ha | >5 |
| 5 | I.1-378 | 250 | g/ha | >5 |
| 6 | I.3-31 | 25 | g/ha | >5 |
| 7 | I.4-75 | 250 | g/ha | >5 |
| 8 | I.4-97 | 250 | g/ha | >5 |
| 9 | I.4-115 | 250 | g/ha | >5 |
| 10 | I.4-136 | 250 | g/ha | >5 |
| 11 | I.4-193 | 250 | g/ha | >5 |
| 12 | I.4-226 | 250 | g/ha | >5 |
| 13 | I.4-227 | 250 | g/ha | >5 |
| 14 | I.4-232 | 250 | g/ha | >5 |
| 15 | I.4-330 | 250 | g/ha | >5 |
| 16 | I.5-22 | 250 | g/ha | >5 |

In the above tables:
BRSNS=*Brassica napes*
HORVS=*Hordeum vulgare*
TRZAS=*Triticum aestivum*
ZEAMX=*Zea mays*

Similar results were also achieved with further compounds of the formula (I), also in the case of application to different plant species.

The invention claimed is:

1. A method for increasing tolerance to abiotic stress in plants, comprising:
applying, to the plants, the seed thereof, or to the area on which the plants grow, or to genetically modified cultivars, the seed thereof, or to cultivated areas on which these cultivars grow, an effective, non-toxic amount of at least one substituted fused dihydropyrimidinone of the formula (I) or a salt thereof:

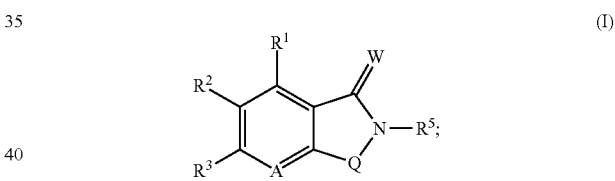

where:
Q represents the moiety:

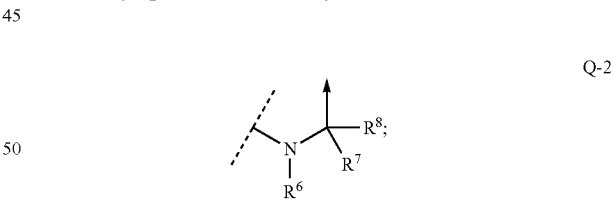

where $R^6$, $R^7$, and $R^8$ are each as defined below; and where the arrow represents a bond to the N—$R^5$ group;

W is oxygen or sulfur;

A is N (nitrogen) or a C—$R^4$ moiety;
where $R^4$ in the C—$R^4$ moiety is in each case as defined below;

$R^1$, $R^2$, and $R^3$ are each independently hydrogen or fluorine;

$R^4$ is nitro, amino, hydroxyl, fluorine, chlorine, bromine, iodine, cyano, hydrothio, ($C_1$-$C_4$)-alkyl, ($C_3$-$C_6$)-cycloalkyl, ($C_2$-$C_6$)-alkenyl, ($C_2$-$C_6$)-alkynyl, aryl, aryl-($C_1$-$C_4$)-alkyl, aryl-($C_2$-$C_6$)-alkenyl, aryl-($C_2$-$C_6$)-alkynyl, heteroaryl, ($C_3$-$C_6$)-cycloalkyl-($C_1$-$C_4$)-alkyl, heteroaryl-($C_2$-$C_6$)-alkenyl, heteroaryl-($C_2$-$C_6$)-alkynyl, ($C_1$-$C_4$)-haloalkyl, ($C_3$-$C_6$)-halocycloalkyl, ($C_2$-$C_6$)-haloalkenyl, ($C_2$-$C_6$)-haloalkylalkynyl, ($C_1$-$C_4$)-trialkylsilyl-($C_2$-$C_6$)-alkynyl, ($C_1$-$C_4$)-alkoxy-($C_1$-$C_4$)-alkyl, ($C_1$-$C_4$)-alkoxy ($C_1$-$C_4$)-haloalkoxy, ($C_2$-$C_6$)-alkenyloxy-($C_1$-$C_4$)-alkyl, aryl-($C_1$-$C_4$)-alkoxy, ($C_1$-$C_6$)-alkylamino, ($C_2$-$C_6$)-alkenylamino, ($C_2$-$C_6$)-alkynylamino, ($C_1$-$C_4$)-alkylthio, ($C_1$-$C_4$)-haloalkylthio, bis-($C_1$-$C_6$)-alkylamino, ($C_3$-$C_6$)-cycloalkylamino, ($C_3$-$C_6$)-haloalkylamino, ($C_1$-$C_6$)-alkylcarbonylamino, ($C_3$-$C_6$)-cycloalkylcarbonylamino, ($C_1$-$C_4$)-haloalkylcarbonylamino, ($C_1$-$C_4$)-alkoxycarbonylamino, ($C_1$-$C_4$)-alkylaminocarbonylamino, ($C_1$-$C_4$)-alkylsulfonylamino, ($C_3$-$C_6$)-cycloalkylsulfonylamino, arylsulfonylamino, hetarylsulfonylamino, ($C_3$-$C_6$)-haloalkylsulfonylamino, ($C_1$-$C_4$)-alkylsulfonyl, ($C_1$-$C_6$)-haloalkylsulfonyl, arylsulfonyl, ($C_1$-$C_4$)alkylsulfinyl, ($C_1$-$C_4$)-haloalkylsulfinyl, arylsulfinyl, ($C_3$-$C_6$)-cycloalkyl-($C_1$-$C_4$)-alkoxy, ($C_1$-$C_6$)-alkynyl-($C_1$-$C_4$)-alkoxy, ($C_2$-$C_6$)-alkenyl-($C_1$-$C_4$)-alkoxy, ($C_2$-$C_6$)-alkenyloxy-($C_1$-$C_4$)-alkoxy, ($C_1$-$C_4$)-alkyloxy-($C_1$-$C_4$)-alkoxy, ($C_1$-$C_4$)-alkylamino-($C_1$-$C_4$)-alkoxy, bis-($C_1$-$C_6$)-alkylamino-($C_1$-$C_4$)-alkoxy, or ($C_3$-$C_6$)-cycloalkylamino-($C_1$-$C_4$)-alkoxy;

$R^5$ is hydrogen ($C_1$-$C_6$)-alkyl, ($C_2$-$C_6$)-alkenyl, ($C_3$-$C_6$)-alkynyl, ($C_3$-$C_6$)-cycloalkyl, ($C_1$-$C_6$)-alkylthio-($C_1$-$C_6$)-alkyl, ($C_1$-$C_6$)-alkoxy-($C_1$-$C_6$)-alkyl, ($C_1$-$C_4$)-haloalkyl, ($C_1$-$C_6$)-cycloalkyl-($C_1$-$C_4$)-alkyl, ($C_1$-$C_6$)-alkoxycarbonyl, ($C_1$-$C_6$)-alkylcarbonyl, ($C_3$-$C_6$)-cycloalkylcarbonyl, ($C_1$-$C_6$)-alkylaminocarbonyl, ($C_3$-$C_6$)-cycloalkylaminocarbonyl, ($C_1$-$C_4$)-haloalkylaminocarbonyl, ($C_2$-$C_6$)-alkynylaminocarbonyl, cyano-($C_1$-$C_6$)-alkylaminocarbonyl, ($C_1$-$C_7$)-heterocycloalkylcarbonyl, heteroaryl-($C_1$-$C_7$)-alkylaminocarbonyl, ($C_2$-$C_6$)-alkenyloxycarbonyl, ($C_3$-$C_7$)-cycloalkyl-($C_1$-$C_4$)-alkoxycarbonyl, ($C_3$-$C_7$)-cycloalkyl-($C_1$-$C_4$)-alkylaminocarbonyl, aryl-($C_1$-$C_4$)-alkylaminocarbonyl, cyano-($C_1$-$C_6$)-alkyl, nitro-($C_1$-$C_6$)-alkyl, ($C_1$-$C_7$)-alkylamino-($C_1$-$C_7$)-alkyl, bis-($C_1$-$C_7$)-alkylamino-($C_1$-$C_7$)-alkyl, aminocarbonyl-($C_1$-$C_7$)-alkyl, ($C_1$-$C_7$)-alkylaminocarbonyl-($C_1$-$C_7$)-alkyl, bis-($C_1$-$C_7$)-alkylaminocarbonyl-($C_1$-$C_7$)-alkyl, or ($C_1$-$C_7$)-alkoxycarbonyl-($C_1$-$C_7$)-alkyl;

$R^6$ is hydrogen, formyl, hydroxyl, amino, ($C_1$-$C_6$)-alkyl, ($C_2$-$C_6$)-alkenyl, ($C_2$-$C_6$)-alkynyl, ($C_3$-$C_6$)-cycloalkyl, ($C_1$-$C_6$)-alkylthio-($C_1$-$C_6$)-alkyl, ($C_1$-$C_6$)-alkoxy-($C_1$-$C_6$)-alkyl, ($C_1$-$C_4$)-haloalkyl, aryl-($C_1$-$C_4$)-alkyl, aryl-($C_2$-$C_6$)-alkenyl, ($C_3$-$C_6$)-cycloalkyl-($C_1$-$C_4$)-alkyl, ($C_1$-$C_6$)-alkoxycarbonyl, ($C_1$-$C_6$)-alkylcarbonyl, ($C_3$-$C_6$)-cycloalkylcarbonyl, ($C_1$-$C_6$)-alkylaminocarbonyl, ($C_3$-$C_6$)-cycloalkylaminocarbonyl, ($C_1$-$C_4$)-haloalkylaminocarbonyl, ($C_2$-$C_6$)-alkynylaminocarbonyl, cyano-($C_1$-$C_6$)-alkylaminocarbonyl, ($C_4$-$C_7$)-heterocycloalkylcarbonyl, heteroaryl-($C_1$-$C_7$)-alkylaminocarbonyl, ($C_2$-$C_6$)-alkenyloxycarbonyl, ($C_3$-$C_7$)-cycloalkyl-($C_1$-$C_4$)-alkoxycarbonyl, ($C_3$-$C_7$)-cycloalkyl-($C_1$-$C_4$)-alkylaminocarbonyl, aryl-($C_1$-$C_4$)-alkylaminocarbonyl, cyano-($C_1$-$C_6$)-alkyl nitro-($C_1$-$C_6$)-alkyl, heteroaryl-($C_1$-$C_4$)-alkyl, ($C_1$-$C_7$)-alkylamino-($C_1$-$C_7$)-alkyl, bis-($C_1$-$C_7$)-alkylamino-($C_1$-$C_7$)-alkyl, aminocarbonyl-($C_1$-$C_7$)-alkyl, ($C_1$-$C_7$)-alkylaminocarbonyl-($C_1$-$C_7$)-alkyl, bis-($C_1$-$C_7$)-alkylaminocarbonyl-($C_1$-$C_7$)-alkyl, or ($C_1$-$C_7$)-alkoxycarbonyl-($C_1$-$C_7$)-alkyl;

$R^7$ is aryl-($C_2$-$C_4$)-alkenyl, aryl-($C_2$-$C_4$)-haloalkenyl, heteroaryl-($C_2$-$C_4$)-alkenyl, heteroaryl-($C_2$-$C_4$)-haloalkenyl, ($C_3$-$C_7$)-heterocycloalkyl-($C_2$-$C_4$)-alkynyl, ($C_3$-$C_7$)-heterocycloalkenyl-($C_2$-$C_4$)-alkynyl, ($C_3$-$C_7$)-heterocycloalkyl-($C_2$-$C_4$)-alkenyl, ($C_3$-$C_7$)-heterocycloalkenyl-($C_2$-$C_4$)-alkenyl, ($C_3$-$C_7$)-heterocycloalkyl-($C_1$-$C_4$)-alkyl, or ($C_3$-$C_7$)-heterocycloalkenyl-($C_1$-$C_4$)-alkyl, where the heteroatom in the heteroaryl, heterocycloalkyl, and heterocycloalkenyl optionally bears a charge; and $R^8$ is hydrogen.

2. The method of claim 1;

where, in formula (I):

$R^1$, $R^2$, and $R^3$ are each independently hydrogen;

$R^4$ is nitro, amino, hydroxyl, fluorine, chlorine, bromine, iodine, cyano, hydrothio, ($C_1$-$C_4$)-alkyl, ($C_3$-$C_6$)-cycloalkyl, ($C_2$-$C_6$)-alkenyl, ($C_2$-$C_6$)-alkynyl, aryl, aryl-($C_1$-$C_4$)-alkyl, aryl-($C_2$-$C_6$)-alkenyl, aryl-($C_2$-$C_6$)-alkynyl, heteroaryl, ($C_3$-$C_6$)-cycloalkyl-($C_1$-$C_4$)-alkyl, heteroaryl-($C_2$-$C_6$)-alkenyl, heteroaryl-($C_2$-$C_6$)-alkynyl, ($C_1$-$C_4$)-haloalkyl, ($C_3$-$C_6$)-halocycloalkyl, ($C_2$-$C_6$)-haloalkenyl, ($C_2$-$C_6$)-haloalkylalkynyl, ($C_1$-$C_4$)-trialkylsilyl-($C_2$-$C_6$)-alkynyl, ($C_1$-$C_4$)-alkoxy-($C_1$-$C_4$)-alkyl, ($C_1$-$C_4$)-alkoxy, ($C_1$-$C_4$)-haloalkoxy, ($C_2$-$C_6$)-alkenyloxy-($C_1$-$C_4$)-alkyl, aryl-($C_1$-$C_4$)-alkoxy, ($C_1$-$C_6$)-alkylamino, ($C_2$-$C_6$)-alkynylamino, ($C_1$-$C_6$)-alkylthio, ($C_1$-$C_4$)-haloalkylthio, bis-($C_1$-$C_6$)-alkylamino, ($C_3$-$C_6$)-cycloalkylamino, ($C_3$-$C_6$)-haloalkylamino, ($C_1$-$C_6$)-alkylcarbonylamino, ($C_3$-$C_6$)-cycloalkylcarbonylamino, ($C_1$-$C_4$)-haloalkylcarbonylamino, ($C_1$-$C_4$)-alkoxycarbonylamino, ($C_1$-$C_4$)-alkylaminocarbonylamino, ($C_1$-$C_4$)-alkylsulfonylamino, ($C_3$-$C_6$)-cycloalkylsulfonylamino, arylsulfonylamino, hetarylsulfonylamino, ($C_3$-$C_6$)-haloalkylsulfonylamino, ($C_1$-$C_4$)-alkylsulfonyl, ($C_1$-$C_6$)-haloalkylsulfonyl, arylsulfonyl, ($C_1$-$C_4$)-alkylsulfinyl, ($C_1$-$C_4$)-haloalkylsulfinyl, ($C_3$-$C_6$)-cycloalkyl-($C_1$-$C_4$)-alkoxy, ($C_1$-$C_6$)-alkynyl-($C_1$-$C_4$)-alkoxy, ($C_2$-$C_6$)-alkenyl-($C_1$-$C_4$)-alkoxy, ($C_2$-$C_6$)-alkenyloxy-($C_1$-$C_4$)-alkoxy, ($C_1$-$C_4$)-alkyloxy-($C_1$-$C_4$)-alkoxy, ($C_1$-$C_4$)-alkylamino-($C_1$-$C_4$)-alkoxy, bis-($C_1$-$C_6$)-alkylamino-($C_1$-$C_4$)-alkoxy, or ($C_3$-$C_6$)-cycloalkylamino-($C_1$-$C_4$)-alkoxy;

$R^5$ is hydrogen or one of the following groups:

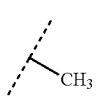

G-1

G-2

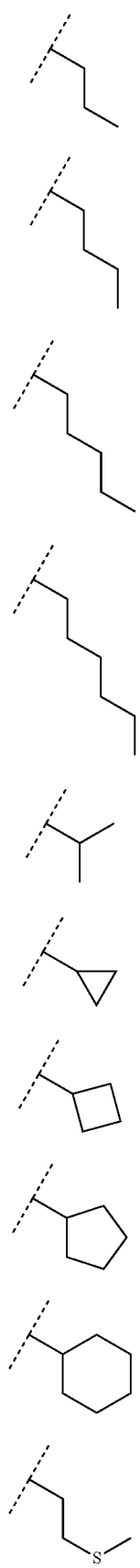
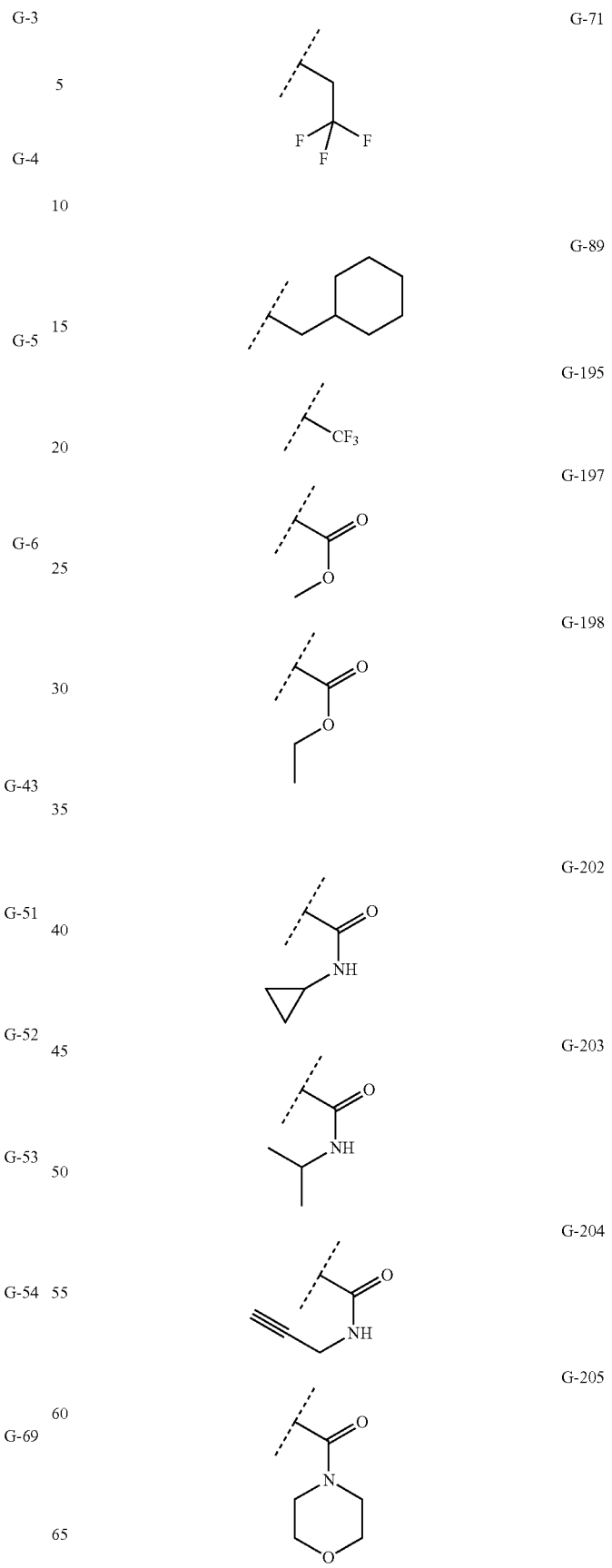

G-206 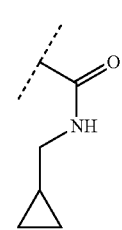
G-207 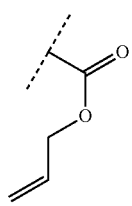
G-208 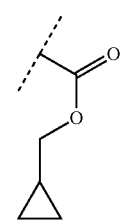
G-209 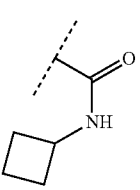
G-210 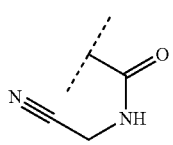
G-212 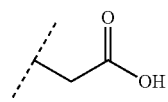
G-213 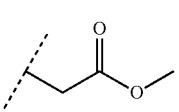
G-214 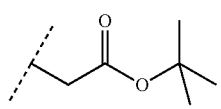
G-215 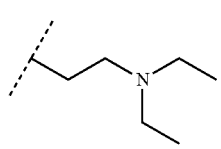
G-216 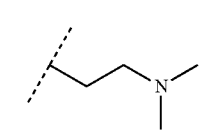
G-222 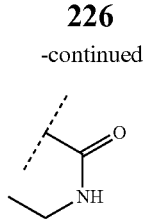
G-223 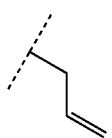
G-224 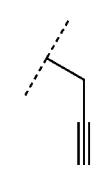
G-225 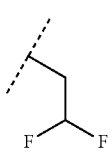
G-226 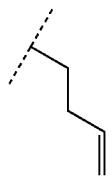
G-227 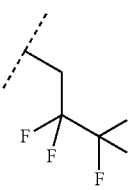
G-228 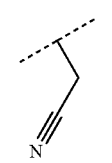
G-229 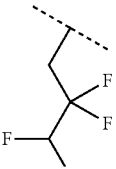
G-230 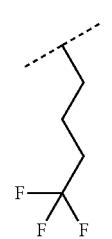

-continued
G-231
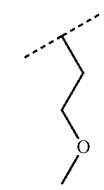
G-232
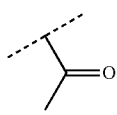
G-233
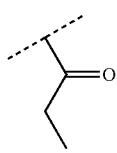
G-234
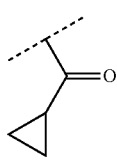
G-235
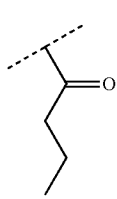
G-236
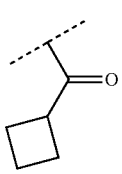
$R^6$ is hydrogen, hydroxyl, or one of the following groups:
G-1
G-2
G-3
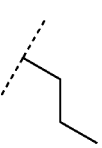
-continued
G-4
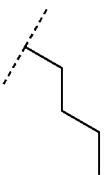
G-5
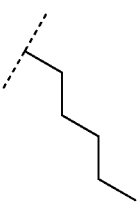
G-6
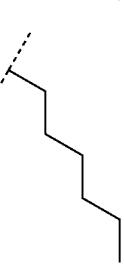
G-43
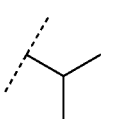
G-51
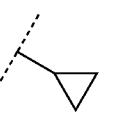
G-52
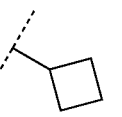
G-53
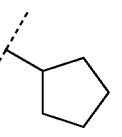
G-54
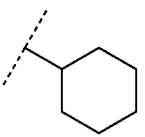
G-69
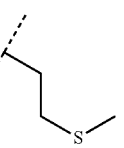
G-71
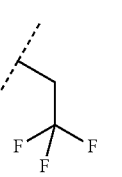

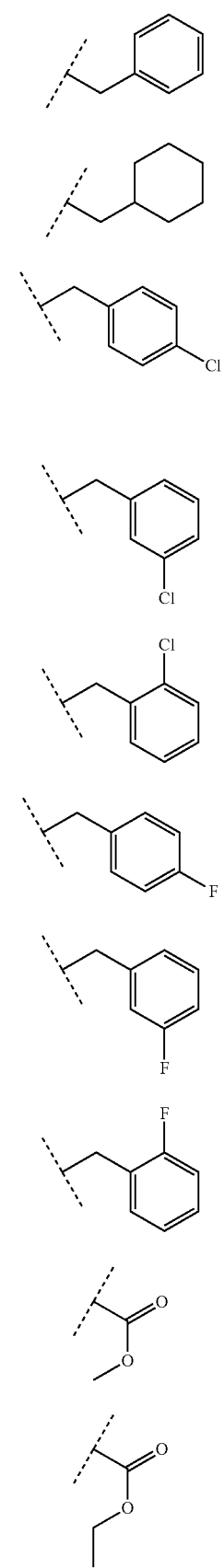
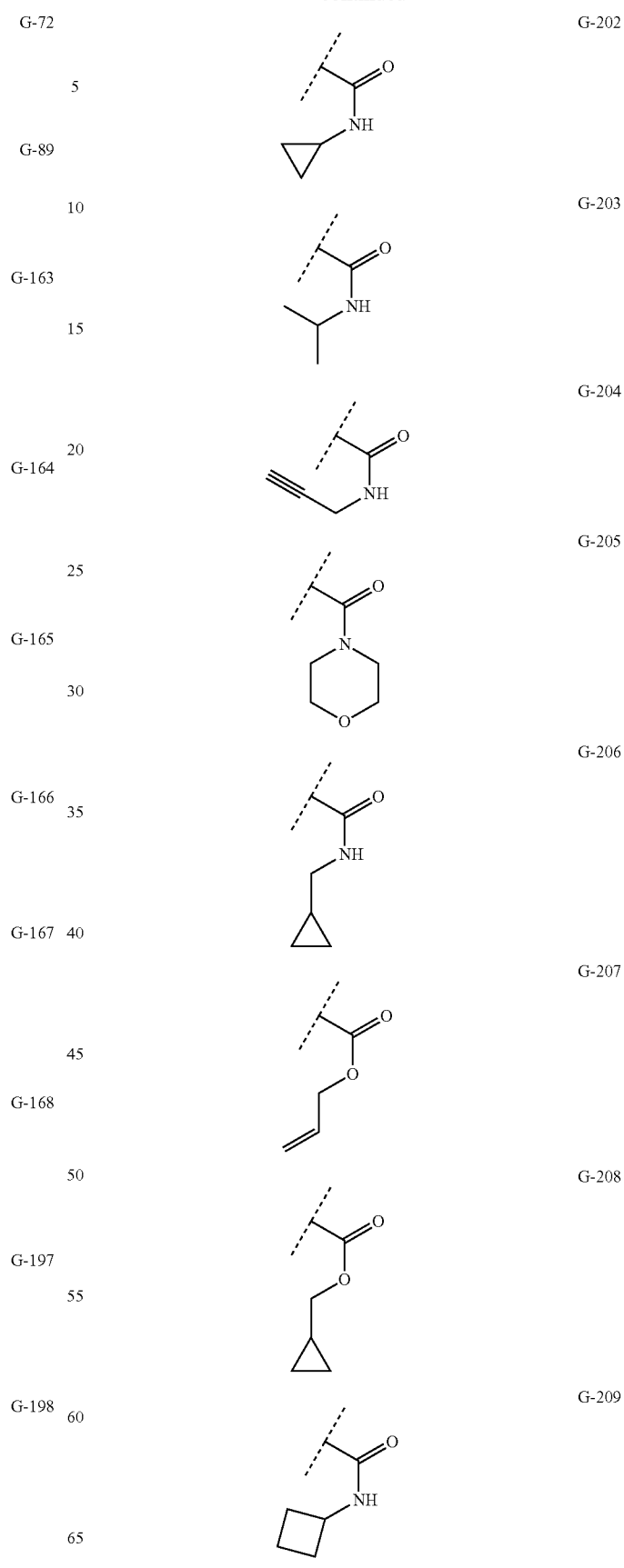

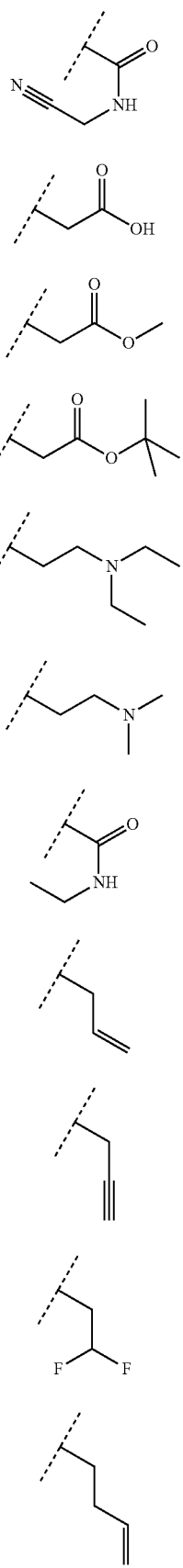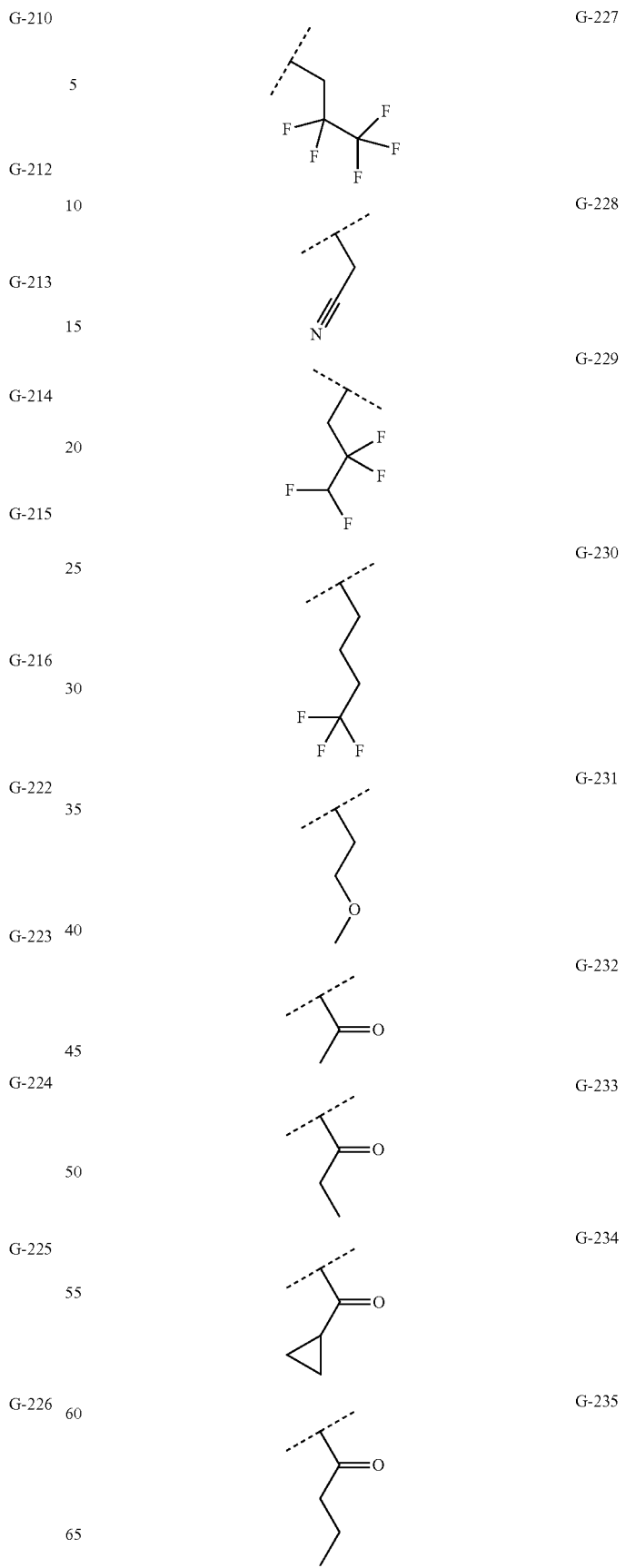

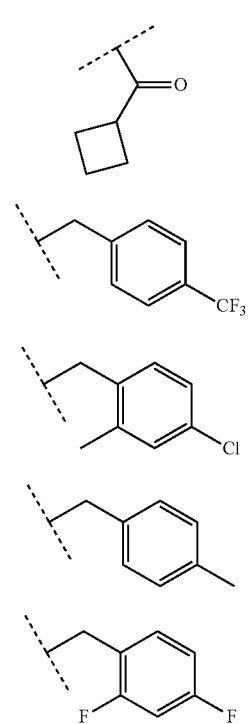
R[7] is one of the following groups:
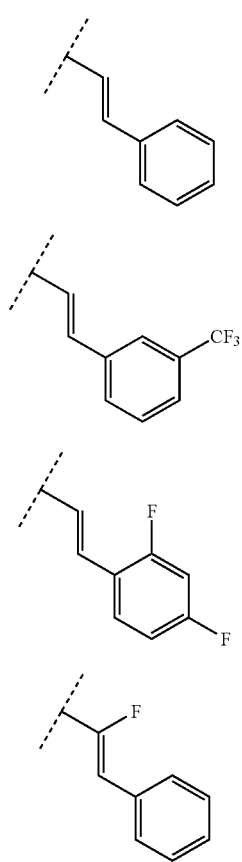
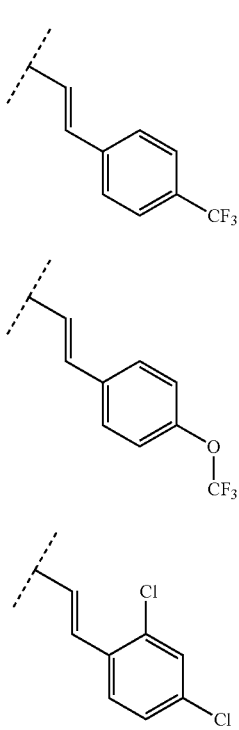
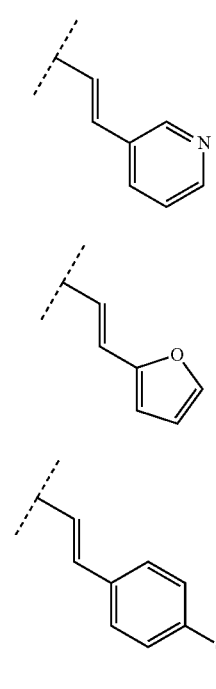
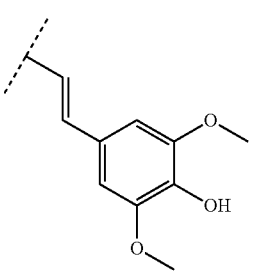

G-131 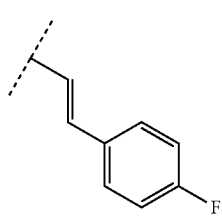
G-132 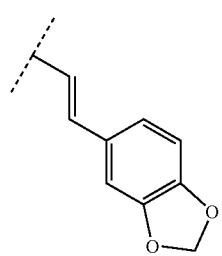
G-138 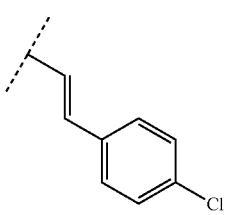
G-139 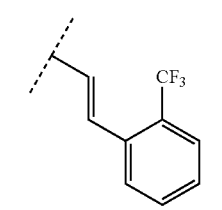
G-140 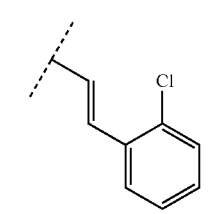
G-141 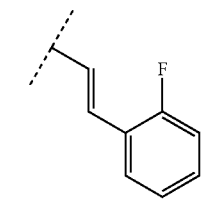
G-142 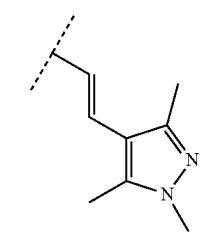
G-143 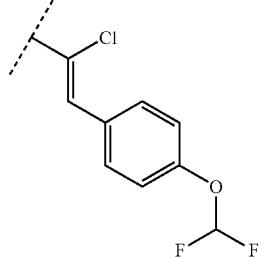
G-144 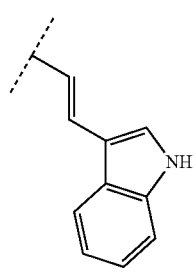
G-185 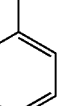
G-247 
G-248 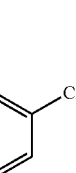
G-249 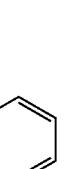
G-250 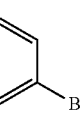

| | |
|---|---|
| G-251 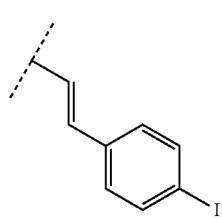 | G-258 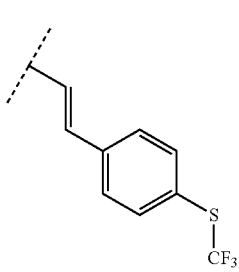 |
| G-252 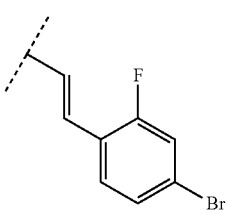 | G-259 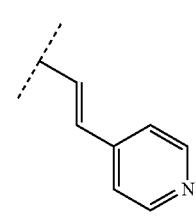 |
| G-253 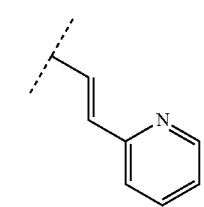 | G-260 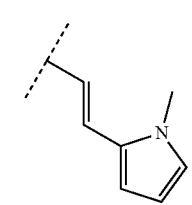 |
| G-254 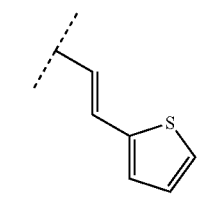 | G-261 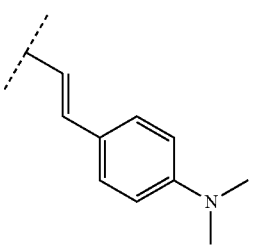 |
| G-255 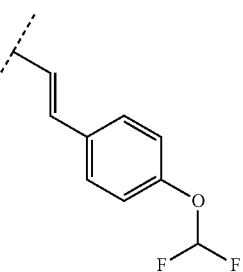 | G-262 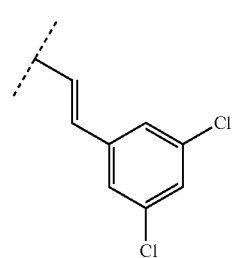 |
| G-256 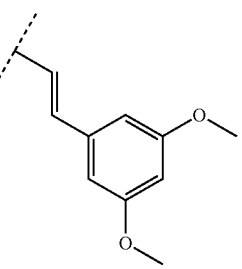 | G-263 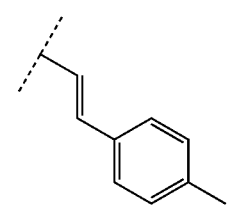 |
| G-257 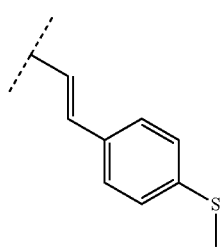 | G-264 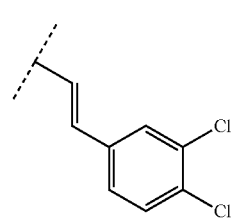 |

239
-continued
G-265
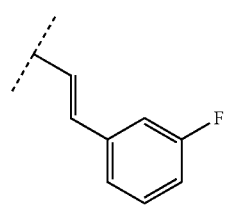
G-266
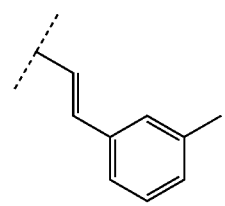
G-267
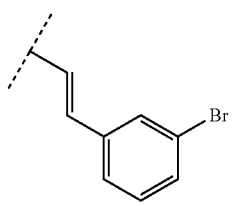
G-268
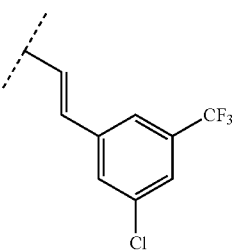
G-269
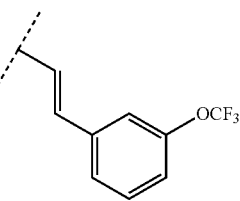
G-270
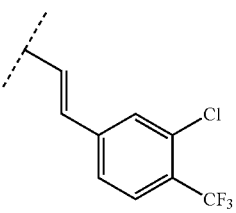
G-271
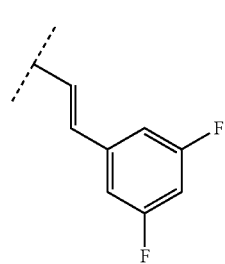
240
-continued
G-272
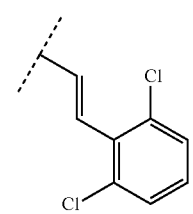
G-273
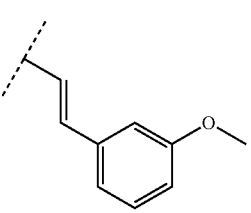
G-274
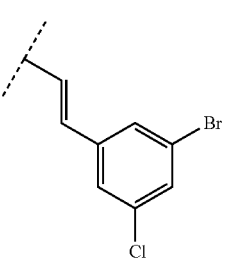
G-275
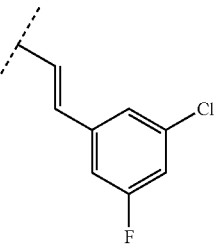
G-276
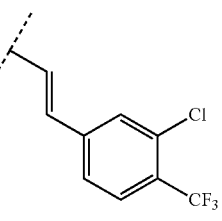
G-277
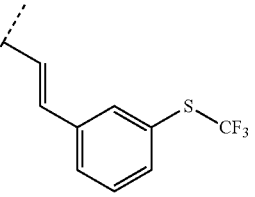
G-278
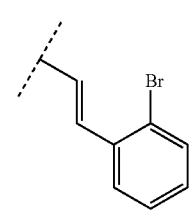

G-279 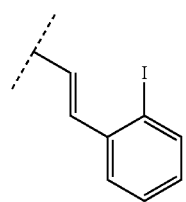

G-280 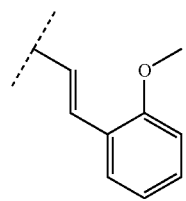

G-281 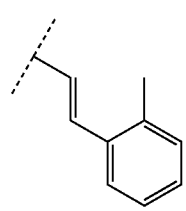

G-282 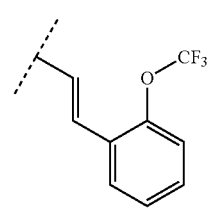

$R^8$ is hydrogen or one of the following groups:

G-1 

G-2 

G-3 

G-4 

G-5 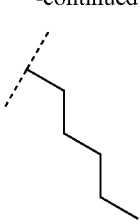

G-6 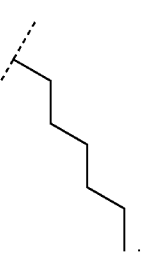

3. The method of claim 1;
wherein the substituted fused dihydropyrimidinone of the formula (I) or salt thereof is applied in a spray application.

4. The method of claim 1;
wherein the substituted fused dihydropyrimidinone of the formula (I) or salt thereof is applied in a spray application in combination with at least one active ingredients selected from the group consisting of insecticides, attractants, acaricides, fungicides, nematicides, herbicides, growth regulators, safeners, substances which influence plant maturity, and bactericides.

5. The method of claim 3;
wherein the substituted fused dihydropyrimidinone of the formula (I) or salts thereof is applied in a spray application to plants and plant parts and applied in combinations with at least one fertilizer.

6. The method of claim 1;
wherein the application is to genetically modified cultivars, the seed thereof, or to cultivated areas on which these cultivars grow.

7. The method of claim 1;
wherein the application is to the plants, the seed thereof or to the area on which the plants grow.

8. The method of claim 1;
wherein the plants are selected from the group consisting of useful plants, ornamental plants, turfgrass types, and trees.

9. The method as claimed in claim 8;
wherein the resistance of the plants thus treated to abiotic stress has been increased by at least 3% compared to untreated plants under otherwise identical physiological conditions.

10. The method of claim 1;
wherein the amount of substituted fused dihydropyrimidinone of the formula (I) or salt thereof applied is an amount effective for enhancing the resistance of plants to abiotic stress factors.

11. The method of claim 10;
wherein the abiotic stress factors comprise at least one condition selected from the group consisting of drought, cold and hot conditions, drought stress, osmotic stress, waterlogging, elevated soil salinity, elevated exposure to minerals, ozone conditions, strong light conditions, limited availability of nitrogen nutrients, and limited availability of phosphorus nutrients.

* * * * *